US007678769B2

(12) United States Patent
Rotman et al.

(10) Patent No.: US 7,678,769 B2
(45) Date of Patent: Mar. 16, 2010

(54) HEPATOCYTE GROWTH FACTOR RECEPTOR SPLICE VARIANTS AND METHODS OF USING SAME

(75) Inventors: Galit Rotman, Herzilya (IL); Merav Beiman, Ness Ziona (IL); Michal Ayalon-Soffer, Ramat-HaSharon (IL); Zurit Levine, Herzlia (IL); Chen Hermesh, Karkur (IL); Anat Oren, Ramat-Aviv (IL); Zohar Tiran, Petach Tikva (IL); Dvir Dahary, Tel-Aviv (IL); Liat Mintz, East Brunswick, NJ (US); Hanqing Xie, Lambertville, NJ (US)

(73) Assignee: Compugen, Ltd., Tel Aviv (IL)

( * ) Notice: Subject to any disclaimer, the term of this patent is extended or adjusted under 35 U.S.C. 154(b) by 0 days.

(21) Appl. No.: 11/781,905

(22) Filed: Jul. 23, 2007
(Under 37 CFR 1.47)

(65) Prior Publication Data
US 2008/0159992 A1 Jul. 3, 2008

Related U.S. Application Data

(63) Continuation-in-part of application No. 10/764,833, filed on Jan. 27, 2004, now abandoned, which is a continuation-in-part of application No. 10/426,002, filed on Apr. 30, 2003, now abandoned, and a continuation-in-part of application No. 10/242,799, filed on Sep. 13, 2002, now abandoned, application No. 11/781,905, which is a continuation-in-part of application No. 11/043,591, filed on Jan. 27, 2005, application No. 11/781,905, which is a continuation-in-part of application No. 11/043,860, filed on Jan. 27, 2005, and a continuation-in-part of application No. PCT/IL2006/001155, filed on Oct. 3, 2006.

(60) Provisional application No. 60/721,961, filed on Sep. 30, 2005, provisional application No. 60/779,408, filed on Mar. 7, 2006, provisional application No. 60/799,319, filed on May 11, 2006, provisional application No. 60/322,285, filed on Sep. 14, 2001, provisional application No. 60/322,359, filed on Sep. 14, 2001, provisional application No. 60/322,506, filed on Sep. 14, 2001, provisional application No. 60/324,524, filed on Sep. 26, 2001, provisional application No. 60/354,242, filed on Feb. 6, 2002, provisional application No. 60/371,494, filed on Apr. 11, 2002, provisional application No. 60/384,096, filed on May 31, 2002, provisional application No. 60/397,784, filed on Jul. 24, 2002, provisional application No. 60/579,202, filed on Jun. 15, 2004, provisional application No. 60/539,128, filed on Jan. 27, 2004, provisional application No. 60/539,129, filed on Jan. 27, 2004.

(51) Int. Cl.
*A61K 38/00* (2006.01)
*C07K 14/00* (2006.01)

(52) U.S. Cl. .............................. 514/12; 514/2; 530/350; 424/9.1; 536/23.1
(58) Field of Classification Search .................. 514/2, 514/12; 530/350; 424/9.1; 536/23.1
See application file for complete search history.

(56) References Cited

U.S. PATENT DOCUMENTS

| 5,571,509 | A | 11/1996 | Comoglio et al. ........... 424/94.5 |
| 2004/0248157 | A1 | 12/2004 | Ayalon-Soffer et al. ......... 435/6 |
| 2005/0233960 | A1 | 10/2005 | Kong-Beltran et al. ........ 514/12 |
| 2005/0272067 | A1 | 12/2005 | Macina et al. .................. 435/6 |
| 2007/0082337 | A1 | 4/2007 | Sorek et al. ..................... 435/6 |

FOREIGN PATENT DOCUMENTS

| EP | 1 243 596 A3 | 2/2003 |
| WO | WO 02/076510 | * 10/2002 |
| WO | WO 2005/016966 | 2/2005 |
| WO | WO 2005/071059 | 8/2005 |
| WO | WO 2005/113596 | 12/2005 |
| WO | WO 2006/119510 | 11/2006 |
| WO | WO 2007/058776 | 5/2007 |
| WO | WO 2007/064437 | 6/2007 |

OTHER PUBLICATIONS

Abounader et al., "In vivo targeting of SF/HGF and c-met expression via U1snRNA/ribozymes inhibits glioma growth and angiogenesis and prompotes apoptosis[1]", *FASEB J.*, 16:108-110 (Jan. 2002).

Baek et al., "Transforming variant of Met receptor confers serum independence and anti-apoptotic property and could be involved in the mouse thymic lymphomagenesis", *Experimental and Molecular Medicine*, 36(4):283-291 (Aug. 2004).

Birchmeier et al, "Met, Metastasis, Motility and More", *Nat. Rev. Mol. Cell Biol.* 4:915-925 (Dec. 2003).

Brockmann et al., "Inhibition of Intracerebral Glioblastoma Growth by Local Treatment with the Scatter Factor/Hepatocyte Growth Factor-Antagonist NK4", *Clin. Cancer Res.*, 9:4578-4585 (Oct. 1, 2003).

Burgess et al., "Fully Human Monoclonal Antibodies to Hepatocyte Growth Factor with Therapeutic Potential Against Hepatocyte Growth Factor/c-Met—Dependent Human Tumors", *Cancer Res.*, 66(3):1721-1729 (Feb. 1, 2006).

Christensen et al., "A Selective Small Molecule Inhibitor of c-Met Kinase Inhibits c-Met-dependent Phenotypes in Vitro and Exhibits Cytoreductive Antitumor Activity in Vivo", *Cancer Res.*, 63:7345-7355 (Nov. 1, 2003).

(Continued)

*Primary Examiner*—Chih-Min Kam
(74) *Attorney, Agent, or Firm*—Fennemore Craig, P.C.

(57) ABSTRACT

Novel polypeptides that are splice variants of c-Met, the receptor for hepatocyte growth factor and polynucleotides encoding same are provided. Methods and pharmaceutical compositions which can be used to treat various disorders such as cancer, immunological-related, blood-related and skin-related disorders using the polypeptides and polynucleotides of the present invention, are also provided.

6 Claims, 76 Drawing Sheets

OTHER PUBLICATIONS

Christensen et al., "c-Met as a target for human cancer and characterization of inhibitors for therapeutic intervention", *Cancer Letters*, 225:1-26 (2005).

Huh et al., "Generation of a 'Floxed' Conditional Mutant Mouse for the HGF Receptor Gene C-*MET*: Impact of Selective Inactivation in Liver and Mammary Gland", (Abstract only) *Hepatology*, 34(4) (2001).

Kim et al., "Systemic Anti-Hepatocyte Growth Factor Monoclonal Antibody Therapy Induces the Regression of Intracranial Glioma Xenografts", *Clin. Cancer Res.*, 12(4):1292-1298 (Feb. 15, 2006).

Kong-Beltran M et al.; "The Sema domain of Met is necessary for receptor dimerization and activation", *Cancer Cell*, 6:75-84 (Jul. 2004).

Lal et al., "Targeting the c-Met Pathway Potentiates Glioblastoma Responses to γ-Radiation", *Clin. Cancer Res.*, 11(12):4479-4486 (Jun. 15, 2005).

Lin et al., "Intron-exon structure of the *MET* gene and cloning of an alternatively-spliced MET isoform reveals frequent exon-skipping of a single large internal exon", *Oncogene*, 16:833-842 (1998).

Ma et al., "A Selective Small Molecule c-MET Inhibitor, PHA665752, Cooperates with Rapamycin", *Clin. Cancer Res.*, 11:2312-2319 (Mar. 15, 2005).

Ma et al., "c-Met: Structure, functions and potential for therapeutic inhibition", *Cancer and Metastasis Reviews*, 22:309-325 (2003).

Mark, et al., "Expression and Characterization of Hepatocyte Growth Factor Receptor-IgG Fusion Proteins", *J Biol Chem.*, 267(36):26166-26171 (1992).

Maulik et al., "Role of the hepatocyte growth factor receptor, c-Met, in oncogenesis and potential for therapeutic inhibition", *Cytokine & Growth Factor Reviews*, 13:41-59 (2002).

Michieli et al., "Targeting the tumor and its microenvironment by a dual-function decoy Met receptor", *Cancer Cell*, 6(1(:61-73 (Jul. 2004).

Saimura et al., "Intraperitoneal injection of adenovirus-mediated *NK4* gene suppresses peritoneal dissemination of pancreatic cancer cell line AsPC-1 in nude mice", *Cancer Gene Therapy*, 9:799-806 (2002).

Tomioka et al., "Inhibition of Growth, Invasion, and Metasis of Human Pancreatic Carcinoma Cells by NK4 in an Orthotopic Mouse Model", *Cancer Research.*, 61:7518-7524 (Dec. 15, 2001).

Trusolino et al., "Interactions between scatter factors and their receptors: hints for therapeutic applications", *FASEB J.*, 12: 1267-1280 (Oct. 1998).

Webb et al., "The Geldanamyciines Are Potent Inhibitors of the Hepatocyte Growth Factor/Scatter Factor-Met-Urokinase Plasminogen Activator-Plasmin Proteolytic Network", *Cancer Research*, 60:342-349 (Jan. 15, 2000).

Wickramasinghe et al., "Met Activation and Receptor Dimerization in Cancer", *Cell Cycle*, 4:683-685 (May 2005).

Zhang et al., "Met decoys: Will cancer take the bait?", *Cancer Cell*, 6:5-6 (Jul. 2004).

Zhang et al., "HGF/SF-Met Signaling in the Control of Branching Morphogenesis and Invasion", *J. Cell. Biochem.*, 88:408-417 (2003).

Database Geneseq, "Receptor tyrosine kinase protein—SEQ ID 19", XP002414706 Retrieved from EBI accession No. GSP: ADY28129 Database accession No. ADY28129 (May 5, 2005).

Evans et al., "Blocking cytokines with genes", J Leuk Biol, 64:55-61 (Jul. 1998).

Hasan et al., "VEGF antagonists", Expert Opin. Biol, Ther., 1(4):703-718 (2001).

Lin et al., "Intron-exon structure of the MET gene and doing of an alternatively-spliced Met Isoform reveals frequent exon-skipping of a single large internal exon", Oncogene, 16:833-842 (1998).

Muller-Newen et al., "Soluble Receptors for Cytokines and Growth Factors", Int Arch Allergy Immunol, 111:99-106 (1996).

Rodrigues et al., "Isoforms of the met receptor tyrosine kinase", EXS, 65:167-179 (1993).

Rodrigues et al., "Alternative Splicing Generates Isoforms of the met Receptor Tyrosine Kinase Which Undergo Differential Processing", Mol Cell Biol, 11:2962-2970.

Australian Office Action dated Oct. 13, 2009 for corresponding Australian patent application No. 2005206389 (3 pages).

\* cited by examiner

FIG. 1A

```
  1 MKAPAVLAPGILVLLFTLVQRSNGECKEALAKSEMNVNMKYQLPNFTAET   50
    ||||||||||||||||||||||||||||||||||||||||||||||||||
  1 MKAPAVLAPGILVLLFTLVQRSNGECKEALAKSEMNVNMKYQLPNFTAET   50

51 PIQNVILHEHHIFLGATNYIYVLNEEDLQKVAEYKTGPVLEHPDCFPCQD  100
    ||||||||||||||||||||||||||||||||||||||||||||||||||
 51 PIQNVILHEHHIFLGATNYIYVLNEEDLQKVAEYKTGPVLEHPDCFPCQD  100

101 CSSKANLSGGVWKDNINMALVVDTYYDDQLISCGSVNRGTCQRHVFPHNH  150
    ||||||||||||||||||||||||||||||||||||||||||||||||||
101 CSSKANLSGGVWKDNINMALVVDTYYDDQLISCGSVNRGTCQRHVFPHNH  150

151 TADIQSEVHCIFSPQIEEPSQCPDCVVSALGAKVLSSVKDRFINFFVGNT  200
    ||||||||||||||||||||||||||||||||||||||||||||||||||
151 TADIQSEVHCIFSPQIEEPSQCPDCVVSALGAKVLSSVKDRFINFFVGNT  200

201 INSSYFPDHPLHSISVRRLKETKDGFMFLTDQSYIDVLPEFRDSYPIKYV  250
    ||||||||||||||||||||||||||||||||||||||||||||||||||
201 INSSYFPDHPLHSISVRRLKETKDGFMFLTDQSYIDVLPEFRDSYPIKYV  250

251 HAFESNNFIYFLTVQRETLDAQTFHTRIIRFCSINSGLHSYMEMPLECIL  300
    ||||||||||||||||||||||||||||||||||||||||||||||||||
251 HAFESNNFIYFLTVQRETLDAQTFHTRIIRFCSINSGLHSYMEMPLECIL  300
```

FIG. 1A (cont'd)

```
301 TEKRKKRSTKKEVENILQAAYVSKPGAQLARQIGASLNDDILFGVFAQSK    350
    ||||||||||||||||||||||||||||||||||||||||||||||||||
301 TEKRKKRSTKKEVENILQAAYVSKPGAQLARQIGASLNDDILFGVFAQSK    350

351 PDSAEPMDRSAMCAFPIKYVNDFFNKIVNKNNVRCLQHFYGPNHEHCFNR    400
    ||||||||||||||||||||||||||||||||||||||||||||||||||
351 PDSAEPMDRSAMCAFPIKYVNDFFNKIVNKNNVRCLQHFYGPNHEHCFNR    400

401 TLLRNSSGCEARRDEYRTEFTTALQRVDLFMGQFSEVLLTSISTFIKGDL    450
    ||||||||||||||||||||||||||||||||||||||||||||||||||
401 TLLRNSSGCEARRDEYRTEFTTALQRVDLFMGQFSEVLLTSISTFIKGDL    450

451 TIANLGTSEGRFMQVVVSRSGPSTPHVNFLLDSHPVSPEVIVEHTLNQNG    500
    ||||||||||||||||||||||||||||||||||||||||||||||||||
451 TIANLGTSEGRFMQVVVSRSGPSTPHVNFLLDSHPVSPEVIVEHTLNQNG    500

501 YTLVITGKKITKIPLNGLGCRHFQSCSQCLSAPPFVQCGWCHDKCVRSEE    550
    ||||||||||||||||||||||||||||||||||||||||||||||||||
501 YTLVITGKKITKIPLNGLGCRHFQSCSQCLSAPPFVQCGWCHDKCVRSEE    550

551 CLSGTWTQQICLPAIYKVFPNSAPLEGGTRLTICGWDFGFRRNNKFDLKK    600
    ||||||||||||||||||||||||||||||||||||||||||||||||||
551 CLSGTWTQQICLPAIYKVFPNSAPLEGGTRLTICGWDFGFRRNNKFDLKK    600

601 TRVLLGNESCTLTLSESTMNTLKCTVGPAMNKHFNMSIIISNGHGTTQYS    650
```

FIG. 1A (cont'd)

```
601 TRVLLGNESCTLTLSESTMNTLKCTVGPAMNKHFNMSIIISNGHGTTQYS 650

651 TFSYVDPVITSISPKYGPMAGGTLLLTLTGNYLNSGNSRHISIGGKTCTLK 700
    ||||||||||||||||||||||||||||||||||||||||||||||||||
651 TFSYVDPVITSISPKYGPMAGGTLLLTLTGNYLNSGNSRHISIGGKTCTLK 700

701 SVSNSILECYTPAQTISTEFAVKLKIDLANRETSIFSYREDPIVYEIHPT 750
    ||||||||||||||||||||||||||||||||||||||||||||||||||
701 SVSNSILECYTPAQTISTEFAVKLKIDLANRETSIFSYREDPIVYEIHPT 750

751 KSFISGGSTITGVGKNLNSVSVPRMVINVHEAGRNFTVACQHRSNSEIIC 800
    ||||||||||||||||||||||||||||||||||||||||||||||||||
751 KSFISGGSTITGVGKNLNSVSVPRMVINVHEAGRNFTVACQHRSNSEIIC 800

801 CTTPSLQQLNLQLPLKTKAFFMLDGILSKYFDLIYVHNPVFKPFEKPVMI 850
    ||||||||||||||||||||||||||||||||||||||||||||||||||
801 CTTPSLQQLNLQLPLKTKAFFMLDGILSKYFDLIYVHNPVFKPFEKPVMI 850

851 SMGNENVLEIKVRNALNTVLNHQLKLN
    |||||||||||
851 SMGNENVLEIK.......
```

FIG. 1B

```
  1  MKAPAVLAPGILVLLFTLVQRSNGECKEALAKSEMNVNMKYQLPNFTAET   50
     ||||||||||||||||||||||||||||||||||||||||||||||||||
  1  MKAPAVLAPGILVLLFTLVQRSNGECKEALAKSEMNVNMKYQLPNFTAET   50

51  PIQNVILHEHHIFLGATNYIYVLNEEDLQKVAEYKTGPVLEHPDCFPCQD  100
     ||||||||||||||||||||||||||||||||||||||||||||||||||
 51  PIQNVILHEHHIFLGATNYIYVLNEEDLQKVAEYKTGPVLEHPDCFPCQD  100

101  CSSKANLSGGVWKDNINMALVVDTYYDDQLISCGSVNRGTCQRHVFPHNH  150
     ||||||||||||||||||||||||||||||||||||||||||||||||||
101  CSSKANLSGGVWKDNINMALVVDTYYDDQLISCGSVNRGTCQRHVFPHNH  150

151  TADIQSEVHCIFSPQIEEPSQCPDCVVSALGAKVLSSVKDRFINFFVGNT  200
     ||||||||||||||||||||||||||||||||||||||||||||||||||
151  TADIQSEVHCIFSPQIEEPSQCPDCVVSALGAKVLSSVKDRFINFFVGNT  200

201  INSSYFPDHPLHSISVRRLKETKDGFMFLTDQSYIDVLPEFRDSYPIKYV  250
     ||||||||||||||||||||||||||||||||||||||||||||||||||
201  INSSYFPDHPLHSISVRRLKETKDGFMFLTDQSYIDVLPEFRDSYPIKYV  250

251  HAFESNNFIYFLTVQRETLDAQTFHTRIIRFCSINSGLHSYMEMPLECIL  300
     ||||||||||||||||||||||||||||||||||||||||||||||||||
251  HAFESNNFIYFLTVQRETLDAQTFHTRIIRFCSINSGLHSYMEMPLECIL  300
```

FIG. 1B (cont'd)

```
301  TEKRKKRSTKKEVFNILQAAYVSKPGAQLARQIGASLNDDILFGVFAQSK  350
     ――――――――――――――――――――――――――――――――――――――――――――――――――
301  TEKRKKRSTKKEVFNILQAAYVSKPGAQLARQIGASLNDDILFGVFAQSK  350

351  PDSAEPMDRSAMCAFPIKYVNDFFNKIVNKNNVRCLQHFYGPNHEHCFNR  400
     ――――――――――――――――――――――――――――――――――――――――――――――――――
351  PDSAEPMDRSAMCAFPIKYVNDFFNKIVNKNNVRCLQHFYGPNHEHCFNR  400

401  TLLRNSSGCEARRDEYRTEFTTALQRVDLFMGQFSEVLLTSISTFIKGDL  450
     ――――――――――――――――――――――――――――――――――――――――――――――――――
401  TLLRNSSGCEARRDEYRTEFTTALQRVDLFMGQFSEVLLTSISTFIKGDL  450

451  TIANLGTSEGRFMQVVVSRSGPSTPHVNFLLDSHPVSPEVIVEHTLNQNG  500
     ――――――――――――――――――――――――――――――――――――――――――――――――――
451  TIANLGTSEGRFMQVVVSRSGPSTPHVNFLLDSHPVSPEVIVEHTLNQNG  500

501  YTLVITGKKITKIPLNGLGCRHFQSCSQCLSAPPFVQCGWCHDKCVRSEE  550
     ――――――――――――――――――――――――――――――――――――――――――――――――――
501  YTLVITGKKITKIPLNGLGCRHFQSCSQCLSAPPFVQCGWCHDKCVRSEE  550

551  CLSGTWTQQICLPAIYKVFPNSAPLEGGTRLTICGWDFGFRRNNKFDLKK  600
     ――――――――――――――――――――――――――――――――――――――――――――――――――
551  CLSGTWTQQICLPAIYKVFPNSAPLEGGTRLTICGWDFGFRRNNKFDLKK  600

601  TRVLLGNESCTLTLSESTMNTLKCTVGPAMNKHFNMSIIISNGHGTTQYS  650
```

FIG. 1B (cont'd)

```
601 TRVLLGNESCTLTLSESTMNTLKCTVGPAMNKHFNMSIIISNGHGTTQYS 650
    ||||||||||||||||||||||||||||||||||||||||||||||||||

651 TFSYVDPVITSISPKYGPMAGGTLLTLTGNYLNSGNSRHISIGGKTCTLK 700
    ||||||||||||||||||||||||||||||||||||||||||||||||||
651 TFSYVDPVITSISPKYGPMAGGTLLTLTGNYLNSGNSRHISIGGKTCTLK 700

701 SVSNSILECYTPAQTISTEFAVKLKIDLANRETSIFSYREDPIVYEIHPT 750
    ||||||||||||||||||||||||||||||||||||||||||||||||||
701 SVSNSILECYTPAQTISTEFAVKLKIDLANRETSIFSYREDPIVYEIHPT 750

751 KSFISGGSTITGVGKNLNSVSVPRMVINVHEAGRNFTVACQHRSNSEIIC 800
    ||||||||||||||||||||||||||||||||||||||||||||||||||
751 KSFISGGSTITGVGKNLNSVSVPRMVINVHEAGRNFTVACQHRSNSEIIC 800

801 CTTPSLQQLNLQLPLKTKAFFMLDGILSKYFDLIYVHNPVFKPFEKPVMI 850
    ||||||||||||||||||||||||||||||||||||||||||||||||||
801 CTTPSLQQLNLQLPLKTKAFFMLDGILSKYFDLIYVHNPVFKPFEKPVMI 850

851 SMGNENVLEIKGNDIDPEAVKGEVLKVGNKSCENIHLHSEAVLCTVPNDL 900
    ||||||||||||||||||||||||||||||||||||||||||||||||||
851 SMGNENVLEIKGNDIDPEAVKGEVLKVGNKSCENIHLHSEAVLCTVPNDL 900

901 LKLNSELNIEVGFLHSSHDVNKEASVIMLFSGLK
    |||||||||||
901 LKLNSELNIE...
```

FIG. 1C

```
  1 MKAPAVLAPGILVLLFTLVQRSNGECKEALAKSEMNVNMKYQLPNFTAET  50
    ||||||||||||||||||||||||||||||||||||||||||||||||||
  1 MKAPAVLAPGILVLLFTLVQRSNGECKEALAKSEMNVNMKYQLPNFTAET  50

51 PIQNVILHEHHIFLGATNYIYVLNEEDLQKVAEYKTGPVLEHPDCFPCQD 100
    ||||||||||||||||||||||||||||||||||||||||||||||||||
 51 PIQNVILHEHHIFLGATNYIYVLNEEDLQKVAEYKTGPVLEHPDCFPCQD 100

101 CSSKANLSGGVWKDNINMALVVDTYYDDQLISCGSVNRGTCQRHVFPHNH 150
    ||||||||||||||||||||||||||||||||||||||||||||||||||
101 CSSKANLSGGVWKDNINMALVVDTYYDDQLISCGSVNRGTCQRHVFPHNH 150

151 TADIQSEVHCIFSPQIEEPSQCPDCVVSALGAKVLSSVKDRFINFFVGNT 200
    ||||||||||||||||||||||||||||||||||||||||||||||||||
151 TADIQSEVHCIFSPQIEEPSQCPDCVVSALGAKVLSSVKDRFINFFVGNT 200

201 INSSYFPDHPLHSISVRRLKETKDGFMFLTDQSYIDVLPEFRDSYPIKYV 250
    ||||||||||||||||||||||||||||||||||||||||||||||||||
201 INSSYFPDHPLHSISVRRLKETKDGFMFLTDQSYIDVLPEFRDSYPIKYV 250

251 HAFESNNFIYFLTVQRETLDAQTFHTRIIRFCSINSGLHSYMEMPLECIL 300
    ||||||||||||||||||||||||||||||||||||||||||||||||||
251 HAFESNNFIYFLTVQRETLDAQTFHTRIIRFCSINSGLHSYMEMPLECIL 300
```

FIG. 1C (cont'd)

```
301 TEKRKKRSTKKEVFNILQAAYVSKPGAQLARQIGASLNDDILFGVFAQSK 350
    |||||||||||||||||||||||||||||||||||||||||||||||||
301 TEKRKKRSTKKEVFNILQAAYVSKPGAQLARQIGASLNDDILFGVFAQSK 350

351 PDSAEPMDRSAMCAFPIKYVNDFFNKIVNKNNVRCLQHFYGPNHEHCFNR 400
    |||||||||||||||||||||||||||||||||||||||||||||||||
351 PDSAEPMDRSAMCAFPIKYVNDFFNKIVNKNNVRCLQHFYGPNHEHCFNR 400

401 TLLRNSSGCEARRDEYRTEFTTALQRVDLFMGQFSEVLLTSISTFIKGDL 450
    |||||||||||||||||||||||||||||||||||||||||||||||||
401 TLLRNSSGCEARRDEYRTEFTTALQRVDLFMGQFSEVLLTSISTFIKGDL 450

451 TIANLGTSEGRFMQVVVSRSGPSTPHVNFLLDSHPVSPEVIVEHTLNQNG 500
    |||||||||||||||||||||||||||||||||||||||||||||||||
451 TIANLGTSEGRFMQVVVSRSGPSTPHVNFLLDSHPVSPEVIVEHTLNQNG 500

501 YTLVITGKKITKIPLNGLGCRHFQSCSQCLSAPPFVQCGWCHDKCVRSEE 550
    |||||||||||||||||||||||||||||||||||||||||||||||||
501 YTLVITGKKITKIPLNGLGCRHFQSCSQCLSAPPFVQCGWCHDKCVRSEE 550

551 CLSGTWTQQICLPAIYKVFPNSAPLEGGTRLTICGWDFGFRRNNKFDLKK 600
    |||||||||||||||||||||||||||||||||||||||||||||||||
551 CLSGTWTQQICLPAIYKVFPNSAPLEGGTRLTICGWDFGFRRNNKFDLKK 600
```

FIG. 1C (cont'd)

```
601 TRVLLGNESCTLTLSESTMNTLKCTVGPAMNKHFNMSIIISNGHGTTQYS 650
    |||||||||||||||||||||||||||||||||||||||||||||||||||
601 TRVLLGNESCTLTLSESTMNTLKCTVGPAMNKHFNMSIIISNGHGTTQYS 650

651 TFSYVDPVITSISPKYGPMAGGTLLTGNYLNSGNSRHISIGGKTCTLK 700
    |||||||||||||||||||||||||||||||||||||||||||||||||
651 TFSYVDPVITSISPKYGPMAGGTLLTGNYLNSGNSRHISIGGKTCTLK 700

701 SVSNSILECYTPAQTISTEFAVKLKIDLANRETSIFSYREDPIVYEIHPT 750
    |||||||||||||||||||||||||||||||||||||||||||||||||
701 SVSNSILECYTPAQTISTEFAVKLKIDLANRETSIFSYREDPIVYEIHPT 750

751 KSFISGGSTITGVGKNLNSVSVPRMVINVHEAGRNFTVACQHRSNSEIIC 800
    |||||||||||||||||||||||||||||||||||||||||||||||||
751 KSFISGGSTITGVGKNLNSVSVPRMVINVHEAGRNFTVACQHRSNSEIIC 800

801 CTTPSLQQLNLQLPLKTKAFFMLDGILSKYFDLIYVHNPVFKPFEKPVMI 850
    |||||||||||||||||||||||||||||||||||||||||||||||||
801 CTTPSLQQLNLQLPLKTKAFFMLDGILSKYFDLIYVHNPVFKPFEKPVMI 850

851 SMGNENVLEIKVGFLHSSHDVNKEASVIMLFSGLK.............. 885
    ||||||||||||
851 SMGNENVLEIK..........................GNDIDPEAVKGEVLK 876

877 VGNKSCENIHLHSEAVLCTVPNDLLKLNSELNIEWKQAISSTVLGKVIVQ 926
```

FIG. 1C (cont'd)

```
 927 PDQNFTGLIAGVVSISTALLLLLGFFLWLKKRKQIKDLGSELVRYDARVH   976
 977 TPHLDRLVSARSVSPTTEMVSNESVDYRATFPEDQFPNSSQNGSCRQVQY  1026
1027 PLTDMSPILTSGDSDISSPLLQNTVHIDLSALNPELVQAVQHVVIGPSSL  1076
1077 IVHFNEVIGRGHFGCVYHGTLLDNDGKKIHCAVKSLNRITDIGEVSQFLT  1126
1127 EGIIMKDFSHPNVLSLLGICLRSEGSPLVVLPYMKHGDLRNFIRNETHNP  1176
1177 TVKDLIGFGLQVAKGMKYLASKKFVHRDLAARNCMLDEKFTVKVADFGLA  1226
1227 RDMYDKEYYSVHNKTGAKLPVKWMALESLQTQKFTTKSDVWSFGVLWEL  1276
```

FIG. 1C (cont'd)

```
1277 MTRGAPPYPDVNTFDITVYLLQGRRLLQPEYCPDPLYEVMLKCWHPKAEM 1326

1327 RPSFSELVSRISAIFSTFIGEHYVHVNATYVNVKCVAPYPSLLSSEDNAD 1376

1377 DEVDTRPASFWETS    1390
```

FIG. 1D

```
  1  MKAPAVLAPGILVLLFTLVQRSNGECKEALAKSEMNVNMKYQLPNFTAET   50
     ||||||||||||||||||||||||||||||||||||||||||||||||||
  1  MKAPAVLAPGILVLLFTLVQRSNGECKEALAKSEMNVNMKYQLPNFTAET   50

51  PIQNVILHEHHIFLGATNYIYVLNEEDLQKVAEYKTGPVLEHPDCFPCQD  100
     ||||||||||||||||||||||||||||||||||||||||||||||||||
 51  PIQNVILHEHHIFLGATNYIYVLNEEDLQKVAEYKTGPVLEHPDCFPCQD  100

101  CSSKANLSGGVWKDNINMALVVDTYYDDQLISCGSVNRGTCQRHVFPHNH  150
     ||||||||||||||||||||||||||||||||||||||||||||||||||
101  CSSKANLSGGVWKDNINMALVVDTYYDDQLISCGSVNRGTCQRHVFPHNH  150

151  TADIQSEVHCIFSPQIEEPSQCPDCVVSALGAKVLSSVKDRFINFFVGNT  200
     ||||||||||||||||||||||||||||||||||||||||||||||||||
151  TADIQSEVHCIFSPQIEEPSQCPDCVVSALGAKVLSSVKDRFINFFVGNT  200

201  INSSYFPDHPLHSISVRRLKETKDGFMFLTDQSYIDVLPEFRDSYPIKYV  250
     ||||||||||||||||||||||||||||||||||||||||||||||||||
201  INSSYFPDHPLHSISVRRLKETKDGFMFLTDQSYIDVLPEFRDSYPIKYV  250
```

FIG. 1D (cont'd)

```
251 HAFESNNFIYFLTVQRETLDAQTFHTRIIRFCSINSGLHSYMEMPLECIL  300
    ||||||||||||||||||||||||||||||||||||||||||||||||||
251 HAFESNNFIYFLTVQRETLDAQTFHTRIIRFCSINSGLHSYMEMPLECIL  300

301 TEKRKKRSTKKEVFNILQAAYVSKPGAQLARQIGASLNDDILFGVFAQSK  350
    |||||||||||||||||||||||||||||||||||||||||||||||||
301 TEKRKKRSTKKEVFNILQAAYVSKPGAQLARQIGASLNDDILFGVFAQSK  350

351 PDSAEPMDRSAMCAFPIKYVNDFFNKIVNKNNVRCLQHFYGPNHEHCFNR  400
    |||||||||||||||||||||||||||||||||||||||||||||||||
351 PDSAEPMDRSAMCAFPIKYVNDFFNKIVNKNNVRCLQHFYGPNHEHCFNR  400

401 TLLRNSSGCEARRDEYRTEFTTALQRVDLFMGQFSEVLLTSISTFIKGDL  450
    |||||||||||||||||||||||||||||||||||||||||||||||||
401 TLLRNSSGCEARRDEYRTEFTTALQRVDLFMGQFSEVLLTSISTFIKGDL  450

451 TIANLGTSEGRFMQ. . . . . . . . . . . . . . . . . . . . . . . . . . . . . . . . . . .  464
    ||||||||||||||
451 TIANLGTSEGRFMQVVVSRSGPSTPHVNFLLDSHPVSPEVIVEHTLNQNG  500

464 . . . . . . . . . . . . . . . . . . . . . . . . . . . . . . . . . . . . . . . . . . . . . . . .  464

501 YTLVITGKKITKIPLNGLGCRHFQSCSQCLSAPPFVQCGWCHDKCVRSEE  550

```
551 CLSGTWTQQICLPAIYKVFPNSAPLEGGTRLTICGWDFGFRRNNKFDLKK 600
464                                                  464
601 TRVLLGNESCTLTLSESTMNTLKCTVGPAMNKHFNMSIIISNGHGTTQYS 650
464                                                  464
651 TFSYVDPVITSISPKYGPMAGGTLLTLTGNYLNSGNSRHISIGGKTCTLK 700
464                                                  464
701 SVSNSILECYTPAQTISTEFAVKLKIDLANRETSIFSYREDPIVYEIHPT 750
464                                                  464
751 KSFISGGSTITGVGKNLNSVSVPRMVINVHEAGRNFTVACQHRSNSEIIC 800
464                                                  464
801 CTTPSLQQLNLQLPLKTKAFFMLDGILSKYFDLIYVHNPVFKPFEKPVMI 850
464                                                  464
851 SMGNENVLEIKGNDIDPEAVKGEVLKVGNKSCENIHLHSEAVLCTVPNDL 900
464                                                  464
```

FIG. 1D (cont'd)

```
 901 LKLNSELNIEWKQAISSTVLGKVIVQPDQNFTGLIAGVVSISTALLLLLG   950
 464 ..................................................  464

951 FFLWLKKRKQIKDLGSELVRYDARVHTPHLDRLVSARSVSPTTEMVSNES  1000
 464 ..................................................  464

1001 VDYRATFPEDQFPNSSQNGSCRQVQYPLTDMSPILTSGDSDISSPLLQNT  1050
 464 ..................................................  464

1051 VHIDLSALNPELVQAVQHVVIGPSSLIVHFNEVIGRGHFGCVYHGTLLDN  1100
 464 ..................................................  464

1101 DGKKIHCAVKSLNRITDIGEVSQFLTEGIIMKDFSHPNVLSLLGICLRSE  1150
 464 ..................................................  464

1151 GSPLVVLPYMKHGDLRNFIRNETHNPTVKDLIGFGLQVAKGMKYLASKKF  1200
 464 ..................................................  464

1201 VHRDLAARNCMLDEKFTVKVADFGLARDMYDKEYYSVHNKTGAKLPVKWM  1250
```

FIG. 1D (cont'd)

```
 465 ........................WSFGVLLWELMTRGAPPYPDVNTFDITVYLLQGR  498
                             |||||:||||||||||||||||||||||||||||
1251 ALESLQTQKFTTKSDVWSFGVVLWELMTRGAPPYPDVNTFDITVYLLQGR 1300

499 RLLQPEYCPDPLYEVMLKCWHPKAEMRPSFSELVSRISAIFSTFIGEHYV  548
     ||||||||||||||||||||||||||||||||||||||||||||||||||
1301 RLLQPEYCPDPLYEVMLKCWHPKAEMRPSFSELVSRISAIFSTFIGEHYV 1350

549 HVNATYVNVKCVAPYPSLLSSEDNADDEVDTRPASFWETS            588
     |||||||||||||||||||||||||||||||||||||||
1351 HVNATYVNVKCVAPYPSLLSSEDNADDEVDTRPASFWETS           1390
```

FIG. 1E

```
  1 MKAPAVLAPGILVLLFTLVQRSNGECKEALAKSEMNVNMK
    ||||||||||||||||||||||||||||||||||||||||
  1 MKAPAVLAPGILVLLFTLVQRSNGECKEALAKSEMNVNMK

41 YQLPNFTAETPIQNVILEHHIFLGATNYIYVLNEEDLQK
    ||||||||||||||||||||||||||||||||||||||
 41 YQLPNFTAETPIQNVILEHHIFLGATNYIYVLNEEDLQK

81 VAEYKTGPVLEHPDCFPCQDCSSKANLSGGVWKDNINMAL
    |||||||||||||||||||||||||||||||||||||||
 81 VAEYKTGPVLEHPDCFPCQDCSSKANLSGGVWKDNINMAL

121 VVDTYDDQLISCGSVNRGTCQRHVFPHNHTADIQSEVHC
    ||||||||||||||||||||||||||||||||||||||
121 VVDTYDDQLISCGSVNRGTCQRHVFPHNHTADIQSEVHC

161 IFSPQIEEPSQCPDCVVSALGAKVLSSVKDRFINFFVGNT
    |||||||||||||||||||||||||||||||||||||||
161 IFSPQIEEPSQCPDCVVSALGAKVLSSVKDRFINFFVGNT

201 INSSYFPDHPLHSISVRRLKETKDGFMFLTDQSYIDVLPE
    |||||||||||||||||||||||||||||||||||||||
201 INSSYFPDHPLHSISVRRLKETKDGFMFLTDQSYIDVLPE
```

FIG. 1E (cont'd)

```
241  FRDSYPIKYVHAFESNNFIYFLTVQRETLDAQTFHTRIIR
     ||||||||||||||||||||||||||||||||||||||||
241  FRDSYPIKYVHAFESNNFIYFLTVQRETLDAQTFHTRIIR

281  FCSINSGLHSYMEMPLECILTEKRKKRSTKKEVFNILQAA
     ||||||||||||||||||||||||||||||||||||||||
281  FCSINSGLHSYMEMPLECILTEKRKKRSTKKEVFNILQAA

321  YVSKPGAQLARQIGASLNDDILFGVFAQSKPDSAEPMDRS
     ||||||||||||||||||||||||||||||||||||||||
321  YVSKPGAQLARQIGASLNDDILFGVFAQSKPDSAEPMDRS

361  AMCAFPIKYVNDFFNKIVNKNNVRCLQHFYGPNHEHCFNR
     ||||||||||||||||||||||||||||||||||||||||
361  AMCAFPIKYVNDFFNKIVNKNNVRCLQHFYGPNHEHCFNR

401  TLLRNSSGCEARRDEYRTEFTTALQRVDLFMGQFSEVLLT
     ||||||||||||||||||||||||||||||||||||||||
401  TLLRNSSGCEARRDEYRTEFTTALQRVDLFMGQFSEVLLT

441  SISTFIKGDLTIANLGTSEGRFMQ----------------
     ||||||||||||||||||||||||
441  SISTFIKGDLTIANLGTSEGRFMQVVVSRSGPSTPHVNFL

481  LDSHPVSPEVIVEHTLNQNGYTLVITGKKITKIPLNGLGC
```

FIG. 1E (cont'd)

```
521  RHFQSCSQCLSAPPFVQCGWCHDKCVRSEECLSGTWTQQI

561  CLPAIYKVFPNSAPLEGGTRLTICGWDFGFRRNNKFDLKK

601  TRVLLGNESCTLTLSESTMNTLKCTVGPAMNKHFNMSIII

641  SNGHGTTQYSTFSYVDPVITSISPKYGPMAGGTLLTLTGN

681  YLNSGNSRHISIGGKTCTLKSVSNSILECYTPAQTISTEF

721  AVKLKIDLANRETSIFSYREDPIVYEIHPTKSFISGGSTI

761  TGVGKNLNSVSVPRMVINVHEAGRNFTVACQHRSNSEIIC

801  CTTPSLQQLNLQLPLKTKAFFMLDGILSKYFDLIYVHNPV

841  FKPFEKPVMISMGNENVLEIKGNDIDPEAVKGEVLKVGNK
```

FIG. 1E (cont'd)

```
881  SCENIHLHSEAVLCTVPNDLLKLNSELNIEWKQAISSTVL

921  GKVIVQPDQNFTGLIAGVVSISTALLLLLGFFLWLKKRKQ

961  IKDLGSELVRYDARVHTPHLDRLVSARSVSPTTEMVSNES

1001 VDYRATFPEDQFPNSSQNGSCRQVQYPLTDMSPILTSGDS

1041 DISSPLLQNTVHIDLSALNPELVQAVQHVVIGPSSLIVHF

1081 NEVIGRGHFGCVYHGTLLDNDGKKIHCAVKSLNRITDIGE

1121 VSQFLTEGIIMKDFSHPNVLSLLGICLRSEGSPLVVLPYM

1161 KHGDLRNFIRNETHNPTVKDLIGFGLQVAKGMKYLASKKF

1201 VHRDLAARNCMLDEKFTVKVADFGLARDMYDKEYYSVHNK
```

FIG. 1E (cont'd)

```
 465  ------------------------------------------WSFGVLLWELMTRG
                                                ||||||||||||||
1241  TGAKLPVKWMALESLQTQKFTTKSDVWSFGVLLWELMTRG

479  APPYPDVNTFDITVYLLQGRRLLQPEYCPDPLYEVMLKCW
      ||||||||||||||||||||||||||||||||||||||||
1281  APPYPDVNTFDITVYLLQGRRLLQPEYCPDPLYEVMLKCW

519  HPKAEMRPSFSELVSRISAIFSTFIGEHYVHVNATYVNVK
      ||||||||||||||||||||||||||||||||||||||||
1321  HPKAEMRPSFSELVSRISAIFSTFIGEHYVHVNATYVNVK

559  CVAPYPSLLSSEDNADDEVDTRPASFWETS
      |||||||||||||||||||||||||||||
1361  CVAPYPSLLSSEDNADDEVDTRPASFWETS
```

FIG. 2A

```
Met-877    1   MKAPAVLAPGIILVLLFTLVQRSNGECKEALAKSEMNVNMKYQLPNFTAETPIQNV    55
RB-Met     1   MKAPAVLAPGIILVLLFTLVQRSNGECKEALAKSEMNVNMKYQLPNFTAETPIQNV    55

Met-877   56   ILHEHHIFLGATNYIYVLNEEDLQKVAEYKTGPVLEHPDCFPCQDCSSKANLSGG   110
RB-Met    56   ILHEHHIFLGATNYIYVLNEEDLQKVAEYKTGPVLEHPDCFPCQDCSSKANLSGG   110

Met-877  111   VWKDNINMALVVDTYYDDQLISCGSVNRGTCQRHVFPHNHTADIQSEVHCIFSPQ   165
RB-Met   111   VWKDNINMALVVDTYYDDQLISCGSVNRGTCQRHVFP NHTADIQSEVHCIFSPQ   165
                                                   R
Met-877  166   IEEPSQCPDCVVSALGAKVLSSVKDRFINFFVGNTINSSYFPDHPLHSISVRRLK   220
RB-Met   166   IEEPSQCPDCVVSALGAKVLSSVKDRF TNFFVGNTINSSYFPDHPLHSISVRRLK   220

Met-877  221   ETKDGFMFLTDQSYIDVLPEFRDSYPIKYVHAFESNNFIYFLTVQRETLDAQTFH   275
RB-Met   221   ETKDGFMFLTDQSYIDVLPEFRDSYPIKYVHAFESNNFIYFLTVQRETLDAQTFH   275

Met-877  276   TRIIRFCSINSGLHSYMEMPLECILTEKRKKRSTKKEVFNILQAAYVSKPGAQLA   330
RB-Met   276   TRIIRFCSINSGLHSYMEMPLECILTEKRKKRSTKKEVFNILQAAYVSKPGAQLA   330
```

FIG. 2A (cont'd)

```
Met-877  331  RQIGASLNDDILFGVFAQSKPDSAEPMDRSAMCAFPIKYVNDFFNKIVNKNNVRC  385
RB-Met   331  RQIGAS NDDILFGVFAQSKPDSAEPMDRSAMCAFPIKYVNDFFNKIVNKNNVRC
         331  RQIGASPNDDILFGVFAQSKPDSAEPMDRSAMCAFPIKYVNDFFNKIVNKNNVRC  385

Met-877  386  LQHFYGPNHEHCFNRTLLRNSSGCEARRDEYRTEFTTALQRVDLFMGQFSEVLLT  440
RB-Met   386  LQHFYGPNHEHCFNRTLLRNSSGCEARRDEYRTEFTTALQRVDLFMGQFSEVLLT
              LQHFYGPNHEHCFNRTLLRNSSGCEARRDEYRTEFTTALQRVDLFMGQFSEVLLT  440

Met-877  441  SISTFIKGDLTIANLGTSEGRFMQVVVSRSGPSTPHVNFLLDSHPVSPEVIVEHT  495
RB-Met   441  SISTFIKGDLTIANLGTSEGRFMQVVVSRSGPSTPHVNFLLDSHPVSPEVIVEHT
              SISTFIKGDLTIANLGTSEGRFMQVVVSRSGPSTPHVNFLLDSHPVSPEVIVEHT  495

Met-877  496  LNQNGYTLVITGKKITKIPLNGLGCRHFQSCSQCLSAPPFVQCGWCHDKCVRSEE  550
RB-Met   496  LNQNGYTLVITGKKITKIPLNGLGCRHFQSCSQCLSAPPFVQCGWCHDKCVRSEE
              LNQNGYTLVITGKKITKIPLNGLGCRHFQSCSQCLSAPPFVQCGWCHDKCVRSEE  550

Met-877  551  CLSGTWTQQICLPAIYKVFPNSAPLEGGTRLTICGWDFGFRRNNKFDLKKTRVLL  605
RB-Met   551  CLSGTWTQQICLPAIYKVFPNSAPLEGGTRLTICGWDFGFRRNNKFDLKKTRVLL
              CLSGTWTQQICLPAIYKVFPNSAPLEGGTRLTICGWDFGFRRNNKFDLKKTRVLL  605

Met-877  606  GNESCTLTLSESTMNTLKCTVGPAMNKHFNMSIIISNGHGTTQYSTFSYVDPVIT  660
RB-Met   606  GNESCTLTLSESTMNTLKCTVGPAMNKHFNMSIIISNGHGTTQYSTFSYVDPVIT
              GNESCTLTLSESTMNTLKCTVGPAMNKHFNMSIIISNGHGTTQYSTFSYVDPVIT  660

Met-877  661  SISPKYGPMAGGTLLTLTGNYLNSGNSRHISIGGKTCTLKSVSNSILECYTPAQT  715
RB-Met   661  SISPKYGPMAGGTLLTLTGNYLNSGNSRHISIGGKTCTLKSVSNSILECYTPAQT
              SISPKYGPMAGGTLLTLTGNYLNSGNSRHISIGGKTCTLKSVSNSILECYTPAQT  715
```

FIG. 2A (cont'd)

```
Met-877  716  ISTEFAVKLKIDLANRETSIFSYREDPIVYEIHPTKSFISGGSTITGVGKNLNSV  770
RB-Met        ISTEFAVKLKIDLANRETSIFSYREDPIVYEIHPTKSFISGGSTITGVGKNLNSV
         716  ISTEFAVKLKIDLANRETSIFSYREDPIVYEIHPTKSFISGGSTITGVGKNLNSV  770

Met-877  771  SVPRMVINVHEAGRNFTVACQHRSNSEIICCTTPSLQQLNLQLPLKTKAFFMLDG  825
RB-Met        SVPRMVINVHEAGRNFTVACQHRSNSEIICCTTPSLQQLNLQLPLKTKAFFMLDG
         771  SVPRMVINVHEAGRNFTVACQHRSNSEIICCTTPSLQQLNLQLPLKTKAFFMLDG  825

Met-877  826  ILSKYFDLIYVHNPVFKPFEKPVMISMGNENVLEIKVRNALNTVLNHQLKLN  877
RB-Met        ILSKYFDLIYVHNPVFKPFEKPVMISMGNENVLEIKVRNALNTVLNHQLKLN
         826  ILSKYFDLIYVHNPVFKPFEKPVMISMGNENVLEIKVRNALNTVLNHQLKLN  877
```

FIG. 2B

```
Met-885    1    MKAPAVLAPGIILVLLFTLVQRSNGECKEALAKSEMNVNMKYQLPNFTAETPIQNVILHEH    60
RB-Met     1    MKAPAVLAPGIILVLLFTLVQRSNGECKEALAKSEMNVNMKYQLPNFTAETPIQNVILHEH    60

Met-885   61    HIFLGATNYIYVLNEEDLQKVAEYKTGPVLEHPDCFPCQDCSSKANLSGGVWKDNINMAL   120
RB-Met    61    HIFLGATNYIYVLNEEDLQKVAEYKTGPVLEHPDCFPCQDCSSKANLSGGVWKDNINMAL   120

Met-885  121    VVDTYDDQLISCGSVNRGTCQRHVFPHNHTADIQSEVHCIFSPQIEEPSQCPDCVVSAL   180
RB-Met   121    VVDTYDDQLISCGSVNRGTCQRHVFP NHTADIQSEVHCIFSPQIEEPSQCPDCVVSAL   180

Met-885  181    GAKVLSSVKDRFINFFVGNTINSSYFPDHPLHSISVRRLKETKDGFMFLTDQSYIDVLPE   240
RB-Met   181    GAKVLSSVKDRF NFFVGNTINSSYFPDHPLHSISVRRLKETKDGFMFLTDQSYIDVLPE   240

Met-885  241    FRDSYPIKYVHAFESNNFIYFLTVQRETLDAQTFHTRIIRFCSINSGLHSYMEMPLECIL   300
RB-Met   241    FRDSYPIKYVHAFESNNFIYFLTVQRETLDAQTFHTRIIRFCSINSGLHSYMEMPLECIL   300

Met-885  301    TEKRKKRSTKKEVFNILQAAYVSKPGAQLARQIGASLNDDILFGVFAQSKPDSAEPMDRS   360
```

FIG. 2B (cont'd)

```
RB-Met    301  TEKRKKRSTKKEVFNILQAAYVSKPGAQLARQIGASPNDDILFGVFAQSKPDSAEPMDRS    360

Met-885   361  AMCAFPIKYVNDFFNKIVNKNNVRCLQHFYGPNHEHCFNRTLLRNSSGCEARRDEYRTEF    420
RB-Met    361  AMCAFPIKYVNDFFNKIVNKNNVRCLQHFYGPNHEHCFNRTLLRNSSGCEARRDEYRTEF    420

Met-885   421  TTALQRVDLFMGQFSEVLLTSISTFIKGDLTIANLGTSEGRFMQVVVSRSGPSTPHVNFL    480
RB-Met    421  TTALQRVDLFMGQFSEVLLTSISTFIKGDLTIANLGTSEGRFMQVVVSRSGPSTPHVNFL    480

Met-885   481  LDSHPVSPEVIVEHTLNQNGYTLVITGKKITKIPLNGLGCRHFQSCSQCLSAPPFVQCGW    540
RB-Met    481  LDSHPVSPEVIVEHTLNQNGYTLVITGKKITKIPLNGLGCRHFQSCSQCLSAPPFVQCGW    540

Met-885   541  CHDKCVRSEECLSGTWTQQICLPAIYKVFPNSAPLEGGTRLTICGWDFGFRRNNKFDLKK    600
RB-Met    541  CHDKCVRSEECLSGTWTQQICLPAIYKVFPNSAPLEGGTRLTICGWDFGFRRNNKFDLKK    600

Met-885   601  TRVLLGNESCTLTLSESTMNTLKCTVGPAMNKHFNMSIIISNGHGTTQYSTFSYVDPVIT    660
RB-Met    601  TRVLLGNESCTLTLSESTMNTLKCTVGPAMNKHFNMSIIISNGHGTTQYSTFSYVDPVIT    660

Met-885   661  SISPKYGPMAGGTLLTLTGNYLNSGNSRHISIGGKTCTLKSVSNSILECYTPAQTISTEF    720
RB-Met    661  SISPKYGPMAGGTLLTLTGNYLNSGNSRHISIGGKTCTLKSVSNSILECYTPAQTISTEF    720

Met-885   721  AVKLKIDLANRETSIFSYREDPIVYEIHPTKSFISGGSTITGVGKNLNSVSVPRMVINVH    780
RB-Met         AVKLKIDLANRETSIFSYREDPIVYEIHPTKSFISGGSTITGVGKNLNSVSVPRMVINVH
```

FIG. 2B (cont'd)

```
RB-Met   721  AVKLKIDLANRETSIFSYREDPIVYEIHPTKSFISGGSTITGVGKNLNSVSVPRMVINVH  780

Met-885  781  EAGRNFTVACQHRSNSEIICCTTPSLQQLNLQLPLKTKAFFMLDGILSKYFDLIYVHNPV  840
RB-Met   781  EAGRNFTVACQHRSNSEIICCTTPSLQQLNLQLPLKTKAFFMLDGILSKYFDLIYVHNPV  840

Met-885  841  FKPFEKPVMISMGNENVLEIKVGFLHSSHDVNKEASVIMLFSGLK  885
RB-Met   841  FKPFEKPVMISMGNENVLEIKV
              FKPFEKPVMISMGNENVLEIKVRNALNTVLNHQLKLN  877
```

FIG. 2C

```
Met-934    1  MKAPAVLAPGIILVLLFTLVQRSNGECKEALAKSEMNVNMKYQLPNFTAETPIQNVILHEH   60
RB-Met     1  MKAPAVLAPGIILVLLFTLVQRSNGECKEALAKSEMNVNMKYQLPNFTAETPIQNVILHEH   60

Met-934   61  HIFLGATNYIYVLNEEDLQKVAEYKTGPVLEHPDCFPCQDCSSKANLSGGVWKDNINMAL  120
RB-Met    61  HIFLGATNYIYVLNEEDLQKVAEYKTGPVLEHPDCFPCQDCSSKANLSGGVWKDNINMAL  120

Met-934  121  VVDTYYDDQLISCGSVNRGTCQRHVFPHNHTADIQSEVHCIFSPQIEEPSQCPDCVVSAL  180
RB-Met   121  VVDTYYDDQLISCGSVNRGTCQRHVFP NHTADIQSEVHCIFSPQIEEPSQCPDCVVSAL
              VVDTYYDDQLISCGSVNRGTCQRHVFPRNHTADIQSEVHCIFSPQIEEPSQCPDCVVSAL  180
```

FIG. 2C (cont'd)

```
Met-934  181  GAKVLSSVKDRFINFFVGNTINSSYFPDHPLHSISVRRLKETKDGFMFLTDQSYIDVLPE  240
RB-Met   181  GAKVLSSVKDRF NFFVGNTINSSYFPDHPLHSISVRRLKETKDGFMFLTDQSYIDVLPE  240

Met-934  241  FRDSYPIKYVHAFESNNFIYFLTVQRETLDAQTFHTRIIRFCSINSGLHSYMEMPLECIL  300
RB-Met   241  FRDSYPIKYVHAFESNNFIYFLTVQRETLDAQTFHTRIIRFCSINSGLHSYMEMPLECIL  300

Met-934  301  TEKRKKRSTKKEVFNILQAAYVSKPGAQLARQIGASLNDDILFGVFAQSKPDSAEPMDRS  360
RB-Met   301  TEKRKKRSTKKEVFNILQAAYVSKPGAQLARQIGAS NDDILFGVFAQSKPDSAEPMDRS  360

Met-934  361  AMCAFPIKYVNDFFNKIVNKNNVRCLQHFYGPNHEHCFNRTLLRNSSGCEARRDEYRTEF  420
RB-Met   361  AMCAFPIKYVNDFFNKIVNKNNVRCLQHFYGPNHEHCFNRTLLRNSSGCEARRDEYRTEF  420

Met-934  421  TTALQRVDLFMGQFSEVLLTSISTFIKGDLTIANLGTSEGRFMQVVSRSGPSTPHVNFL  480
RB-Met   421  TTALQRVDLFMGQFSEVLLTSISTFIKGDLTIANLGTSEGRFMQVVSRSGPSTPHVNFL  480

Met-934  481  LDSHPVSPEVIVEHTLNQNGYTLVITGKKITKIPLNGLGCRHFQSCSQCLSAPPFVQCGW  540
RB-Met   481  LDSHPVSPEVIVEHTLNQNGYTLVITGKKITKIPLNGLGCRHFQSCSQCLSAPPFVQCGW  540

Met-934  541  CHDKCVRSEECLSGTWTQQICLPAIYKVFPNSAPLEGGTRLTICGWDFGFRRNNKFDLKK  600
RB-Met   541  CHDKCVRSEECLSGTWTQQICLPAIYKVFPNSAPLEGGTRLTICGWDFGFRRNNKFDLKK  600
```

FIG. 2C (cont'd)

```
Met-934  601  TRVLLGNESCTLTLSESTMNTLKCTVGPAMNKHFNMSIIISNGHGTTQYSTFSYVDPVIT  660
RB-Met   601  TRVLLGNESCTLTLSESTMNTLKCTVGPAMNKHFNMSIIISNGHGTTQYSTFSYVDPVIT  660

Met-934  661  SISPKYGPMAGGTLLTLTGNYLNSGNSRHISIGGKTCTLKSVSNSILECYTPAQTISTEF  720
RB-Met   661  SISPKYGPMAGGTLLTLTGNYLNSGNSRHISIGGKTCTLKSVSNSILECYTPAQTISTEF  720

Met-934  721  AVKLKIDLANRETSIFSYREDPIVYEIHPTKSFISGGSTITGVGKNLNSVSVPRMVINVH  780
RB-Met   721  AVKLKIDLANRETSIFSYREDPIVYEIHPTKSFISGGSTITGVGKNLNSVSVPRMVINVH  780

Met-934  781  EAGRNFTVACQHRSNSEIICCTTPSLQQLNLQLPLKTKAFFMLDGILSKYFDLIYVHNPV  840
RB-Met   781  EAGRNFTVACQHRSNSEIICCTTPSLQQLNLQLPLKTKAFFMLDGILSKYFDLIYVHNPV  840

Met-934  841  FKPFEKPVMISMGNENVLEIKGNDIDPEAVKGEVLKVGNKSCENIHLHSEAVLCTVPNDL
              LKLNSELNIEVGFLHSSHDVNKEASVIMLFSGLK    934
RB-Met   841  FKPFEKPVMISMGNENVLEIKVRNALNTVLNHQLKLN    877
```

FIG. 2D

```
Met-588    1    MKAPAVLAPGILVLLFTLVQRSNGECKEALAKSEMNVNMKYQLPNFTAETPIQNVILHEH     60
RB-Met     1    MKAPAVLAPGILVLLFTLVQRSNGECKEALAKSEMNVNMKYQLPNFTAETPIQNVILHEH     60

Met-588   61    HIFLGATNYIYVLNEEDLQKVAEYKTGPVLEHPDCFPCQDCSSKANLSGGVWKDNINMAL    120
RB-Met    61    HIFLGATNYIYVLNEEDLQKVAEYKTGPVLEHPDCFPCQDCSSKANLSGGVWKDNINMAL    120

Met-588  121    VVDTYYDDQLISCGSVNRGTCQRHVFPHNHTADIQSEVHCIFSPQIEEPSQCPDCVVSAL    180
RB-Met   121    VVDTYYDDQLISCGSVNRGTCQRHVFP NHTADIQSEVHCIFSPQIEEPSQCPDCVVSAL    180

Met-588  181    GAKVLSSVKDRFINFFVGNTINSSYFPDHPLHSISVRRLKETKDGFMFLTDQSYIDVLPE    240
RB-Met   181    GAKVLSSVKDRF NFFVGNTINSSYFPDHPLHSISVRRLKETKDGFMFLTDQSYIDVLPE    240

Met-588  241    FRDSYPIKYVHAFESNNFIYFLTVQRETLDAQTFHTRIIRFCSINSGLHSYMEMPLECIL    300
RB-Met   241    FRDSYPIKYVHAFESNNFIYFLTVQRETLDAQTFHTRIIRFCSINSGLHSYMEMPLECIL    300

Met-588  301    TEKRKKRSTKKEVFNILQAAYVSKPGAQLARQIGASLNDDILFGVFAQSKPDSAEPMDRS    360
RB-Met   301    TEKRKKRSTKKEVFNILQAAYVSKPGAQLARQIGASPNDDILFGVFAQSKPDSAEPMDRS    360
```

FIG. 2D (cont'd)

```
Met-588  361  AMCAFPIKYVNDFFNKIVNKNNVRCLQHFYGPNHEHCFNRTLLRNSSGCEARRDEYRTEF  420
RB-Met   361  AMCAFPIKYVNDFFNKIVNKNNVRCLQHFYGPNHEHCFNRTLLRNSSGCEARRDEYRTEF  420
              AMCAFPIKYVNDFFNKIVNKNNVRCLQHFYGPNHEHCFNRTLLRNSSGCEARRDEYRTEF

Met-588  421  TTALQRVDLFMGQFSEVLLTSISTFIKGDLTIANLGTSEGRFMQWSFGVLLWELMTRGAPP
              YPDVNTFDITVYLLQGRRLLQPEYCPDPLYEVMLKCWHPKAEMRPSFSELVSRISAIFSTF
              IGEHYVHVNATYVNVKCVAPYPSLLSSEDNADDEVDTRPASFWETS       588
              TTALQRVDLFMGQFSEVLLTSISTFIKGDLTIANLGTSEGRFMQ

RB-Met   421  TTALQRVDLFMGQFSEVLLTSISTFIKGDLTIANLGTSEGRFMQVVVSRSGPSTPHVNFLL
              DSHPVSPEVIVEHTLNQNGYTLVITGKKITKIPLNGLGCRHFQSCSQCLSAPPFVQCGWCH
              DKCVRSEECLSGTWTQQICLPAIYKVFPNSAPLEGGTRLTICGWDFGFRRNNKFDLKKTRV
              LLGNESCTLTLSESTMNTLKCTVGPAMNKHFNMSIIISNGHGTTQYSTFSYVDPVITSISP
              KYGPMAGGTLLTLTGNYLNSGNSRHISIGGKTCTLKSVSNSILECYTPAQTISTEFAVKLK
              IDLANRETSIFSYREDPIVYEIHPTKSFISGGSTITGVGKNLNSVSVPRMVINVHEAGRNF
              TVACQHRSNSEIICCTTPSLQQLNLQLPLKTKAFFMLDGILSKYFDLIYVHNPVEKPFEKP
              VMISMGNENVLEIKVRNALNTVLNHQLKLN       877
```

FIG. 5A

GAATTCGCCACCATGAAGGCCCCTGCCGTGCTGGCCCCTGGCATCCTGGTGCTGCTGTTC
ACCCTGGTGCAGAGAAGCAACGGCGAGTGTAAGGAGGCCCTGGCCAAGAGCGAGATGAAC
GTGAACATGAAGTACCAGCTGCCCAACTTCACCGCCGAGACACCCATCCAGAACGTGATC
CTGCACGAGCACCACATCTTCCTGGGCGCCACCAACTACATCTACGTGCTGAACGAGGAG
GACCTGCAGAAGGTGGCCGAGTACAAGACCGGCCCTGTGCTGGAGCACCCTGACTGCTTC
CCTTGCCAGGACTGTAGCAGCAAGGCCAACCTGAGCGGCGAGTGTGGAAGGACAACATC
AACATGGGCCCTGGTGGTGCCAGAACGACCTACTACGACACCAACACCGCCGATATCCAGAGC
AATAGAGGCACCTGCCAGAGACACGTGTTCCCCACAACCACACCGCCCAGTGCCCGACTGTGTG
GAGGTGCACTGCAATCTTCAGCCCCCCAGATCGAGGAGCCCCAGTGCCGGTTCATCAATTTCTTT
GTGTCCGCCCTGGGAGCCAAGTGCTGTCCAGCGTGAAGACGTCACCCCCTGCACAGCATCTCTGTG
GTGGGCAACACCATCAACAGCAGCTACTTCCCCGATCCATGTTCCTGACCGACCAGCTACATCGAT
AGGCGGCTGAAGGAGACAAAGGACGGCTTACCCCCATCAAGTACGTGCACGCCTTCGAGAGCAAC
GTGCTGCCCGAGTTCAGAGACACAGCTACCCCGAGCGGAGACACTGACGCGCCAGATGAGATCCCACC
AACTTCATCATCTACTTTCTGACCGGTTCTGCTCCATCAATAGCGGCCTGCACAGCTACAGCTGAGATGCCCCTG
CGGATCATCCGGTTCTGCTCGAGAAGCGGAAGAAGCGGTTCCACCAGCTGCCAAGAAGGAGTGTTCAACATC
GAGTGTATCCTGACCGCCTACGTGTCCAAGCTGTCCCAAGCTGGCCGCAGACATCGGCGCCAGC
CTGCAGGCCGCGATATCCTGTTCGCGTGTTCGCCCAGAGCAAGCCCGACAGCGCCGAGCCC
ATGGATAGAAGCGCCACATGTGCCTTCCCTATCAAGTATGTGAACGACTTCTTCAACAAG
ATCGTGAACAAGAACAATGTGAGATGCCTGCAGCACTTCTACGGCCCCAATCACGAGCAC
TGCTTCAACCGAGTTCACCACCGCCCTGCTGAGAAACAGCCGGCCTGTGAGGCCCAGTTCAGCGAG
AGGACCGAGTTCACCACCGCCCTGCTGAGATCTGTTCATGGGCCAGTTCATGCAGCGAGAG
GTGCTGCTGACCAGCATCAGCACCTTCATCAAGGAGACCTGCCAACCTGGGC
ACCAGCGAGGGCAGATTCATGCAGGTGGTGTCCAGTGTCCAGAAGCGCCCCAGCACCCCTCAAC

FIG. 5A (cont'd)

```
GTGAACTTCCTGCTGGACAGCCACCCTGTGAGCCCTGAGGTGATCGTGGAGCACACCCTG
AACCAGAACGGCTACACCCTGGTGATCACCGGCAAGAAGATCACCAAGATCCCCCTGAAC
GGCCTGGGCTGTGTAGACACTTCCAGACTGCTCCCAGTGCCTGCCTGAGCGCCCCTCCGTG
CAGTGCGGCTGGTGCCACGACAAGTGTGTGAGGAGCGAGGAGTGTCTGAGCGGCACCTGG
ACCCAGCAGATCTGCCTGCCCCGCCATCTACACAAGTGTTCCCAACAGCGCCCCTCTGGAG
GGCGGCACCAGACTGTGCCTGTGGCTGGGACTTCGGCTTCCGGCGAACAACAAGTTC
GACCTGAAGAGAAAACCAGGGTGCTGCTGGGCAATGAGAGCTGTACCCTGACCCTGAGCGAG
AGCACCATGAACAACACCCTGAAGTGCACAGTGGGCCCTGCCATGAACAAGCACTTCAACATG
AGCATCATCAACGGCCACAAGCGGCCCCAGTACAGCACCTTCTCCTACGTGGAC
CCCGTGATCATCAAGAGCATCAGCCCCAAGTACGGCCCTATGGCCGGAGAACCCTGCTGACC
CTGACCGGCAACTACCTGAACAGCGGCACATCAGCATCAGCATCGGCGGCAAGACA
TGTACCCTGAAGAGAGCGTGTCCAACAGCATCCTGGAGTGCTACACCCCCTGCCAGACCATC
AGCACCGAGTTCGCCGTGAAGCTGAAGATCGAAGATCGACCTGGCCAACCGGGAGACATCCATCTTC
AGCTACCGGGAGGACCCTATCGTGTAGGGCAAGAACTTCACCACCACCAAGAGCTTCATCAGCGGC
GGCAGCAGCACCATCACCGGAGTGCCGGCAGAAACTCTGTGACCTGGCCTGCAGCAGCCAACCTGA
ATCAACGTGCACGAGGCCCCGGCCAGCAGCCCTGATTCACCGTGCCAGCACAGAAGCAACTCC
GAGATCATCTGCTGTACCACCCCTAGCCTGCAGCAGCCTGAACCTGCAGCTGCCCCCTGAAA
ACCAAGGCCTTTCATGCTGTTCAAGCCCGTCTGGACGGCATCTGAGCAAGTACTTCGACCTGATCTATGTA
CACAACCCCGTGTTCAAGGGCAACGACATCGATCCTGGAGAAGCCCCGTGATGATCAGCAGCGAAGAAC
GTGCTGGAGATCAAGAGCTGTGAGAACATCCACCTGCACAGCGGCCGTGCTGTGTACCGTG
GTGGGCAACAAGAGCTGTGAAGCTGAACAGCGAGCTGAACATCGAAGTGGGCCTTTCTGCACAGC
CCCAACGACCTGCTGAAGCTGAACAAGAGGCCAGCGTGATCATGCTGTTCAGCGGCCTGAAGTTCGAA
AGCCACGACGTGAACAAAGAGGCCAGCGTGATCATGCTGTTCAGCGGCCTGAAGTTCGAA
CCCAAGAGCTGTGACAAGAACCCACACCTGCCCCCTTGCCCCTGAGCTGCTGGGC
GGACCCAGCCGGTGTTCCTGTTCCCTCCCAAGCCTAAGGACACCCTGATGATCAGCAGAACC
CCCGAGGTGACCTGTGTGGTGGATGTGCACAATGCCAAGACCCCGAGGTGAAGTTCAAC
TGGTACGTGGACGGCGTGGAGGTGCACAATGCCAAGACAAGCCCAGGAGGAGCAGTAC
AACAGCACCTACCGGGTGGTGTCCGTGCTGACCGTGCTGCACCAGGATTGGCTGAACGGC
```

FIG. 5A (cont'd)

```
AAGGAATACAAGTGTAAGGTGTCCAACAAGGCCCTGCCTGCCCCTATCGAGAAAACCATC
AGCAAGGCCAAGGCCAGCCTAGGGAGCCCCAGTGTATACACCCTGCCCCCTAGCAGAGAT
GAGCTGACCAAGAATCAGGTGTCCCTGACCTGCCTGGTGAAGGGCTTCTACCCCAGCGAC
ATCGCCGTGGAGTGGGAGAGCAACGGCCAGCCCGAGAACAACTACAAGACCACCCCCCCT
GTGCTGGACAGCGATGGCAGCTTCTTCCTGTACAGCAAGCTGACCGTGGATAAGAGCAGA
TGGCAGCAGGGCAACGTGTTCAGCTGCTCCGTGATGCACGAGGCCCTGCACAATCACTAC
ACCCAGAAGAGCCTGAGCCTGTCCCCTGGCAAGTGATGAGCGGCCGC
```

FIG. 5B

```
MKAPAVLAPGILVLLFTLVQRSNGECKEALAKSEMNVNMKYQLPNFTAET
PIQNVILHEHHIFLGATNYIYVLNEEDLQKVAEYKTGPVLEHPDCFPCQD
CSSKANLSGGVWKDNINMALVVDTYDDQLISCGSVNRGTCQRHVFPHNH
TADIQSEVHCIFSPQIEEPSQCPDCVVSALGAKVLSSVKDRFINFFVGNT
INSSYFPDHPLHSISVRRLKETKDGFMFLTDQSYIDVLPEFRDSYPIKYV
HAFESNNFIYFLTVQRETLDAQTFHTRIIRFCSINSGLHSYMEMPLECIL
TEKRKRSTKKEVFNILQAAYVSKPGAQLARQIGASLNDDILFGVFAQSK
PDSAEPMDRSAMCAFPIKYVNDFFNKIVNKNNVRCLQHFYGPNHEHCFNR
TLLRNSSGCEARRDEYRTEFTTALQRVDLFMGQFSEVLLTSISTFIKGDL
TIANLGTSEGRFMQVVVSRSGPSTPHVNFLLDSHPVSPEVIVEHTLNQNG
YTLVITGKKITKIPLNGLGCRHFQSCSQCLSAPPFVQCGWCHDKCVRSEE
CLSGTWTQQICLPAIYKVFPNSAPLEGGTRLTICGWDFEGFRRNNKFDLKK
TRVLLGNESCTLTLSESTMNTLKCTVGPAMNKHFNMSIIISNGHGTTQYS
TFSYVDPVITSISPKYGPMAGGTLLTLTGNYLNSGNSRHISIGGKTCTLK
SVSNSILECYTPAQTISTEFAVKLKIDLANRETSIFSYREDPIVYEIHPT
KSFISGGSTITGVGKNLNSVSVPRMVINVHEAGRNFTVACQHRSNSEIIC
```

FIG. 5B (cont'd)

CTTPSLQQLNLQLPLKTKAFFMLDGILSKYEDLIYVHNPVEKPFEKPVMI
SMGNENVLEIKGNDIDPEAVKGEVLKVGNKSCENIHLHSEAVLCTVPNDL
LKLNSELNIEVGFLHSSHDVNKEASVIMLFSGLKFEPKSCDKTHTCPPCP
APELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVMHE
ALHNHYTQKSLSLSPGK

FIG. 7A

GAATTCGCCACCATGAAGGCCCCCTGCCGTGCTGCCCCTGCTGGTGCTGCT
GTTCACCCTGGTGCAGAGAAGCAACGGCGAGTGTAAGGAGGCCCTGGCCAAGAGCGAGAT
GAACGTGAACATGAAGTACCAGCTGCCCAACTTCACCGCCGAGACACCCATCCAGAACGT
GATCCTGCACGAGCACCACATCTTCCTGGGCGCCACCAACTACATCTACGTGCTGAACGA
GGAGGACCTGCAGAAGGTGGCCGAGTACAAGACCGGCCCCTGTGCTGGAGCACCCTGACTG
CTTCCCCTTGCCAGGACTGTAGCAGCAAGGCCAACCTGAGCGGCGAGTGTGGAAGGACAA
CATCAACATGGCCCCTGGTGGTGGACACCTACTACGACCAGCTGATCAGCTGTGGCAG
CGTGAATAGAGGCACCTGCCAGAGACACCTGTTCCCCCACAACCACCGCCGATATCCA
GAGCGAGGTGCACTGCATCTTCAGCCCCCAGATCGAGGAGCCCAGCCAGTGCCCCGACTG
TGTGGTGTCCGCCTGGGAGCCAAGGTGCTGTCCAGCGTGAAGGACCGGTTCATCAATTT
CTTTGTGGGCAACACCATCAACAGCAGCTACTTCCCCGATCACCCCTGCACAGCATCTC
TGTGAGGCGGCTGAAGGAGACAAAGACGGCTTCATGTTCCTGACCAGAGCCAGAGACTACAT
CGATGTGCTGCTGCCCGAGTTCAGAGACAGCTACCCCCATCAAGTACGTGCACGCCTTCGAGAG
CAACAACTTCATCTACTTTCTGACCGTGCAGCGGAGACACTGGAGACGCCCAGACCTTCCA
CACCCGGATCATCCGGTTCTGCTCCATCAATAGCGGCCTGCACAGCTACAGCTACAGCTAGATGCC
CCTGGAGTGTATCCTGCCTACGTGTCCAAGCCTGGCGCCCAGCCTGCCACCAGGAGGTGTTCAA
CATCCTGCAGGCCCTACGATATCCTGTTCGCGTCCCAAGCCTGGCCAGAGCCCGACAGCGCCGA
CAGCCTGAAACGACGATATCCTGTTCGGCGTGTCGCCTATCAAGTATGTGAACGACTTCTTCAA
GCCCATGGATAGAAGCCCATGTGTGCCATGTGAGATGTGAACAATGTGAGATGTTCTACGGCCCCAATCACGA
CAAGATCGTGAACAAGAACAATGTGAGATGCCTGCAGCACTTCTACGGCCCCAATCACGA
GCACTGCTTCAACCGGAGTTCACCACCGGAGTTCACCACCGCCCTGTGAGAAACAGCAGCGCGTGTGAGCCGGCTGTGTGAGCCGGGTGTGAGCCCAGTTCAG
GTACAGGACCGAGTTCACCACCGGAGTTCACCACCGCCCTGTGAGCCGGCTGTGTGAGCCGCCAGTTCAG
CGAGGTGCTGCTGACCAGCATCAGCAGCCACCTTCATCAAGGAGACCTGACCATCGCCAACCT
GGGCACCACCAGCGAGGGCAGATTCATGCAGCCCACCCTGTGGTGGTGTCCAGAAGCGGCCCCAGCACCCC
TCACGTGAACTTCCTGCTGGACAGCTACACCCCTGTGATCGAGCCCGAGGTGATCGTGGAGCACAC
CCTGAACCAGAGAACGGCTACACCCCCTGGTGATCACCGGCAAGAAGATCACCAAGATCCCCCT

FIG. 7A (cont'd)

```
GAACGGCCTGGGCTGTAGACACTTCCAGAGCTGCTCCCAGTGCCTGAGCGCCCCTCCCTT
CGTGCAGTGCCGCTGGTGCCACGACAAGTGTGTGAGGAGCGAGGAGTGTCTGAGCGGCAC
CTGGACCCAGCAGATCTGCCTGCCCCGCCATCTACAAGGTGTTCCCAACAGCGCCCCTCT
GGAGGCGGCACCAGACTGACCATCTGTGGCTGGACTTCCGGCTTCCGGCGGAACAACAA
GTTCGACCTGAAGAAAACCAGGGTGCTGCTGGGCAATGAGAGCTGTACCCTGACCCTGAG
CGAGAGCACCATGAACACCCTGAAGTGCACAGTGGGCCCTGCCATGAACAAGCACTTCAA
CATGAGCATCATCATCAGCAACGGCCACGGCCACCACCCAGTACAGCACCTTCTCCTACGT
GGACCCCGTGATCACAAGCATCAGCCCCAAGTACGGCCCTATGCCGGAGGAACCCTGCT
GACCCTGACCGGCAACTACCTGAACAGCGGCAACAGCAGCCGGCACATCAGCGGCGGCAA
GACATGTACCCTGAAGAGCGTGTCCAACAGCATCCTGGAGTGCTACACCCCCTGCCCAGAC
CATCAGCAGCGAGTTCGCCGTGAAGCTGAAGATCGAAAGATCTGGCCAACCTGGAGACATCCAT
CTTCAGCTACCGGGAGGACCCCTATCGTGTACGAGAACCTGAACTCTGTGAGCGTGCCCCGGAT
CGGCGGCAGCAGCCATCACCGGAGTGGGCAAGAAACTTCACCGTGGCCTGCCAGCACAGAAGCAA
GGTGATCAACGTGCACGAGGCCGGTGTACCACCCCCTAGCCTGACCAGCCATCTGCCCCCT
CTCCGAGATCATCTGCTGCTTCTTCATGCTGGACGGCATCCTGAGCAGGCATCTCGACCTGATCTA
GAAAACCAAGGCCTTCTTCATGCTGTTCAAGCCCTTCGAGAAGCCCGTGATGATCAGCAGCAACGA
TGTACACAACCCGTGTTCAAGCCCTTCGAGAAGCCCGTGATGATCAGCAGCATGGGCAACGA
GAACGTGCTGGAGATCAAGGTGGGCTTTCTGCACAGCAGCCACGACGTGAACAAAGAGGC
CAGCGTGATCATGCTGTTCAGCGGCCTGAAGCCCTGGAGCCACCCCTCAGTTCGAGAAAAC
CGGCCACCATGATCACCACCATCACCACGGCGGCCAGTGATAAGCGCCGC
```

FIG. 7B

MKAPAVLAPGILVLLFTLVQRSNGECKEALAKSEMNVNMKYQLPNFTAET
PIQNVILHEHHIFLGATNYIYVLNEEDLQKVAEYKTGPVLEHPDCFPCQD
CSSKANLSGGVWKDNINMALVVDTYYDDQLISCGSVNRGTCQRHVFPHNH
TADIQSEVHCIFSPQIEEPSQCPDCVVSALGAKVLSSVKDRFINFFVGNT
INSSYFPDHPLHSISVRRLKETKDGFMFLTDQSYIDVLPEFRDSYPIKYV
HAFESNNFIYFLTVQRETLDAQTFHTRIIRFCSINSGLHSYMEMPLECIL
TEKRKKRSTKKEVNILQAAYVSKPGAQLARQIGASLNDDILFGVFAQSK
PDSAEPMDRSAMCAFFIKYVNDFFNKIVNKNNVRCLQHFYGPNHEHCFNR
TLLRNSSGCEARRDEYRTEFTTALQRVDLFMGQFSEVLLTSISTFIKGDL
TIANLGTSEGRFMQVVVSRSGPSTPHVNFLLDSHPVSPEVIVEHTLNQNG
YTLVITGKKITKIPLNGLGCRHFQSCSQCLSAPPFVQCWCHDKCVRSEE
CLSGTWTQQICLPAIYKVFPNSAPLEGGTRLTICGWDEGFRRNNKFDLKK
TRVLLGNESCTLTLSESTMNTLKCTVGPAMNKHFNMSIIISNGHGTTQYS
TFSYVDPVITSISPKYGPMAGGTLLTGNYLNSGNSRHISIGGKTCTLK
SVSNSILECYTPAQTISTEFAVKLKIDLANRETSIFSYREDPIVYEIHPT
KSFISGGSTITGVGKNLNSVSVPRMVINVHEAGRNFTVACQHRSNSEIIC
CTTPSLQQLNLQLPLKTKAFFMLDGILSKYFDLIYVHNPVFKPFEKPVMI
SMGNENVLEIKVGFLHSSHDVNKEASVIMLFSGLKPWSHPQFEKTGHHHH
HHHHGGQ

FIG. 8A

GAATTCGCCACCATGAAGGCCCCTGCCGTGCTGGCCCCTGGCCATCCTGGTGCTGCTGTTC
ACCCTGGTGCAGAGAAGCAACGGCGAGTGTAAGGAGGCCCTGGCCAAGAGCGAGATGAAC

FIG. 8A (cont'd)

```
GTGAACATGAAGTACCAGCTGCCCAACTTCACCGCCGAGACACCCATCCAGAACGTGATC
CTGCACGAGCACCACATCTTCCTGGGCGCCACCAACTACATCTACGTGCTGAACGAGGAG
GACCTGCAGAAGGTGGCCGAGTACAAGAGACCGGCCCTGTGCTGGAGCACCCTGACTGCTTC
CCTTGCCAGGACTGTAGCAGCAAGGCCAACCTGAGCGGCGGAGTGTGGAAGGACAACATC
AACATGGCCCTGGTGTGGTGGACAGAGACACGTGTTCCCCACAACCACCGCCGATATCCAGAGC
AATAGAGGCACCTGCATCTTCAGCCCCCCAGATCGAGGAGCCCAGCCAGTGCCCCGACTGTGTG
GAGGTGCACTGCACTTTCAGCCCCCCAGATCGAGGAGCCCAGCCAGTGCCCCGACTGTGTG
GTGTCCGCCCTGGGAGCCAAGGTGCTGTCCAGCGTGAAGGACCGGTTCATCAATTTCTTT
GTGGGCAACACCATCAACAGCAGCTACTTCCCCGATCACCCCTGCACCAGAGCATCTCTGTG
AGGCGGCTGAAGGAGACAAAGGACGCGCTTCATGTTCCTGACCGACCAGAGCTACATCGAT
GTGCTGCCCGAGTTCAGAGACAGCAGCTACCCCATCAAGTACGTGCACGCCCTTCGAGAGCAAC
AACTTCATCTACTTTCTGACCGTGCAGCGGGAGACACTGGACGCCCAGACCTTCCACACC
CGGATCATCATCCGGTTCTGCTCCATCAATAGCGGCTACATGGAAGAAGGAGATGCCCCTG
GAGTGTATCCTGACCGAGAAGCGGAAAGCCGGTCCACCAAGAAGGAGGTGTTCAACATC
CTGCAGGCCCGCTACGTGTCCAAGCCTGGCGTGTTCGCCCAGAGCAAGCCCGACGCCCAGCCCGAGCCC
CTGAACGACGATATCCTGTTCGGCGTGTTCGCCCTATCAAGTATGTGAACGACTTCTTCAACAAG
ATGGATAGAAGCGCCATGTTGAGATGCCAGCACTTCTACGCCCCAATCACGAGCAC
ATCGTGAACAAGAACAATGTGAGATGCCAGCACTTCTACGCCCCAATCACGAGCAC
TGCTTCAACCGGACCCCTGCTGAGAAACAGCAGCGGCTGTGAGGCCAGGAGGACGAGTAC
AGGACCGAGTTCATCACCGCCGTGCAGCGCGTGATCTGTTCATGGGCCAGTTCAGCGAG
GTGCTGCTGACCGAGGGCAGATCAGCACCCTTCATCAAGGGAGACCTGCTGACCATCGCCAACCTGGGC
ACCAGCGAGGGCAGATTCATGCAGGTGGTGTCCAGAAGCGGCCCAGCACCCTCAC
GTGAACTTCCTGCTGGACAGCACCACCCTGTGAGCCCGAGGTGATCGTGAGCACACCCTG
AACCAGAACGGCTACACCCTGGTGATCACCGGCAAGAAGATCACCAAGATCCCCCTGAAC
GGCCTGGGCTGGCTGTAGACACTTCCAGACGTGCTCCCAGTGCTGGAGGAGTGTCTGAGCGGCACCGTG
CAGTGCGGCTGGTGCCACGACAAGTGTGTGGAGGAGCGAGGAGTGTTCCCAACAGCGCCCCTCTGGAG
ACCCAGCAGATCTGCCTGCCCGCCATCTACAAGGTGTTCCCGGCTTCGGCTTCGGCTTCGGCACCTTCGGAG
GGCGGCACCAGACTGTGTGACCATCGGCTGGGACTTCGGCTTCGGCTTCGGCGGAACAAGTTC
```

FIG. 8A (cont'd)

```
GACCTGAAGAAAACCAGGGTGCTGCTGGGCAATGAGAGCTGTACCCTGACCCTGAGCGAG
AGCACCATGAACACCCTGAAGTGCACAGTGGGCCCTGAACAAGCACTTCAACATG
AGCATCATCAGCAACGGCCACGGCACCACCCAGTACAGCACCTTCTCCTACGTGGAC
CCCGTGATCACAAGCATCAGCCCCAAGTACGGCCCCTATGCCGGAGGAACCCTGCTGACC
CTGACCGGCAACTACCTGAACAGCGGCACAGCCGGCACATCAGCGGCGGCAAGACA
TGTACCCTGAAGAGCGTGTCCAACAGCATCCTGAGTGCTACACCCCTGCCCAGACCATC
AGCACCGAGTTCGCCGTGAAGCTGAAGATCGACCTGGCCAACCGGGAGACATCCATCTTC
AGCTACCGGGAGGACCCCTATCGTGTACGAGATCCACCCACCAAGAGCTTCATCAGCGGC
GGCAGCACCATCACCGGAGTGGGCAGAAGCTCTGTGAGCGTGCCCCGGATGGTG
ATCAACGTGCACGAGGCCGGACAGAAACTTCACCGTGCCTGCCAGCACAGAAGCAACTCC
GAGATCATCTGCTGTACCACCCCTAGCCTGCAGCAGCTGAACCTGCAGCTGCCCCTGAAA
ACCAAGGCCTTTCTTCATGCTGGACGGCATCCTGAGCAAGTACTTCGACCTGATCTATGTA
CACAACCCCGTGTTCAAGCCCTTCGAGAAGCCCGTGATGATCAGCAGCCCGCAACGAGAAC
GTGCTGGAGATCAAGGTGGGCTTTCTGCACAGCAGCACGACGTGAACAAAGAGGCCAGC
GTGATCATGCTGTTCAGCGGCCTGAAGTTCGAACCCAAGAGCTGTGACAAGACCCACACC
TGCCCCCCCTTGCCCTGAGCTGCTGGGCGGAACCCCCGAGGTGACCTGTGTGGTGGTGGAT
AAGCCTAAGGACACCCTGATGATCAGCAGGACCCCCGAGGTGACCTGTGTGGTGGTGGAT
GTGAGCCACGAGGACCCTGAGGTGAAGTTCAACTGGTACGTGGACGGCGTGGAGGTGCAC
AATGCCAAGACCAAGCCCAGGGAGGAGCAGTACAACAGCACCTACCGGGTGGTGTCCGTG
CTGACCGTGCTGCACCAGGATTGGCTGAACGGCAAGGAATACAAGTGTAAGGTGTCCAAC
AAGGCCCTGCCCTGCCCATCGAGAAAACCATCAGCAAGGCTGACCAAGAATCAGGTGTCCCTG
ACCCAGGTGTACACCCTGCCCCCAGCACCACCCCCCCCAGCAGATGAGCCGTGGAGTGGGAGAGCAATGGGC
CAGCCCGAGAACAACTACAAGACAACCCCTGCCCCCCAGCACCACCCCCCCCCAGCAGATGAGCCGTGGAGTGGGAGAGCAACGGC
CTGTACAGCAAGCTGACCGTGGATAAGAGACAGATGGCCAGCAGGCAACGTGTTCAGCTGC
TCCGTGATGCACGAGGCCCTGCACAATCACTACACACCAGAAGAGCCTGAGCCTGTCCCCT
GGCAAGTGATGAGCGGCCGC
```

FIG. 8B

MKAPAVLAPGILVLLFTLVQRSNGECKEALAKSEMNVNMKYQLPNFTAET
PIQNVILHEHHIFLGATNYIYVLNEEDLQKVAEYKTGPVLEHPDCFPCQD
CSSKANLSGGVWKDNINMALVVDTYDDQLISCGSVNRGTCQRHVFPHNH
TADIQSEVHCIFSPQIEEPSQCPDCVVSALGAKVLSSVKDRFINFFVGNT
INSSYFPDHPLHSISVRRLKETKDGFMFLTDQSYIDVLPEFRDSYPIKYV
HAFESNNFIYFLTVQRETLDAQTEHTRIRFCSINSGLHSYMEMPLECIL
TEKRKKRSTKKEVNILQAAYVSKPGAQLARQIGASLNDDILFGVFAQSK
PDSAEPMDRSAMCAFPIKYVNDFFNKIVNKNNVRCLQHFYGPNHEHCFNR
TLLRNSSGCEARRDEYRTEFTTALQRVDLFMGQFSEVLLTSISTFIKGDL
TIANLGTSEGRFMQVVVSRSGPSTPHVNFLLDSHPVSPEVIVEHTLNQNG
YTLVITGKKITKIPLNGLGCRHFQSCSQCLSAPPFVQCGWCHDKCVRSEE
CLSGTWTQQICLPAIYKVFPNSAPLEGGTRLTICGWDFGFRRNNKFDLKK
TRVLLGNESCTLTLSESTMNTLKCTVGPAMNKHFNMSIIISNGHGTTQYS
TFSYVDPVITSISPKYGPMAGGTLLTLTGNYLNSGNSRHISIGGKTCTLK
SVSNSILECYTPAQTISTEFAVKLKIDLANRETSIFSYREDPIVYEIHPT
KSFISGGSTITGVGKNLNSVSVPRMVINVHEAGRNFTVACQHRSNSEIIC
CTTPSLQQLNLQLPLKTKAFFMLDGILSKYFDLIYVHNPVFKFEKPVMI
SMGNENVLEIKVGFLHSSHDVNKEASVIMLFSGLKFEPKSCDKTHTCPPC
PAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSVMH
EALHNHYTQKSLSLSPGK

FIG. 12

CCAGCCCAAACCATTTCAACTGAGTTTGCTGTCTGTTAAATTGAAAATTGACTTAGCCAACCGAGAGACAAGCATC
TTCAGTTACCGTGAAGATCCCATTGTCTGTCTATGAAATTCATCCAACCAAATCTTTTATTGTGGTGGGAGCACAA
TAACAGGTGTTGGGAAAAACCTGAATTCAGTTAGTGTCCCGAGAATGGTCATAAATGTCATGAAGCAGGAA
GGAACTTTACAGTGGCATGTCAACATCGCTCTAATTCAGAGATAATCTGTTGTACCACTCCTTCCCTGCAACA
GCTGAATCTGCAACTCCCCCTGAAAACCAAAGCCTTTTCATGTTAGATGGGATCCTTTCCAAATACTTTGATC
TCATTTATGTACATAATCCTGTGTTTAAGCCCTTTTGAAAAGCCAGTGATCTCAATGGGCAATGAAAAATGT
ACTGGAAATTAAGGTAAGAAATGCTTTAAACACTGTCTTTAAATCATCAGCTCAAACTTAATTGACTTCATAG
CTGGATCCGC

FIG. 13A

<u>GAATT</u>GCCACC<u>ATGAAG</u>CCCCTGCCGTGCTGGCCCCTGGTGCTGCTGTTC
ACCCTGGTGCAGAGAAGCCAACGGGCGAGTGTAAGGAGCCCTGGCCAAGAGCGAGATGAAC
GTGAACATGAAGTACCAGCTGCCCAACTTCACCGCCCGAGACACCCATCCAGAACGTGATC
CTGCACGAGCACCACATCTTCCTGGGCGCCACCAACTACATCTACGTGCTGAACGAGGAG
GACCTGCAGAAGGTGGCCGAGTACAAGACCGGCCCTGTGCTGGAGCACCCTGACTGCTTC
CCTTGCCGTGGGACTGTAGCAGCAAGGCACCTGAGCGCGGACCAGCTGATCAGCTGTGGCAGCGTG
AACATGGCCCTGGTGGTGGACACCTACGACACCCCCACAACCACACCGCCAGTGCCCGATATCCAGAGC
AATAGAGGCACCTGCATCTGCAGATCTTCAGCCCCCAGATCGAGGAGCCCAGCGAGCCCAGTGCCCGACTGTGTG
GAGGTGCACTGCATCTTCAGCCCCCAGATCGAGGAGCCCAGCGAGCCCAGTGCCCGACTGTGTG
GTGTCCCGGGAGCCAAGGTGCTGTCCAGCGTGAAGACCGTTCATCAATTTCTTT
GTGGGCAACACCATCAACAGCAGCACTTCCCGATCACCCCTGCACACAGCATCTCTGTG
AGGCGGGCTGAAGGAGACAAAGGACGGCTTCATGTTCCTGACCGACCAGAGCTACATCGAT

FIG. 13A (cont'd)

```
GTGCTGCCCGAGTTCAGAGACAGCTACCCCATCAAGTACGTGCACGCCCTTCGAGAGCAAC
AACTTCATCTACTTTCTGACCGTGCAGCGTGGGAGACACTGGACGCCCAGACCTTCCACACC
CGGATCATCCGGTTCTGCTCCATCAATAGCGGCCTGCACAGCTACATGGAGATGCCCCTG
GAGTGTATCCTGACCGAGAAGCGGAAGAAGCGGTCCACCAAGAAGGAGTGTTCAACATC
CTGCAGGCCGCCTACGTGTCCAAGCCTGGCGCCCAGCTGGCCAGACAGATCGGCGCCAGC
CTGAACGACGATATCCTGTTCGGCGTGTTCGCCTATCAAGTATGTGAACGACTTCTTCAACAAG
ATGGATAGAAGCGCCATGTGTGCCTTCCCTATCAAGTATGTGAACGACTTCTTCAACAAG
ATCGTGAACAAGAACAATGTGAGATGCCTGCAGAAACAGCAGCGCGTGGAGGCCAGGAGGACGAGTAC
TGCTTCAACCGACCCTGCTGAGACACCGCGTGGATCTGTTCATGGGCCAGTTCAGCGAG
AGGACCGAGTTCACCACCGCCCTGCAGCGCGTGGATCTGTTCATGGGCCAGTTCAGCGAG
GTGCTGCTGACCAGCAGCATCAGCACCTTCATCAAGGAGACCTGACCATCGCCAACCTGGGC
ACCAGCGAGGGCAGATTCATGCAGGTGGTGGTTGTCCAGAAGCGGCCCACCACCCCTCAC
GTGAACTTCCTGCTGGACAGCCACCCTGTGAGCCCGAGGTGATCGTGAGCACACCCTG
AACCAGAAACGGCTACACCCCTGGTGATCACCGGCAAGAAGATCACCAAGATCCCCCTGAAC
GGCCTGGGCTGTAGACACTTCCAGACTGCTCCCAGTGCCTGAGCGCCCCTCCCTTCGTG
CAGTGCGGCTGGTGGTGCCACGACGAAGTGTGTGAGGCGCAGGAGTGTCTGAGCGCCCACCTGG
ACCCAGCAGATCTGCCTGCCCGCCATCTACAAGGTGTTCCCCAACAGCGCCCCTCTGGAG
GGGCACCAGACTGACCATCTGTGCCTGGGACTTCGGCTTCCGGCGAACAACAAGTTC
GACCTGAAGAAAACCAGGGTGCTGCTGGGCAATGAGAGCTGTACCCTGACCCTGAGCGAG
AGCACCATGAACATCATCAGCAACGGCCACCCAGTACGCACCTTCTCCTACGTGAC
AGCATCATCATCACAAGCATCAGCCCCAAGTACGGCCCTATGGCCGGAGAACCCTGCTGACC
CCCGTGATCACAAGCATCAGCCCCAAGTACGGCCCTATGGCCGCACATCAGCATCGGCGGCAAGACA
CTGACCGGCAACTACCTGAAGAGCGTGTCCAACAGCATCCTGGAGTGCTACACCCCTGCCCAGACCATC
TGTACCCTGAAGAGCGTTCGCCGTGAAGCTGAAGATCGAACCTGGCCAACCTGGACACCGGGAGACATCTTC
AGCACCGGGAGGACCCTATCGTGTACGAGATCGTGTACGAGATCCACCCCACCAAGAGCTTCATCAGCGGC
```

FIG. 13A (cont'd)

```
GGCAGCACCATCACCGGAGTGGGCAAGAACCTGAACTCTGTGAGCGTGCCCCGGATGGTG
ATCAACGTGCACGAGGCCGGGCAGAGAAACTTCACCGTGGCCTGCCAGCACAGAAGCAACTCC
GAGATCATCTGCTGTACCACCCCTAGCCTGCAGCAGCTGAACCTGCAGCTGCCCCTGAAA
ACCAAGGCCTTCTTCATGCTGGACGGCATCCTGAGCAAGTACTTCGACCTGATCTATGTA
CACAACCCCGTGTTCAAGCCCTTCGAGAAGCCCGTGATGATCAGCATGGGCAACGAGAAC
GTGCTGGAGATCAAGGTGAGGAACGCCCTGAACACCGTGCTGAATCACCGTCGAAGCTG
AACCCCTGGAGCCACCCTCAGTTCGAGAAAAACCGGCCACCACCATCACCACCATCACCAC
GGCGGCCAGTGATAAGCGGCCGC
```

FIG. 13B

```
MKAPAVLAPGILVLLFTLVQRSNGECKEALAKSEMNVNMKYQLPNFTAETPIQNVILHEH
HIFLGATNYIYVLNEEDLQKVAEYKTGPVLEHPDCFPCQDCSSKANLSGGVWKDNINMAL
VVDTYYDDQLISCGSVNRGTCQRHVFPHNHTADIQSEVHCIFSPQIEEPSQCPDCVVSAL
GAKVLSSVKDRFINFFVGNTINSSYFPDHPLHSISVRRLKETKDGFMFLTDQSYIDVLPE
FRDSYPIKYVHAFESNNFIYFLTVQRETLDAQTFHTRIIRFCSINSGLHSYMEMPLECIL
TEKRKKRSTKKEVFNILQAAYVSKPGAQLARQIGASLNDDILFGVFAQSKPDSAEPMDRS
AMCAFPIKYVNDFFNKIVNKNNVRCLQHFYGPNHEHCFNRTLLRNSSGCEARRDEYRTEF
TTALQRVDLFMGQFSEVLLTSISTFIKGDLTIANLGTSEGRFMQVVVSRSGPSTPHVNFL
LDSHPVSPEVIVEHTLNQNGYTLVITGKKITKIPLNGLGCRHFQSCSQCLSAPPFVQCGW
CHDKCVRSEECLSGTWTQQICLPAIYKVFPNSAPLEGGTRLTICGWDFGFRRNNKFDLKK
TRVLLGNESCTLTLSESTMNTLKCTVGPAMNKHFNMSIIISNGHGTTQYSTFSYVDPVIT
SISPKYGPMAGGTLLTLTGNYLNSGNSRHISIGGKTCTLKSVSNSILECYTPAQTISTEF
AVKLKIDLANRETSIFSYREDPIVYEIHPTKSFISGGSTITGVGKNLNSVSVPRMVINVH
EAGRNFTVACQHRSNSEIICCTTPSLQQLNLQLPLKTKAFFMLDGILSKYFDLIYVHNPV
FKPFEKPVMISMGNENVLEIKVRNALNTVLNHQLKLNPWSHPQFEKTGHHHHHHGGQ
```

FIG. 18A

GAATTCGCCACCATGAAGGCCCCCTGCCGTGCTGGCCATCCTGGTGCTGCTGTTC
ACCCTGGTGCAGAGAAGCAACGGCGAGTGTAAGGAGGCCCTGGCCAAGAGCGAGATGAAC
GTGAACATGAAGTACCAGCTGCCCAACTTCACCGCCGAGACACCCATCCAGAACGTGATC
CTGCACGAGCACCACCATCTTCCTGGGCGCCACCAACTACATCTACGTGCTGAACGAGGAG
GACCTGCAGAAGGTGGCCGAGTACAAGACCGGCCCTGTGCTGGAGCACCCTGACTGCTTC
CCTTGCCAGGACTGTAGCAGCAAGGCCAACCTGAGCGGCGGAGTGTGGAAGGACAACATC
AACATGGCCCTGTGGTGACACCTACGACGACCAGCTGATCAGCTGTGGCAGCGTG
AATAGAGGCACCTGCCAGAGACACGTGTTCCCCACAACCACCGCCGATATCCAGAGC
GAGGTGCACTGCATCTTCAGCCCCCAGATCGAGGAGCCCAGTGCCCCGACTGTGTG
GTGTCCGCCCTGGGAGCCAAGGTGCTGTCCAGCGTGAAGGACCGGTTCATCAATTTCTTT
GTGGGCAACACCATCAACAGCAGCAGCTACTTCCCCGATCACCCCTGACCGATCTCTGTG
AGGCGGCTGAAGGAGAGACAAAGGACAGCTACCCCATCAAGTACGTGCACGAGCATCGAT
GTGCTGCCCGAGTTCAGAGACACTTCTGACCGTTCTGCTCCATCAATAGCGGCCTGACCAGAGCCTTCGAGACCAAC
AACTTCATCTCATCCGGTTCTGCTCCATCAATAGCGGCCTACAAGCCTCCACCACC
CGGATCATCCGGTTCTGCTCCATCAATAGCGGCCTACAGCAGCTACATGGAGATGCCCCTG
GAGTGTATCCTGCCGCCTACGTGTCCAAGAAGCCGGTCCACCAAGAGGAGGTGTTCAACATC
CTGCAGGCCCGCCTACGTGTCCAAGCCTGGCCCAGACAGATCGGCGCCAGC
CTGAACGACGATATCCTGTTCGCGCCAAGCAAGCCCAGAGCAAGCGCCCGAGCCC
ATGGATAGAAGCGCCATGTGTGCCTTCCCTATCAAGTATGTGAACGACTTCTTCAACAAG
ATCGTGAACAAGAACAATGTGAGATGCCTGCAGCACTTCTACGGCCACCCCAATCACGAGCAC
TGCTTCAACCGGACCCCTGCTGAGAAACAGCAGCGGCTGTGAGGCCAGGAGGACGAGTAC
AGGACCGAGTTCACCACCGCCGTGGATCTGTTCATGGGCCAGTTCAGCGAG

FIG. 18A (cont'd)

```
GTGCTGCTGACCAGCAGCATCAGCACCTTCATCAAGGGAGACCTGACCATCGCCAACCTGGGC
ACCAGCGAGGGCAGATTCATGCAGGTGGTGTGTCCAGAAGCGGCCCCAGCACCCCCTCAC
GTGAACTTCCTGCTGACAGCCACCCTGTGAGCCCGAGTGATCGTGGAGCACACCCTG
AACCAGAACGGCTACACCCTGGTGATCACCGGCAAGAAGATCACCAAGATCCCCCTGAAC
GGCCCTGGGCTGTGTAGACACTTCCAGAGCTGCTCCCAGTGCCTGAGCGCCCCTTCGTG
CAGTGCGGCTGGTGCCACGACAAGTGTGTGAGGAGCGAGGAGTGTCTGAGCGGCACCTGG
ACCCAGCAGATCTGCCTGCCCGCCATCTACAAGGTGTTCCCAACAGCGCCCCTCTGGAG
GGCGGCACCGACTGACCATCTGTGGCTGGGACTTCGGCTTCCGGCGAACAACAAGTTC
GACCTGAAGAAAAACCAGGGTGCTGCTGGGCAATGAGAGAGCTGTACCCTGAGCGAG
AGCACCATGAACACCCTGAAGTGCACAGTGGCCCTGCCATGAACAAGCACTTCAACATG
AGCATCATCAGCAAGCGCCAACGGCCACCCAGTACAGCACCTTCTCTACGTGGAC
CCCGTGATCACAAGAGCATCAGCGCAACTACCTGAACAGCGGCACATCAGCGGCAAGACA
CTGACCGGCAACTACCTGAAGAACTGAGATCAGCGGCACATCAGCGGCAAGACA
TGTACCCTGAAGAGCGTGTCCAACAGCATCCTGGAGTGCTACACCCCTGCCCAGACCATC
AGCACCGAGTTCGCCGTGAAGCTGAAGATCGACCTGGCCAACCGGGAGACATCCATCTTC
AGCTACCGGGAGGACCCCTATCGTGTACGAGATCTGAGAACCTGAACTCTGTGCCCCGGATGGTG
GGCAGCACCATCACCGGAGTGCCGGCCAGAAACTTCACCGTGGCCTGCCAGCACAGAAGCAACTCC
ATCAACGTGCAGGGCACGAGGCCGGCCATCCTGGACCAGCTGAACCTGCTGCCCCCTGAAA
GAGATCATCTGCTGTACCACCCCTGGACGGCATCCTGAGACGGCAAGTACTTCGACCTGATCTATGTA
ACCAAGGCCTTCTTCATGCTGAAGGTTCAAGCCCTTCGAGAAGCCCGTGATGATCAGCAACGAGAAC
CACAACCCGTGTTCAAGCCCTTCGAGAAGCCCGTGATGATCAGCAACGAGAAC
GTGCTGGAGATCAAGGTTGAGGAACGCCCTGAACACCGTGCTGAATCAGCTGCTGAAGCTG
AACCCCTGGAGCCACCCCAGTTCGAACCCAAGAGTGTGACAAGACCCACACCTGCCCC
CCTTGCCCTGCCCCTGAGCTGCTGGGCGGACCCAGCGTGTTCCTGTTCCTCCCCAAGCCT
```

FIG. 18A (cont'd)

```
AAGGACACCCTGATGATCAGCAGAGAACCCCCGAGGTGACCTGTGTGTGGATGTGAGC
CACGAGGACCCTGAGGTGAAGTTCAACTGGTACGTGGACGGCGTGGAGGTGCACAATGCC
AAGACCAAGCCCAGGGAGGAGCAGTACAACAGCACCTACCGGGTGGTGTCCGTGCTGACC
GTGCTGCACCAGGATTGGCTGAACGGCAAGGAATACAAGTGTAAGGTGTCCAACAAGGCC
CTGCCTGCCCCTATCGAGAAAACCATCAGCAAGGCCAAGGGCCAGCCCAGGGAGCCCCAG
GTGTACACCCTGCCCCCTAGCAGAGATGAGCTGACCAAGAATCAGGTGTCCCTGACCTGC
CTGGTGAAGGGCTTCTACCCCAGCGACATCGCCGTGGAGTGGGAGAGCAACGGCCAGCCC
GAGAACAACTACAAGACCACCCCCCCTGTGCTGGACAGCGATGGCAACGTGTTCAGCTGC
AGCAAGCTGACCGTGGATAAGAGCAGATGGCAGCAGGGCAACGTGTTCAGCTGCTCCGTG
ATGCACGAGGCCCTGCACAATCACTACACCCAGAAGAGCCTGAGCCTGTCCCCCTGGCAAG
TGATGAGCGGCCGC
```

FIG 18B

```
MKAPAVLAPGILVLLFTLVQRSNGECKEALAKSEMNVNMKYQLPNFTAET
PIQNVILHEHHIFLGATNYIYVLNEEDLQKVAEYKTGPVLEHPDCFPCQD
CSSKANLSGGVWKDNINMALVVDTYYDDQLISCGSVNRGTCQRHVFPHNH
TADIQSEVHCIFSPQIEEPSQCPDCVVSALGAKVLSSVKDRFINFFVGNT
INSSYFPDHPLHSISVRRLKETKDGFMFLTDQSYIDVLPEFRDSYPIKYV
HAFESNNFIYFLTVQRETLDAQTFHTRIIRFCSINSGLHSYMEMPLECIL
TEKRKKRSTKKEVFNILQAAYVSKPGAQLARQIGASLNDDILFGVFAQSK
PDSAEPMDRSAMCAFPIKYVNDFFNKIVNKNNVRCLQHFYGPNHEHCFNR
TLLRNSSGCEARRDEYRTEFTTALQRVDLFMGQFSEVLLTSISTFIKGDL
TIANLGTSEGRFMQVVVSRSGPSTPHVNFLLDSHPVSPEVIVEHTLNQNG
```

FIG. 18B (cont'd)

YTLVITGKKITKIPLNGLGCRHFQSCSQCLSAPPFVQCGWCHDKCVRSEE
CLSGTWTQQICLPAIYKVFPNSAPLEGGTRLTICGWDFGFRRNKFDLKK
TRVLLGNESCTLTLSESTMNTLKCTVGPAMNKHFNMSIIISNGHGTTQYS
TFSYVDPVITSISPKYGPMAGGTLLTLTGNYLNSGNSRHISIGGKTCTLK
SVSNSILECYTPAQTISTEFAVKLKIDLANRETSIFSYREDPIVYEIHPT
KSFISGGSTITGVGKNLNSVSVPRMVINVHEAGRNFTVACQHRSNSEIIC
CTTPSLQQLNLQLPLKTKAFFMLDGILSKYFDLIYVHNPVFKPFEKPVMI
SMGNENVLEIKVRNALNTVLNHQLKLNPWSHPQFEPKSCDKTHTCPPCPA
PELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEA
LHNHYTQKSLSLSPGK

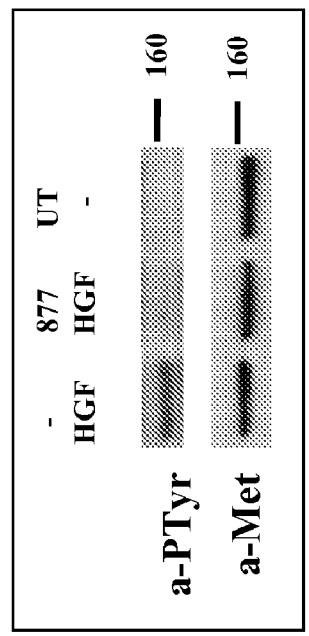
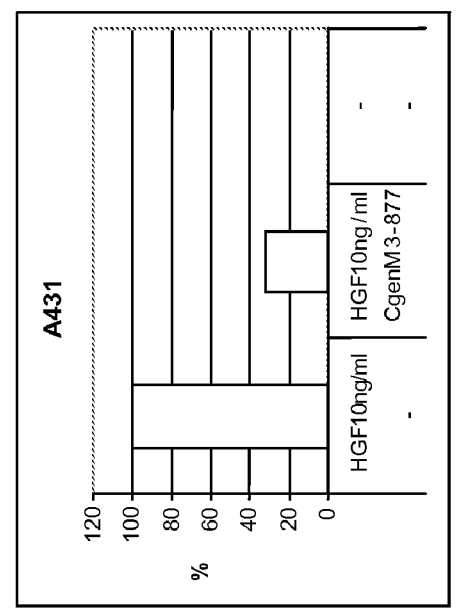
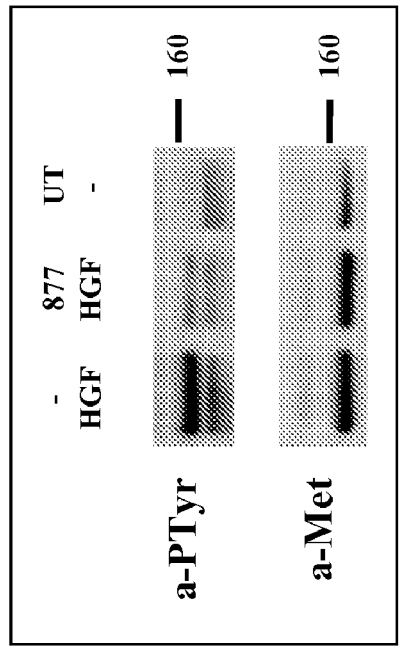
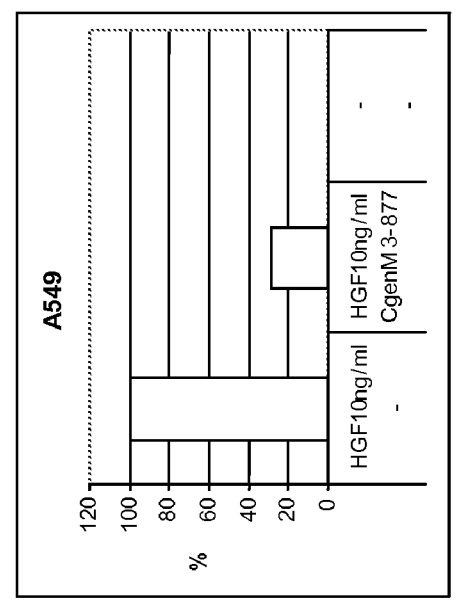
FIG. 22A
FIG. 22B

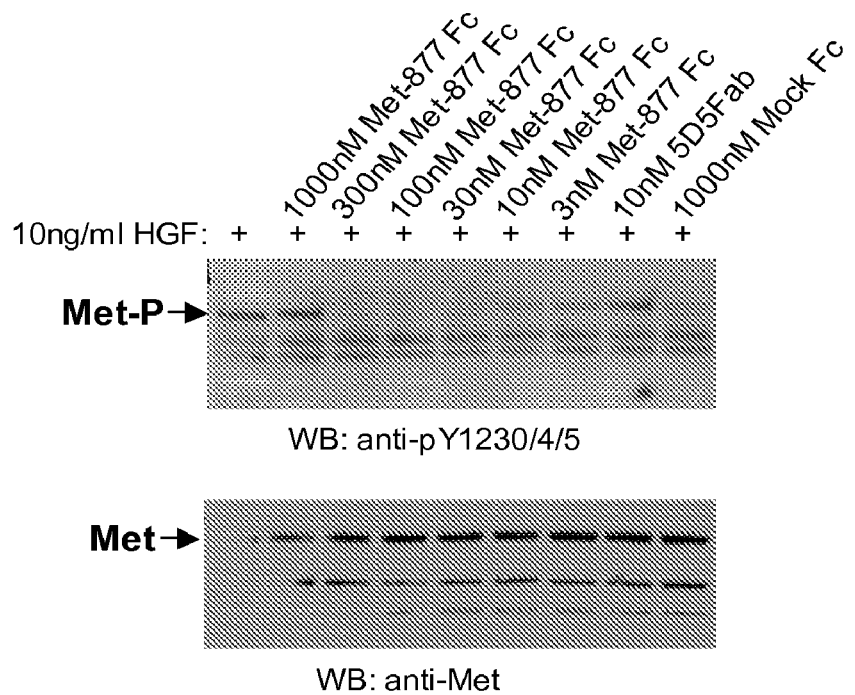
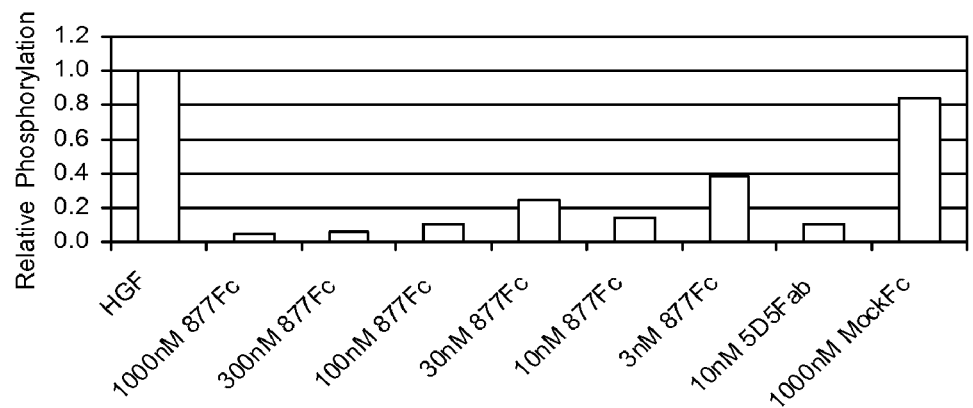
FIG. 23C

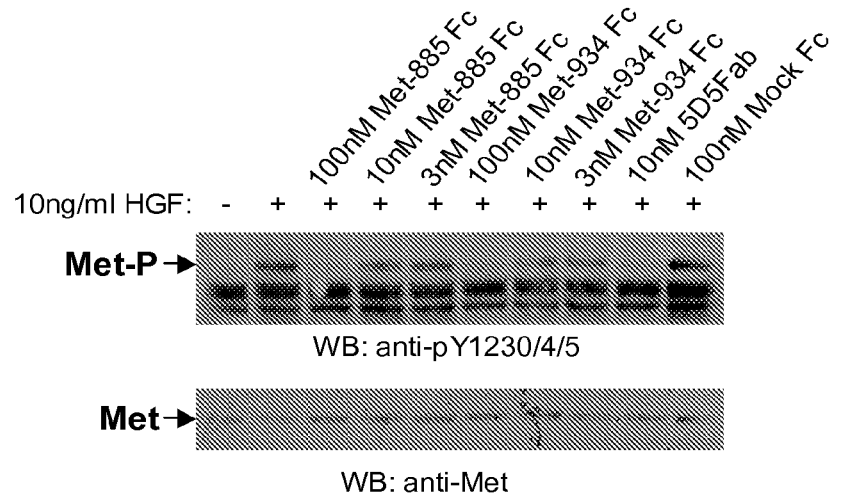
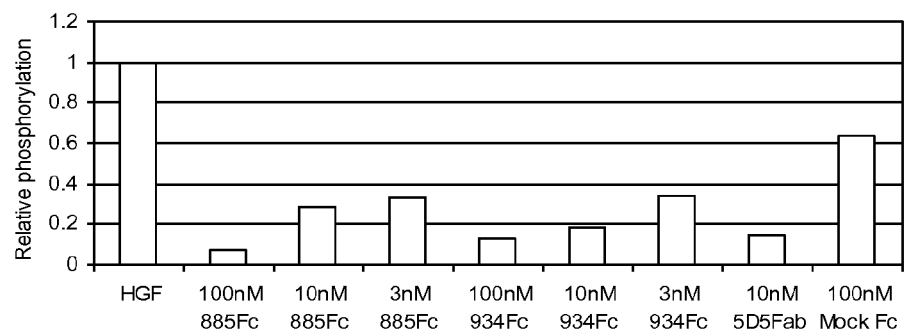
FIG. 23D

FIG. 25A

| | 1 | 2 | 3 | 4 | 5 | 6 | 7 | 8 | 9 | 10 | 11 | 12 |
|---|---|---|---|---|---|---|---|---|---|---|---|---|
| A | | | | | | | | | | | | |
| B | | no HGF | no HGF | no HGF | FC 934 100ug/ml | FC 934 100ug/ml | FC 934 100ug/ml | | | | | |
| C | HGF P27 1:50 100ug/ml | HGF P27 1:50 | HGF P27 1:50 | | FC 934 30 ug/ml | FC 934 30 ug/ml | FC 934 30 ug/ml | Met 877 FC Br1A 10ug/ml | Met 877 FC Br1A 10ug/ml | Met 877 FC Br1A 10ug/ml | 877 BR4A 10ug/ml | |
| D | CGM877 in PBS 100ug/ml | CGM877 in PBS 100ug/ml | CGM877 in PBS 100ug/ml | | FC 934 10 ug/ml | FC 934 10 ug/ml | FC 934 10 ug/ml | 877 Br1B 100ug/ml | 877 Br1B 100ug/ml | 877 Br1B 100ug/ml | 877 BR4A 10ug/ml | |
| E | CGM877 in PBS 30ug/ml | CGM877 in PBS 30ug/ml | CGM877 in PBS 30ug/ml | | MockFC 100ug/ml | MockFC 100ug/ml | MockFC 100ug/ml | 877 Br1B 30ug/ml | 877 Br1B 30ug/ml | 877 Br1B 30ug/ml | HGF P27 1:50 | |
| F | CGM877 in PBS 10ug/ml | CGM877 in PBS 10ug/ml | CGM877 in PBS 10ug/ml | | Met 877 FCBr1A 100ug/ml | Met 877 FCBr1A 100ug/ml | Met 877 FCBr1A 100ug/ml | 877 Br1B 10ug/ml | 877 BR4A 100ug/ml | 877 BR4A 100ug/ml | HGF P27 1:50 | |
| G | MockN PBS 100ug/ml | MockN PBS 100ug/ml | MockN PBS 100ug/ml | | Met 877 FCBr1A 30ug/ml | Met 877 FCBr1A 30ug/ml | Met 877 FCBr1A 30ug/ml | 877 BR4A 30ug/ml | 877 BR4A 30ug/ml | 877 BR4A 30ug/ml | HGF P27 1:50 | |
| H | | | | | | | | | | | | |

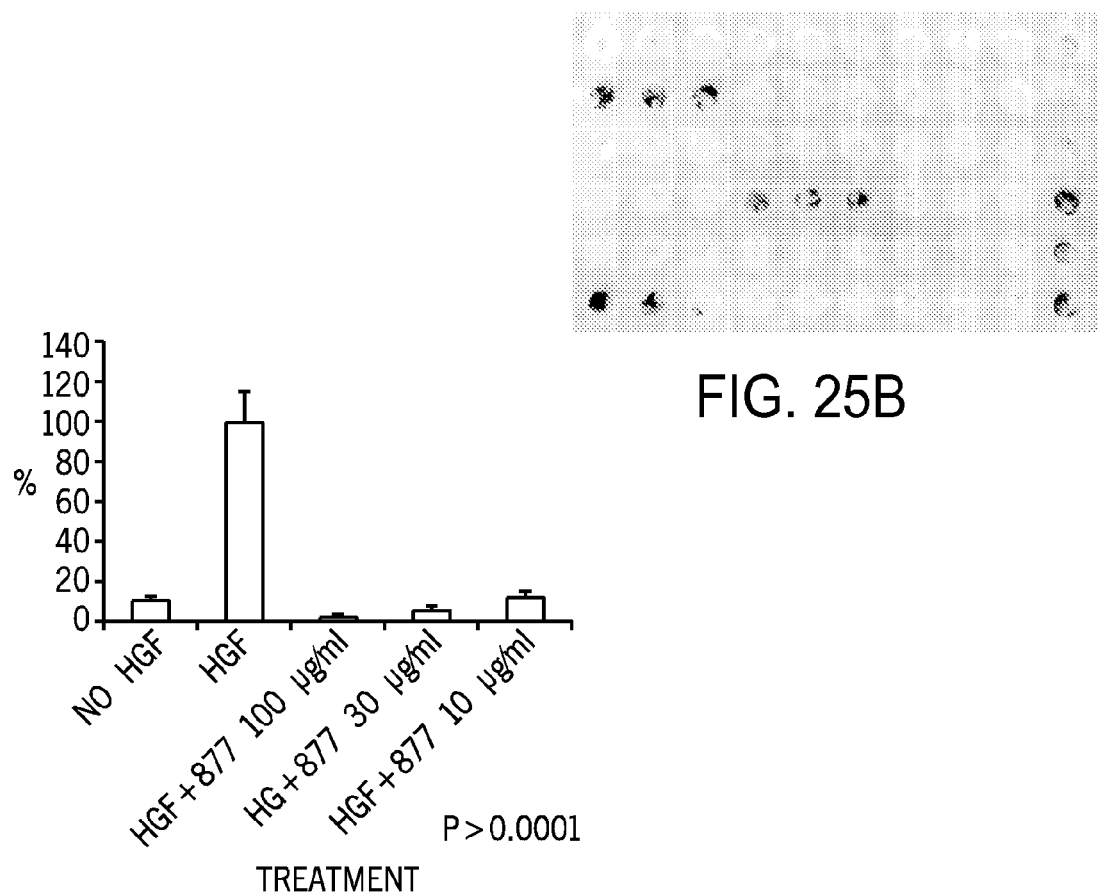
FIG. 25B
FIG. 25C
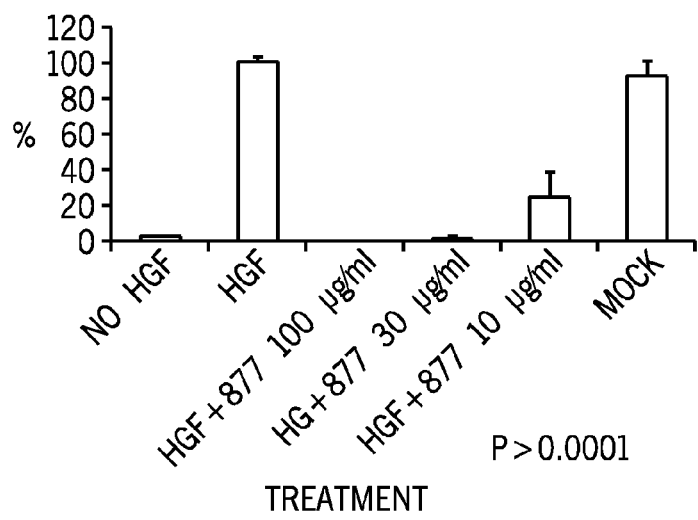
FIG. 25D

- ♦ 877 Fc
- ■ 885 Fc
- ▲ 934 Fc

HEPATOCYTE GROWTH FACTOR RECEPTOR SPLICE VARIANTS AND METHODS OF USING SAME

RELATED APPLICATION DATA

This application is a continuation-in-part of U.S. Non-provisional application Ser. No. 10/764,833 filed on Jan. 27, 2004, now abandoned, which is a continuation-in-part of U.S. Non-provisional application Ser. Nos. 10/426,002 filed on Apr. 30, 2003, now abandoned, and 10/242,799 filed on Sep. 13, 2002, now abandoned, and claims the benefit of priority from U.S. Provisional Application Nos. 60/322,285 filed on Sep. 14, 2001, 60/322,359 filed on Sep. 14, 2001, 60/322,506 filed on Sep. 14, 2001, 60/324,524 filed on Sep. 26, 2001, 60/354,242 filed on Feb. 6, 2002, 60/371,494 filed on Apr. 11, 2002, 60/384,096 filed on May 31, 2002, and 60/397,784 filed on Jul. 24, 2002; and is also a continuation-in-part of U.S. Non-provisional application Ser. No. 11/043,591 filed on Jan. 27, 2005, which claims the benefit of priority from U.S. Provisional Application Nos. 60/579,202 filed on Jun. 15, 2004, and 60/539,128 filed on Jan. 27, 2004; and is also a continuation-in-part of U.S. Non-provisional application Ser. No. 11/043,860 filed on Jan. 27, 2005, now abandoned, which claims the benefit of priority from U.S. Provisional Application No. 60/539,129 filed on Jan. 27, 2004; and is also a continuation-in-part of International Application No. PCT/IL06/01155 filed on Oct. 3, 2006, which claims the benefit of priority from U.S. Provisional Application Nos. 60/721,961 filed on Sep. 30, 2005, 60/779,408 filed on Mar. 7, 2006 and 60/799,319 filed on May 11, 2006, the content of each which is expressly incorporated herein in its entirety by this reference.

FIELD OF THE INVENTION

The present invention relates to hepatocyte growth factor receptor splice variant polypeptides, and polynucleotides encoding same, vectors and host cells comprising same and more particularly, to therapeutic and diagnostic compositions and methods utilizing same.

BACKGROUND OF THE INVENTION

The protein product of c-Met oncogene is the tyrosine kinase receptor for hepatocyte growth factor (HGF) also known as scatter factor (SF). HGF and its receptor c-Met are widely expressed in a variety of tissues, and their expression is normally confined to cells of mesenchymal and epithelial origin, respectively. The HGF-Met pathway is involved in a wide range of biological effects, including cell proliferation and survival, cell adhesion, cell migration and invasion, morphogenic differentiation, organization of tubular structures and angiogenesis. Such paracrine signaling is vital to normal embryogenic development, wound healing and tissue maintenance and regeneration (reviewed in Christensen et al, 2005, Cancer Letters 225: 1-26).

While HGF-Met signaling plays a key role during normal development, inappropriate activation of this signaling pathway has been implicated in tumor development and progression. Aberrant c-Met signaling has been described in a variety of human cancers, including solid tumors and hematologic malignancies. Met activation may be involved in different stages of tumor progression, such as tumor cell proliferation and survival in primary tumors, induction of angiogenesis, stimulation of cell motility to form micrometastases, induction of invasive phenotype, and regaining the proliferation phenotype to form overt metastases (Birchmeier et al 2003, Nat. Rev. Mol. Cell. Biol. 4: 915-925).

Several mechanisms cause dysregulation of the HGF-Met pathway in tumor cells, such as overexpression of c-Met and/or HGF, constitutive kinase activation of c-Met in the presence or absence of gene amplification, activating mutations of c-Met, and autocrine activation of c-Met by HGF. c-Met is expressed in most carcinomas, but the degree of expression varies among distinct tumor types. High expression is detected in renal and colorectal carcinomas, and lung adenocarcinomas. Overexpression of ligand and/or receptor correlates with high tumor grade and poor prognosis. c-Met mutations have been reported in several types of tumors, such as hereditary and sporadic human papillary renal carcinomas, as well as ovarian cancer, childhood hepatocellular carcinoma, head and neck squamous cell carcinomas, gastric and lung cancers (reviewed in Maulik et al, 2002. Cytokine & Growth Factor Rev. 13: 41-59; Ma et al, 2003. Cancer and Metastasis Rev. 22: 309-325).

The HGF-Met pathway is involved in cell scattering. HGF was discovered as a secretory product of fibroblasts and smooth muscle cells that induces dissociation and motility of epithelial cells. It is able to induce cell dissociation and mutual repulsion in a similar manner to semaphorins. HGF-Met signaling is also involved in cell motility. The key events regulating cell motility are polymerization of actin, formation of actin stress fibers, and focal adhesion formation. HGF has been shown to induce branching morphogenesis of kidney, mammary and bile ductular cells. In response to HGF, Met-expressing cells form branches in three-dimensional matrigel or tubule-like structures in collagen gels. This process is mediated through changes in cell shape, asymmetric polarization of the cells in the direction of branching, branch elongation, cell-cell contact, cell-ECM communication, ECM remodeling, controlled proteolysis and cell motility (Zhang et al. 2003. J. Cell. Biochem., 88:408-417; Ma et al, 2003. ibid). HGF acts as a potent angiogenic factor. HGF stimulation of vascular endothelial cells promotes migration, proliferation, protease production, invasion, and organization into capillary-like tubes. HGF can also promote the expression of angiogenic factors by tumor cells (Ma et al, 2003. ibid).

HGF-Met signaling has been strongly implicated in the promotion of the invasive/metastatic tumor phenotype. An HGF-stimulated pathway involving MAPK1/2 signaling is important in the up-regulation of expression of the serine protease urokinase (uPA) and its receptor (uPAR), resulting in an increase of uPA on the cell surface. Certain components of the ECM can be directly degraded by uPA, and more importantly, uPA cleaves plasminogen into the broader-specificity protease plasmin, which is able to efficiently degrade several ECM and basement membrane (BM) components. Plasmin also activates metalloproteinases, which have potent ECM/BM degrading abilities. HGF has been reported to promote attachment of tumor cells to endothelium, an important step in the metastatic cascade. This activity may be mediated by HGF induced up-regulation of CD44 expression on endothelium cells, and integrin expression on tumor cells.

The human Met gene, which includes 21 exons, is located on chromosome 7 band 7q21-q31 and spans more than 120 kb in length. The primary Met transcript produces a 150 kDa polypeptide (1390 amino acids) that is partially glycosylated to produce a 170 kDa precursor protein. This 170 kDa precursor is further glycosylated and then cleaved into a 50 kDa α-chain and a 140 kDa β-chain which are disulfide-linked. The α-subunit of the mature Met heterodimer is highly glycosylated and is entirely extracellular, while the β-subunit contains a large extracellular region, a membrane spanning segment, and an intracellular tyrosine kinase domain (Ma et al, 2003. ibid).

Met is the prototypic member of a subfamily of heterodimeric receptor tyrosine kinases which include Met, Ron, and Sea. Members of the Met receptor subfamily have been shown to share homology with semaphorins and semaphorin receptors (plexin), which play a role in cell scattering (Reviewed in Trusolino et al. 1998, FASEB J. 12: 1267-1280). All semaphorins contain a conserved 500 amino acid extracellular domain (Sema domain), which spans the cysteine-rich Met related sequence (MRS), containing the consensus motif C—X(5-6)-C—X(2)-C—X(6-8)-C—X(2)-C—X(3-5)-C. The extracellular portions of Met, Ron, and Sea contain a region of homology to semaphorins including the N-terminal Sema domain and the MRS. Other domains identified in the extracellular portion of Met are the PSI domain and the IPT/TIG repeat domain. The PSI domain is found in plexins, semaphorins and integrins while the IPT repeats (also known as TIG domains) are found within immunoglobulin, plexins and transcription factors. The C-terminus intracellular tyrosine kinase domain shares homology with Ron and Sea.

The Sema domain plays a critical role in ligand binding and is also necessary for receptor dimerization (Kong-Beltran et al 2004, Cancer Cell, 6: 75-84; Wickramasinghe and Kong-Beltran, 2005, Cell Cycle, 4: 683-685). Treatment of Met-overexpressing tumor cells with a recombinant Sema protein construct (rSema, which contains also the PSI domain) inhibits both ligand dependent and independent activation of Met-mediated signal transduction, cell motility and migration, in a manner similar to the antagonistic anti-Met Fab 5D5 (Kong-Beltran et al 2004. ibid). Decoy Met (the entire extracellular domain of Met, produced as a truncated soluble receptor) interferes with HGF binding to Met, and with receptor dimerization. Similarly, a chimeric soluble protein containing the extracellular domain of Met fused to the constant region of IgG heavy chain, binds HGF with an affinity similar to that of the authentic, membrane-associated receptor, and inhibits the binding of HGF to Met, expressed on A549 cells (Mark, et al., 1992, J Biol. Chem. 267:26166-26171). Local or systemic delivery of decoy Met in mice, by lentiviral vector technology, inhibits tumor cell proliferation and survival in a variety of human xenografts, impairs tumor angiogenesis, suppresses or prevents the formation of spontaneous metastases, and synergizes with radiotherapy in inducing tumor regression (Michieli et al, 2004, Cancer Cell 6: 61-73). These data suggest that the extracellular domain of Met may not only represent a novel anticancer therapeutic target, but also acts as a biotherapeutic itself (reviewed in Zhang et al 2004, Cancer Cell 6: 5-6).

Various inhibitory strategies have been employed to therapeutically target the HGF-Met pathway (reviewed in Christensen et al, 2005, Cancer Letters 225: 1-26), and several candidates are under development. Three main approaches have been employed for selective anticancer drug development: antagonism of HGF/Met interaction, inhibition of tyrosine kinase catalytic activity of Met, and blockade of intracellular Met/effectors interactions. Among the current developments are a humanized anti-HGF mAb AMG-102 (Amgen); NK4, a proteolytic cleavage fragment of HGF that acts as a competitive HGF antagonist (Kringle Pharma); and small molecule inhibitors of the c-Met receptor, such as XL880 (Exelixis), ARQ 197 (Arqule), SU11274, PHA665752, PF-02341066 of Pfizer; a series of small molecules of Methylgene, and others.

WO 2005/113596 assigned to Receptor Biologix Inc, discloses several in silico predicted polypeptides that are isoforms of cell surface receptors, including, inter alia, Met receptor, wherein each polypeptide comprises at least one domain of the receptor, operatively linked to at least one amino acid encoded by an intron of a relevant gene; and the polypeptide lacks a transmembrane domain, protein kinase domain and at least one additional domain compared to the wt receptor, whereby the membrane localization and protein kinase activity of the polypeptide is reduced or abolished compared to the receptor. It is further speculated that these isoforms may be useful in treating or preventing metastatic cancer, inhibiting angiogenesis, treating lung cancer, malignant peripheral nerve sheath tumors, colon cancer, gastric cancer, cutaneous malignant melanoma and prevention of malaria. WO 2005/113596 mentions that the Met isoforms might be provided in pharmaceutical compositions as conjugates between the isoform and another agent, including coupling to an Fc fragment of an antibody that binds to a specific cell surface marker to induce killer T cell activity in neturophils, natural killer cells and macrophages. However, no guidance is provided for production of any conjugates, nor are there any examples for actual biological activities of said Met isoforms.

U.S. Pat. No. 5,571,509 assigned to Farmitalia Carlo Erba S. R. L., discloses a carboxy-terminal truncated form of the c-Met oncogene. The truncated form results in a beta chain of the receptor, which is 75 to 85 kDa long that acts as an antagonist of the HGF receptor. U.S. Pat. No. 5,571,509 reveals that this soluble Met protein is released in the culture medium by proteolytic cleavage of the membrane-bound Met proteins. However, these proteolytic fragments are not novel splice variants of cMet.

US Patent Application Publication No. 2005/0233960 assigned to GENETECH, INC. discloses c-Met antagonists for modulating the HGF/c-met signaling pathway. The c-Met antagonists of US 2005/0233960 are particularly peptides comprising at least a portion of c-Met Sema domain or variant thereof.

There is an unmet need to develop therapies which target the HGF-Met pathway and Met signaling via Met receptor tyrosine kinase, and which inhibit Met receptor action and/or its physiological effects.

SUMMARY OF THE INVENTION

The present invention provides splice variants of the Met receptor tyrosine kinase, derivatives thereof and vectors encoding same. Specifically, the present invention provides soluble Met receptor splice variants or derivatives thereof having inhibitory effects on Met tyrosine kinase activity. The invention further provides pharmaceutical compositions, fusion proteins and host cells comprising said splice variants and vector encoding said splice variants. In addition, the present invention provides methods of treating, preventing and diagnosing cancers and non-cancerous proliferative disorders reliant on Met signaling, using said splice variants.

The Met variant products (splice variants) of the present invention are devoid of transmembrane and intracellular domains while retaining the extracellular region of Met (i.e., HGF binding site). Without wishing to be bound by a single theory, these splice variants are likely to compete for HGF binding to the membrane bound Met receptor and as a consequence may block Met activation and the signaling pathway. Alternatively, Met soluble splice variants can interfere with constitutive Met signaling in cancer cells, in an HGF-independent manner. Therefore, Met splice variants of the present invention can serve as antagonists (i.e., inhibitors) of HGF dependent or independent Met signaling.

According to a first aspect the present invention provides an isolated polynucleotide encoding Met splice variant protein comprising an amino acid sequence as set forth in any one of SEQ ID NO:36 (Met588 protein) and SEQ ID NO:37 (Met877 protein).

According to one embodiment, the present invention provides an isolated polynucleotide encoding Met splice variant protein having a nucleic acid sequence as set forth in any one of SEQ ID NO:1 (Met588) and SEQ ID NO:3 (Met877).

According to another embodiment, the isolated polynucleotide further comprises an Fc fragment coding sequence wherein the expression of the polynucleotide leads to the formation of a fusion protein with an Fc fragment.

According to yet another embodiment, the isolated polynucleotide comprising the Fc fragment encodes a MET splice variant fusion protein comprising an amino acid sequence as set forth in SEQ ID NO:79 (Met877-Fc protein).

According to yet a further embodiment, the isolated polynucleotide comprising the Fc fragment coding sequence comprises a nucleic acid sequence as set forth in SEQ ID NO:78 (Met877-Fc).

According to yet another embodiment, the isolated polynucleotide further comprises a tag coding sequence wherein the expression of the polynucleotide leads to the formation of a fusion protein with a tag.

According to one embodiment, the isolated polynucleotide comprising a tag sequence encodes a MET splice variant fusion protein comprising an amino acid sequence as set forth in SEQ ID NO:47 (Met877-His-tag protein).

According to another embodiment, the isolated polynucleotide comprising a tag coding sequence comprises a nucleic acid sequence as set forth in SEQ ID NO:46 (Met877-His tag).

According to another aspect, the present invention provides an isolated Met splice variant polypeptide having an amino acid sequence as set forth in any one of SEQ ID NOS:36 (Met588 protein) or 37 (Met877 protein).

According to one embodiment, the isolated polypeptide further comprises an Fc fragment contiguously joined thereto. According to another embodiment, the isolated polypeptide further comprises a tag contiguously joined thereto.

According to another embodiment, the isolated Met splice variant comprising an Fc fragment is having an amino acid sequence as set forth in SEQ ID NO:79 (Met877Fc protein).

According to yet another embodiment, the isolated Met splice variant comprising a tag is having an amino acid sequence as set forth in SEQ ID NO:47 (Met877-His-tag protein).

According to yet another aspect, the present invention provides an isolated polynucleotide encoding Met splice variant tagged protein comprising a first nucleic acid sequence encoding a Met splice variant having an amino acid sequence as set forth in any one of SEQ ID NO:66 (Met885 protein) and SEQ ID NO:38 (Met934 protein) and a second nucleic acid sequence encoding a tag sequence.

According to one embodiment, the polynucleotide encoding Met splice variant tagged protein, wherein the protein comprises a sequence as set forth in SEQ ID NO:75 (Met885-His-tag protein).

According to other embodiments, the polynucleotide encoding Met splice variant tagged protein comprises a nucleic acid sequence as set forth in SEQ ID NO:74 (Met885-His-tag).

According to yet another aspect, the present invention provides an isolated polynucleotide encoding a Met splice variant fusion protein comprising a first nucleic acids sequence encoding a Met splice variant having an amino acid sequence as set forth in any one of SEQ ID NO:66 (Met885 protein) and SEQ ID NO:38 (Met934 protein) and a second nucleic acid sequence encoding an Fc fragment.

According to one embodiment, the isolated polynucleotide encodes a fusion protein comprising an amino acid sequence as set forth in any of SEQ ID NO:77 (Met885-Fc protein) and SEQ ID NO:68 (Met934-Fc protein). According to another embodiment, the isolated polynucleotide comprising an Fc fragment coding sequence is having the nucleic acid sequence as set forth in any of SEQ ID NO:76 (Met885-Fc) and SEQ ID NO:67 (Met934-Fc).

According to a further aspect, the present invention provides an isolated Met splice variant tagged protein comprising a first fragment having an amino acid sequence as set forth in any one of SEQ ID NO:66 (Met885 protein) and SEQ ID NO:38 (Met934 protein) and a second fragment contiguously joined thereto, wherein the second fragment is a tag.

According to one embodiment, the tagged protein comprises an amino acid as set forth in SEQ ID NO:75 (Met885-His-tag protein).

According to yet another aspect, the present invention provides isolated Met splice variant fusion protein comprising a first fragment having an amino acid sequence as set forth in any one of SEQ ID NO:66 (Met885 protein) and SEQ ID NO:38 (Met934 protein) and a second fragment contiguously joined thereto, wherein the second fragment is an Fc fragment.

According to one embodiment, the isolated Met splice variant having an Fc fragment coding sequence contiguously joined thereto comprises an amino acid sequence as set forth in any one of SEQ ID NO:77 (Met885-Fc protein) and SEQ ID NO:68 (Met934-Fc protein).

According to alternative embodiments, the present invention further provides derivatives of the Met receptor tyrosine kinase variants and modified Met receptor tyrosine kinase variants. According to some embodiments the derivatives are obtained by glycosylation and/or phosphorylation and/or chemical modifications. According to other embodiments, the derivatives are fusion proteins. According to certain embodiments the modified splice variants are fused to an Fc fragment of Ig. According to certain embodiments the modified Met receptor tyrosine kinase variants are obtained by addition of C-terminal His/StrepII tag.

According to certain embodiments, the protein variants of the present invention can be modified to form synthetically modified variants.

Advantageously, the protein variants of the present invention comprise modifications that enhance their inhibitory and/or therapeutic effect including, e.g., enhanced affinity, improved pharmacokinetics properties (such as half life, stability, clearance rate), and reduced toxicity to the subject. Such modifications include, but are not limited to, modifications involving glycosylation, pegylation, substitution with non-naturally occurring but functionally equivalent amino acid and linking groups.

According to additional aspects, the present invention provides vectors, cells, liposomes and compositions comprising the isolated nucleic acids of this invention.

According to further aspects, the present invention provides pharmaceutical compositions comprising the novel splice variant polypeptides of this invention.

According to yet additional aspects, the present invention provides pharmaceutical compositions comprising the novel splice variant polynucleotides of this invention.

According to yet other aspects, the present invention provides pharmaceutical compositions comprising an expression vector, wherein the expression vector contains the nucleic acid sequence encoding Met variant of the present invention. According to still further aspects the present invention provides pharmaceutical compositions comprising host cells containing the expression vectors of the invention.

According to yet another aspect, the present invention provides a method for treating a Met-related disease, comprising administering an agent selected from: Met variant therapeutic protein, variant peptide, nucleic acid sequence encoding Met variant of the present invention, expression vector containing the nucleic acid sequence encoding Met variant of the present invention or host cells containing the expression vector as above, to a subject in need of treatment thereof.

According to certain embodiment, Met-related diseases including, but not limited to, diseases wherein Met receptor tyrosine kinase is involved in the etiology or pathogenesis of the disease process, as will be explained in detail hereinbelow. Optionally, the transcripts of novel Met variants of the present invention are useful as therapeutic agents for treatment of Met-related diseases.

In particular, Met-related diseases include, but are not limited to, disorders or conditions that would benefit from treatment with a molecule or method of the invention. These include chronic and acute disorders or diseases, such as pathological conditions which predispose to the disorder in question. Non-limiting examples of the disorders to be treated herein include malignant and benign tumors; lymphoid malignancies; neuronal, glial, astrocytal, hypothalamic and other glandular, macrophagal, epithelial, stromal and blastocoelic disorders; and angiogenesis-related disorders.

Examples of cancer include but are not limited to, carcinoma, lymphoma, leukemia, sarcoma and blastoma. According to certain preferred embodiments, the methods of the present invention are useful in treating primary and metastatic cancer such as breast cancer, colon cancer, colorectal cancer, gastrointestinal tumors, esophageal cancer, cervical cancer, ovarian cancer, endometrial or uterine carcinoma, vulval cancer, liver cancer, hepatocellular cancer, bladder cancer, kidney cancer, hereditary and sporadic papillary renal cell carcinoma, pancreatic cancer, various types of head and neck cancer, lung cancer (e.g., non-small cell lung cancer, small cell lung cancer, squamous cell carcinoma, lung adenocarcinoma), prostate cancer, thyroid cancer, brain tumors, glioblastoma, glioma, malignant peripheral nerve sheath tumors, cancer of the peritoneum, cutaneous malignant melanoma, and salivary gland carcinoma.

Met-related diseases also consist of diseases in which anti-angiogenic activity plays a favorable role, including but not limited to, diseases having abnormal quality and/or quantity of vascularization as a characteristic feature. Dysregulation of angiogenesis can lead to many disorders that can be treated by compositions and methods of the invention. These disorders include both non-neoplastic and neoplastic conditions. Neoplastic include but are not limited to the type of primary and metastatic cancers described above. Non-neoplastic disorders include but are not limited to inflammatory and autoimmune disorders, such as aberrant hypertrophy, arthritis, psoriasis, sarcoidosis, scleroderma, atherosclerosis, synovitis, dermatitis, Crohn's disease, ulcerative colitis, inflammatory bowel disease, respiratory distress syndrome, uveitis, meningitis, encephalitis, Sjorgen's syndrome, systemic lupus erythematosus, diabetes mellitus, multiple sclerosis, juvenile onset diabetes; allergic conditions, eczema and asthma; proliferative retinopathies, including but not limited to diabetic retinopathy, retinopathy of prematurity, retrolental fibroplasia, neovascular glaucoma, age-related macular degeneration, diabetic macular edema, cornal neovascularization, corneal graft neovascularization and/or rejection, ocular neovascular disease; and various other disorders in which anti-angiogenic activity plays a favorable role including but not limited to vascular restenosis, arteriovenous malformations, meningioma, hemangioma, angiofibroma, thyroid hyperplasia, hypercicatrization in wound healing, hypertrophic scars.

The compositions and methods of the present invention can be further employed in combination with surgery or cytotoxic agents, or other anti-cancer agents, such as chemotherapy or radiotherapy and/or in combination with anti-angiogenesis drugs.

Additionally or alternatively, Met receptor tyrosine kinase variants according to the present invention may be useful for diagnosis of diseases wherein Met receptor tyrosine kinase is involved in the etiology or pathogenesis of the disease process, and/or disease in which Met expression is altered as compared to the normal level, as will be explained in detail hereinbelow. Furthermore, the novel variants may be useful for diagnosis of any disease or condition where Met receptor tyrosine kinase is known to serve as a diagnostic or prognostic marker.

Examples of diseases where the novel variants may be useful for diagnosis include, but are not limited to, cancer, such as hereditary and sporadic papillary renal carcinoma, breast cancer, ovarian cancer, childhood hepatocellular carcinoma, metastatic head and neck squamous cell carcinomas, lung cancer (e.g., non-small cell lung cancer, small cell lung cancer), prostate cancer, pancreatic cancer and gastric cancer, diabetic retinopathy, regenerative processes such as wound healing and conditions, which require enhanced angiogenesis such as atherosclerotic diseases, ischemic conditions and diabetes, and diseases of the liver such as hepatic cirrhosis and hepatic dysfunction.

According to yet another aspect, the present invention provides a kit for detecting a variant-detectable disease, comprising a kit detecting specific expression of a splice variant according to any of the above embodiments.

US Patent Application Publication No. 2004/0248157, assigned to the applicant of the present invention (and hereby incorporated by reference as if fully set forth herein) discloses polynucleotides and their respective encoded polypeptides. One of several transcripts disclosed therein is a Met-934 variant (denoted herein SEQ ID NO: 2 and SEQ ID NO:38, for mRNA and protein sequences, respectively), which results from alternative splicing of the c-Met gene, thereby causing an extension of exon 12 (the last exon before the transmembrane region encoding exon) leading to an insertion of a stop codon and the generation of a truncated Met protein which terminates just before the transmembrane domain. Met splice variant has an open reading frame (ORF) of 934 amino acids including 910 amino acids of the wild-type (w.t.) Met protein and a unique sequence of 24 amino acids at the C-terminus of the protein. It contains nearly the complete extracellular portion of Met (910 amino acids of 933 of the w.t. protein) and therefore comprises all its structural domains (the Sema, PSI and TIG domains). Met-934 is predicted to be a secreted protein since it retains the original N-terminal signal peptide (amino acids 1-24) and lacks the transmembrane domain (amino acids 933-955 of the w.t.). The Met-934 secreted isoform was suggested to function as an antagonist (i.e., inhibitor) of Met-HGF interaction by competing with the membrane-bound receptor for the ligand-HGF. Met-934 splice variant was suggested to be useful in the treatment and/or diagnosis of cancers such as, hereditary and sporadic papillary renal carcinoma, breast cancer, ovarian cancer, childhood hepatocellular carcinoma, metastatic head and neck squamous cell carcinomas, lung cancer (e.g., non-small cell lung cancer, small cell lung cancer), prostate cancer, pancreatic cancer, gastric cancer and other diseases such as diabetic retinopathy.

WO 05/071059 and U.S. patent application Ser. No. 11/043,591 (both of which are hereby incorporated by reference as if fully set forth herein) assigned to the applicant of the present invention disclose polynucleotides and their respective encoded polypeptides. One among the hundreds of polynucleotide transcripts disclosed therein is HSU08818_orig_trans_9_drop_nodes_28_new_num_15_tr0_r1_1_gPRT (denoted herein SEQ ID NO:48) which encodes an amino acid sequence termed hereinafter Met-885 (SEQ ID NO:66). This splice isoform was generated through exon skipping and it contains the first 11 exons of the c-Met gene, skips the 12th exon and enters the intron following the 12th exon, leading to an insertion of a stop codon and the generation of a truncated Met protein which terminates just before the transmembrane domain. The derived protein contains 885 amino acids, that includes 861 amino acids of the wild-type and a unique sequence of 24 intron-derived amino acids at the C-terminus of the protein. The Met-885 (SEQ ID NO:66) secreted isoform was suggested to be useful for treatment of Papillary Renal Carcinoma, head and neck cancers and other cancers.

These and additional features of the invention will be better understood in conjunction with the figures description, examples and claims which follow.

BRIEF DESCRIPTION OF DRAWINGS

FIGS. 1A-E demonstrate amino acid sequence comparison between the Met variants of the invention and the known Met receptor protein kinase. FIG. 1A demonstrates the comparison between Met-877 variant of the invention (SEQ ID NO:37) and the known Met receptor protein kinase (SEQ ID NO:34). FIG. 1B demonstrates the comparison between Met-934 variant of the invention (SEQ ID NO:38) and the known Met receptor protein kinase (SEQ ID NO:34). FIG. 1C demonstrates the comparison between Met-885 variant of the invention (SEQ ID NO:66) and the known Met receptor protein kinase (SEQ ID NO:34). FIG. 1D demonstrates the comparison between Met-588 variant of the invention (SEQ ID NO:36) and the known Met receptor protein kinase MET_HUMAN (SEQ ID NO:34). FIG. 1E demonstrates the comparison between Met-588 variant of the invention (SEQ ID NO:36) and the known Met receptor protein kinase MET_HUMAN_V1 (SEQ ID NO:35).

FIGS. 2A-D demonstrates amino acid sequence comparison between the Met variants of the invention and a Met variant previously disclosed by Receptor Biologix Inc. (RB). The unique amino acids are marked in bold. FIG. 2A demonstrates the comparison between Met-877 variant of the invention (SEQ ID NO:37) and the RB Met variant (SEQ ID NO:40). FIG. 2B demonstrates the comparison between Met-885 variant of the invention (SEQ ID NO:66) and the RB Met variant (SEQ ID NO:40). FIG. 2C demonstrates the comparison between Met-934 variant of the invention (SEQ ID NO:38) and the RB Met variant (SEQ ID NO:40). FIG. 2D demonstrates the comparison between Met-588 variant of the invention (SEQ ID NO:36) and the RB Met variant (SEQ ID NO:40).

FIG. 5A shows the Met-934-Fc sequence that was codon optimized to boost protein expression in mammalian system (SEQ ID NO:67). The bold part of the nucleotide sequence shows the relevant ORF (open reading frame) including the tag sequence.

FIG. 5B shows the optimized Met-934-Fc protein sequence (SEQ ID NO:68). The bold part of the sequence is the Fc tag.

FIG. 7A shows the optimized nucleotide sequences of Met885 StrepHis (SEQ ID NO:74). The bold part of the nucleotide sequence shows the relevant ORF (open reading frame) including the tag sequence. The Strep-His tag is underlined.

FIG. 7B shows the optimized protein sequences of Met885 StrepHis (SEQ ID NO:75). The Strep-His tag is underlined.

FIG. 8A shows the optimized nucleotide sequences of Met-885-Fc (SEQ ID NO:76). The bold part of the nucleotide sequence shows the relevant ORF (open reading frame) including the tag sequence. The Fc-tag is underlined.

FIG. 8B shows the optimized Met-885-Fc protein sequence (SEQ ID NO:77). The Fc-tag is underlined.

FIG. 12 shows the Met-877 (SEQ ID NO:45) PCR product sequence. The sequences of the primers used for the RT-PCR in Figure, are shown in bold.

FIG. 13A shows the Met-877 (SEQ ID NO:46) sequence that was codon optimized to boost protein expression in mammalian system. The bold part of the nucleotide sequence shows the relevant ORF (open reading frame) including the tag sequence.

FIG. 13B shows the optimized Met-877 His tag (SEQ ID NO:47) amino acid sequence. In bold there is the Strep tag, following the amino acid Pro (Strep II tag: WSHPQFEK); and His tag (8 His residues—HHHHHHHH) sequences which are separated by a linker of two amino acids (Thr-Gly). The 8 His tag is followed by Gly-Gly-Gln.

FIG. 18A shows the optimized nucleotide sequences of Met-877-Fc (SEQ ID NO:78). The bold part of the nucleotide sequence shows the relevant ORF (open reading frame) including the tag sequence. The Fc-tag is underlined.

FIG. 18B shows the optimized protein sequence of Met-877-Fc (SEQ ID NO: 79). The bold part of the sequence represents the Fc tag.

FIG. 19 demonstrates the COOMASSIE staining results of SDS-PAGE gel of Met-Fc variants.

FIGS. 22A-22B demonstrate the influence of Met-877 on HGF induced Met phosphorylation, using A431 (epidermoid carcinoma) or A549 (non-small cell lung carcinoma) cells treated with 10 ng/ml HGF (R&D) for 10 min, in the presence or absence of 100 μg/ml Met-877. UT=untreated cells. Immunoprecipitation of Met was followed by immunoblotting with anti-Ptyr Ab. After stripping, the same membrane was immunoblotted with anti-Met Ab. FIG. 22A shows the autoradiograms. FIG. 22B demonstrates the densitometry results of the scanned autoradiograms. The level of P-tyr on Met upon HGF-induction was defined as 100%. FIG. 22C shows the autoradiogram, FIG. 22D demonstrates the densitometry results of the scanned autoradiogram.

FIGS. 23A-23D demonstrate the influence of Met-877-Fc, -885-Fc and 934-Fc (SEQ ID NOS:79, 77 and 68, respectively) on HGF-induced phosphorylation of specific Met tyrosine residues (Y1230, 1234 and 1235) using an antibody that recognizes Met when it is phosphorylated at these residues. A549 (non-small cell lung carcinoma) or MDA-MB-231 (breast carcinoma) cells (in FIGS. 23A-B or 23C-D, respectively) were treated with 10 ng/ml HGF for 10 min, in the presence or absence of various concentrations of Met variants. Lysates of treated cells were immunoblotted with an anti-pY1230/4/5 specific Ab. After stripping, the same membrane was immunoblotted with anti-Met Ab. Densitometry was carried out on the scanned autoradiograms and levels of phosphorylated Met were normalized to levels of Met expression. The level of pY1230/4/5 on Met upon HGF-induction was defined as 1.0. The histograms show the relative levels of Met phosphorylation following the various inhibitory treatments.

FIGS. 25A-25G present the influence of Met-variants on HGF-induced invasion of DA3 cells. FIGS. 25A and 25B show the plate layout and the scanned filter of a representative experiment. FIGS. 25C and 25D show the results of two separate experiments carried out with Met-877, at doses of 10-100 μg/ml.

FIGS. 25E-25G show results of three separate experiments carried out with different batches and various doses (10, 30 and 100 μg/ml) of Met variants, and respective Mock preparations. The following batches of Met-877 were used: 877Br2B-Fr2, 877Bt2, and 877Br4A. Other proteins tested were Met-877-Fc (SEQ ID NO:79), Met-934-Fc (SEQ ID NO:68) and Met-885-Fc (SEQ ID NO:77). Shown in each graph is the relative level of DA3 migration obtained in response to different doses of Met-variants or Mock preparations, where migration in response to 100 ng/ml HGF and absence of inhibitors is defined as 100%.

FIG. 26A shows the calibration of the assay with various doses of HGF. The Met variants were subsequently tested at an HGF concentration of 10 ng/ml. FIG. 26B shows the effect of Met-877-Fc (SEQ ID NO:79) on HGF-induced urokinase upregulation, indicating a strong inhibition at doses higher than 10 nM. FIG. 26C shows that similar results were obtained in a separate experiment, and also with Met-885-Fc (SEQ ID NO:77) and Met-934-Fc (SEQ ID NO:68). FIG. 26D indicates similar inhibitory activity among these variants.

FIG. 27A shows the effect of Met-877-Fc (SEQ ID NO: 79) on proliferation of H441 upon induction by 10 ng/ml HGF. FIGS. 27B and 27C depict more clearly the level of inhibition by Met-877-Fc (SEQ ID NO:79) and Met-885-Fc (SEQ ID NO:77), respectively. In these figures, the induction of proliferation by 10 ng/ml HGF is defined as 1.0, and shown are the levels of the inhibition of this induction exerted by various doses of Met-variants. FIG. 27D shows the effect of Met-877-Fc (SEQ ID NO:79) on the proliferation of AsPC-1 cells (as measured by BrdU incorporation), upon induction with various doses of HGF, while FIG. 27E indicates the levels of inhibition of the induction of proliferation when HGF was used at 10 ng/ml. FIG. 27F shows the results of a proliferation assay, similar to the one depicted in FIG. 27D, but measured by MTT.

DESCRIPTION OF THE PREFERRED EMBODIMENTS

The present invention provides hepatocyte growth factor receptor (MET_HUMAN) variants, which may optionally be used for therapeutic applications and/or as diagnostic markers.

Preferably, but without wishing to be limited, these therapeutic protein variants are inhibitory peptides antagonistic to the activity of Met receptor protein kinase and as such are useful as therapeutic proteins or peptides for diseases in which Met receptor protein kinase is involved either in the etiology or pathogenesis of the disease or disorder.

Figure 3:
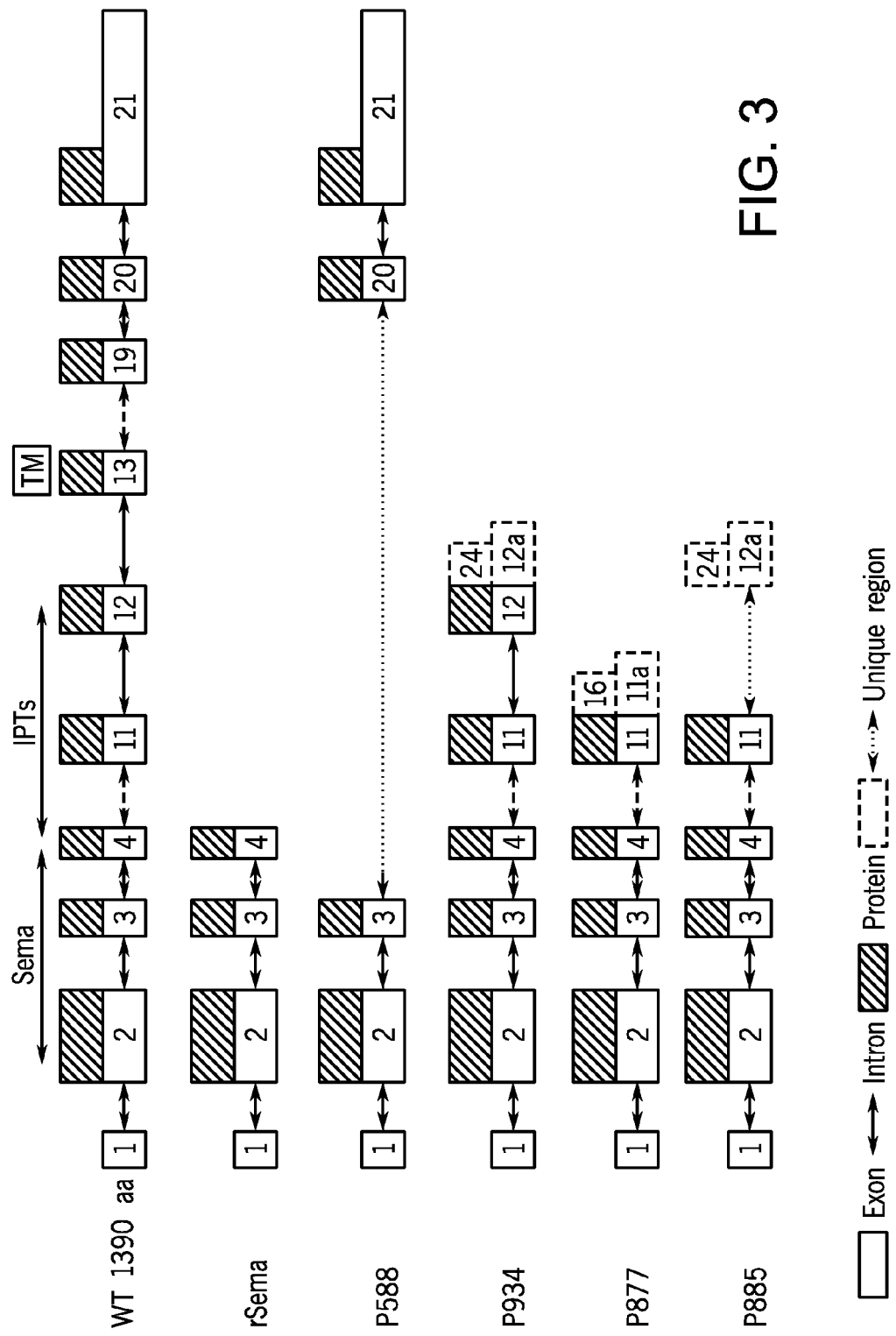
FIG. 3 shows schematic mRNA and protein structure of Met. "WT 1390aa" represents the known Met receptor protein kinase (SEQ ID NO:34). "rSEMA" represents the recombinant SEMA domain of the Met extracellular region (Kong-Beltran et al., 2004, Cancer Cell 6, 75-84), SEQ ID NO:39. "P588" represents the Met-588 variant of the present invention (SEQ ID NO:1 and 36, for mRNA and protein, respectively). "P934" represents the Met-934 variant previously disclosed in U.S. patent application Ser. No. 10/764,833 publication No. 2004/0248157 assigned to the applicant of the present invention (SEQ ID NO:2 and 38, for mRNA and protein, respectively). "P877" represents the Met-877 variant of the present invention (SEQ ID NO:3 and 37, for mRNA and protein, respectively). "P885" represents the Met-885 variant previously disclosed in WO 05/071059 and U.S. patent application Ser. No. 11/043,591 assigned to the applicant of the present invention (SEQ ID NO:48 and 66, for mRNA and protein, respectively). Exons are represented by white boxes, while introns are represented by two headed arrows. Dotted lines between exons mean that all exons between them are present with no changes. Proteins are shown in boxes with upper right to lower left fill. The unique regions are represented by white boxes with dashed frame. SEMA domain, transmembrane domain (TM), and immunoglobulin-plexin-transcription factor domain (IPT) are identified accordingly.

According to a currently preferred embodiment the Met variant of the invention, denoted Met-877 (SEQ ID NO:3) represents a splice variant that is encoded by exons 1-11 of the Met receptor protein kinase gene with the addition of unique nucleic acid sequence, as depicted in SEQ ID NO:82, referred as "exon 11a" in FIG. 3. It should be noted that inclusion of exon 11a encodes a polypeptide containing amino acids 1-861 of the wild type or native Met (SEQ ID NO:35) with 16 additional unique amino acids residues, as set fourth in SEQ ID NO:83, and the remainder of the polypeptide is terminated. This embodiment is represented herein by SEQ ID NO:37. Thus, the mature secretory variant Met-877 will have 877 amino acid residues in total, and is represented herein by SEQ ID NO:37.

According to another currently preferred embodiment the Met variant of the invention, denoted Met-588 (SEQ ID NO:1) represents a splice variant that is encoded by exons 1-3, 20 and 21 of the Met receptor protein kinase gene, generating a polypeptide containing amino acids 1-464 and 1267-1390 of the wild type or native Met (SEQ ID NO: 35) generating a unique junction between amino acid residues 464 and 1267. This embodiment is represented herein by SEQ ID NO:36. Thus, the mature secretory variant Met-588 will have 588 amino acid residues in total, and is represented herein by SEQ ID NO:36.

According to another currently preferred embodiment the Met variant of the invention, denoted Met-885 (SEQ ID NO:48) represents a splice variant that is encoded by exons 1-11 of the Met receptor protein kinase gene with the addition of unique nucleic acid sequence as set forth in SEQ ID NO:80, referred to as exon 12a in FIG. 3. It should be noted that inclusion of exon 12a encodes a polypeptide containing amino acids 1-861 of the wild type or native Met (SEQ ID NO:35) with 24 additional unique amino acids residues as set fourth in SEQ ID NO:81, and the remainder of the polypeptide is terminated. This embodiment is represented herein by SEQ ID NO:66. Thus, the mature secretory variant Met-885 will have 885 amino acid residues in total, and is represented herein by SEQ ID NO:66.

According to another aspect, the present invention provides an isolated nucleic acid molecule encoding for a splice variant according to the present invention, having a nucleotide sequence as set forth in any one of SEQ ID NOS: 1 and 3 (for Met588 and Met877, respectively); SEQ ID NOS: 67, 76, and 78 (for Met-934-Fc, Met885-Fc and Met 877-Fc, respectively); SEQ ID NOS: 74 and 46 (for Met885-tag and Met877-tag, respectively) or a sequence complementary thereto.

The variant polypeptides and polynucleotides encoding same are useful for the diagnosis and treatment of a wide range of Met-related diseases, in which Met activity and/or expression contribute to disease onset and/or progression, such that treating the disease may involve blocking Met activity and/or expression. Met-related diseases include, but are not limited to, all disorders or conditions that would benefit from treatment with a substance/molecule or method of the invention. These include chronic and acute disorders or diseases, including pathological conditions which predispose to the disorder in question. Non-limiting examples of the disorders to be treated herein include malignant and benign tumors; non-leukemias and lymphoid malignancies; neuronal, glial, astrocytal, hypothalamic and other glandular, macrophagal, epithelial, stromal and blastocoelic disorders; and angiogenesis-related disorders.

The term "Tumor", as used herein, refers to all neoplastic cell growth and proliferation, whether malignant or benign, and all pre-cancerous and cancerous cells and tissues. Examples of cancer include but are not limited to, carcinoma, lymphoma, leukemia, sarcoma and blastoma. While the terms "Tumor" or "Cancer" as used herein is not limited to any one specific form of the disease, it is believed that the methods will be particularly effective for cancers which are found to be accompanies by increased levels of HGF, or over expression or other activation of the Met receptor. Examples of such cancers include primary and metastatic cancer such as breast cancer, colon cancer, colorectal cancer, gastrointestinal tumors, esophageal cancer, cervical cancer, ovarian cancer, endometrial or uterine carcinoma, vulval cancer, liver cancer, hepatocellular cancer, bladder cancer, kidney cancer, hereditary and sporadic papillary renal cell carcinoma, pancreatic cancer, various types of head and neck cancer, lung cancer (e.g., non-small cell lung cancer, small cell lung cancer, squamous cell carcinoma, lung adenocarcinoma), prostate cancer, thyroid cancer, brain tumors, glioblastoma, glioma, malignant peripheral nerve sheath tumors, cancer of the peritoneum, cutaneous malignant melanoma, and salivary gland carcinoma.

Met-related diseases also consist of diseases in which anti-angiogenic activity plays a favorable role, including but not limited to, diseases having abnormal quality and/or quantity of vascularization as a characteristic feature. Dysregulation of angiogenesis can lead to many disorders that can be treated by compositions and methods of the invention. These disorders include both non-neoplastic and neoplastic conditions. Neoplastics include but are not limited to the type of primary and metastatic cancers described above. Non-neoplastic disorders include but are not limited to inflammatory and autoimmune disorders, such as aberrant hypertrophy, arthritis, psoriasis, sarcoidosis, scleroderma, sclerosis, atherosclerosis, synovitis, dermatitis, Crohn's disease, ulcerative colitis, inflammatory bowel disease, respiratory distress syndrome, uveitis, meningitis, encephalitis, Sjorgen's syndrome, systemic lupus erythematosus, diabetes mellitus, multiple sclerosis, juvenile onset diabetes; allergic conditions such as eczema and asthma; proliferative retinopathies, including but not limited to diabetic retinopathy, retinopathy of prematurity, retrolental fibroplasia, neovascular glaucoma, age-related macular degeneration, diabetic macular edema, cornal neovascularization, corneal graft neovascularization and/or rejection, ocular neovascular disease; and various other disorders in which anti-angiogenic activity plays a favorable role including but not limited to vascular restenosis, arteriovenous malformations, meningioma, hemangioma, angiofibroma, thyroid hyperplasia, hypercicatrization in wound healing, hyperthrophic scars.

The compositions and methods of the present invention can be further employed in combination with surgery or cytotoxic agents, or other anti-cancer agents, such as chemotherapy or radiotherapy and/or in combination with anti-angiogenesis drugs.

The present invention is of novel hepatocyte growth factor receptor (MET_HUMAN) variant polypeptides and polynucleotides encoding same, which can be used for the diagnosis of a wide range of diseases wherein Met receptor tyrosine kinase is involved in the etiology or pathogenesis of the disease process, and/or disease in which Met expression is altered as compared to the normal level, as will be explained in detail hereinbelow. Furthermore, the novel variants may be useful for diagnosis of any disease or condition where Met receptor tyrosine kinase is known to serve as a diagnostic or prognostic marker.

Examples of diseases where the novel variants may be useful for diagnosis, include, but are not limited to, regenerative processes such as wound healing and conditions, which require enhanced angiogenesis such as atherosclerotic diseases, ischemic conditions and diabetes, and diseases of the liver such as hepatic cirrhosis and hepatic dysfunction.

According to still other preferred embodiments, the present invention optionally and preferably encompasses any amino acid sequence or fragment thereof encoded by a nucleic acid sequence corresponding to a splice variant protein as described herein, including any oligopeptide or peptide relating to such an amino acid sequence or fragment, including but not limited to the unique amino acid sequences of these proteins that are depicted as tails, heads, insertions, edges or bridges. The present invention also optionally encompasses antibodies capable of recognizing, and/or being elicited by, such oligopeptides or peptides.

The present invention also optionally and preferably encompasses any nucleic acid sequence or fragment thereof, or amino acid sequence or fragment thereof, corresponding to a splice variant of the present invention as described above, optionally for any application.

In another embodiment, the present invention relates to bridges, tails, heads and/or insertions, and/or analogs, homologs and derivatives of such peptides. Such bridges, tails, heads and/or insertions are described in greater detail below with regard to the Examples.

As used herein a "tail" refers to a peptide sequence at the end of an amino acid sequence that is unique to a splice variant according to the present invention. Therefore, a splice variant having such a tail may optionally be considered as a chimera, in that at least a first portion of the splice variant is typically highly homologous (often 100% identical) to a portion of the corresponding known protein, while at least a second portion of the variant comprises the tail.

As used herein a "head" refers to a peptide sequence at the beginning of an amino acid sequence that is unique to a splice variant according to the present invention. Therefore, a splice variant having such a head may optionally be considered as a chimera, in that at least a first portion of the splice variant comprises the head, while at least a second portion is typically highly homologous (often 100% identical) to a portion of the corresponding known protein.

As used herein "an edge portion" refers to a connection between two portions of a splice variant according to the present invention that were not joined in the wild type or known protein. An edge may optionally arise due to a join between the above "known protein" portion of a variant and the tail, for example, and/or may occur if an internal portion of the wild type sequence is no longer present, such that two portions of the sequence are now contiguous in the splice variant that were not contiguous in the known protein. A "bridge" may optionally be an edge portion as described above, but may also include a join between a head and a "known protein" portion of a variant, or a join between a tail and a "known protein" portion of a variant, or a join between an insertion and a "known protein" portion of a variant.

As used herein the phrase "known protein" refers to a known database provided sequence of a specific protein, including, but not limited to, SwissProt, National Center of Biotechnology Information (NCBI), PIR, A Database of Human Unidentified Gene-Encoded Large Proteins, Nuclear Protein Database, human mitochondrial protein database, and University Protein Resource (UniProt).

In another embodiment, this invention provides antibodies specifically recognizing the splice variants and polypeptide fragments thereof of this invention. Preferably such antibodies differentially recognize splice variants of the present invention but do not recognize a corresponding known protein (such known proteins are discussed with regard to their splice variants in the Examples below).

In another embodiment, this invention provides an isolated nucleic acid molecule encoding for a splice variant according to the present invention, having a nucleotide sequence as set forth in any one of the sequences listed herein, or a sequence complementary thereto. In another embodiment, this invention provides an isolated nucleic acid molecule, having a nucleotide sequence as set forth in any one of the sequences listed herein, or a sequence complementary thereto. In another embodiment, this invention provides an oligonucleotide of at least about 12 nucleotides, specifically hybridizable with the nucleic acid molecules of this invention. In another embodiment, this invention provides vectors, cells, liposomes and compositions comprising the isolated nucleic acids of this invention.

Description of the Methodology Undertaken to Uncover the Biomolecular Sequences of the Present Invention Human ESTs and cDNAs were obtained from GenBank versions 145 (Dec. 23, 2004) and NCBI genome assembly of Aug. 26, 2005 (Build 35). Novel splice variants were predicted using the LEADS clustering and assembly system as described in U.S. Pat. No. 6,625,545, U.S. patent application Ser. No. 10/426,002, both of which are hereby incorporated by reference as if fully set forth herein. Briefly, the software cleans the expressed sequences from repeats, vectors and immunoglobulins. It then aligns the expressed sequences to the genome taking alternative splicing into account and clusters overlapping expressed sequences into "clusters" that represent genes or partial genes.

These were annotated using the GeneCarta (Compugen, Tel-Aviv, Israel) platform. The GeneCarta platform includes a rich pool of annotations, sequence information (particularly of spliced sequences), chromosomal information, alignments, and additional information such as SNPs, gene ontology terms, expression profiles, functional analyses, detailed domain structures, known and predicted proteins and detailed homology reports.

Brief description of the methodology used to obtain annotative sequence information is summarized infra (for detailed description see U.S. patent application Ser. No. 10/426,002, published as US20040101876).

The ontological annotation approach—An ontology refers to the body of knowledge in a specific knowledge domain or discipline such as molecular biology, microbiology, immunology, virology, plant sciences, pharmaceutical chemistry, medicine, neurology, endocrinology, genetics, ecology, genomics, proteomics, cheminformatics, pharmacogenomics, bioinformatics, computer sciences, statistics, mathematics, chemistry, physics and artificial intelligence.

An ontology includes domain-specific concepts—referred to, herein, as sub-ontologies. A sub-ontology may be classified into smaller and narrower categories. The ontological annotation approach is effected as follows.

First, biomolecular (i.e., polynucleotide or polypeptide) sequences are computationally clustered according to a progressive homology range, thereby generating a plurality of clusters each being of a predetermined homology of the homology range.

Progressive homology is used to identify meaningful homologies among biomolecular sequences and to thereby assign new ontological annotations to sequences, which share requisite levels of homologies. Essentially, a biomolecular sequence is assigned to a specific cluster if displays a predetermined homology to at least one member of the cluster (i.e., single linkage). A "progressive homology range" refers to a range of homology thresholds, which progress via predetermined increments from a low homology level (e.g. 35%) to a high homology level (e.g. 99%).

Following generation of clusters, one or more ontologies are assigned to each cluster. Ontologies are derived from an annotation preassociated with at least one biomolecular sequence of each cluster; and/or generated by analyzing (e.g., text-mining) at least one biomolecular sequence of each cluster thereby annotating biomolecular sequences.

The hierarchical annotation approach—"Hierarchical annotation" refers to any ontology and subontology, which can be hierarchically ordered, such as, a tissue expression hierarchy, a developmental expression hierarchy, a pathological expression hierarchy, a cellular expression hierarchy, an intracellular expression hierarchy, a taxonomical hierarchy, a functional hierarchy and so forth.

The hierarchical annotation approach is effected as follows. First, a dendrogram representing the hierarchy of interest is computationally constructed. A "dendrogram" refers to a branching diagram containing multiple nodes and representing a hierarchy of categories based on degree of similarity or number of shared characteristics.

Each of the multiple nodes of the dendrogram is annotated by at least one keyword describing the node, and enabling literature and database text mining, such as by using publicly available text mining software. A list of keywords can be obtained from the GO Consortium. However, measures are taken to include as many keywords, and to include keywords which might be out of date. For example, for tissue annotation, a hierarchy is built using all available tissue/libraries sources available in the GenBank, while considering the following parameters: ignoring GenBank synonyms, building anatomical hierarchies, enabling flexible distinction between tissue types (normal versus pathology) and tissue classification levels (organs, systems, cell types, etc.).

In a second step, each of the biomolecular sequences is assigned to at least one specific node of the dendrogram.

The biomolecular sequences can be annotated biomolecular sequences, unannotated biomolecular sequences or partially annotated biomolecular sequences.

Annotated biomolecular sequences can be retrieved from pre-existing annotated databases as described hereinabove.

For example, in GenBank, relevant annotational information is provided in the definition and keyword fields. In this case, classification of the annotated biomolecular sequences to the dendrogram nodes is directly effected. A search for suitable annotated biomolecular sequences is performed using a set of keywords which are designed to classify the biomolecular sequences to the hierarchy (i.e., same keywords that populate the dendrogram).

In cases where the biomolecular sequences are unannotated or partially annotated, extraction of additional annotational information is effected prior to classification to dendrogram nodes. This can be effected by sequence alignment, as described hereinabove. Alternatively, annotational information can be predicted from structural studies. Where needed, nucleic acid sequences can be transformed to amino acid sequences to thereby enable more accurate annotational prediction.

Finally, each of the assigned biomolecular sequences is recursively classified to nodes hierarchically higher than the specific nodes, such that the root node of the dendrogram encompasses the full biomolecular sequence set, which can be classified according to a certain hierarchy, while the offspring of any node represent a partitioning of the parent set.

For example, a biomolecular sequence found to be specifically expressed in "rhabdomyosarcoma", will be classified also to a higher hierarchy level, which is "sarcoma", and then to "Mesenchymal cell tumors" and finally to a highest hierarchy level "Tumor". In another example, a sequence found to be differentially expressed in endometrium cells, will be classified also to a higher hierarchy level, which is "uterus", and then to "women genital system" and to "genital system" and finally to a highest hierarchy level "genitourinary system". The retrieval can be performed according to each one of the requested levels.

Annotating gene expression according to relative abundance—Spatial and temporal gene annotations are also assigned by comparing relative abundance in libraries of different origins. This approach can be used to find genes, which are differentially expressed in tissues, pathologies and different developmental stages. In principal, the presentation of a contigue in at least two tissues of interest is determined and significant over or under representation of the contigue in one of the at least two tissues is assessed to identify differential expression. Significant over or under representation is analyzed by statistical pairing.

Annotating spatial and temporal expression can also be effected on splice variants. This is effected as follows. First, a contigue which includes exonal sequence presentation of the at least two splice variants of the gene of interest is obtained. This contigue is assembled from a plurality of expressed sequences. Then, at least one contigue sequence region, unique to a portion (i.e., at least one and not all) of the at least two splice variants of the gene of interest, is identified. Identification of such unique sequence region is effected using computer alignment software. Finally, the number of the plurality of expressed sequences in the tissue having the at least one contigue sequence region is compared with the number of the plurality of expressed sequences not-having the at least one contigue sequence region, to thereby compare the expression level of the at least two splice variants of the gene of interest in the tissue.

Data concerning therapies, indications and possible pharmacological activities of the polypeptides of the present invention was obtained from PharmaProject (PJB Publications Ltd) and public databases, including LocusLink and Swissprot. Functional structural analysis of the polypeptides of the present invention was effected using Interpro domain analysis software (Interpro default parameters, the analyses that were run are HMMPfam, HMMSmart, ProfileScan, FprintScan, and BlastProdom). Subcellular localization was analyzed using ProLoc software (Einat Hazkani-Covo, Erez Y. Levanon, Galit Rotman, Dan Graur, Amit Novik. Evolution of multicellularity in metazoa: comparative analysis of the subcellular localization of proteins in Saccharomyces, Drosophila and Caenorhabditis. Cell Biology International (2004; 28(3): 171-8).

Prediction of Cellular Localization

Information given in the text with regard to cellular localization was determined according to four different software programs: (i) tmhmm (from Center for Biological Sequence Analysis, Technical University of Denmark DTU) or (ii) tmpred (from EMBnet, maintained by the ISREC Bionformatics group and the LICR Information Technology Office, Ludwig Institute for Cancer Research, Swiss Institute of Bioinformatics) for transmembrane region prediction; (iii) signalp_hmm and (iv) signalp_nn (both from Center for Biological Sequence Analysis, Technical University of Denmark DTU) for signal peptide prediction. The terms "signalp_hmm" and "signalp_nn" refer to two modes of operation for the program SignalP: hmm refers to Hidden Markov Model, while nn refers to neural networks. Localization was also determined through manual inspection of known protein localization and/or gene structure, and the use of heuristics by the individual inventor. In some cases for the manual inspection of cellular localization prediction, inventors used the ProLoc computational platform [Einat Hazkani-Covo, Erez Levanon, Galit Rotman, Dan Graur and Amit Novik; (2004) Evolution of multicellularity in metazoa: comparative analysis of the subcellular localization of proteins in Saccharomyces, Drosophila and Caenorhabditis. Cell Biology International 2004; 28 (3): 171-8.], which predicts protein localization based on various parameters including, protein domains (e.g., prediction of trans-membranous regions and localization thereof within the protein), pI, protein length, amino acid composition, homology to pre-annotated proteins, recognition of sequence patterns which direct the protein to a certain organelle (such as, nuclear localization signal, NLS, mitochondria localization signal), signal peptide and anchor modeling and using unique domains from Pfam that are specific to a single compartment.

Single Nucleotide Polymorphisms

Information is given in the text with regard to SNPs (single nucleotide polymorphisms). A description of the abbreviations is as follows. "T->C", for example, means that the SNP results in a change at the position given in the table from T to C. Similarly, "M->Q", for example, means that the SNP has caused a change in the corresponding amino acid sequence, from methionine (M) to glutamine (Q). If, in place of a letter at the right hand side for the nucleotide sequence SNP, there is a space, it indicates that a frameshift has occurred. A frameshift may also be indicated with a hyphen (-). A stop codon is indicated with an asterisk at the right hand side (*). As part of the description of an SNP, a comment may be found in parentheses after the above description of the SNP itself. This comment may include an FTId, which is an identifier to a SwissProt entry that was created with the indicated SNP. An FTId is a unique and stable feature identifier, which allows construction of links directly from position-specific annotation in the feature table to specialized protein-related databases. The FTId is always the last component of a feature in the description field, as follows: FTId=XXX_number, in which XXX is the 3-letter code for the specific feature key, separated by an underscore from a 6-digit number. In the table of the amino acid mutations of the wild type proteins of the selected splice variants of the invention, the header of the first column is "SNP position(s) on amino acid sequence", representing a position of a known mutation on amino acid sequence. For each given SNP, it was determined whether it was previously known by using dbSNP build 122 from NCBI, released on Aug. 13, 2004.

Information given in the text with regard to the Homology to the wild type was determined by Smith-Waterman version 5.1.2

Using Special (non default) parameters as follows:

model=sw.model

GAPEXT=0

GAPOP=100.0

MATRIX=blosum100

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). All of these are hereby incorporated by reference as if fully set forth herein.

As used herein, the following terms have the meanings ascribed to them unless specified otherwise.

TERMS AND DEFINITIONS

As used herein the phrase "disease" includes any type of pathology and/or damage, including both chronic and acute damage, as well as a progress from acute to chronic damage.

The term "biologically active", as used herein, refers to a protein having structural, regulatory, or biochemical functions of a naturally occurring molecule. Likewise, "immunologically active" refers to the capability of the natural, recombinant, or synthetic ligand, or any oligopeptide thereof, to induce a specific immune response in appropriate animals or cells and to bind with specific antibodies.

The term "modulate", as used herein, refers to a change in the activity of at least one receptor-mediated activity. For example, modulation may cause an increase or a decrease in protein activity, binding characteristics, or any other biological, functional or immunological properties of a ligand.

Nucleic Acids

A "nucleic acid fragment" or an "oligonucleotide" or a "polynucleotide" are used herein interchangeably to refer to a polymer of nucleic acid residues. A polynucleotide sequence of the present invention refers to a single or double stranded nucleic acid sequences which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is composed of genomic and cDNA sequences. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

Thus, the present invention encompasses nucleic acid sequences described hereinabove; fragments thereof, sequences hybridizable therewith, sequences homologous thereto [e.g., at least 90%, at least 95% or more identical to the nucleic acid sequences set forth herein], sequences encoding similar polypeptides with different codon usage, altered sequences characterized by mutations, such as deletion, insertion or substitution of one or more nucleotides, either naturally occurring or man induced, either randomly or in a targeted fashion. The present invention also encompasses homologous nucleic acid sequences (i.e., which form a part of a polynucleotide sequence of the present invention), which include sequence regions unique to the polynucleotides of the present invention.

In cases where the polynucleotide sequences of the present invention encode previously unidentified polypeptides, the present invention also encompasses novel polypeptides or portions thereof, which are encoded by the isolated polynucleotide and respective nucleic acid fragments thereof described hereinabove.

Thus, the present invention also encompasses polypeptides encoded by the polynucleotide sequences of the present invention. The present invention also encompasses homologues of these polypeptides, such homologues can be at least 90%, at least 95% or more homologous to the amino acid sequences set forth below, as can be determined using BlastP software of the National Center of Biotechnology Information (NCBI) using default parameters. Finally, the present invention also encompasses fragments of the above described polypeptides and polypeptides having mutations, such as deletions, insertions or substitutions of one or more amino acids, either naturally occurring or man induced, either randomly or in a targeted fashion.

As mentioned hereinabove, biomolecular sequences uncovered using the methodology of the present invention can be efficiently utilized as tissue or pathological markers and as putative drugs or drug targets for treating or preventing a disease.

Oligonucleotides designed for carrying out the methods of the present invention for any of the sequences provided herein (designed as described above) can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art.

Oligonucleotides used according to this aspect of the present invention are those having a length selected from a range of about 10 to about 200 bases preferably about 15 to about 150 bases, more preferably about 20 to about 100 bases, most preferably about 20 to about 50 bases.

The oligonucleotides of the present invention may comprise heterocyclic nucleosides consisting of purines and the pyrimidines bases, bonded in a 3' to 5' phosphodiester linkage.

Preferable oligonucleotides are those modified in either backbone, internucleoside linkages or bases, as is broadly described hereinunder. Such modifications can oftentimes facilitate oligonucleotide uptake and resistivity to intracellular conditions.

Specific examples of preferred oligonucleotides useful according to this aspect of the present invention include oligonucleotides containing modified backbones or non-natural internucleoside linkages. Oligonucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other oligonucleotides which can be used according to the present invention, are those modified in both sugar and the internucleoside linkage, i.e., the backbone, of the nucleotide units are replaced with novel groups. The base units are maintained for complementation with the appropriate polynucleotide target. An example for such an oligonucleotide mimetic, includes peptide nucleic acid (PNA). A PNA oligonucleotide refers to an oligonucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present invention, are disclosed in U.S. Pat. No. 6,303,374.

Oligonucleotides of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science and Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Such bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi Y S et al. (1993) Antisense Research and Applications, CRC Press, Boca Raton 276-278] and are presently preferred base substitutions, even more particularly when combined with 2'-O-methoxyethyl sugar modifications.

Another modification of the oligonucleotides of the invention involves chemically linking to the oligonucleotide one or more moieties or conjugates, which enhance the activity, cellular distribution or cellular uptake of the oligonucleotide. Such moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety, as disclosed in U.S. Pat. No. 6,303,374.

It is not necessary for all positions in a given oligonucleotide molecule to be uniformly modified, and in fact more than one of the aforementioned modifications may be incorporated in a single compound or even at a single nucleoside within an oligonucleotide.

Antibodies:

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad-immunoglobulin variable region genes. Antibodies exist, e.g., as intact immunoglobulins or as a number of well characterized fragments produced by digestion with various peptidases. This includes, e.g., Fab' and F(ab)'2 fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, CH1, CH2 and CH3, but does not include the heavy chain variable region.

The functional fragments of antibodies, such as Fab, F(ab') 2, and Fv that are capable of binding to macrophages, are described as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')$_2$, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. (1959. Biochem. J. 73:119-126). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. (1972. Proc. Nat'l Acad. Sci. USA 69:2659-62). Alternatively, the variable chains can be linked by an inter-molecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula 1991. Methods 2:97-105; Bird et al., 1988. Science 242:423-426; Pack et al., 1993. Bio/Technology 11:1271-77; and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry (1991. Methods, 2:106-10).

Humanized forms of non-human (e.g., murine) antibodies are chimeric molecules of immunoglobulins, immunoglobulin chains or fragments thereof (such as Fv, Fab, Fab', F(ab') or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321: 522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., Bio/Technology 10:779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Monoclonal antibody development may optionally be performed according to any method that is known in the art. The methods described in WO 2005/072049 are expressly incorporated by reference as if fully set forth herein.

Oligonucleotides

Oligonucleotides according to the present invention may optionally be used as molecular probes as described herein. Such probes are useful for hybridization assays, and also for NAT assays (as primers, for example).

Thus, the present invention encompasses nucleic acid sequences described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

Typically, detection of a nucleic acid of interest in a biological sample is effected by hybridization-based assays using an oligonucleotide probe.

The term "oligonucleotide" refers to a single stranded or double stranded oligomer or polymer of ribonucleic acid (RNA) or deoxyribonucleic acid (DNA) or mimetics thereof. This term includes oligonucleotides composed of naturally-occurring bases, sugars and covalent internucleoside linkages (e.g., backbone) as well as oligonucleotides having non-naturally-occurring portions which function similarly to respective naturally-occurring portions. An example of an oligonucleotide probe which can be utilized by the present invention is a single stranded polynucleotide which includes a sequence complementary to the unique sequence region of any variant according to the present invention, including but not limited to a nucleotide sequence coding for an amino sequence of a bridge, tail, head and/or insertion according to the present invention, and/or the equivalent portions of any nucleotide sequence given herein (including but not limited to a nucleotide sequence of a node, segment or amplicon described herein).

Alternatively, an oligonucleotide probe of the present invention can be designed to hybridize with a nucleic acid sequence encompassed by any of the above nucleic acid sequences, particularly the portions specified above, including but not limited to a nucleotide sequence coding for an amino sequence of a bridge, tail, head and/or insertion according to the present invention, and/or the equivalent portions of any nucleotide sequence given herein (including but not limited to a nucleotide sequence of a node, segment or amplicon described herein).

Oligonucleotides designed according to the teachings of the present invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphoramidite followed by deprotection, desalting and purification by for example, an automated trityl-on method or HPLC.

Oligonucleotides of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Such bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi Y S et al. (1993) Antisense Research and Applications, CRC Press, Boca Raton 276-278] and are presently preferred base substitutions, even more particularly when combined with 2'-O-methoxyethyl sugar modifications.

It will be appreciated that oligonucleotides of the present invention may include further modifications which increase bioavailability, therapeutic efficacy and reduce cytotoxicity. Such modifications are described in Younes (2002) Current Pharmaceutical Design 8:1451-1466.

The isolated polynucleotides of the present invention can optionally be detected (and optionally quantified) by using hybridization assays. Thus, the isolated polynucleotides of the present invention are preferably hybridizable with any of the above described nucleic acid sequences under moderate to stringent hybridization conditions.

Moderate to stringent hybridization conditions are characterized by a hybridization solution such as containing 10% dextran sulfate, 1 M NaCl, 1% SDS and $5 \times 10^6$ cpm $^{32}$P labeled probe, at 65° C., with a final wash solution of 0.2× SSC and 0.1% SDS and final wash at 65° C. and whereas moderate hybridization is effected using a hybridization solution containing 10% dextran sulfate, 1 M NaCl, 1% SDS and $5 \times 10^6$ cpm $^{32}$P labeled probe, at 65° C., with a final wash solution of 1×SSC and 0.1% SDS and final wash at 50° C.

Hybridization based assays which allow the detection of the biomarkers of the present invention (i.e., DNA or RNA) in a biological sample rely on the use of oligonucleotides which can be 10, 15, 20, or 30 to 100 nucleotides long, preferably from 10 to 50, and more preferably from 40 to 50 nucleotides.

Hybridization of short nucleic acids (below 200 bp in length, e.g. 17-40 bp in length) can be effected using the following exemplary hybridization protocols which can be modified according to the desired stringency; (i) hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 1-1.5° C. below the $T_m$, final wash solution of 3 M TMACl, 0.01 M sodium phosphate (pH 6.8), 1 mM EDTA (pH 7.6), 0.5% SDS at 1-1.5° C. below the $T_m$; (ii) hybridization solution of 6×SSC and 0.1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 2-2.5° C. below the $T_m$, final wash solution of 3 M TMACl, 0.01 M sodium phosphate (pH 6.8), 1 mM EDTA (pH 7.6), 0.5% SDS at 1-1.5° C. below the $T_m$, final wash solution of 6×SSC, and final wash at 22° C.; (iii) hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature.

The detection of hybrid duplexes can be carried out by a number of methods. Typically, hybridization duplexes are separated from unhybridized nucleic acids and the labels bound to the duplexes are then detected. Such labels refer to radioactive, fluorescent, biological or enzymatic tags or labels of standard use in the art. A label can be conjugated to either the oligonucleotide probes or the nucleic acids derived from the biological sample (target).

For example, oligonucleotides of the present invention can be labeled subsequent to synthesis, by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent. Alternatively, when fluorescently-labeled oligonucleotide probes are used, fluorescein, lissamine, phycoerythrin, rhodamine (Perkin Elmer Cetus), Cy2, Cy3, Cy3.5, Cy5, Cy5.5, Cy7, FluorX (Amersham) and others [e.g., Kricka et al. (1992), Academic Press San Diego, Calif.] can be attached to the oligonucleotides.

Traditional hybridization assays include PCR, RT-PCR, Real-time PCR, RNase protection, in-situ hybridization, primer extension, Southern blots (DNA detection), dot or slot blots (DNA, RNA), and Northern blots (RNA detection) (NAT type assays are described in greater detail below). More recently, PNAs have been described (Nielsen et al. 1999, Current Opin. Biotechnol. 10:71-75). Other detection methods include kits containing probes on a dipstick setup and the like.

Although the present invention is not specifically dependent on the use of a label for the detection of a particular nucleic acid sequence, such a label might be beneficial, by increasing the sensitivity of the detection.

Furthermore, it enables automation. Probes can be labeled according to numerous well known methods (Sambrook et al., 1989, supra). Non-limiting examples of radioactive labels include 3H, 14C, 32P, and 35S. Non-limiting examples of detectable markers include ligands, fluorophores, chemiluminescent agents, enzymes, and antibodies. Other detectable markers for use with probes, which can enable an increase in sensitivity of the method of the invention, include biotin and radio-nucleotides. It will become evident to the person of ordinary skill that the choice of a particular label dictates the manner in which it is bound to the probe.

As commonly known, radioactive nucleotides can be incorporated into probes of the invention by several methods. Non-limiting examples thereof include kinasing the 5' ends of the probes using gamma ATP and polynucleotide kinase, using the Klenow fragment of Pol I of $E\ coli$ in the presence of radioactive dNTP (i.e. uniformly labeled DNA probe using random oligonucleotide primers in low-melt gels), using the SP6/T7 system to transcribe a DNA segment in the presence of one or more radioactive NTP, and the like.

Those skilled in the art will appreciate that wash steps may be employed to wash away excess target DNA or probe as well as unbound conjugate. Further, standard heterogeneous assay formats are suitable for detecting the hybrids using the labels present on the oligonucleotide primers and probes.

It will be appreciated that a variety of controls may be usefully employed to improve accuracy of hybridization assays. For instance, samples may be hybridized to an irrelevant probe and treated with RNAse A prior to hybridization, to assess false hybridization.

Probes of the invention can be utilized with naturally occurring sugar-phosphate backbones as well as modified backbones including phosphorothioates, dithionates, alkyl phosphonates and a-nucleotides and the like. Modified sugar-phosphate backbones are generally taught by Miller, 1988, Ann. Reports Med. Chem. 23:295 and Moran et al., 1987, Nucleic acid molecule. Acids Res., 14:5019. Probes of the invention can be constructed of either ribonucleic acid (RNA) or deoxyribonucleic acid (DNA), and preferably of DNA.

Detection (and optionally quantification) of a nucleic acid of interest in a biological sample may also optionally be effected by NAT-based assays, which involve nucleic acid amplification technology, such as PCR for example (or variations thereof such as real-time PCR for example).

Amplification of a selected, or target, nucleic acid sequence may be carried out by a number of suitable methods. See generally Kwoh et al., 1990, Am. Biotechnol. Lab. 8:14 Numerous amplification techniques have been described and can be readily adapted to suit particular needs of a person of ordinary skill. Non-limiting examples of amplification techniques include polymerase chain reaction (PCR), ligase chain reaction (LCR), strand displacement amplification (SDA), transcription-based amplification, the q3 replicase system and NASBA (Kwoh et al., 1989, Proc. Natl. Acad. Sci. USA 86, 1173-1177; Lizardi et al., 1988, BioTechnology 6:1197-1202; Malek et al., 1994, Methods Mol. Biol., 28:253-260; and Sambrook et al., 1989, supra).

Polymerase chain reaction (PCR) is carried out in accordance with known techniques, as described for example, in U.S. Pat. Nos. 4,683,195; 47683,202; 4,800,159; and 4,965,188 (the disclosures of all three U.S. patents are incorporated herein by reference). In general, PCR involves a treatment of a nucleic acid sample (e.g., in the presence of a heat stable DNA polymerase) under hybridizing conditions, with one oligonucleotide primer for each strand of the specific sequence to be detected. An extension product of each primer, which is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample is analyzed to assess whether the sequence or sequences to be detected are present. Detection of the amplified sequence may be carried out by visualization following EtBr staining of the DNA following gel electrophoresis, or using a detectable label in accordance with known techniques, and the like. For a review of PCR techniques, see PCR Protocols, A Guide to Methods and Amplifications, Michael et al. Eds, Acad. Press, 1990.

As used herein, a "primer" defines an oligonucleotide which is capable of annealing to a target sequence, thereby creating a double stranded region which can serve as an initiation point for DNA synthesis under suitable conditions.

Ligase chain reaction (LCR) is carried out in accordance with known techniques (Weiss, 1991, Science 254:1292). Adaptation of the protocol to meet the desired needs can be carried out by a person of ordinary skill. Strand displacement amplification (SDA) is also carried out in accordance with known techniques or adaptations thereof to meet the 15 particular needs (Walker et al., 1992, Proc. Natl. Acad. Sci. USA 89:392-396; and ibid., 1992, Nucleic Acids Res. 20:1691-1696).

The terminology "amplification pair" refers herein to a pair of oligonucleotides (oligos) of the present invention, which are selected to be used together in amplifying a selected nucleic acid sequence by one of a number of types of amplification processes, preferably a polymerase chain reaction. Other types of amplification processes include ligase chain reaction, strand displacement amplification, or nucleic acid sequence-based amplification, as explained in greater detail below. As commonly known in the art, the oligos are designed to bind to a complementary sequence under selected conditions.

In one particular embodiment, amplification of a nucleic acid sample from a patient is amplified under conditions which favor the amplification of the most abundant differentially expressed nucleic acid. In one preferred embodiment, RT-PCR is carried out on an mRNA sample from a patient under conditions which favor the amplification of the most abundant mRNA. In another preferred embodiment, the amplification of the differentially expressed nucleic acids is carried out simultaneously. Of course, it will be realized by a person skilled in the art that such methods could be adapted for the detection of differentially expressed proteins instead of differentially expressed nucleic acid sequences.

The nucleic acid (i.e. DNA or RNA) for practicing the present invention may be obtained according to well known methods.

Oligonucleotide primers of the present invention may be of any suitable length, depending on the particular assay format and the particular needs and targeted genomes employed. In general, the oligonucleotide primers are at least 12 nucleotides in length, preferably between 15 and 24 molecules, and they may be adapted to be especially suited to a chosen nucleic acid amplification system. As commonly known in the art, the oligonucleotide primers can be designed by taking into consideration the melting point of hybridization thereof with its targeted sequence (see below and in Sambrook et al., 1989, Molecular Cloning—A Laboratory Manual, 2nd Edition, CSH Laboratories; Ausubel et al., 1989, in Current Protocols in Molecular Biology, John Wiley & Sons Inc., N.Y.).

It will be appreciated that antisense oligonucleotides may be employed to quantify expression of a splice isoform of interest. Such detection is effected at the pre-mRNA level. Essentially the ability to quantitate transcription from a splice site of interest can be effected based on splice site accessibility. Oligonucleotides may compete with splicing factors for the splice site sequences. Thus, low activity of the antisense oligonucleotide is indicative of splicing activity [see Sazani and Kole (2003), supra].

Polymerase chain reaction (PCR)-based methods may be used to identify the presence of mRNA of the markers of the present invention. For PCR-based methods a pair of oligonucleotides is used, which is specifically hybridizable with the polynucleotide sequences described hereinabove in an opposite orientation so as to direct exponential amplification of a portion thereof (including the hereinabove described sequence alteration) in a nucleic acid amplification reaction. For example, oligonucleotide pairs of primers specifically hybridizable with nucleic acid sequences according to the present invention are described in greater detail with regard to the Examples below.

The polymerase chain reaction and other nucleic acid amplification reactions are well known in the art (various non-limiting examples of these reactions are described in greater detail below). The pair of oligonucleotides according to this aspect of the present invention are preferably selected to have compatible melting temperatures (Tm), e.g., melting temperatures which differ by less than that 7° C., preferably less than 5° C., more preferably less than 4° C., most preferably less than 3° C., ideally between 3° C. and 0° C.

Hybridization to oligonucleotide arrays may be also used to determine expression of the biomarkers of the present invention (hybridization itself is described above). Such screening has been undertaken in the BRCA1 gene and in the protease gene of HIV-1 virus [see Hacia et al., (1996) Nat Genet. 1996; 14(4):441-447; Shoemaker et al., (1996) Nat Genet. 1996; 14(4):450-456; Kozal et al., (1996) Nat Med 1996; 2(7):753-759]. Optionally and preferably, such hybridization is combined with amplification as described herein.

The nucleic acid sample which includes the candidate region to be analyzed is preferably isolated, amplified and labeled with a reporter group. This reporter group can be a fluorescent group such as phycoerythrin. The labeled nucleic acid is then incubated with the probes immobilized on the chip using a fluidics station. For example, Manz et al. (1993) Adv in Chromatogr. 1993; 33:1-66 describe the fabrication of fluidics devices and particularly microcapillary devices, in silicon and glass substrates.

Once the reaction is completed, the chip is inserted into a scanner and patterns of hybridization are detected. The hybridization data is collected, as a signal emitted from the reporter groups already incorporated into the nucleic acid, which is now bound to the probes attached to the chip. Since the sequence and position of each probe immobilized on the chip is known, the identity of the nucleic acid hybridized to a given probe can be determined.

It will be appreciated that when utilized along with automated equipment, the above described detection methods can be used to screen multiple samples for ferretin light chain variant detectable disease both rapidly and easily.

According to various preferred embodiments of the methods of the present invention, determining the presence and/or level of any specific nucleic or amino acid in a biological sample obtained from, for example, a patient is effected by any one of a variety of methods including, but not limited to, a signal amplification method, a direct detection method and detection of at least one sequence change.

The signal amplification methods according to various preferred embodiments of the present invention may amplify, for example, a DNA molecule or an RNA molecule. Signal amplification methods which might be used as part of the present invention include, but are not limited to PCR, LCR (LAR), Self-Sustained Synthetic Reaction (3SR/NASBA) or a Q-Beta (Qβ) Replicase reaction.

Peptides

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

Polypeptide products can be biochemically synthesized such as by employing standard solid phase techniques. Such methods include exclusive solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry.

Solid phase polypeptide synthesis procedures are well known in the art and further described by John Morrow Stewart and Janis Dillaha Young, Solid Phase Peptide Syntheses (2nd Ed., Pierce Chemical Company, 1984).

Synthetic polypeptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of a polypeptide are desired, it can be generated using recombinant techniques such as described by Bitter et al., (1987) Methods in Enzymol. 153: 516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

It will be appreciated that peptides identified according to the teachings of the present invention may be degradation products, synthetic peptides or recombinant peptides as well as peptidomimetics, typically, synthetic peptides and peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C.A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted by synthetic non-natural acid such as Phenylglycine, TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Since the peptides of the present invention are preferably utilized in therapeutics which require the peptides to be in soluble form, the peptides of the present invention preferably include one or more non-natural or natural polar amino acids, including but not limited to serine and threonine which are capable of increasing peptide solubility due to their hydroxyl-containing side chain.

The peptides of the present invention are preferably utilized in a linear form, although it will be appreciated that in cases where cyclization does not severely interfere with peptide characteristics, cyclic forms of the peptide can also be utilized.

The peptides of the present invention can be biochemically synthesized such as by using standard solid phase techniques. These methods include exclusive solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry.

Solid phase peptide synthesis procedures are well known in the art and further described by John Morrow Stewart and Janis Dillaha Young, Solid Phase Peptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of the peptides of the present invention are desired, the peptides of the present invention can be generated using recombinant techniques such as described by Bitter et al., (1987) Methods in Enzymol. 153: 516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

Expression Systems

To enable cellular expression of the polynucleotides of the present invention, a nucleic acid construct according to the present invention may be used, which includes at least a coding region of one of the above nucleic acid sequences, and further includes at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Any suitable promoter sequence can be used by the nucleic acid construct of the present invention.

Preferably, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166). The nucleic acid construct of the present invention can further include an enhancer, which can be adjacent or distant to the promoter sequence and can function in up regulating the transcription therefrom.

The nucleic acid construct of the present invention preferably further includes an appropriate selectable marker and/or an origin of replication. Preferably, the nucleic acid construct utilized is a shuttle vector, which can propagate both in E. coli (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (www.invitrogen.com). Examples of retroviral vector and packaging systems are those sold by Clontech, San Diego, Calif., including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5'LTR promoter.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element (s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of the present invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Variant Recombinant Expression Vectors and Host Cells

Another aspect of the invention pertains to vectors, preferably expression vectors, containing a nucleic acid encoding a variant protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., variant proteins, mutant forms of variant proteins, fusion proteins, etc.).

The recombinant expression vectors of the invention can be designed for production of variant proteins in prokaryotic or eukaryotic cells. For example, variant proteins can be expressed in bacterial cells such as *Escherichia coli*, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, to the amino or C terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, PreScission, TEV and enterokinase. Typical fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET 11d (Studier et al., Gene Expression Technology: Methods in Enzymology 185, Academic Press, San Diego, Calif. (1990) 60-89)—not accurate, pET11a-d have N terminal T7 tag.

One strategy to maximize recombinant protein expression in *E. coli* is to express the protein in a host bacterium with an impaired capacity to proteolytically cleave the recombinant protein. See, e.g., Gottesman, Gene Expression Technology:

Methods in Enzymology 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (see, e.g., Wada, et al., 1992. Nucl. Acids Res. 20: 2111-2118). Such alteration of nucleic acid sequences of the invention can be carried out by standard DNA synthesis techniques. Another strategy to solve codon bias is by using BL21-codon plus bacterial strains (Invitrogen) or Rosetta bacterial strain (Novagen), these strains contain extra copies of rare *E. coli* tRNA genes.

In another embodiment, the expression vector encoding for the variant protein is a yeast expression vector. Examples of vectors for expression in yeast *Saccharomyces cerivisae* include pYepSec1 (Baldari, et al., 1987. EMBO J. 6: 229-234), pMFa (Kurjan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.).

Alternatively, variant protein can be produced in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In yet another embodiment, a nucleic acid of the invention is expressed in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195), pIRESpuro (Clontech), pUB6 (Invitrogen), pCEP4 (Invitrogen) pREP4 (Invitrogen), pcDNA3 (Invitrogen). When used in mammalian cells, the expression vector's control functions are often provided by viral regulatory elements. For example, commonly used promoters are derived from polyoma, adenovirus 2, cytomegalovirus, Rous Sarcoma Virus, and simian virus 40. For other suitable expression systems for both prokaryotic and eukaryotic cells see, e.g., Chapters 16 and 17 of Sambrook, et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banerji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the alpha-fetoprotein promoter (Campes and Tilghman, 1989. Genes Dev. 3: 537-546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to mRNA encoding for variant protein. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," Reviews-Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, variant protein can be produced in bacterial cells such as *E. coli*, insect cells, yeast, plant or mammalian cells (such as Chinese hamster ovary cells (CHO) or COS or 293 cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin, puromycin, blasticidin and methotrexate. Nucleic acids encoding a selectable marker can be introduced into a host cell on the same vector as that encoding variant protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express)

variant protein. Accordingly, the invention further provides methods for producing variant protein using the host cells of the invention. In one embodiment, the method comprises culturing the host cell of the present invention (into which a recombinant expression vector encoding variant protein has been introduced) in a suitable medium such that variant protein is produced. In another embodiment, the method further comprises isolating variant protein from the medium or the host cell.

For efficient production of the protein, it is preferable to place the nucleotide sequences encoding the variant protein under the control of expression control sequences optimized for expression in a desired host. For example, the sequences may include optimized transcriptional and/or translational regulatory sequences (such as altered Kozak sequences).

Protein Modifications

Fusion Proteins

A fusion protein may be prepared from a variant protein according to the present invention by fusion with a portion of an immunoglobulin comprising a constant region of an immunoglobulin. More preferably, the portion of the immunoglobulin comprises a heavy chain constant region which is optionally and more preferably a human heavy chain constant region. The heavy chain constant region is most preferably an IgG heavy chain constant region, and optionally and most preferably is an Fc chain, most preferably an IgG Fc fragment that comprises CH2 and CH3 domains. Although any IgG subtype may optionally be used, the IgG1 subtype is preferred. The Fc chain may optionally be a known or "wild type" Fc chain, or alternatively may be mutated. Non-limiting, illustrative, exemplary types of mutations are described in US Patent Application No. 20060034852, published on Feb. 16, 2006, hereby incorporated by reference as if fully set forth herein. The term "Fc chain" also optionally comprises any type of Fc fragment.

One reason for adding the Fc fragment is to increase the in vivo half-life of the therapeutic protein.

Several of the specific amino acid residues that are important for antibody constant region-mediated activity in the IgG subclass have been identified. Inclusion, substitution or exclusion of these specific amino acids therefore allows for inclusion or exclusion of specific immunoglobulin constant region-mediated activity. Furthermore, specific changes may result in aglycosylation for example and/or other desired changes to the Fc chain. At least some changes may optionally be made to block a function of Fc which is considered to be undesirable, such as an undesirable immune system effect, as described in greater detail below.

Non-limiting, illustrative examples of mutations to Fc which may be made to modulate the activity of the fusion protein include the following changes (given with regard to the Fc sequence nomenclature as given by Kabat, from Kabat E A et al: Sequences of Proteins of Immunological Interest. US Department of Health and Human Services, NIH, 1991): 220C->S; 233-238 ELLGGP->EAEGAP; 265D->A, preferably in combination with 434N->A; 297N->A (for example to block N-glycosylation); 318-322 EYKCK->AYACA; 330-331AP->SS; or a combination thereof (see for example M. Clark, "Chemical Immunol and Antibody Engineering", pp 1-31 for a description of these mutations and their effect). The construct for the Fc chain which features the above changes optionally and preferably comprises a combination of the hinge region with the CH2 and CH3 domains.

The above mutations may optionally be implemented to enhance desired properties or alternatively to block non-desired properties. For example, aglycosylation of antibodies was shown to maintain the desired binding functionality while blocking depletion of T-cells or triggering cytokine release, which may optionally be undesired functions (see M. Clark, "Chemical Immunol and Antibody Engineering", pp 1-31). Substitution of 331 proline for serine may block the ability to activate complement, which may optionally be considered an undesired function (see M. Clark, "Chemical Immunol and Antibody Engineering", pp 1-31). Changing 330 alanine to serine in combination with this change may also enhance the desired effect of blocking the ability to activate complement.

Residues 235 and 237 were shown to be involved in antibody-dependent cell-mediated cytotoxicity (ADCC), such that changing the block of residues from 233-238 as described may also block such activity if ADCC is considered to be an undesirable function.

Residue 220 is normally a cysteine for Fc from IgG1, which is the site at which the heavy chain forms a covalent linkage with the light chain. Optionally, this residue may be changed to a serine, to avoid any type of covalent linkage (see M. Clark, "Chemical Immunol and Antibody Engineering", pp 1-31).

The above changes to residues 265 and 434 may optionally be implemented to reduce or block binding to the Fc receptor, which may optionally block undesired functionality of Fc related to its immune system functions (see "Binding site on Human IgG1 for Fc Receptors", Shields et al, vol 276, pp 6591-6604, 2001).

The above changes are intended as illustrations only of optional changes and are not meant to be limiting in any way. Furthermore, the above explanation is provided for descriptive purposes only, without wishing to be bound by a single hypothesis.

Addition of Groups

If a variant according to the present invention is a linear molecule, it is possible to place various functional groups at various points on the linear molecule which are susceptible to or suitable for chemical modification. Functional groups can be added to the termini of linear forms of the variant. In some embodiments, the functional groups improve the activity of the variant with regard to one or more characteristics, including but not limited to, improvement in stability, penetration (through cellular membranes and/or tissue barriers), tissue localization, efficacy, decreased clearance, decreased toxicity, improved selectivity, improved resistance to expulsion by cellular pumps, and the like. For convenience sake and without wishing to be limiting, the free N-terminus of one of the sequences contained in the compositions of the invention will be termed as the N-terminus of the composition, and the free C-terminal of the sequence will be considered as the C-terminus of the composition. Either the C-terminus or the N-terminus of the sequences, or both, can be linked to a carboxylic acid functional groups or an amine functional group, respectively.

Non-limiting examples of suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the active ingredient attached thereto into a cell, for example, by reducing the hydrophilicity and increasing the lipophilicity of the active ingredient, these being an example for "a moiety for transport across cellular membranes".

These moieties can optionally and preferably be cleaved in vivo, either by hydrolysis or enzymatically, inside the cell. (Ditter et al., J. Pharm. Sci. 57:783 (1968); Ditter et al., J.

Pharm. Sci. 57:828 (1968); Ditter et al., J. Pharm. Sci. 58:557 (1969); King et al., Biochemistry 26:2294 (1987); Lindberg et al., Drug Metabolism and Disposition 17:311 (1989); and Tunek et al., Biochem. Pharm. 37:3867 (1988), Anderson et al., Arch. Biochem. Biophys. 239:538 (1985) and Singhal et al., FASEB J. 1:220 (1987)). Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a composition of the present invention is protected, preferably with a methyl, ethyl, benzyl or substituted benzyl ester, more preferably as a benzyl ester.

Non-limiting, illustrative examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include but are not limited to acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—, Adamantan, naphthalen, myristoleyl, toluen, biphenyl, cinnamoyl, nitrobenzoy, toluoyl, furoyl, benzoyl, cyclohexane, norbornane, or Z-caproic. In order to facilitate the N-acylation, one to four glycine residues can be present in the N-terminus of the molecule.

The carboxyl group at the C-terminus of the compound can be protected, for example, by a group including but not limited to an amide (i.e., the hydroxyl group at the C-terminus is replaced with —$NH_2$, —$NHR_2$ and —$NR_2R_3$) or ester (i.e. the hydroxyl group at the C-terminus is replaced with —$OR_2$). $R_2$ and $R_3$ are optionally independently an aliphatic, substituted aliphatic, benzyl, substituted benzyl, aryl or a substituted aryl group. In addition, taken together with the nitrogen atom, $R_2$ and $R_3$ can optionally form a C4 to C8 heterocyclic ring with from about 0-2 additional heteroatoms such as nitrogen, oxygen or sulfur. Non-limiting suitable examples of suitable heterocyclic rings include piperidinyl, pyrrolidinyl, morpholino, thiomorpholino or piperazinyl. Examples of C-terminal protecting groups include but are not limited to —$NH_2$, —$NHCH_3$, —$N(CH_3)_2$, —NH(ethyl), —N(ethyl)$_2$, —N(methyl) (ethyl), —NH(benzyl), —N(C1-C4 alkyl)(benzyl), —NH(phenyl), —N(C1-C4 alkyl)(phenyl), —$OCH_3$, —O-(ethyl), —O-(n-propyl), —O-(n-butyl), —O-(iso-propyl), —O-(sec-butyl), —O-(t-butyl), —O-benzyl and —O-phenyl.

Substitution by Peptidomimetic Moieties

A "peptidomimetic organic moiety" can optionally be substituted for amino acid residues in the composition of this invention both as conservative and as non-conservative substitutions. These moieties are also termed "non-natural amino acids" and may optionally replace amino acid residues, amino acids or act as spacer groups within the peptides in lieu of deleted amino acids. The peptidomimetic organic moieties optionally and preferably have steric, electronic or configurational properties similar to the replaced amino acid and such peptidomimetics are used to replace amino acids in the essential positions, and are considered conservative substitutions. However such similarities are not necessarily required. According to preferred embodiments of the present invention, one or more peptidomimetics are selected such that the composition at least substantially retains its physiological activity as compared to the native variant protein according to the present invention.

Peptidomimetics may optionally be used to inhibit degradation of the peptides by enzymatic or other degradative processes. The peptidomimetics can optionally and preferably be produced by organic synthetic techniques. Non-limiting examples of suitable peptidomimetics include D amino acids of the corresponding L amino acids, tetrazol (Zabrocki et al., J. Am. Chem. Soc. 110:5875-5880 (1988)); isosteres of amide bonds (Jones et al., Tetrahedron Lett. 29:3853-3856 (1988)); LL-3-amino-2-propenidone-6-carboxylic acid (LL-Acp) (Kemp et al., J. Org. Chem. 50:5834-5838 (1985)). Similar analogs are shown in Kemp et al., Tetrahedron Lett. 29:5081-5082 (1988) as well as Kemp et al., Tetrahedron Lett. 29:5057-5060 (1988), Kemp et al., Tetrahedron Lett. 29:4935-4938 (1988) and Kemp et al., J. Org. Chem. 54:109-115 (1987). Other suitable but exemplary peptidomimetics are shown in Nagai and Sato, Tetrahedron Lett. 26:647-650 (1985); Di Maio et al., J. Chem. Soc. Perkin Trans., 1687 (1985); Kahn et al., Tetrahedron Lett. 30:2317 (1989); Olson et al., J. Am. Chem. Soc. 112:323-333 (1990); Garvey et al., J. Org. Chem. 56:436 (1990). Further suitable exemplary peptidomimetics include hydroxy-1,2,3,4-tetrahydroisoquinoline-3-carboxylate (Miyake et al., J. Takeda Res. Labs 43:53-76 (1989)); 1,2,3,4-tetrahydro-isoquinoline-3-carboxylate (Kazmierski et al., J. Am. Chem. Soc. 133:2275-2283 (1991)); histidine isoquinolone carboxylic acid (HIC) (Zechel et al., Int. J. Pep. Protein Res. 43 (1991)); (2S,3S)-methyl-phenylalanine, (2S,3R)-methyl-phenylalanine, (2R,3S)-methyl-phenylalanine and (2R,3R)-methyl-phenylalanine (Kazmierski and Hruby, Tetrahedron Lett. (1991)).

Exemplary, illustrative but non-limiting non-natural amino acids include beta-amino acids (beta3 and beta2), homo-amino acids, cyclic amino acids, aromatic amino acids, Pro and Pyr derivatives, 3-substituted Alanine derivatives, Glycine derivatives, ring-substituted Phe and Tyr Derivatives, linear core amino acids or diamino acids. They are available from a variety of suppliers, such as Sigma-Aldrich (USA) for example.

Chemical Modifications

In the present invention any part of a variant protein may optionally be chemically modified, i.e. changed by addition of functional groups. For example the side amino acid residues appearing in the native sequence may optionally be modified, although as described below alternatively other part(s) of the protein may optionally be modified, in addition to or in place of the side amino acid residues. The modification may optionally be performed during synthesis of the molecule if a chemical synthetic process is followed, for example by adding a chemically modified amino acid. However, chemical modification of an amino acid when it is already present in the molecule ("in situ" modification) is also possible.

The amino acid of any of the sequence regions of the molecule can optionally be modified according to any one of the following exemplary types of modification (in the peptide conceptually viewed as "chemically modified"). Non-limiting exemplary types of modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxyl groups to an amino group on a sugar (Garg and Jeanloz, Advances in Carbohydrate Chemistry and Biochemistry, Vol. 43, Academic Press (1985); Kunz, Ang. Chem. Int. Ed. English 26:294-308 (1987)). Acetal and ketal bonds can also optionally be formed between amino acids and carbohydrates. Fatty acid acyl derivatives can optionally be made, for example, by acylation of a free amino group (e.g., lysine) (Toth et al., Peptides: Chemistry, Structure and Biology, Rivier and Marshal, eds., ESCOM Publ., Leiden, 1078-1079 (1990)).

As used herein the term "chemical modification", when referring to a protein or peptide according to the present invention, refers to a protein or peptide where at least one of its amino acid residues is modified either by natural processes, such as processing or other post-translational modifications, or by chemical modification techniques which are well known in the art. Examples of the numerous known modifications typically include, but are not limited to: acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process.

Other types of modifications optionally include the addition of a cycloalkane moiety to a biological molecule, such as a protein, as described in PCT Application No. WO 2006/050262, hereby incorporated by reference as if fully set forth herein. These moieties are designed for use with biomolecules and may optionally be used to impart various properties to proteins.

Furthermore, optionally any point on a protein may be modified. For example, pegylation of a glycosylation moiety on a protein may optionally be performed, as described in PCT Application No. WO 2006/050247, hereby incorporated by reference as if fully set forth herein. One or more polyethylene glycol (PEG) groups may optionally be added to O-linked and/or N-linked glycosylation. The PEG group may optionally be branched or linear. Optionally any type of water-soluble polymer may be attached to a glycosylation site on a protein through a glycosyl linker.

Altered Glycosylation

Variant proteins of the invention may be modified to have an altered glycosylation pattern (i.e., altered from the original or native glycosylation pattern). As used herein, "altered" means having one or more carbohydrate moieties deleted, and/or having at least one glycosylation site added to the original protein.

Glycosylation of proteins is typically either N-linked or O-linked. N-linked refers to the attachment of the carbohydrate moiety to the side chain of an asparagine residue. The tripeptide sequences, asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to variant proteins of the invention is conveniently accomplished by altering the amino acid sequence of the protein such that it contains one or more of the above-described tripeptide sequences (for N-linked glycosylation sites). The alteration may also be made by the addition of, or substitution by, one or more serine or threonine residues in the sequence of the original protein (for O-linked glycosylation sites). The protein's amino acid sequence may also be altered by introducing changes at the DNA level.

Another means of increasing the number of carbohydrate moieties on proteins is by chemical or enzymatic coupling of glycosides to the amino acid residues of the protein. Depending on the coupling mode used, the sugars may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston, CRC Crit. Rev. Biochem., 22: 259-306 (1981).

Removal of any carbohydrate moieties present on variant proteins of the invention may be accomplished chemically or enzymatically. Chemical deglycosylation requires exposure of the protein to trifluoromethanesulfonic acid, or an equivalent compound. This treatment results in the cleavage of most or all sugars except the linking sugar (N-acetylglucosamine or N-acetylgalactosamine), leaving the amino acid sequence intact. Chemical deglycosylation is described by Hakimuddin et al., Arch. Biochem. Biophys., 259: 52 (1987); and Edge et al., Anal. Biochem., 118: 131 (1981). Enzymatic cleavage of carbohydrate moieties on proteins can be achieved by the use of a variety of endo- and exo-glycosidases as described by Thotakura et al., Meth. Enzymol., 138: 350 (1987).

Methods of Treatment

As mentioned hereinabove the novel therapeutic protein variants of the present invention and compositions derived therefrom (i.e., peptides, oligonucleotides) can be used to treat cluster, variant or protein-related diseases, disorders or conditions.

Thus, according to an additional aspect of the present invention there is provided a method of treating cluster, variant or protein-related disease, disorder or condition in a subject.

The subject according to the present invention is a mammal, preferably a human which is diagnosed with one of the disease, disorder or conditions described hereinabove, or alternatively is predisposed to at least one type of the cluster, variant or protein-related disease, disorder or conditions described hereinabove.

As used herein the term "treating" refers to preventing, curing, reversing, attenuating, alleviating, minimizing, suppressing or halting the deleterious effects of the above-described diseases, disorders or conditions.

Treating, according to the present invention, can be effected by specifically upregulating the expression of at least one of the polypeptides of the present invention in the subject.

Optionally, upregulation may be effected by administering to the subject at least one of the polypeptides of the present invention (e.g., recombinant or synthetic) or an active portion thereof, as described herein. However, since the bioavailability of large polypeptides may potentially be relatively small due to high degradation rate and low penetration rate, administration of polypeptides is optionally confined to small peptide fragments (e.g., about 100 amino acids). The polypeptide or peptide may optionally be administered in as part of a pharmaceutical composition, described in more detail below.

It will be appreciated that treatment of the above-described diseases according to the present invention may be combined with other treatment methods known in the art (i.e., combination therapy). Thus, treatment of malignancies using the agents of the present invention may be combined with, for example, radiation therapy, antibody therapy and/or chemotherapy.

Alternatively or additionally, an upregulating method may optionally be effected by specifically upregulating the amount (optionally expression) in the subject of at least one of the polypeptides of the present invention or active portions thereof.

As is mentioned hereinabove and in the Examples section which follows, the biomolecular sequences of this aspect of the present invention may be used as valuable therapeutic tools in the treatment of diseases, disorders or conditions in which altered activity or expression of the wild-type gene product (known protein) is known to contribute to disease, disorder or condition onset or progression. For example, in case a disease is caused by overexpression of a membrane bound-receptor, a soluble variant thereof may be used as an antagonist which competes with the receptor for binding the ligand, to thereby terminate signaling from the receptor. Examples of such diseases are listed in the Examples section which follows.

Pharmaceutical Compositions and Delivery Thereof

The present invention features a pharmaceutical composition comprising a therapeutically effective amount of a therapeutic agent according to the present invention, which is preferably a therapeutic protein variant as described herein. Optionally and alternatively, the therapeutic agent could be an antibody or an oligonucleotide that specifically recognizes and binds to the therapeutic protein variant, but not to the corresponding full length known protein.

According to the present invention the therapeutic agent could be any one of novel Met receptor protein tyrosine kinase variant polypeptides and polynucleotides of the present invention. Optionally and alternatively, the therapeutic agent could be an antibody or an oligonucleotide that specifically recognizes and binds to the novel Met receptor protein tyrosine kinase variant polypeptides and polynucleotides of the present invention.

According to the present invention the therapeutic agent could be used for the treatment or prevention of a wide range of diseases, as described in greater detail below.

Alternatively, the pharmaceutical composition of the present invention includes a therapeutically effective amount of at least an active portion of a therapeutic protein variant polypeptide.

The pharmaceutical composition according to the present invention is preferably used for the treatment of cluster-related (variant-related) diseases, which includes but is not limited to diseases wherein Met receptor protein tyrosine kinase is involved in the etiology or pathogenesis of the disease process as described herein.

"Treatment" refers to both therapeutic treatment and prophylactic or preventative measures. Those in need of treatment include those already with the disorder as well as those in which the disorder is to be prevented. Hence, the mammal to be treated herein may have been diagnosed as having the disorder or may be predisposed or susceptible to the disorder. "Mammal" for purposes of treatment refers to any animal classified as a mammal, including humans, domestic and farm animals, and zoo, sports, or pet animals, such as dogs, horses, cats, cows, etc. Preferably, the mammal is human.

A "disorder" is any condition that would benefit from treatment with the agent according to the present invention. This includes chronic and acute disorders or diseases including those pathological conditions which predispose the mammal to the disorder in question.

The term "therapeutically effective amount" refers to an amount of agent according to the present invention that is effective to treat a disease or disorder in a mammal.

The therapeutic agents of the present invention can be provided to the subject per se, or as part of a pharmaceutical composition where they are mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the preparation accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections. Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Pharmaceutical compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Met-variants of the present invention can be used as carriers or targetors of cytotoxic drugs, and can be useful as anticancer therapeutic and/or diagnostic agents. Thus, according to an optional embodiment of the present invention, the variants of the present invention can optionally be conjugated to a bioactive moiety, preferably selected from the group consisting of but not limited to a cytotoxic compound, a cytostatic compound, an antisense compound, an anti-viral agent, a specific antibody, an imaging agent and a biodegradable carrier.

Diagnostic Methods

The term "marker" in the context of the present invention refers to a nucleic acid fragment, a peptide, or a polypeptide, which is differentially present in a sample taken from patients having or predisposed to a Met-related disease, disorder or condition as compared to a comparable sample taken from subjects who do not have a such a disease, disorder or condition.

According to the present invention the marker could be any one of novel Met variant polypeptides and polynucleotides of the present invention. Optionally and alternatively, the marker could be an antibody or an oligonucleotide that specifically recognizes and binds to the novel Met variant polypeptides and polynucleotides of the present invention.

According to the present invention the marker could be used for the diagnosis, prognosis, prediction, screening, early diagnosis, determination of progression, therapy selection and treatment monitoring of a wide range of diseases, as described in greater detail below.

Typically the level of the marker in a biological sample obtained from the subject is different (i.e., increased or decreased) from the level of the same variant in a similar sample obtained from a healthy individual.

In another embodiment, this invention provides antibodies specifically recognizing the splice variants and polypeptide fragments thereof of this invention. Preferably such antibodies differentially recognize splice variants of the present invention but do not recognize a corresponding known protein (such known proteins are discussed with regard to their splice variants in the Examples below).

In another embodiment, this invention provides a method for detecting a splice variant according to the present invention in a biological sample, comprising: contacting a biological sample with an antibody specifically recognizing a splice variant according to the present invention under conditions whereby the antibody specifically interacts with the splice variant in the biological sample but do not recognize known corresponding proteins (wherein the known protein is discussed with regard to its splice variant(s) in the Examples below), and detecting the interaction; wherein the presence of an interaction correlates with the presence of a splice variant in the biological sample.

In another embodiment, this invention provides a method for detecting a splice variant nucleic acid sequences in a biological sample, comprising: hybridizing the isolated nucleic acid molecules or oligonucleotide fragments of at least about a minimum length to a nucleic acid material of a biological sample and detecting a hybridization complex; wherein the presence of a hybridization complex correlates with the presence of a splice variant nucleic acid sequence in the biological sample.

According to the present invention, any known in the art method could be used for the diagnosis, prognosis, prediction, screening, early diagnosis, determination of progression, therapy selection and treatment monitoring of a wide range of diseases. Such method can be selected from the group consisting of but not limited to: immunoassays, immunohistochemical analysis, radioimmunoassay, radioimaging methods, Western blot analysis, ELISA, or nucleic acid based technologies (eg., PCR, RT-PCR, in situ PCR, LCR, LAR, 3SR/NASBA, CPR, Branched DNA, RFLPs, ASO, Denaturing/Temperature Gradient Gel Electrophoresis (DGGE/TGGE), SSCP, Dideoxy fingerprinting (ddF), Reverse dot blot).

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above description, illustrate the invention in a non limiting fashion.

Example 1

Description for Met Clusters HSU08818 and Z40018

Cluster HSU08818 features 3 transcripts HSU08818_PEA_1_T9 (SEQ ID NO:1); HSU08818_PEA_1_T14 (SEQ ID NO:2); HSU08818_PEA_1_T15 (SEQ ID NO:3) and 30 segments of interest, the names for which are given in Table 1. The selected protein variants are given in Table 2.

Cluster Z40018 features 1 transcript Z40018_1_T15 (SEQ ID NO:48), encoding the selected protein Z40018_1_P17 (SEQ ID NO:66), and 15 segments of interest, the names for which are given in Table 3.

These sequences are variants of the known protein Hepatocyte growth factor receptor precursor (SEQ ID NO:34) (SwissProt accession identifier MET_HUMAN; known also according to the synonyms EC 2.7.1.112; Met proto-oncogene tyrosine kinase; c-met; HGF receptor; HGF-SF receptor, Met receptor protein tyrosine kinase), referred to herein as the previously known protein.

TABLE 1

Segments of interest
Segment Name

HSU08818_PEA_1_node_0 (SEQ ID NO: 4)
HSU08818_PEA_1_node_4 (SEQ ID NO: 5)
HSU08818_PEA_1_node_11 (SEQ ID NO: 6)
HSU08818_PEA_1_node_13 (SEQ ID NO: 7)
HSU08818_PEA_1_node_18 (SEQ ID NO: 8)
HSU08818_PEA_1_node_22 (SEQ ID NO: 9)
HSU08818_PEA_1_node_24 (SEQ ID NO: 10)
HSU08818_PEA_1_node_29 (SEQ ID NO: 11)
HSU08818_PEA_1_node_32 (SEQ ID NO: 12)
HSU08818_PEA_1_node_57 (SEQ ID NO: 13)
HSU08818_PEA_1_node_60 (SEQ ID NO: 14)
HSU08818_PEA_1_node_61 (SEQ ID NO: 15)
HSU08818_PEA_1_node_62 (SEQ ID NO: 16)
HSU08818_PEA_1_node_63 (SEQ ID NO: 17)
HSU08818_PEA_1_node_65 (SEQ ID NO: 18)
HSU08818_PEA_1_node_67 (SEQ ID NO: 19)
HSU08818_PEA_1_node_15 (SEQ ID NO: 20)
HSU08818_PEA_1_node_16 (SEQ ID NO: 21)
HSU08818_PEA_1_node_20 (SEQ ID NO: 22)
HSU08818_PEA_1_node_27 (SEQ ID NO: 23)
HSU08818_PEA_1_node_30 (SEQ ID NO: 24)

TABLE 1-continued

Segments of interest
Segment Name

HSU08818_PEA_1_node_33 (SEQ ID NO: 25)
HSU08818_PEA_1_node_52 (SEQ ID NO: 26)
HSU08818_PEA_1_node_53 (SEQ ID NO: 27)
HSU08818_PEA_1_node_54 (SEQ ID NO: 28)
HSU08818_PEA_1_node_55 (SEQ ID NO: 29)
HSU08818_PEA_1_node_58 (SEQ ID NO: 30)
HSU08818_PEA_1_node_59 (SEQ ID NO: 31)
HSU08818_PEA_1_node_64 (SEQ ID NO: 32)
HSU08818_PEA_1_node_66 (SEQ ID NO: 33)

TABLE 2

Proteins of interest

| Protein Name | Corresponding Transcript |
| --- | --- |
| HSU08818_PEA_1_P8 (Met588, SEQ ID NO: 36) | HSU08818_PEA_1_T9 (SEQ ID NO: 1) |
| HSU08818_PEA_1_P12 (Met877, SEQ ID NO: 37) | HSU08818_PEA_1_T15 (SEQ ID NO: 3) |
| HSU08818_PEA_1_P16 (Met934, SEQ ID NO: 38) | HSU08818_PEA_1_T14 (SEQ ID NO: 2) |

TABLE 3

Segments of interest
Segment Name

Z40018_1_N6 (SEQ ID NO: 49)
Z40018_1_N13 (SEQ ID NO: 50)
Z40018_1_N15 (SEQ ID NO: 51)
Z40018_1_N20 (SEQ ID NO: 52)
Z40018_1_N24 (SEQ ID NO: 53)
Z40018_1_N26 (SEQ ID NO: 54)
Z40018_1_N31 (SEQ ID NO: 55)
Z40018_1_N0 (SEQ ID NO: 56)
Z40018_1_N1 (SEQ ID NO: 57)
Z40018_1_N2 (SEQ ID NO: 58)
Z40018_1_N17 (SEQ ID NO: 59)
Z40018_1_N18 (SEQ ID NO: 60)
Z40018_1_N22 (SEQ ID NO: 61)
Z40018_1_N29 (SEQ ID NO: 62)
Z40018_1_N35 (SEQ ID NO: 63)

Known polymorphisms for Met receptor protein tyrosine kinase sequence are as shown in Table 4.

TABLE 4

Amino acid mutations for Known Protein

| SNP position(s) on amino acid sequence | Comment |
| --- | --- |
| 320 | A -> V. /FTId = VAR_006285. |
| 1131 | M -> T (in HPRC; germline mutation). /FTId = VAR_006286. |
| 1188 | V -> L (in HPRC; germline mutation). /FTId = VAR_006287. |
| 1195 | L -> V (in HPRC; somatic mutation). /FTId = VAR_006288. |
| 1220 | V -> I (in HPRC; germline mutation). /FTId = VAR_006289. |
| 1228 | D -> N (in HPRC; germline mutation). /FTId = VAR_006290. |
| 1228 | D -> H (in HPRC; somatic mutation). /FTId = VAR_006291. |
| 1230 | Y -> C (in HPRC; germline mutation). /FTId = VAR_006292. |
| 1230 | Y -> H (in HPRC; somatic mutation). /FTId = VAR_006293. |
| 1250 | M -> T (in HPRC; somatic mutation). /FTId = VAR_006294. |
| 1191 | G -> A |
| 1267 | W -> V |

Cluster HSU08818 and/or cluster Z40018 transcripts, proteins and derived peptides are useful as therapeutic agents for Met-related diseases Met-related diseases include, but are not limited to, all disorders or conditions that would benefit from treatment with a substance/molecule or method of the invention. These include chronic and acute disorders or diseases, including pathological conditions which predispose to the disorder in question. Non-limiting examples of the disorders to be treated herein include malignant and benign tumors; non-leukemias and lymphoid malignancies; neuronal, glial, astrocytal, hypothalamic and other glandular, macrophagal, epithelial, stromal and blastocoelic disorders; and angiogenesis-related disorders.

The term "Tumor", as used herein, refers to all neoplastic cell growth and proliferation, whether malignant or benign, and all pre-cancerous and cancerous cells and tissues. Examples of cancer include but are not limited to, carcinoma, lymphoma, leukemia, sarcoma and blastoma. While the terms "Tumor" or "Cancer" as used herein is not limited to any one specific form of the disease, it is believed that the methods will be particularly effective for cancers which are found to be accompanies by increased levels of HGF, or over expression or other activation of the Met receptor. Examples of such cancers include primary and metastatic cancer such as breast cancer, colon cancer, colorectal cancer, gastrointestinal tumors, esophageal cancer, cervical cancer, ovarian cancer, endometrial or uterine carcinoma, vulval cancer, liver cancer, hepatocellular cancer, bladder cancer, kidney cancer, hereditary and sporadic papillary renal cell carcinoma, pancreatic cancer, various types of head and neck cancer, lung cancer (e.g., non-small cell lung cancer, small cell lung cancer, squamous cell carcinoma, lung adenocarcinoma), prostate cancer, thyroid cancer, brain tumors, glioblastoma, glioma, malignant peripheral nerve sheath tumors, cancer of the peritoneum, cutaneous malignant melanoma, and salivary gland carcinoma.

Met-related diseases also consist of diseases in which anti-angiogenic activity plays a favorable role, including but not limited to, diseases having abnormal quality and/or quantity of vascularization as a characteristic feature. Dysregulation of angiogenesis can lead to many disorders that can be treated by compositions and methods of the invention. These disorders include both non-neoplastic and neoplastic conditions. Neoplastics include but are not limited to the type of primary and metastatic cancers described above. Non-neoplastic disorders include but are not limited to inflammatory and autoimmune disorders, such as aberrant hyperthrophy, arthritis, psoriasis, sarcoidosis, scleroderma, sclerosis, atherosclerosis, synovitis, dermatitis, Crohn's disease, ulcerative colitis, inflammatory bowel disease, respiratory distress syndrome, uveitis, meningitis, encephalitis, Sjorgen's syndrome, systemic lupus erythematosus, diabetes mellitus, multiple sclerosis, juvenile onset diabetes; allergic conditions such as eczema and asthma; proliferative retinopathies, including but not limited to diabetic retinopathy, retinopathy of prematurity, retrolental fibroplasia, neovascular glaucoma, age-related macular degeneration, diabetic macular edema, cornal neovascularization, corneal graft neovascularization and/or rejection, ocular neovascular disease; and various other disorders in which anti-angiogenic activity plays a favorable role including but not limited to vascular restenosis, arteriovenous malformations, meningioma, hemangioma, angiofibroma, thyroid hyperplasia, hypercicatrization in wound healing, hyperthrophic scars.

The compositions and methods of the present invention can be further employed in combination with surgery or cytotoxic agents, or other anti-cancer agents, such as chemotherapy or radiotherapy and/or in combination with anti-angiogenesis drugs.

Cluster HSU08818 and/or cluster Z40018 can be used as a diagnostic marker according to overexpression of transcripts of this cluster in cancer. Expression of such transcripts in normal tissues is also given according to the previously described methods. The term "number" in the left hand column of table 5 and the numbers on the y-axis of the FIG. 4 refer to weighted expression of ESTs in each category, as "parts per million" (ratio of the expression of ESTs for a particular cluster to the expression of all ESTs in that category, according to parts per million).

Figure 4:
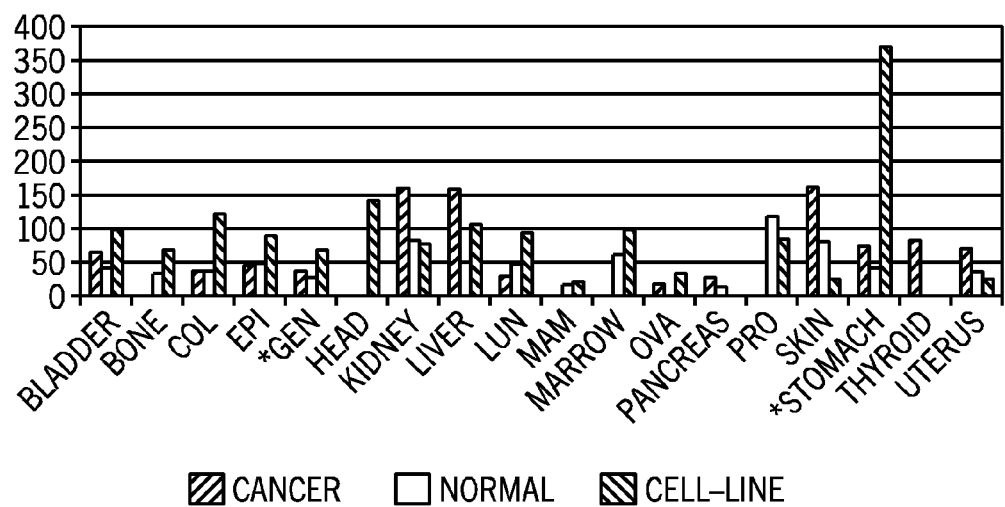
FIG. 4 is a histogram showing cancer and cell-line vs. normal tissue expression for Cluster HSU08818, demonstrating overexpression in a mixture of malignant tumors from different tissues and gastric carcinoma.

Overall, the following results were obtained as shown with regard to the histograms in FIG. 4 and Table 5. P values and ratios for expression in cancerous tissues are shown in Table 6. This cluster is overexpressed (at least at a minimum level) in the following pathological conditions: a mixture of malignant tumors from different tissues and gastric carcinoma.

TABLE 5

Normal tissue distribution

| Name of Tissue | Number |
| --- | --- |
| bladder | 41 |
| bone | 32 |
| colon | 37 |
| epithelial | 49 |
| general | 26 |
| head and neck | 0 |
| kidney | 83 |
| liver | 4 |
| lung | 48 |
| breast | 17 |
| bone marrow | 62 |
| ovary | 0 |
| pancreas | 10 |
| prostate | 120 |
| skin | 83 |
| stomach | 36 |
| Thyroid | 0 |
| uterus | 36 |

TABLE 6

P values and ratios for expression in cancerous tissue

| Name of Tissue | P1 | P2 | SP1 | R3 | SP2 | R4 |
| --- | --- | --- | --- | --- | --- | --- |
| bladder | 7.6e−01 | 4.5e−01 | 6.0e−01 | 1.3 | 4.9e−01 | 1.4 |
| bone | 9.2e−01 | 2.1e−01 | 1 | 0.5 | 6.5e−01 | 1.3 |
| colon | 4.0e−01 | 2.9e−01 | 7.8e−01 | 0.9 | 5.0e−01 | 1.2 |
| epithelial | 7.0e−01 | 9.6e−02 | 7.2e−01 | 0.8 | 5.6e−02 | 1.2 |
| general | 4.7e−01 | 5.3e−03 | 9.2e−02 | 1.2 | 9.6e−06 | 1.8 |
| head and neck | 4.3e−01 | 2.8e−01 | 1 | 1.0 | 4.2e−01 | 1.7 |
| kidney | 7.7e−01 | 7.6e−01 | 1.9e−01 | 1.1 | 3.0e−01 | 1.0 |
| liver | 3.3e−01 | 3.4e−01 | 2.3e−01 | 3.9 | 1.6e−01 | 3.0 |
| lung | 8.6e−01 | 8.2e−01 | 7.8e−01 | 0.7 | 3.3e−01 | 1.0 |

TABLE 6-continued

P values and ratios for expression in cancerous tissue

| Name of Tissue | P1 | P2 | SP1 | R3 | SP2 | R4 |
| --- | --- | --- | --- | --- | --- | --- |
| breast | 9.5e−01 | 6.2e−01 | 1 | 0.7 | 8.2e−01 | 0.9 |
| bone marrow | 8.6e−01 | 8.5e−01 | 1 | 0.3 | 5.6e−01 | 0.9 |
| ovary | 6.2e−01 | 4.2e−01 | 6.8e−01 | 1.5 | 5.9e−01 | 1.6 |
| pancreas | 5.5e−01 | 6.8e−01 | 3.9e−01 | 1.9 | 5.4e−01 | 1.4 |
| prostate | 9.3e−01 | 9.3e−01 | 1 | 0.1 | 1 | 0.3 |
| skin | 6.3e−01 | 7.5e−01 | 3.2e−01 | 1.8 | 9.4e−01 | 0.4 |
| stomach | 5.0e−01 | 2.4e−02 | 5.0e−01 | 1.5 | 5.5e−03 | 3.2 |
| Thyroid | 1.8e−01 | 1.8e−01 | 6.7e−01 | 1.6 | 6.7e−01 | 1.6 |
| uterus | 4.1e−01 | 4.8e−01 | 2.6e−01 | 1.4 | 4.4e−01 | 1.1 |

The amino acid sequence comparison between Met variants of the present invention and the known Hepatocyte growth factor receptor precursor is shown in FIG. 1A-E. FIG. 1A demonstrates the comparison between Met-877 variant of the invention (SEQ ID NO: 37) and the known Met receptor protein kinase (SEQ ID NO: 34). FIG. 1B demonstrates the comparison between Met-934 variant of the invention (SEQ ID NO: 38) and the known Met receptor protein kinase (SEQ ID NO: 34). FIG. 1C demonstrates the comparison between Met-885 variant of the invention (SEQ ID NO: 66) and the known Met receptor protein kinase (SEQ ID NO: 34). FIG. 1D demonstrates the comparison between Met-588 variant of the invention (SEQ ID NO: 36) and the known Met receptor protein kinase MET_HUMAN (SEQ ID NO: 34). FIG. 1E demonstrates the comparison between Met-588 variant of the invention (SEQ ID NO: 36) and the known Met receptor protein kinase MET_HUMAN_V1 (SEQ ID NO: 35).

FIG. 2 shows the amino acid sequence comparison between Met variants of the present invention and a Met variant previously disclosed by Receptor Biologix Inc. (RB). The unique amino acids are marked in bold. FIG. 2A demonstrates the comparison between Met-877 variant of the invention (SEQ ID NO: 37) and the RB Met variant (SEQ ID NO: 40). FIG. 2B demonstrates the comparison between Met-885 variant of the invention (SEQ ID NO: 66) and the RB Met variant (SEQ ID NO: 40). FIG. 2C demonstrates the comparison between Met-934 variant of the invention (SEQ ID NO: 38) and the RB Met variant (SEQ ID NO: 40). FIG. 2D demonstrates the comparison between Met-588 variant of the invention (SEQ ID NO: 36) and the RB Met variant (SEQ ID NO: 40).

The comparison report between Met variants of the present invention and the known Hepatocyte growth factor receptor precursor is given below:

Variant protein HSU08818_PEA_1_P8 (SEQ ID NO:36) according to the present invention is encoded by transcript HSU08818_PEA_1_T9 (SEQ ID NO:1). A brief description of the relationship of the variant protein according to the present invention to the aligned protein is as follows:

Comparison report between HSU08818_PEA_1_P8 (SEQ ID NO:36) and MET_HUMAN_V1 (SEQ ID NO:35), as demonstrated in FIG. 1E:

1. An isolated chimeric polypeptide encoding for HSU08818_PEA_1_P8 (SEQ ID NO:36), comprising a first amino acid sequence being at least 90% homologous to MKAPAVLAPGILVLLFTLVQRSNGECK-EALAKSEMNVNMKYQLPNFTAETPIQNVILHE HHI-FLGATNYIYVLNEEDLQKVAEYKTGPV-LEHPDCFPCQDCSSKANLSGGVWKDNIN MALVVDTYYDDQLISCGSVNRGTCQRH-VFPHNHTADIQSEVHCIFSPQIEEPSQCPDCVV SAL-GAKVLSSVKDRFINFFVGNTINSSYFP- DHPLHSISVRRLKETKDGFMFLTDQSYIDVL
PEFRDSYPIKYVHAFESNNFIY-
FLTVQRETLDAQTFHTRIIRFCSINS-
GLHSYMEMPLECIL TEKRKKRSTKKEVF-
NILQAAYVSKPGAQLARQIGASLNDDILFGVFAQSK
PDSAEPMDR SAMCAFPIKYVNDFFNKIVNKNNVR-
CLQHFYGPNHEHCFNRTLLRNSSGCEARRDEYRT
EFTTALQRVDLFMGQFSEVLLTSIST-
FIKGDLTIANLGTSEGRFMQ corresponding to amino acids 1-464 of MET_HUMAN_Vi (SEQ ID NO:35), which also corresponds to amino acids 1-464 of HSU08818_PEA__1_P8 (SEQ ID NO:36), a second amino acid sequence being at least 90% homologous to—WSFGVLLWELMTRGAP-PYPDVNTFDITVYLLQGRRLLQPEYCPD-PLYEVMLKCWHPKA EMRPSFSELVSRISAIFSTFIGE-HYVHVNATYVNVKCVAPYPSLLSSEDNADDEVDTR PAS FWETS corresponding to amino acids 1267-1390 of MET_HUMAN_V1, which also corresponds to amino acids 465-588 of HSU08818_PEA__1_P8 (SEQ ID NO:36), wherein said first amino acid sequence and second amino acid sequence are contiguous and in a sequential order.

2. An isolated chimeric polypeptide encoding for an edge portion of HSU08818_PEA__1_P8 (SEQ ID NO:36), comprising a polypeptide having a length "n", wherein n is at least about 10 amino acids in length, optionally at least about 20 amino acids in length, preferably at least about 30 amino acids in length, more preferably at least about 40 amino acids in length and most preferably at least about 50 amino acids in length, wherein at least two amino acids comprise QW, having a structure as follows: a sequence starting from any of amino acid numbers 464-x to 464; and ending at any of amino acid numbers 465+((n−2)−x), in which x varies from 0 to n−2.

Comparison report between HSU08818_PEA__1_P8 (SEQ ID NO:36) and MET_HUMAN (SEQ ID NO:34), as demonstrated in FIG. 1D:

1. An isolated chimeric polypeptide encoding for HSU08818_PEA__1_P8 (SEQ ID NO:36), comprising a first amino acid sequence being at least 90% homologous to MKAPAVLAPGILVLLFTLVQRSNGECK-
EALAKSEMNVNMKYQLPNFTAETPIQNVILHE HHI-
FLGATNYIYVLNEEDLQKVAEYKTGPV-
LEHPDCFPCQDCSSKANLSGGVWKDNIN
MALVVDTYYDDQLISCGSVNRGTCQRH-
VFPHNHTADIQSEVHCIFSPQIEEPSQCPDCVV SAL-
GAKVLSSVKDRFINFFVGNTINSSYFP-
DHPLHSISVRRLKETKDGFMFLTDQSYIDVL
PEFRDSYPIKYVHAFESNNFIY-
FLTVQRETLDAQTFHTRIIRFCSINS-
GLHSYMEMPLECIL TEKRKKRSTKKEVF-
NILQAAYVSKPGAQLARQIGASLNDDILFGVFAQSKP
DSAEPMDR SAMCAFPIKYVNDFFNKIVNKNNVR-
CLQHFYGPNHEHCFNRTLLRNSSGCEARRDEYRT
EFTTALQRVDLFMGQFSEVLLTSIST-
FIKGDLTIANLGTSEGRFMQ corresponding to amino acids 1-464 of MET_HUMAN (SEQ ID NO:34), which also corresponds to amino acids 1-464 of HSU08818_PEA__1_P8 (SEQ ID NO:36), a second amino acid sequence being at least 90% homologous to WSFGV corresponding to amino acids 1267-1271 of MET_HUMAN (SEQ ID NO:34), which also corresponds to amino acids 465-469 of HSU08818_PEA__1_P8 (SEQ ID NO:36), a bridging amino acid L corresponding to amino acid 470 of HSU08818_PEA__1_P8 (SEQ ID NO:36), and a third amino acid sequence being at least 90% homologous to—LWELMTRGAPPYPDVNT-FDITVYLLQGRRLLQPEYCPDPLYEVM-
LKCWHPKAEMRPSF SELVSRISAIFSTFIGEHYVH-VNATYVNVKCVAPYPSLLSSEDNADDEVDTRPASFW
ETS corresponding to amino acids 1273-1390 of MET_HUMAN (SEQ ID NO:34), which also corresponds to amino acids 471-588 of HSU08818_PEA__1_P8 (SEQ ID NO:36), wherein said first amino acid sequence, second amino acid sequence, bridging amino acid and third amino acid sequence are contiguous and in a sequential order.

2. An isolated chimeric polypeptide encoding for an edge portion of HSU08818_PEA__1_P8 (SEQ ID NO:36), comprising a polypeptide having a length "n", wherein n is at least about 10 amino acids in length, optionally at least about 20 amino acids in length, preferably at least about 30 amino acids in length, more preferably at least about 40 amino acids in length and most preferably at least about 50 amino acids in length, wherein at least two amino acids comprise QW, having a structure as follows: a sequence starting from any of amino acid numbers 464-x to 464; and ending at any of amino acid numbers 465+((n−2)−x), in which x varies from 0 to n−2.

The location of the variant protein was determined according to results from a number of different software programs and analyses, including analyses from SignalP and other specialized programs. The variant protein is secreted.

Variant protein HSU08818_PEA__1_P8 (SEQ ID NO:36) also has the following non-silent SNPs (Single Nucleotide Polymorphisms) as listed in Table 7, (given according to their positions on the amino acid sequence, with the alternative amino acids listed; the last column indicates whether the SNP is known or not; the presence of known SNPs in variant protein HSU08818_PEA__1_P8 (SEQ ID NO:36) sequence provides support for the deduced sequence of this variant protein according to the present invention).

TABLE 7

Amino acid mutations

| SNP position(s) on amino acid sequence | Alternative amino acid(s) | Previously known SNP |
|---|---|---|
| 230 | T -> A | No |
| 292 | M -> V | No |
| 322 | V -> A | No |
| 410 | E -> G | No |
| 470 | L -> V | No |

The glycosylation sites of variant protein HSU08818_PEA__1_P8 (SEQ ID NO:36), as compared to the known protein Hepatocyte growth factor receptor precursor (SEQ ID NO:34), are described in Table 8 (given according to their positions on the amino acid sequence in the first column; the second column indicates whether the glycosylation site is present in the variant protein; and the last column indicates whether the position is different on the variant protein).

TABLE 8

Glycosylation site(s)

| Position(s) on known amino acid sequence | Present in variant protein | Position in variant protein |
|---|---|---|
| 635 | no | |
| 879 | no | |
| 405 | yes | 405 |
| 149 | yes | 149 |
| 399 | yes | 399 |
| 202 | yes | 202 |
| 607 | no | |

TABLE 8-continued

Glycosylation site(s)

| Position(s) on known amino acid sequence | Present in variant protein | Position in variant protein |
|---|---|---|
| 106 | yes | 106 |
| 930 | no | |
| 785 | no | |
| 45 | yes | 45 |

The phosphorylation sites of variant protein HSU08818_PEA_1_P8 (SEQ ID NO:36), as compared to the known protein Hepatocyte growth factor receptor precursor (SEQ ID NO:34), are described in Table 9 (given according to their positions on the amino acid sequence in the first column; the second column indicates whether the phosphorylation site is present in the variant protein; and the last column indicates whether the position is different on the variant protein).

TABLE 9

Phosphorylation site

| Position(s) on known amino acid sequence | Present in variant protein | Position in variant protein |
|---|---|---|
| 1235 | no | |

Variant protein HSU08818_PEA_1_P8 (SEQ ID NO:36) is encoded by transcript HSU08818_PEA_1_T_9 (SEQ ID NO:1), for which the coding portion starts at position 195 and ends at position 1958. The transcript also has the following SNPs as listed in Table 10 (given according to their position on the nucleotide sequence, with the alternative nucleic acid listed; the last column indicates whether the SNP is known or not; the presence of known SNPs in variant protein HSU08818_PEA_1_P8 (SEQ ID NO:36) sequence provides support for the deduced sequence of this variant protein according to the present invention).

TABLE 10

Nucleic acid SNPs

| SNP position on nucleotide sequence | Alternative nucleic acid | Previously known SNP |
|---|---|---|
| 2 | A -> G | No |
| 78 | A -> T | Yes |
| 79 | T -> A | Yes |
| 338 | G -> A | Yes |
| 882 | A -> G | No |
| 1068 | A -> G | No |
| 1159 | T -> C | No |
| 1423 | A -> G | No |
| 1601 | G -> C | No |
| 1602 | C -> G | No |
| 1646 | T -> C | No |
| 1805 | A -> G | Yes |
| 1880 | A -> G | Yes |
| 1996 | T -> A | No |
| 2001 | A -> | No |
| 2001 | A -> C | No |
| 2050 | -> C | No |
| 2645 | G -> A | Yes |
| 2989 | A -> G | No |
| 3287 | G -> A | No |
| 3389 | A -> G | No |
| 3500 | T -> | No |
| 4158 | A -> | No |

Variant protein HSU08818_PEA_1_P12 (SEQ ID NO:37) according to the present invention is encoded by transcripts HSU08818_PEA_1_T15 (SEQ ID NO:3). A brief description of the relationship of the variant protein according to the present invention to aligned known protein is as follows:

Comparison report between HSU08818_PEA_1_P12 (SEQ ID NO:37) and MET_HUMAN (SEQ ID NO:34), as demonstrated in FIG. 1A:

1. An isolated chimeric polypeptide encoding for HSU08818_PEA_1_P12 (SEQ ID NO:37), comprising a first amino acid sequence being at least 90% homologous to MKAPAVLAPGILVLLFTLVQRSNGECK-EALAKSEMNVNMKYQLPNFTAETPIQNVILHE HHI-FLGATNYIYVLNEEDLQKVAEYKTGPV-LEHPDCFPCQDCSSKANLSGGVWKDNIN MALVVDTYYDDQLISCGSVNRGTCQRH-VFPHNHTADIQSEVHCIFSPQIEEPSQCPDCVV SAL-GAKVLSSVKDRFINFFVGNTINSSYFP-DHPLHSISVRRLKETKDGFMFLTDQSYIDVL PEFRDSYPIKYVHAFESNNFIY-FLTVQRETLDAQTFHTRIIRFCSINS-GLHSYMEMPLECIL TEKRKKRSTKKEVF-NILQAAYVSKPGAQLARQIGASLNDDILFGVFAQSKP DSAEPMDR SAMCAFPIKYVNDFFNKIVNKNNVR-CLQHFYGPNHEHCFNRTLLRNSSGCEARRDEYRT EFTTALQRVDLFMGQFSEVLLTSIST-FIKGDLTIANLGTSEGRFMQVVVSRSGPSTPHVNF LLDSHPVSPEVIVEHTLNQNGYTLVIT-GKKITKIPLNGLGCRHFQSCSQCLSAPPFVQCG WCH-DKCVRSEECLSGTWTQQICLPAIYKVFP-NSAPLEGGTRLTICGWDFGFRRNNKFDL KKTRVLLGNESCTLTLSEST-MNTLKCTVGPAMNKHFNMSIIISNGHGT-TQYSTFSYVDPV ITSISPKYGPMAGGTLLTLTG-NYLNSGNSRHISIGGKTCTLKSVSNSILECYTPAQTIS TEF AVKLKIDLANRETSIFSYRED-PIVYEIHPTKSFISGGSTITGVGKNLNS-VSVPRMVINVHEA GRNFTVACQHRSNSEIICCT-TPSLQQLNLQLPLKTKAFFMLDGILSKYFDLIYVHNP VFKP FEKPVMISMGNENVLEIK corresponding to amino acids 1-861 of MET_HUMAN (SEQ ID NO:34), which also corresponds to amino acids 1-861 of HSU08818_PEA_1_P12 (SEQ ID NO:37), and a second amino acid sequence being at least 70%, optionally at least 80%, preferably at least 85%, more preferably at least 90% and most preferably at least 95% homologous to a polypeptide having the sequence VRNALNTVLNHQLKLN (SEQ ID NO:83) corresponding to amino acids 862-877 of HSU08818_PEA_1_P12 (SEQ ID NO:37), wherein said first amino acid sequence and second amino acid sequence are contiguous and in a sequential order.

2. An isolated polypeptide encoding for a tail of HSU08818_PEA_1_P12 (SEQ ID NO:37), comprising a polypeptide being at least 70%, optionally at least about 80%, preferably at least about 85%, more preferably at least about 90% and most preferably at least about 95% homologous to the sequence VRNALNTVLNHQLKLN (SEQ ID NO:83) in HSU08818_PEA_1_P12 (SEQ ID NO:37).

The location of the variant protein was determined according to results from a number of different software programs and analyses, including analyses from SignalP and other specialized programs. The variant protein is secreted.

Variant protein HSU08818_PEA_1_P12 (SEQ ID NO:37) also has the following non-silent SNPs (Single Nucleotide Polymorphisms) as listed in Table 11, (given according to their positions on the amino acid sequence, with the alternative amino acids listed; the last column indicates whether the SNP is known or not; the presence of known SNPs in variant protein HSU08818_PEA_1_P12 (SEQ ID NO:37) sequence provides support for the deduced sequence of this variant protein according to the present invention).

TABLE 11

Amino acid mutations

| SNP position(s) on amino acid sequence | Alternative amino acid(s) | Previously known SNP |
|---|---|---|
| 230 | T -> A | No |
| 292 | M -> V | No |
| 322 | V -> A | No |
| 410 | E -> G | No |
| 714 | Q -> | No |

The glycosylation sites of variant protein HSU08818_PEA_1_P12 (SEQ ID NO:37), as compared to the known protein Hepatocyte growth factor receptor precursor (SEQ ID NO:34), are described in Table 12 (given according to their positions on the amino acid sequence in the first column; the second column indicates whether the glycosylation site is present in the variant protein; and the last column indicates whether the position is different on the variant protein).

TABLE 12

Glycosylation site(s)

| Position(s) on known amino acid sequence | Present in variant protein | Position in variant protein |
|---|---|---|
| 635 | yes | 635 |
| 879 | no | |
| 405 | yes | 405 |
| 149 | yes | 149 |
| 399 | yes | 399 |
| 202 | yes | 202 |
| 607 | yes | 607 |
| 106 | yes | 106 |
| 930 | no | |
| 785 | yes | 785 |
| 45 | yes | 45 |

The phosphorylation sites of variant protein HSU08818_PEA_1_P12 (SEQ ID NO:37), as compared to the known protein Hepatocyte growth factor receptor precursor (SEQ ID NO:34), are described in Table 13 (given according to their positions on the amino acid sequence in the first column; the second column indicates whether the phosphorylation site is present in the variant protein; and the last column indicates whether the position is different on the variant protein).

TABLE 13

Phosphorylation site(s)

| Position on known amino acid sequence | Present in variant protein | Position in variant protein |
|---|---|---|
| 1235 | no | |

Variant protein HSU08818_PEA_1_P12 (SEQ ID NO:37) is encoded by HSU08818_PEA_1_T15 (SEQ ID NO:3), for which the coding portion starts at position 195 and ends at position 2825. The transcript also has the following SNPs as listed in Table 14 (given according to their position on the nucleotide sequence, with the alternative nucleic acid listed; the last column indicates whether the SNP is known or not; the presence of known SNPs in variant protein HSU08818_PEA_1_P12 (SEQ ID NO:37) sequence provides support for the deduced sequence of this variant protein according to the present invention).

TABLE 14

Nucleic acid SNPs

| SNP position on nucleotide sequence | Alternative nucleic acid | Previously known SNP |
|---|---|---|
| 2 | A -> G | No |
| 78 | A -> T | Yes |
| 79 | T -> A | Yes |
| 338 | G -> A | Yes |
| 882 | A -> G | No |
| 1068 | A -> G | No |
| 1159 | T -> C | No |
| 1423 | A -> G | No |
| 2138 | A -> G | Yes |
| 2335 | A -> | No |

Variant protein HSU08818_PEA_1_P16 (SEQ ID NO:38) according to the present invention is encoded by transcripts HSU08818_PEA_1_T14 (SEQ ID NO:2). A brief description of the relationship of the variant protein according to the present invention to aligned known protein is as follows:

Comparison report between HSU08818_PEA_1_P16 (SEQ ID NO:38) and MET_HUMAN (SEQ ID NO:34), as demonstrated in FIG. 1B:

1. An isolated chimeric polypeptide encoding for HSU08818_PEA_1_P16 (SEQ ID NO:38), comprising a first amino acid sequence being at least 90% homologous to MKAPAVLAPGILVLLFTLVQRSNGECK-EALAKSEMNVNMKYQLPNFTAETPIQNVILHE HHI-FLGATNYIYVLNEEDLQKVAEYKTGPV-LEHPDCFPCQDCSSKANLSGGVWKDNIN MALVVDTYYDDQLISCGSVNRGTCQRH-VFPHNHTADIQSEVHCIFSPQIEEPSQCPDCVV SAL-GAKVLSSVKDRFINFFVGNTINSSYFP-DHPLHSISVRRLKETKDGFMFLTDQSYIDVL PEFRDSYPIKYVHAFESNNFIY-FLTVQRETLDAQTFHTRIIRFCSINS-GLHSYMEMPLECIL TEKRKKRSTKKEVF-NILQAAYVSKPGAQLARQIGASLNDDILFGVFAQSKP DSAEPMDR SAMCAFPIKYVNDFFNKIVNKNNVR-CLQHFYGPNHEHCFNRTLLRNSSGCEARRDEYRT EFTTALQRVDLFMGQFSEVLLTSIST-FIKGDLTIANLGTSEGRFMQVVVSRSGPSTPHVNF LLDSHPVSPEVIVEHTLNQNGYTLVIT-GKKITKIPLNGLGCRHFQSCSQCLSAPPFVQCG WCH-DKCVRSEECLSGTWTQQICLPAIYKVFP-NSAPLEGGTRLTICGWDFGFRRNNKFDL KKTRVLLGNESCTLTLSEST-MNTLKCTVGPAMNKHFNMSIIISNGHGT-TQYSTFSYVDPV ITSISPKYGPMAGGTLLTLTG-NYLNSGNSRHISIGGKTCTLKSVSNSILECYTPAQTIS TEF AVKLKIDLANRETSIFSYRED-PIVYEIHPTKSFISGGSTITGVGKNLNS-VSVPRMVINVHEA GRNFTVACQHRSNSEIICCT-TPSLQQLNLQLPLKTKAFFMLDGILSKYFDLIYVHNP VFKP FEKPVMISMGNENVLEIKGNDIDPEAVK-GEVLKVGNKSCENIHLHSEAVLCTVPNDLLK LNSELNIE corresponding to amino acids 1-910 of MET_HUMAN (SEQ ID NO:34), which also corresponds to amino acids 1-910 of HSU08818_PEA_1_P16 (SEQ ID NO:38), and a second amino acid sequence being at least 70%, optionally at least 80%, preferably at least 85%, more preferably at least 90% and most preferably at least 95% homologous to a polypeptide having the sequence VGFLH-SSHDVNKEASVIMLFSGLK (SEQ ID NO:81) corresponding to amino acids 911-934 of HSU08818_PEA_1_P16 (SEQ ID NO:38), wherein said first amino acid sequence and second amino acid sequence are contiguous and in a sequential order.

2. An isolated polypeptide encoding for a tail of HSU08818_PEA_1_P16 (SEQ ID NO:38), comprising a polypeptide being at least 70%, optionally at least about 80%, preferably at least about 85%, more preferably at least about 90% and most preferably at least about 95% homologous to the sequence VGFLHSSHDVNKEASVIMLFSGLK (SEQ ID NO:81) in HSU08818_PEA_1_P16 (SEQ ID NO:38).

The location of the variant protein was determined according to results from a number of different software programs and analyses, including analyses from SignalP and other specialized programs. The variant protein is believed to be secreted.

Variant protein HSU08818_PEA_1_P16 (SEQ ID NO:38) also has the following non-silent SNPs (Single Nucleotide Polymorphisms) as listed in Table 15, (given according to their positions on the amino acid sequence, with the alternative amino acids listed; the last column indicates whether the SNP is known or not; the presence of known SNPs in variant protein HSU08818_PEA_1_P16 (SEQ ID NO:38) sequence provides support for the deduced sequence of this variant protein according to the present invention).

TABLE 15

Amino acid mutations

| SNP position(s) on amino acid sequence | Alternative amino acid(s) | Previously known SNP |
|---|---|---|
| 230 | T -> A | No |
| 292 | M -> V | No |
| 322 | V -> A | No |
| 410 | E -> G | No |
| 714 | Q -> | No |

The glycosylation sites of variant protein HSU08818_PEA_1_P16 (SEQ ID NO:38), as compared to the known protein Hepatocyte growth factor receptor precursor (SEQ ID NO:34), are described in Table 16 (given according to their positions on the amino acid sequence in the first column; the second column indicates whether the glycosylation site is present in the variant protein; and the last column indicates whether the position is different on the variant protein).

TABLE 16

Glycosylation site(s)

| Position(s) on known amino acid sequence | Present in variant protein | Position in variant protein |
|---|---|---|
| 635 | yes | 635 |
| 879 | yes | 879 |
| 405 | yes | 405 |
| 149 | yes | 149 |
| 399 | yes | 399 |
| 202 | yes | 202 |
| 607 | yes | 607 |
| 106 | yes | 106 |

TABLE 16-continued

Glycosylation site(s)

| Position(s) on known amino acid sequence | Present in variant protein | Position in variant protein |
|---|---|---|
| 930 | no | |
| 785 | yes | 785 |
| 45 | yes | 45 |

The phosphorylation sites of variant protein HSU08818_PEA_1_P16 (SEQ ID NO:38), as compared to the known protein Hepatocyte growth factor receptor precursor (SEQ ID NO:34), are described in Table 17 (given according to their positions on the amino acid sequence in the first column; the second column indicates whether the phosphorylation site is present in the variant protein; and the last column indicates whether the position is different on the variant protein).

TABLE 17

Phosphorylation site(s)

| Position(s) on known amino acid sequence | Present in variant protein | Position in variant protein |
|---|---|---|
| 1235 | no | |

Variant protein HSU08818_PEA_1_P16 (SEQ ID NO:38) is encoded by HSU08818_PEA_1_T14 (SEQ ID NO:2), for which the coding portion starts at position 195 and ends at position 2996. The transcript also has the following SNPs as listed in Table 18 (given according to their position on the nucleotide sequence, with the alternative nucleic acid listed; the last column indicates whether the SNP is known or not; the presence of known SNPs in variant protein HSU08818_PEA_1_P16 (SEQ ID NO:38) sequence provides support for the deduced sequence of this variant protein according to the present invention).

TABLE 18

Nucleic acid SNPs

| SNP position on nucleotide sequence | Alternative nucleic acid | Previously known SNP |
|---|---|---|
| 2 | A -> G | No |
| 78 | A -> T | Yes |
| 79 | T -> A | Yes |
| 338 | G -> A | Yes |
| 882 | A -> G | No |
| 1068 | A -> G | No |
| 1159 | T -> C | No |
| 1423 | A -> G | No |
| 2138 | A -> G | Yes |
| 2335 | A -> | No |

Variant protein Z40018_1_P17 (SEQ ID NO:66) according to the present invention has an amino acid sequence encoded by transcript Z40018_1_T15 (SEQ ID NO:48). FIG. 1C shows an alignment of Z40018_1_P17 (SEQ ID NO:66) (Met-885 (SEQ ID NO:66) to the known protein (Hepatocyte growth factor receptor precursor (SEQ ID NO:34). A brief description of the relationship of the variant protein according to the present invention to aligned protein is as follows:

Comparison report between Z40018_1_P17 (SEQ ID NO:66) and MET_HUMAN (SEQ ID NO:34):

A. An isolated chimeric polypeptide encoding for Z40018_1_P17 (SEQ ID NO:66), comprising a first amino acid sequence being at least 90% homologous to MKAPAVLAPGILVLLFTLVQRSNGECKEALAKSEMNVNMKYQLPNFTAETPIQNVILHE HHIFLGATNYIYVLNEEDLQKVAEYKTGPVLEHPDCFPCQDCSS KANLSGGVWKDNIN MALVVDTYYDDQLISCGSVNRGTCQRHVFPHNHTADIQSEVHCIFSPQIEEPSQCPDCVV SALGAKVLSSVKDRFINFFVGNTINSSYFPDHPLHSISVRRLKETKDGFMFLTD QSYIDVL PEFRDSYPIKYVHAFESNNFIYFLTVQRETLDAQTFHTRIIRFCSINSGLHSYMEMPLECIL TEKRKKRSTKKEVFNILQAAYVSKPGAQLARQIGASLNDDILFGVFAQSKP DSAEPMDR SAMCAFPIKYVNDFFNKIVNKNNVRCLQHFYGPNHEHCFNRTLLRNSSGCEARRDEYRT EFTTALQRVDLFMGQFSEVLLTSISTFIKGDLTIANLGTSEGRFMQVVVSRSGPSTPHVNF LLDSHPVSPEVIVEHTLNQNGYTLVITGKKITKIPLNGLGCRHFQSCSQCLSAPPFVQCG WCHDKCVRSEECLSGTWTQQICLPAIYKVFPNSAPLEGGTRLTICGWDFGFRRNNKFDL KKTRVLLGNESCTLTLSESTMNTLKCTVGPAMNKHFNMSIIISNGHGTTQYSTFSYVDPV ITSISPKYGPMAGGTLLTLTGNYLNSGNSRHISIGGKTCTLKSVSNSILECYTPAQTIS TEF AVKLKIDLANRETSIFSYREDPIVYEIHPTKSFISGGSTITGVGKNLNSVSVPRMVINVHEA GRNFTVACQHRSNSEIICCTTPSLQQLNLQLPLKTKAFFMLDGILSKYFDLIYVHNP VFKP FEKPVMISMGNENVLEIK corresponding to amino acids 1-861 of MET_HUMAN (SEQ ID NO:34), which also corresponds to amino acids 1-861 of Z40018_1_P17 (SEQ ID NO:66), and a second amino acid sequence being at least 70%, optionally at least 80%, preferably at least 85%, more preferably at least 90% and most preferably at least 95% homologous to a polypeptide having the sequence VGFLHSSHDVNKEASVIMLFSGLK (SEQ ID NO:81) corresponding to amino acids 862-885 of Z40018_1_P17 (SEQ ID NO:66), wherein said first amino acid sequence and second amino acid sequence are contiguous and in a sequential order.

B. An isolated polypeptide encoding for an edge portion of Z40018_1_P17 (SEQ ID NO:66), comprising an amino acid sequence being at least 70%, optionally at least about 80%, preferably at least about 85%, more preferably at least about 90% and most preferably at least about 95% homologous to the sequence VGFLHSSHDVNKEASVIMLFSGLK (SEQ ID NO:81) of Z40018_1_P17 (SEQ ID NO:66).

The localization of the variant protein was determined according to results from a number of different software programs and analyses, including analyses from SignalP and other specialized programs. The variant protein is believed to be secreted.

Variant protein Z40018_1_P17 (SEQ ID NO:66) also has the following non-silent SNPs (Single Nucleotide Polymorphisms) as listed in Table 19, (given according to their position(s) on the amino acid sequence, with the alternative amino acid(s) listed; the last column indicates whether the SNP is known or not; the presence of known SNPs in variant protein Z40018_1_P17 (SEQ ID NO:66) sequence provides support for the deduced sequence of this variant protein according to the present invention).

TABLE 19

Amino acid mutations

| SNP position(s) on amino acid sequence | Alternative amino acid(s) | Previously known SNP |
|---|---|---|
| 111 | V -> | No |
| 230 | T -> A | No |
| 292 | M -> V | No |
| 322 | V -> A | No |
| 410 | E -> G | No |
| 715 | T -> | No |

The glycosylation sites of variant protein Z40018_1_P17 (SEQ ID NO:66), as compared to the known protein Hepatocyte growth factor receptor precursor (SEQ ID NO:34), are described in Table 20 (given according to their position(s) on the amino acid sequence in the first column; the second column indicates whether the glycosylation site is present in the variant protein; and the last column indicates whether the position is different on the variant protein).

TABLE 20

Glycosylation site(s)

| Position(s) on known amino acid sequence | Present in variant protein? | Position(s) on variant protein |
|---|---|---|
| 45 | Yes | 45 |
| 106 | Yes | 106 |
| 149 | Yes | 149 |
| 202 | Yes | 202 |
| 399 | Yes | 399 |
| 405 | Yes | 405 |
| 607 | Yes | 607 |
| 635 | Yes | 635 |
| 785 | Yes | 785 |
| 879 | No | |
| 930 | No | |

The phosphorylation sites of variant protein Z40018_1_P17 (SEQ ID NO:66), as compared to the known protein, are described in Table 21 (given according to their position(s) on the amino acid sequence in the first column; the second column indicates whether the phosphorylation site is present in the variant protein; and the last column indicates whether the position is different on the variant protein).

TABLE 21

Phosphorylation site(s)

| Position(s) on known amino acid sequence | Present in variant protein? | Position(s) on variant protein |
|---|---|---|
| 1235 | No | |

The variant protein has the following domains, as determined by using InterPro. The domains are described in Table 22:

TABLE 22

InterPro domain(s)

| Domain description | Analysis type | Position(s) on protein |
|---|---|---|
| Plexin | HMMPfam | 519-562 |
| Plexin | HMMSmart | 519-562 |
| Semaphorin | HMMPfam | 55-500 |

TABLE 22-continued

| | InterPro domain(s) | |
|---|---|---|
| Domain description | Analysis type | Position(s) on protein |
| Cell surface receptor IPT | HMMPfam | 563-655, 657-739, 742-836 |
| Cell surface receptor IPT | HMMSmart | 562-655, 656-739, 741-836 |
| Semaphorin | HMMSmart | 52-496 |

Variant protein Z40018_1_P17 (SEQ ID NO:66) is encoded by Z40018_1_T15 (SEQ ID NO:48), for which the coding portion starts at position 188 and ends at position 2842. The transcript also has the following SNPs as listed in Table 23 (given according to their position on the nucleotide sequence, with the alternative nucleic acid listed; the last column indicates whether the SNP is known or not; the presence of known SNPs in variant protein Z40018_1_P17 (SEQ ID NO:66) sequence provides support for the deduced sequence of this variant protein according to the present invention).

TABLE 23

| Nucleic acid SNPs | | |
|---|---|---|
| SNP position(s) on nucleotide sequence | Alternative nucleic acid(s) | Previously known SNP |
| 71 | A -> T | Yes |
| 72 | T -> A | Yes |
| 331 | G -> A | Yes |
| 519 | T -> | No |
| 875 | A -> G | No |
| 1061 | A -> G | No |
| 1152 | T -> C | No |
| 1416 | A -> G | No |
| 2131 | A -> G | Yes |
| 2330 | A -> | No |

Novel splice variants of Met encode a truncated Met, a soluble receptor, which contains the extracellular portion of the protein but lacks the transmembrane and cytoplasmic domains, as shown in FIG. 3. FIG. 3 shows schematic mRNA and protein structure of Met. "WT 1390aa" represents the known Met receptor protein kinase (SEQ ID NO:34). "rSEMA" represents the recombinant SEMA domain of the Met extracellular region (Kong-Beltran et al., 2004, Cancer Cell 6, 75-84), SEQ ID NO:39. "P588" represents the Met-588 variant of the present invention (SEQ ID NO: 1 and 36, for mRNA and protein, respectively). "P934" represents the Met-934 variant previously disclosed in U.S. patent application Ser. No. 10/764,833, published as US 2004/0248157 assigned to the applicant of the present invention (SEQ ID NO:2 and 38, for mRNA and protein, respectively). "P877" represents the Met-877 variant of the present invention (SEQ ID NO: 3 and 37, for mRNA and protein, respectively). "P885" represents the Met-885 variant previously disclosed in WO 05/071059 and U.S. patent application Ser. No. 11/043,591 assigned to the applicant of the present invention (SEQ ID NO:48 and 66, for mRNA and protein, respectively). Exons are represented by boxes with upper left to lower right fill, while introns are represented by two headed arrows. Proteins are shown in boxes with upper right to lower left fill. The unique regions are represented by white boxes with dashed frame. SEMA domain, transmembrane domain (TM), and immunoglobulin-plexin-transcription factor domain (IPT) are identified accordingly.

Example 2

Met-934 Variant Transcript Validation, Cloning, Protein Production and Purification This Example describes cloning of Met-934 variant (SEQ ID NO:2) in baculovirus and in mammalian expression systems. Different expression systems were used to check expression efficiency, amount of expressed proteins produced and also to characterize the expressed proteins.

Full Length Validation of Met-934:

mRNA from the ES2 cell line was isolated and treated with DNAse I, followed by reverse transcription using random hexamer primer mix and Superscript™.

The Met-934 variant (SEQ ID NO:2) was validated by RT-PCR amplification using Expand High Fidelity PCR System (Roche #3300242) under the following conditions: 2.5 µl—×10 buffer; 5 µl—cDNA; 2 µl—dNTPs (2.5 mM each); 0.5 µl—DNA polymerase; 14 µl—H$_2$O; and 0.5 µl—of each primer (25 µM) in a total reaction volume of 25 µl;

Primers including Met-934 splice variant specific sequences are listed in Table 24 below.

TABLE 24

| Primer ID: | Sequence |
|---|---|
| MetT9For (RT) (SEQ ID NO: 41) | 5' - CTGGGCACCGAAAGATAAAC - 3' |
| MetT9UT - Rev (SEQ ID NO: 42) | 5' - GTTGATGAGCCAAAACCCAC - 3' |

PCR products were run in a 1% agarose gel, TAEX1 solution at 150V, and extracted from gel using QiaQuick™ gel extraction kit (Qiagen™).

The extracted DNA product served as a DNA template for PCR reaction entitled for the cloning Met-934 into mammalian expression vectors.

Cloning and Expression of Met-934-Fc into Mammalian Expression Vector:

The Met-934 was produced as an Fc-fused protein (SEQ ID NO:68). The Met-934 Fc sequence was codon optimized (SEQ ID NO:67) to boost protein expression in mammalian system. The optimized gene was synthesized by GeneArt (Germany) by using their proprietary gene synthesis technology with the addition of DNA sequences encoding human IgG1 Fc at the 3' of the DNA fragment. The gene synthesis technology is a proprietary robust nucleic acid manufacturing platform that makes double stranded DNA molecules. The resultant optimized nucleic acid sequences (SEQ ID NO:67) is shown in FIG. 5A, where the bold part of the nucleotide sequence shows the relevant ORF (open reading frame) including the tag sequence, while the amino acid sequence (SEQ ID NO:68) is shown in FIG. 5B, where the bold part of the sequence is the Fc tag. This protein tag sequences was added so that the expressed protein can be more easily purified.

The DNA fragment was cloned into EcoRI/NotI sites (underlined portions of the nucleotide sequence shown in FIG. 5A) in pIRESpuro3 (Clontech, cat # PT3646-5) and the sequence was verified.

Transfection of M 934 Fc Construct:

The Met-934 Fc construct was transfected into HEK-293T cells (ATCC # CRL-11268) as follows. One day prior to transfection, one well from a 6 well plate was plated with 500,000 cells in 2 ml DMEM. At the day of transfection, the FuGENE 6 Transfection Reagent (Roche, Cat#: 1-814-443) was warmed to ambient temperature and mixed prior to use. 6 µl of FuGENE Reagent were diluted into 100 µl DMEM (Dulbecco's modified Eagle's medium; Biological Industries, Cat#: 01-055-1A). Next, 2 micrograms of construct DNA were added. The contents were gently mixed and incubated at room temperature (RT) for 15 minutes. 100 µl of the complex mixture was added dropwise to the cells and swirled. The cells were incubated overnight at 37° C. with 5% $CO_2$. Following about 48 h, transfected cells were split and subjected to antibiotic selection with 5 microgram/ml puromycin. The surviving cells were propagated for about three weeks.

Expression Analysis of Met-934 Fc:

Met-934 Fc stable pools were analyzed by Western blot analysis using anti IgG antibodies. The supernatant of the puromycin resistant cells expressing the Met-934 Fc recombinant protein (SEQ ID NO:68) was collected and bound to protein A beads as follows. 50 ul Protein A sepharose (Amersham cat# 17-5280-04) was washed twice with water and twice with 100 mM Tris pH 7.4. The beads were centrifuged for 2 min in 5500×g. Next, 1 ml of sample was loaded on the beads, and the sample was gently shaked for 45 min. at RT. Then, the beads were spinned down and washed with 100 mM Tris pH 7.4, and the proteins were eluted with 50 ul SDS sample buffer containing 100 mM Citrate Phosphate pH 3.5. The eluted proteins were incubated for 3 min, at 100° C. and loaded on a 12% SDS-PAGE gel.

Following electrophoresis, proteins on the gel were transferred to nitrocellulose membranes for 60 min at 35V using Invitrogen's transfer buffer and X-Cell II blot module. Following transfer, the blots were blocked with 5% skim milk in wash buffer (0.05% Tween-20 in PBS) for at least 60 minutes at room temperature with shaking. Following blocking, the blots were incubated for 60 min at room temperature with a commercially available anti IgG HRP antibody (SIGMA, Cat# A0170) diluted in 1/5 blocking buffer, followed by washing with wash buffer. Next, the blot incubated with anti IgG was immersed in ECL solution (Enhanced Chemiluminescence) and detection was performed according to the manufacturer's instructions (Amersham; Cat # RPN2209).

Figure 6:
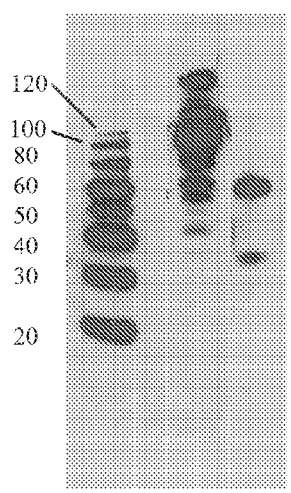
FIG. 6 shows the Western blot result, demonstrating stable Met-934-Fc expression using anti IgG antibodies.

The Western blot result, demonstrating stable Met-934-Fc (SEQ ID NO:68) expression using anti IgG antibodies, is shown in FIG. 6. Lane 1 represents Molecular weight marker (MagicMark LC5602); lane 4 represents Met-934 Fc (SEQ ID NO:68). lane 10 represents Fc control (~100 ng).

Cloning of Met-885 Variant:

Met-885 was cloned in two forms, one with a StrepHis C' terminus tag (SEQ ID NO:74) and the second with IgG1 Fc tag (SEQ ID NO:76).

Met885_Fc was subcloned from the codon optimized Met934 pIRESpuro clone, where its last 24 aas were synthesized by four sequentional PCR reactions according to the following description:

Met934 pIRESpuro DNA was used as a template in the first PCR reaction while the next three PCR reactions were done using the upstream PCR product (by tooth pick) as a template.

The following primer pairs were used:
PCR1—For (100-560) (SEQ ID NO:69) and Rev1 (100-586) (SEQ ID NO:70)
PCR2—For (100-560) (SEQ ID NO:69) and Rev2 (100-587) (SEQ ID NO:71)
PCR3—For (100-560) (SEQ ID NO:69) and Rev3 (100-588) (SEQ ID NO:72)
PCR4—For (100-560) (SEQ ID NO:69) and Rev4 (100-562) (SEQ ID NO:73)

The PCR primer sequences are listed in table 25 below.

TABLE 25

| Primer's name | sequence |
|---|---|
| For (100-560) (SEQ ID NO: 69) | 5' TGGACGGCATCCTGAGCAAG 3' |
| Rev1 (100-586) (SEQ ID NO: 70) | 5' GCTGCTGTGCAGAAAGCCCACCTTGATCTCCAGCACGTTCTC3' |
| Rev2 (100-587) (SEQ ID NO: 71) | 5' GGCCTCTTTGTTCACGTCGTGGCTGCTGTGCAGAAAGCCC3' |
| Rev3 (100-588) (SEQ ID NO: 72) | 5' GCTGAACAGCATGATCACGCTGGCCTCTTTGTTCACGTCGTGG3' |
| Rev4 (100-562) (SEQ ID NO: 73) | 5' CGCTTCGAACTTCAGGCCGCTGAACAGCATGATCAC3' |

The amplification was done using 18 ng of DNA template and Platinum Pfx DNA polymerase (Invitrogen cat#11708-039), under the following conditions: 1 ul—of each primer (10 uM) plus 35 ul—$H_2O$ were added into 5 ul Amplification buffer, 5 ul enhancer solution 0.5 ul MgSO4 (50 mM) 1 ul dNTPs and 1 ul Pfx (205u/ul) tube with a reaction program of 3 minutes at 94° C.; 25 cycles of: [30 seconds at 94° C., 30 seconds at 53° C., 30 seconds at 72° C.] and 10 minutes at 72° C. At the end of each PCR amplification, products were analyzed on agarose gels stained with ethidium bromide and visualized with UV light. The PCR products were then served as a template for the next PCR reaction. The fourth PCR product was digested with BsrGI and BstBI and extracted from agarose gel using QiaQuick™ gel extraction kit (Qiagen, Cat #28706). Next, Met934 pIRESpuro DNA was digested with NheI and BsrGI and 2560 bp fragment was extracted from agarose gel. The two DNA fragments were then ligated into Met934_Fc pIRESpuro previously digested with NheI and BstBI to give the product Met885_Fc pIRESpuro. Positive colonies were selected and sequenced by direct sequencing in order to exclude mutations due to the PCR reactions (Hy-Labs, Israel).

Met885 StrepHis was subcloned as follows: Met885_Fc pIRESpuro was digested with BmgBI and a 6868 bp fragment was extracted from agarose gel using QiaQuick™ gel extraction kit (Qiagen, Cat #28706), in addition, Met934 pIRESpuro was also digested with BmgBI and a 1016 bp fragment was extracted from agarose gel and ligated to the previously digested Met885 Fc pIRESpuro. Positive clones were selected and sequenced.

FIG. 7A shows the optimized nucleotide sequences of Met885 StrepHis (SEQ ID NO:74) and FIG. 8A shows the optimized nucleotide sequences of Met885_Fc (SEQ ID NO:76). FIGS. 7B and 8B show the respective protein sequences of Met885 StrepHis (SEQ ID NO:75) and Met885_Fc (SEQ ID NO:77). DNA sequences in bold show the relevant ORFs (open reading frames) including the underlined tags (StrepHis or Fc) sequences.

Transfection of Met-885 Constructs

The Met885 constructs were transfected into HEK-293T cells (ATCC # CRL-11268) as follows. One day prior to transfection, one well from a 6 well plate was plated with 500,000 cells in 2 ml DMEM. At the day of transfection, the FuGENE 6 Transfection Reagent (Roche, Cat#: 1-814-443) was warmed to ambient temperature and mixed prior to use. 6 µl of FuGENE Reagent were diluted into 100 µl DMEM (Dulbecco's modified Eagle's medium; Biological Industries, Cat#: 01-055-1A). Next, 2 micrograms of construct DNA were added. The contents were gently mixed and incubated at room temperature (RT) for 15 minutes. 100 µl of the complex mixture was added dropwise to the cells and swirled. The cells were incubated overnight at 37° C. with 5% $CO_2$. Following about 48 h, transfected cells were split and subjected to antibiotic selection with 5 microgram/ml puromycin. The surviving cells were propagated for about three weeks.

Expression Analysis

Met-885 stable pools were analyzed by Western blot analysis using anti His and anti IgG antibodies. The supernatants of the Met-885_Fc puromycin resistant cells were collected and were bound to protein A beads as follows: 50 ul Protein A sepharose (Amersham cat# 17-5280-04) was washed twice with water and twice with 100 mM Tris pH 7.4. The beads were centrifuged for 2 min in 4000 rpm. Next, 1 ml sample was loaded on the beads, and gently shaked for 45 min. at RT. Then, the beads were spinned down and washed with 100 mM Tris pH 7.4, and the protein was eluted with 50 ul SB containing 100 mM Citrate Phosphate pH 3.5. The eluted protein was incubated for 3 min, at 100° C. and loaded on a 12% SDS-PAGE. Following electrophoresis, proteins on the gel were transferred to nitrocellulose membranes for 60 min at 35 V using Invitrogen's transfer buffer and X-Cell II blot module. Following transfer, the blot was blocked with 5% skim milk in wash buffer (0.05% Tween-20 in PBS) for at least 60 minutes at room temperature with shaking. Following blocking, the blot was incubated for 60 min at room temperature with a commercially available anti IgG HRP antibody (SIGMA, Cat# A0170) diluted in ⅕ blocking buffer, followed by washing with wash buffer and incubation with the secondary antibody Goat anti mouse HRP (Jackson, Cat# 115-035-146) diluted 1:25,000 in 1/5 blocking buffer. Next, ECL (Enhanced Chemiluminescence) detection was performed according to the manufacturer's instructions (Amersham; Cat # RPN2209).

Figure 9:
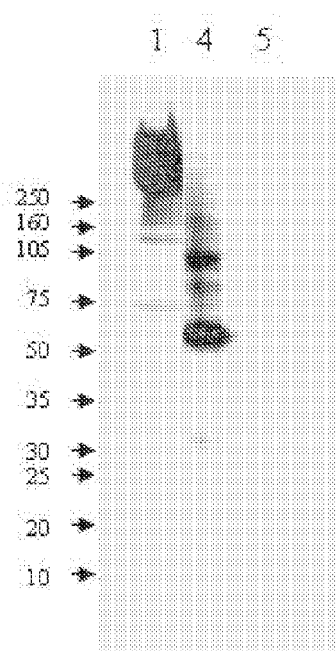
FIG. 9 shows Western blot results, demonstrating stable Met885-Fc (SEQ ID NO:77) expression using anti IgG (lane 1). 100 ng of Fc control is shown in lane 4.

The Western blot results, demonstrating stable Met885_Fc (SEQ ID NO:77) expression using anti IgG, is shown in FIG. 9. FIG. 9 demonstrates the expression of Met885 Fc (SEQ ID NO:77) (lane 1). 100 ng of Fc control is shown in lane 4.

Binding of Met885 StrepHis (SEQ ID NO:75) to Ni-NTA beads was done as follows: 50 ul Ni-NTA agarose (Qiagen #1018244) were washed twice with water and twice with ×1 IMIDAZOLE buffer (Biologicals industries #01-914-5A) and then centrifuged for 5 min at 950×g. 1 ml of cell supernatant was added to the beads and the samples were gently shaken for 45 min. at RT. Then, the samples were spun down and washed with ×1 IMIDAZOLE buffer, and were centrifuged again at 950×g for 5 min. The samples were eluted with 50 ul SDS sample buffer incubated for 5 min. at 100° C. and loaded on a 12% SDS-PAGE.

Following electrophoresis, proteins on the gel were transferred to nitrocellulose membrane for 60 min at 35 V using Invitrogen's transfer buffer and X-Cell II blot module. Following transfer, the blots were blocked with 5% skim milk in wash buffer (0.05% Tween-20 in PBS) for at least 60 min. at room temperature with shaking. Following blocking, the blots were incubated for 60 min at room temperature with a commercially available mouse anti Histidine Tag, (Serotec, Cat# MCA1396) diluted in 1/5 blocking buffer followed by washing with wash buffer and incubation with the secondary antibody Goat anti Mouse HRP, (Jackson, Cat# 115-035-146) diluted 1:25,000 in 1/5 blocking buffer. Next, ECL (Enhanced Chemiluminescence) detection was performed according to the manufacturer's instructions (Amersham; Cat # RPN2209).

Figure 10:
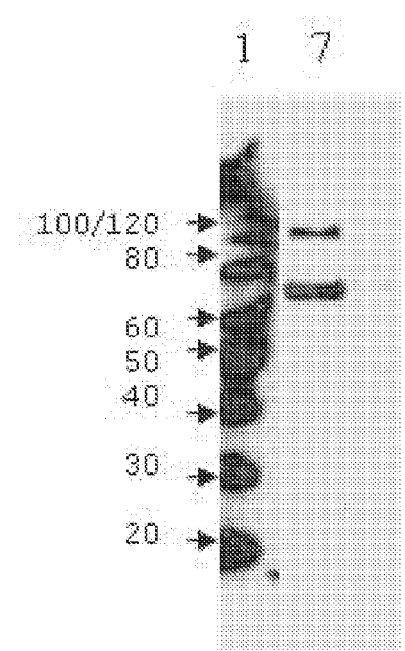
FIG. 10 shows Western blot results, demonstrating stable Met885_StrepHis (SEQ ID NO:75) expression using anti His (lane 7). Molecular weight marker (Rainbow AMERSHAM RPN800) is shown in lane 1.

The Western blot results, demonstrating stable Met885_StrepHis (SEQ ID NO:75) expression using anti His, is shown in FIG. 10. FIG. 10 demonstrates the expression of Met885 StrepHis (SEQ ID NO:75) (lane 7). Molecular weight marker (Rainbow AMERSHAM RPN800) is shown in lane 1.

Example 3

Figure 11:
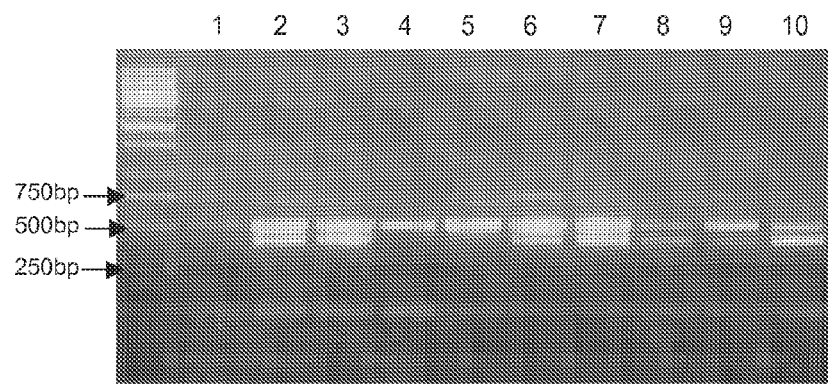
FIG. 11 shows the RT-PCR results of Met-877 (SEQ ID NO:3) variant. The various lanes show RT-PCR products on cDNA prepared from RNA extracted from the following sources: lanes 1-3 colon cell lines, as follows: lane 1—caco; lane 2—CG22 from Ichilov; lane 3—(CG224); lane 4 lung cell line H1299; lane 5 ovary cell line ES2, lane 6 breast cell line MCF7; lane 7 lung tissue A609163, Biochain; lanes 8-9 breast tissues A605151 and A609221, Biochain, respectively; lane 10—293 cell line.

Met-877 Variant Transcript Validation, Cloning, Protein Production and Purification Validation of Met-877 Variant Transcript (SEQ ID NO:3):

Met-877 transcript (SEQ ID NO:3) was validated using a unique tail reverse primer (primer sequences are given in Table 26). The existence of the transcript was checked in the following tissues: colon, lung, ovary and breast, as demonstrated in FIG. 11. FIG. 11 shows the PCR results of Met-877 variant (SEQ ID NO:45). Lanes 1-3 represent cDNA prepared from RNA extracted from colon cell lines, as follows: lane 1—caco; lane 2-CG22; lane 3—CG224; lane 4 represents cDNA prepared from RNA extracted from lung cell line H1299; lane 5 represents cDNA prepared from RNA extracted from ovary cell line ES2, lane 6 represents cDNA prepared from RNA extracted from breast cell line MCF7; lane 7 represents cDNA prepared from RNA extracted from lung tissue A609163, Biochain; lanes 8-9 represent cDNA prepared from RNA extracted from breast tissues A605151 and A609221, Biochain, respectively; lane 10 represents cDNA prepared from RNA extracted from 293 cell line. As demonstrated in FIG. 7, the Met-877 transcript was detected as a unique band only in cDNA prepared from RNA extracted from lung H1299 and ovary ES2 cell lines. The experimental method used is described below. H1299 lung and ES2 ovary RNA was obtained from Ichilov. Total RNA samples were treated with DNaseI (Ambion Cat # 1906).

RT PCR:

Purified RNA (1 µg) was mixed with 150 ng Random Hexamer primers (Invitrogen) and 500 µM dNTP in a total volume of 15.6 µl. The mixture was incubated for 5 min at 65°

C. and then quickly chilled on ice. Thereafter, 5 µl of 5× SuperscriptII first strand buffer (Invitrogen), 2.4 µl 0.1M DTT and 40 units RNasin (Promega) were added, and the mixture was incubated for 10 min at 25° C., followed by further incubation at 42° C. for 2 min. Then, 1 µl (200 units) of SuperscriptII (Invitrogen) was added and the reaction (final volume of 25 µl) was incubated for 50 min at 42° C. and then inactivated at 70° C. for 15 min. The resulting cDNA was diluted 1:20 in TE buffer (10 mM Tris pH=8, 1 mM EDTA pH=8).

The table 26 below shows primers for the reaction and PCR conditions. Orientation for the primers is given as F (forward) or R (reverse).

TABLE 26

| Oligonucleotide sequence (ID) | Orientation | Nucleotide coordinates on target sequence |
|---|---|---|
| 5' CCAGCCCAAACCATTTCAAC - 3' (100-71 MET n24 For (SEQ ID NO: 43)) | F | 2321-2340 |
| 5'GCGGATCCAGCTATGAAGTCAATTAAGTTTGAG-3' (100-72 MET877 n30 Rev (SEQ ID NO: 44)) | R | 2807-2831 |

PCR Amplification and Analysis:

cDNA (5 ul), prepared as described above (RT PCR), was used as a template in PCR reactions. The amplification was done using AccuPower PCR PreMix (Bioneer, Korea, Cat# K2016), under the following conditions: 1 ul—of each primer (10 uM) plus 13 ul —$H_2O$ were added into AccuPower PCR PreMix tube with a reaction program of 5 minutes at 94° C.; 35 cycles of: [30 seconds at 94° C., 30 seconds at 55° C., 60 seconds at 72° C.] and 10 minutes at 72° C. At the end of the PCR amplification, products were analyzed on agarose gels stained with ethidium bromide and visualized with UV light. The PCR reaction yielded one major band. The PCR products were extracted from the gel using QiaQuick™ gel extraction kit (Qiagen, Cat #28706). The extracted DNA products were sequenced by direct sequencing using the gene specific primers described above (Hy-Labs, Israel). The resulted Met-877 PCR product sequence (SEQ ID NO:XXX) is shown in FIG. 12. The sequences of the primers are shown in bold.

Cloning of Met-877 Variant:

The Met-877 sequence was codon optimized to boost protein expression in mammalian system (SEQ ID NO:46). The optimized gene was synthesized by GeneArt (Germany) by using their proprietary gene synthesis technology with the addition of DNA sequences encoding the StrepII and His tags at the 3' of the DNA fragment. The gene synthesis technology is a proprietary robust nucleic acid manufacturing platform that makes double stranded DNA molecules. The resultant optimized nucleic acid sequences (SEQ ID NO:46) is shown in FIG. 13A, where the bold part of the nucleotide sequence shows the relevant ORF (open reading frame) including the tag sequence, while the amino acid sequence (SEQ ID NO:47) is shown in FIG. 13B, where the bold part of the sequence is the Strep tag, following the amino acid Pro (Strep II tag: WSHPQFEK;) and His tag (8 His residues—HHHH-HHHH;) sequences which are separated by a linker of two amino acids (Thr-Gly). The 8 His tag is followed by Gly-Gly-Gln. These protein tag sequences were added so that the expressed protein can be more easily purified.

Figure 14:
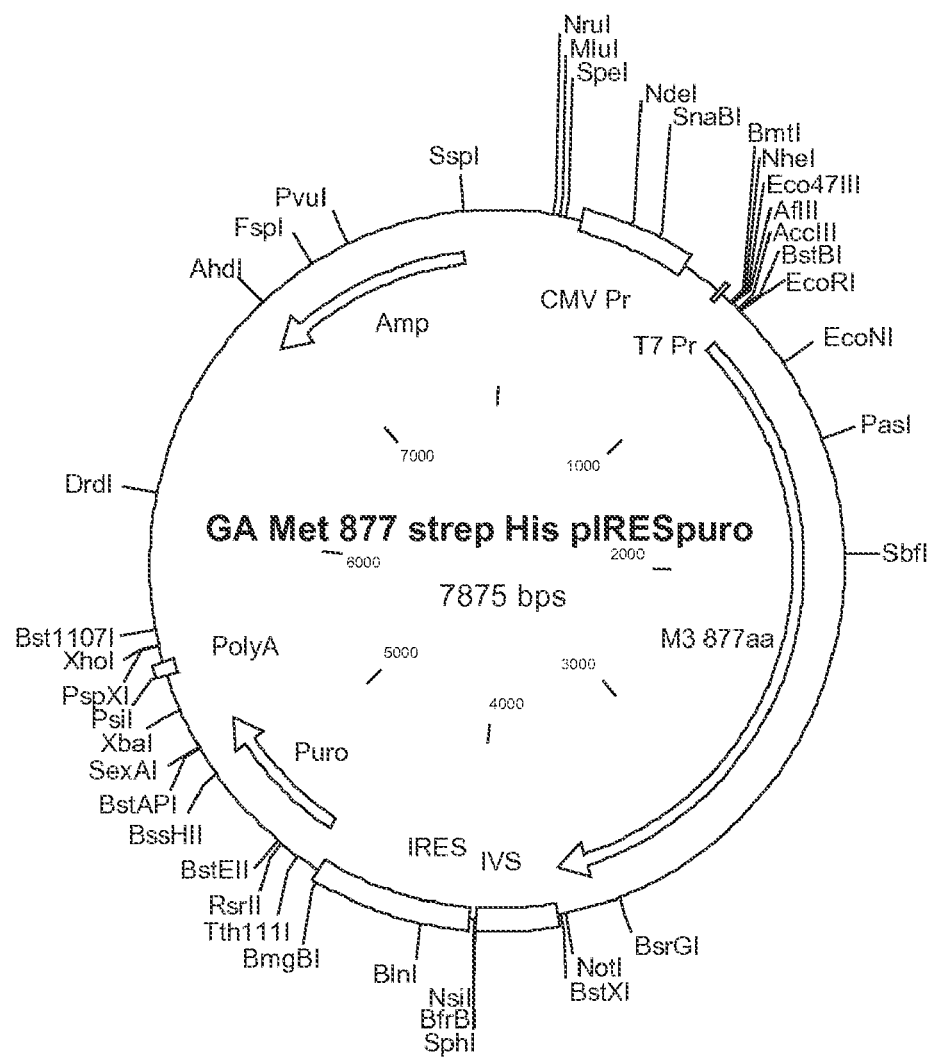
FIG. 14 shows a schematic diagram of the pIRESpuro3 construct containing the Met-877 DNA fragment.

The DNA fragment was cloned into EcoRI/NotI sites (underlined portions of the nucleotide sequence shown in FIG. 13A) in pIRESpuro3 (Clontech, cat # PT3646-5) and the sequence was verified. FIG. 14 shows a schematic diagram of the resultant construct.

Expression of Met-877 Variant Protein:

The construct was transfected to HEK-293T cells (ATCC catalog number CRL-11268) as follows. One day prior to transfection, one well from a 6 well plate was plated with 500,000 cells in 2 ml DMEM. At the day of transfection, the FuGENE 6 Transfection Reagent (Roche, Cat#: 1-814-443) was warmed to ambient temperature and mixed prior to use. 6 µl of FuGENE Reagent were diluted into 100 µl DMEM (Dulbecco's modified Eagle's medium; Biological Industries, Cat#: 01-055-1A). Next, 2 micrograms of construct DNA were added. The contents were gently mixed and incubated at room temperature (RT) for 15 minutes. 100 µl of the complex mixture was added dropwise to the cells and swirled. The cells were incubated overnight at 37° C. with 5% CO2. Following about 48 h, transfected cells were split and subjected to antibiotic selection with 5 microgram/ml puromycin. An empty pIRESpuro vector (containing no insert) was transfected in parallel into HEK-293T cells, to generate "mock" expressing cells.

The surviving cells were propagated for about three weeks. Expression of the desired protein was verified by Western Blot (lane 5 of FIG. 15) according to the following method.

Figure 15:
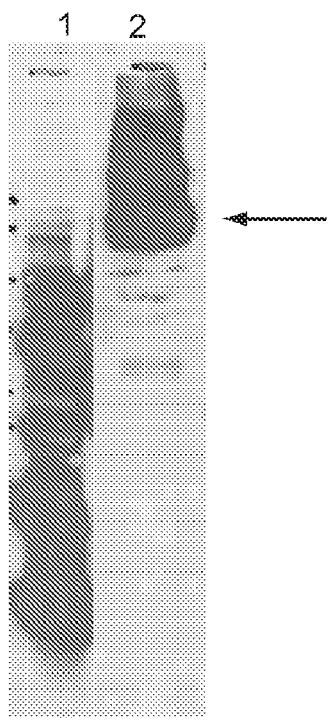
FIG. 15 shows a Western Blot analysis, demonstrating the expression of the cloned Met-877 (SEQ ID NO:47) protein. Lane 1 represent molecular weight marker.

The supernatants of the puromycin resistant cells were concentrated 16 fold with TCA (1 ml conditioned medium was concentrated into 60 ul). 25 ul of the solution was loaded on a 12% SDS-PAGE gel. Following electrophoresis, proteins on the gel were transferred to nitrocellulose membranes for 60 min at 35 V using Invitrogen's transfer buffer and X-Cell II blot module. Following transfer, the blots were blocked with 5% skim milk in wash buffer (0.05% Tween-20 in PBS) for at least 60 min. at room temperature with shaking. Following blocking, the blots were incubated for 60 min at room temperature with a commercially available anti His antibody (Serotec, Cat. # MCA1396) diluted in ⅕ blocking buffer, followed by washing with wash buffer and incubating for another 60 min at room temperature with respective peroxidase-conjugated antibodies. Next, the blots were washed again with wash buffer, followed by ECL (Enhanced Chemiluminescence) detection performed according to the manufacturer's instructions (Amersham; Cat # RPN2209) The results are shown in FIG. 15 lane 2. Lane 1 is the molecular weight marker.

Production of Met-877 Protein:

In order to produce sufficient amounts of the protein, the cells were further propagated in serum-free medium as described below. HEK293T cells expressing Met-877 according to the present invention are taken from a T-80 flask containing serum supplemented medium after trypsinization, and were transferred into shake flasks containing serum free medium (EX-CELL293, JRH) supplemented with 4 mM glutamine and selection antibiotics (5 ug/ml puromycin). Cells were propagated in suspension in shake flasks at 37° C., 100-120 rpm agitation and culture volume was increased by sequential passages. Production-phase growth was carried out in a stirred-tank bioreactor (Applikon) operated in perfusion mode. Seeding cell density was about 1.5 10$^6$ cells/ml and during production cell density was kept at 8-16 10$^6$ cells/ml, fed at perfusion rate of 0.7-1.4 replacements per day with the same medium as detailed above.

HEK-293T cells transfected previously with empty pIRE-Spuro vector were propagated similarly, in order to produce mock preparation.

Met-877 Protein Purification

Met-877 protein (SEQ ID NO:47) according to the present invention was purified by affinity chromatography using Ni-NTA (nickel-nitrilotriacetic acid) resin. This type of chromatography is based on the interaction between a transition Ni$^{2+}$ ion immobilized on a matrix and the histidine side chains of His-tagged proteins. His-tag fusion proteins can be eluted from the matrix by adding free imidazole for example, as described below. The purification method preferably uses the Strep/6× Histidine system (double-tag) to ensure purification of recombinant proteins at high purity under standardized conditions. A protein according to the present invention, carrying the 8× Histidine-tag and the Strep-tag II at the C-terminus, can be initially purified by IMAC (Immobilized metal ion affinity chromatography) based on the 8× Histidine-tag-Ni-NTA interaction. After elution from the Ni-NTA matrix with imidazole, the protein (which also carries the Strep-tag II epitope) can be loaded directly onto a Strep-Tactin matrix. No buffer exchange is required. After a short washing step, the recombinant protein can be eluted from the Strep-Tactin matrix using desthiobiotin. Met-877 Purification Method:

Met-877 protein (SEQ ID NO:47) according to the present invention was purified by affinity chromatography using Ni-NTA resin, according to the following protocol:

6 L of culture was concentrated to 670 ml by ultrafiltration. pH was adjusted to 8.0 by adding 3 ml of Tris 1 M pH 8.5. Imidazole was added to the sample to final concentration of 10 mM and the sup was filtered through a 0.22 um filter (Millipore, Cat# SCGP U11 RE);). The supernatant was transferred to 3×250 ml centrifuge tubes. Six ml of Ni-NTA Superflow beads (Ni-NTA Superflow®, QIAGEN) were equilibrated with 10 column volumes of WFI (Teva Medical #AWF7114) and 10 column volumes of Buffer A (50 mM NaH$_2$PO$_4$, 300 mM NaCl, 10 mM imidazole, pH 8.0). The beads were added to the filtered supernatant, and the tube was incubated overnight on a rocking platform at 4° C.

The Ni-NTA beads in the 3×250 ml centrifuge tube were separated from the supernatant and packed in a 6 ml column of Ni-NTA Superflow. Beads were washed with buffer A at a flow rate of 1 column volume per minute, until O.D 280 nm was lower than 0.005. The Met-877 protein was eluted with buffer B (50 mM NaH$_2$PO$_4$, 300 mM NaCl, 250 mM imidazole, pH 8.0) at a flow rate not higher than 1 ml/min. Imidazole was removed from the purified protein by dialysis against 1×PBS (Dulbecoo's Phosphate Buffered Saline, concentrate ×10, Biological Industries, Cat # 020235A) at 4° C. The protein was aliquoted with or without 0.1% BSA and stored at –70° C.

Figure 16:
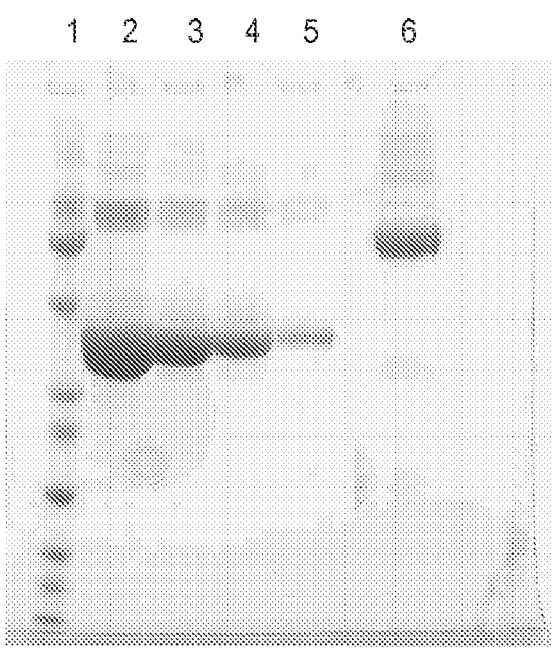
FIG. 16 demonstrates the analysis of the purified Met-877 His tag (SEQ ID NO:47) protein by SDS-PAGE stained by Coomassie (lane 6). Lane 1 represent molecular weight marker. Lanes 2-5 represent BSA in different concentrations for quantity reference.
Figure 17:
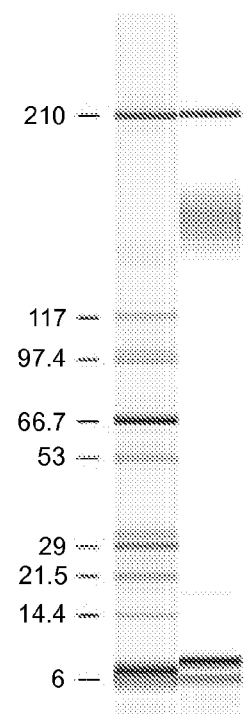
FIG. 17 demonstrates the analysis of the purified Met-877 His tag (SEQ ID NO:47) protein by the Bioanalyzer (Agilent).

The purified protein was analyzed by SDS-PAGE stained by Coomassie (lane 6 in FIG. 16) and by the Bioanalyzer (Agilent) (lane 11 in FIG. 17), and found to be approximately 98% pure. The identity of the protein was verified by LC-MS/MS.

Culture supernatant from mock cells underwent the same purification protocol. The same fractions were collected during "elution" from the column, dialyzed similarly against 1×PBS and aliquoted, either with or without 0.1% BSA and stored at –70° C. These fractions are referred to as "mock".

Met 877 Fc Cloning:

The Met-877 Fc sequence was codon optimized to boost protein expression in mammalian system. The optimized gene was synthesized by GeneArt (Germany) by using their proprietary gene synthesis technology with the addition of DNA sequences encoding human IgG1 Fc at the 3' of the DNA fragment. The gene synthesis technology is a proprietary robust nucleic acid manufacturing platform that makes double stranded DNA molecules. The resultant optimized nucleic acid sequences (SEQ ID NO:78) is shown in FIG. 18A, where the bold part of the nucleotide sequence shows the relevant ORF (open reading frame) including the tag sequence, while the amino acid sequence (SEQ ID NO:79) is shown in FIG. 18B, where the bold part of the sequence is the Fc tag. This protein tag sequences was added so that the expressed protein can be more easily purified.

The DNA fragment was cloned into EcoRI/NotI sites (underlined portions of the nucleotide sequence shown in FIG. 18A) in pIRESpuro3 (Clontech, cat # PT3646-5) and the sequence was verified.

Met-Fc Variant Protein Production and Purification:

Description of Propagation Process

In order to produce sufficient amounts of the proteins, cells expressing Met-877 Fc (SEQ ID NO:79), Met-934 Fc (SEQ ID NO:68) or Met-885 Fc (SEQ ID NO:77) were propagated to a final volume of 2000 ml. When the cells reached a density of about 2.7×106 cells/ml, the cultures were harvested by centrifugation and the sup filtered through a 0.22 um filter and used for protein purification. Harvested culture medium was concentrated approximately 5-10 fold and filtered through a 0.22 um filter.

Purification:

Met variants were purified using affinity chromatography with Protein A. The starting culture supernatant (sup) containing the Met variants was pH adjusted to 7.4 with 2M Tris-HCl pH 8.5 (approximately 2.5% of the final volume), and filtered through 0.22 μm filter. 1 ml nProtein-A sepharose previously equilibrated with 10 CV of buffer B (100 mM Citrate-Phosphate, pH 3.5) and 15 CV of buffer A (100 mM Tris.HCl, pH 7.5) was added to the sup and incubated overnight on a rolling platform at 4° C. The next day, 0.5/5 cm column was packed with the beads. The packed Protein-A column was connected to the FPLC AKTA at the "Wash Unbound" stage, at the program: "Protein A 1 ml Fc Purification". Wash was carried out with buffer A—up to 80 CV until O.D 280 nm is lower than 0.01 mAU. The elution step was performed with buffer B. The protein was expected to elute in up to 5 CV, represented as the peak of the chromatography. Elution was collected in 1 ml fractions and pH of the elution was immediately (within 5 min) neutralized with addition of 1/10 volume of buffer C (2M Tris, pH 8.5) to each elution fraction tube. The column was regenerated and stored according to the manufacturer's instructions. Collected elution fractions were analyzed by SDS-PAGE to identify the protein-rich fractions (NuPage Bis-Tris 12% gels, MES-SDS Running buffer). SDS-PAGE was followed by Coomassie staining (Simply Blue SafeStain-Invitrogen; results not shown).

Fractions containing the protein (analyzed by SDS-PAGE) were pooled and dialyzed twice against 5 L buffer D (1×PBS)

4-18 hrs each time, using Dialysis Membrane cassette, 10 kDa cutoff (PIERCE). BSA was added to a final concentration of 0.1% and the purified proteins were dialyzed extensively against PBS, filtered through sterile 0.45 μm PVDF filter and divided into sterile low binding Eppendorf tubes.

Purified Product Analysis

The MW, concentration and purity of the final products were analyzed by Bioanalyser according to manufacturer instructions. The results are summarized in Table 27 below.

TABLE 27

| Variant | Purity % | Concentration (μg/ml) |
|---|---|---|
| Met-934-Fc BrA1 (SEQ ID NO: 68) | 100 (average) | 3111 (average) |
| Met-877-Fc BrA1 (SEQ ID NO: 79) | 91.7 | 2016 |
| Met-885-Fc Bt1(SEQ ID NO: 77) | 90.6 (average) | 1479 (average) |

Figure 19A:
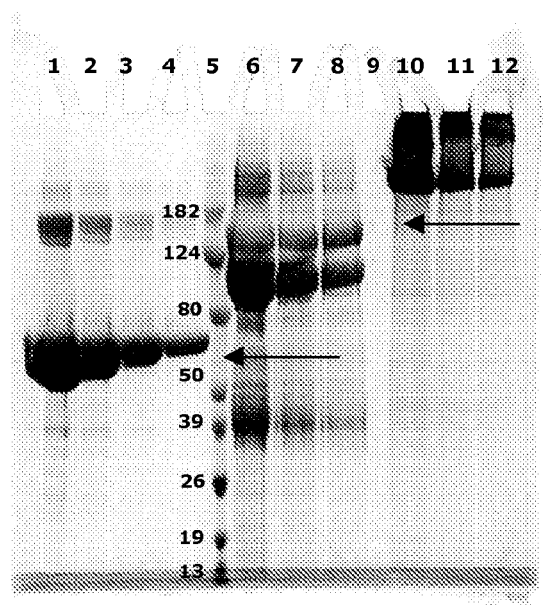
FIG. 19A demonstrates the SDS-PAGE results of Met-885-Fc (SEQ ID NO:77)
Figure 19B:
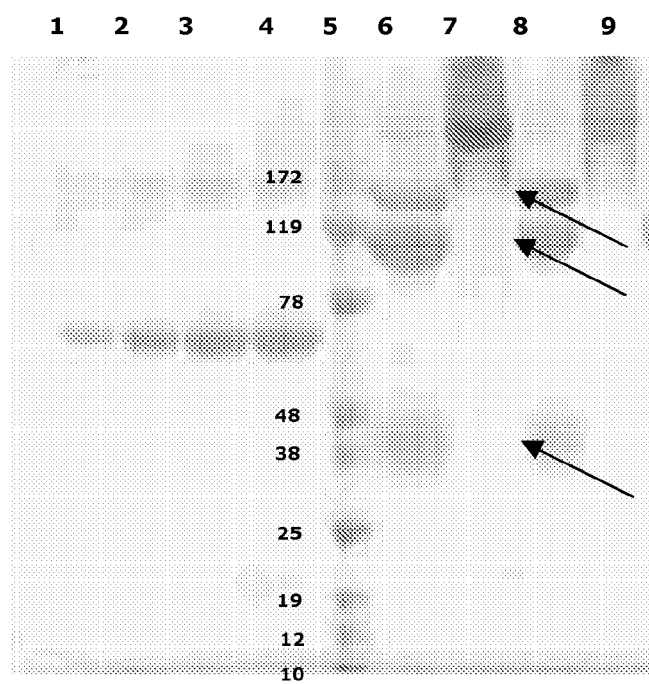
FIG. 19B demonstrates SDS-PAGE results of Met-934 Fc (SEQ ID NO:68)
Figure 19C:
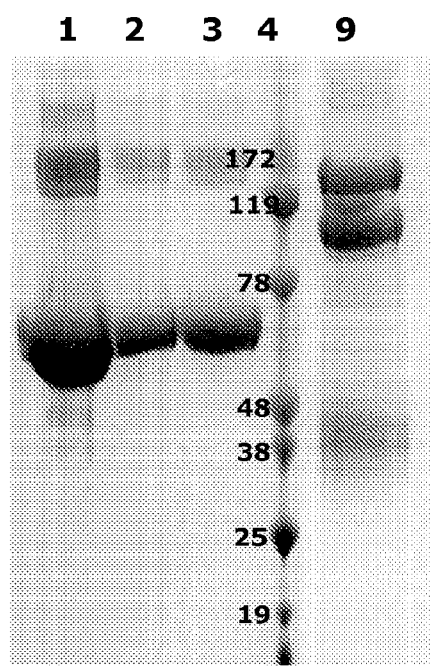
FIG. 19C demonstrates SDS-PAGE results of Met877-Fc (SEQ ID NO:79).

Quantitative SDS-PAGE was performed including 4 concentrations of BSA standards (100, 500, 1000, 2000 μg/ml). FIGS. 19A-C demonstrate the COOMASSIE staining results of SDS-PAGE gel of Met-Fc variants. FIG. 19A demonstrates the SDS-PAGE results of Met-885 Fc (SEQ ID NO:77); FIG. 19B demonstrates SDS-PAGE results of Met-934 Fc (SEQ ID NO:68); FIG. 19C demonstrates SDS-PAGE results of Met877-Fc (SEQ ID NO:79). Tables 28-30 describe the samples loaded in each lane of the SDS-PAGE. In all cases the analysis was carried out on proteins after dialysis using 4-12% BT SDS-PAGE.

TABLE 28

| Lane | SAMPLE |
|---|---|
| 1 | BSA 2 mg/ml |
| 2 | BSA 1 mg/ml |
| 3 | BSA 0.5 mg/ml |
| 4 | BSA 0.25 mg/ml |
| 5 | Markers MW |
| 6 | 314Met885Fc Bt1 reduced, 2 mg/ml |
| 7 | 314Met885Fc Bt1 reduced, 1:2 |
| 8 | 314Met885Fc Bt1 reduced, 1:3 |
| 10 | 314Met885Fc Bt1 nonreduced 2 mg/ml |
| 11 | 314Met885Fc Bt1 nonreduced, 1:2 |
| 12 | 314Met885Fc Bt1 nonreduced, 1:3 |

TABLE 29

| Lane | SAMPLE |
|---|---|
| 1 | BSA 0.5 mg/ml |
| 2 | BSA 1 mg/ml |
| 3 | BSA 1.5 mg/ml |
| 4 | BSA 2 mg/ml |
| 5 | Markers MW |
| 6 | 278 MET Fc 934 BrA1 |
| 7 | 278 MET Fc 934 BrA1, -DTT |
| 8 | 278 MET Fc 934 BrA1 1:2 |
| 9 | 278 MET Fc 934 BrA1 1:2, -DTT |

TABLE 30

| Lane | SAMPLE |
|---|---|
| 1 | BSA 2.0 mg/ml |
| 2 | BSA 0.5 mg/ml |
| 3 | BSA 1.0 mg/ml |
| 4 | MW Markers (combrex Prosieve) |
| 9 | 309-Met-Fc-877 Bt1 |

Example 4

Establishment of Assay-HGF-Induced Met Phosphorylation

The following set of experiments was performed to set up the necessary controls for testing the effect of Met variants according to the present invention. The following cell lines were used: NCI-H441 (ATCC cat no: HTB-174), MDA-MB-435S (ATCC cat no: HTB-129), MDA-MB-231 (ATCC cat no: HTB-26), A431 (ATCC cat no: CRL-1555) and A549 (ATCC cat no: CCL-185).

Cell Treatment and Preparation of Cell Lysate

Cells were seeded at a concentration of 250,000 cells/well in 2 ml of DMEM 10% FCS in 6-well plates and allowed to adhere for 24 hours. Then the cells were serum starved for 3 days in medium without FBS, followed by addition of HGF at concentrations of 10 to 100 ng/ml for 10 min in 0.5 ml. Washing of the cells was done twice with ice-cold PBS. 500 ul of ice-cold PBS were then added and the cells were scraped with a rubber policeman. The cell suspension was removed to 1.5 ml eppendorf and the scraping was repeated with another 500 ul of ice-cold PBS. The cells were spinned 5 min at 14.000 rpm, and the supernatant was discarded. 200 μl of lysis buffer (50 mM Tris pH 7.4, 1% Nonidet 40, 2 mM EDTA, 150 mM NaCl), containing protease and phosphatase inhibitors, was added to the cell pellet, followed by incubation on ice for 30 minutes and centrifugation for 10 min at 12,000 rpm. The cell lysates were transferred to new tubes and used immediately. HGF used was from Calbiochem (Cat. 375228, Lot. B59912) or R&D (Cat. No. 294-HGN, Lot QF025022). HGF from both sources was diluted to final concentration—2 μg/ml and stored at −70° C. in 200 ul aliquots.

Immunoprecipitation (IP) Using Anti (α)-Met:

Agarose conjugated anti-Met (C-28) (SC-161, Santa Cruz) beads were washed three times with PBS, spun for 1 min at 2000 rpm, and (5 μl×n) were taken for further experiments, where n=2× number of reactions. Then 20 μl of redissolved beads were added to each tube and incubated for 2 hour at RT, rotating, followed by precipitation of the beads at 2000 rpm for 1 min. The supernatant was stored for further analysis. Beads were washed in lysis buffer three times and then were dissolved in 70 μl of 2× sample buffer, containing 10% DTT 1M, boiled for 5 minutes and centrifuged. Half of the extracts were run on 4-12% Bis-Tris gel in MOPS buffer (Invitrogen).

Immunoblotting with Anti-Phospho-Tyr:

IP samples were boiled for 5 min and span down before running. Samples were run (20 μl of each) on 12 wells 4-12% Bis-Tris gel in MOPS buffer (Invitrogen) and transferred to nitrocellulose membrane. Blocking was carried out with 5% non-fat milk (Difco, Cat. 232100 Lot: 41184250 Exp: Dec. 5, 2009) in 0.1% Tween-20 in PBS for one hour at room temperature. Membranes were probed with anti-phospho-Tyr mAb (4G10, Upstate, Cat. No. 05-321, Lot. 28818) in 1:1000 dilution, for one hour at room temperature while rocking. Secondary antibody, goat anti-rabbit IgG conjugated to HRP (Jackson ImmunoResearch, Cat. No. 115-035-146) was used at 1:40,000 dilution (5% non-fat milk+0.1% Tween-20 in PBS 1 h RT). Signal was detected using ECL system (EZ-ECL, Biol. Ind., Cat. No. 20-500-120). Equal volume of each solution were mixed, incubated at RT for 5 min, the blot was immersed in final solution for 3 min and exposed to film.

Immunoblotting with Anti-Met:

Membranes previously immunoblotted with anti-phospho Tyr, were stripped with Ponceau S solution (P-7170, Lot.

093K4356) for 5 minutes, followed by washing in distilled water for 5 minutes at RT. Blocking was carried out with 5% non-fat milk in 0.1% Tween-20 in PBS for one hour at room temperature. Proteins were detected with anti-Met rabbit Ab in 1:1000 dilution (C-12, Santa Cruz, SC-10, Lot. J2504) for one hour at room temperature with rocking. The membranes were rinsed with 0.1% Tween-20 in PBS ×2 and washed with 0.1% Tween-20 in PBS 5 min four times. Secondary goat anti-rabbit IgG antibody conjugated to HRP (Jackson ImmunoResearch, Cat. No. 111-035-144) was used at 1:50.000 dilution. The membranes were rinsed with 0.1% Tween-20 in PBS ×2, followed by four 5 min washes with 0.1% Tween-20 in PBS. Signal was detected using ECL system (EZ-ECL, Biol. Ind., Cat No. 20-500-120). Equal volumes of each solution were mixed, incubated at RT for 5 min, the blot was immersed in final solution for 3 min and exposed to film.

Figure 20:
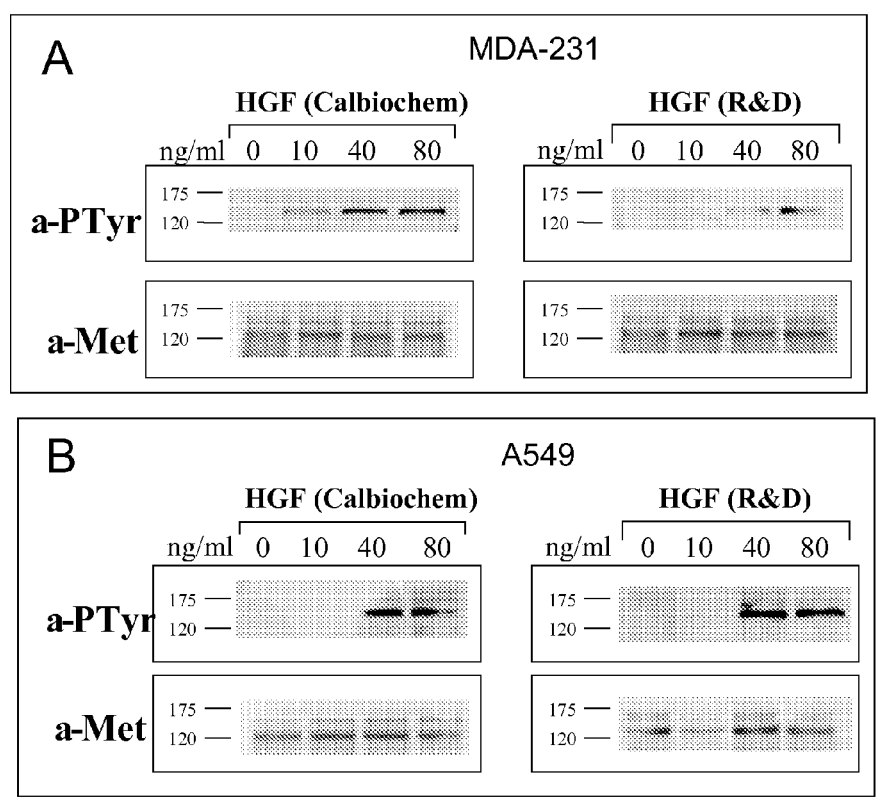
FIG. 20 shows immunoprecipitation and immunoblotting results, demonstrating HGF induction of Met phosphorylation in two different cell lines, MDA-231 and A549, using HGF from two different commercial sources (R&D and Calbiochem). The results demonstrate the calibration of minimal HGF concentration required to induce Met phosphorylation.

FIG. 20 shows analysis of HGF-induced Met phosphorylation that was detected with anti-Phospho-Tyr antibody after immunoprecipitation of Met. Two commercial sources of HGF were checked for bioactivity. Both HGF (Calbiochem) and HGF (R&D) show significant activity on A549 and MDA-MB-231 cell lines. Stimulation of Met phosphorylation was detected in HGF concentrations ranging from 10 to 80 ng/ml. Met protein was detected using anti-Met antibody in the same membranes after stripping, indicating its presence in all lanes at similar levels.

Figure 21:
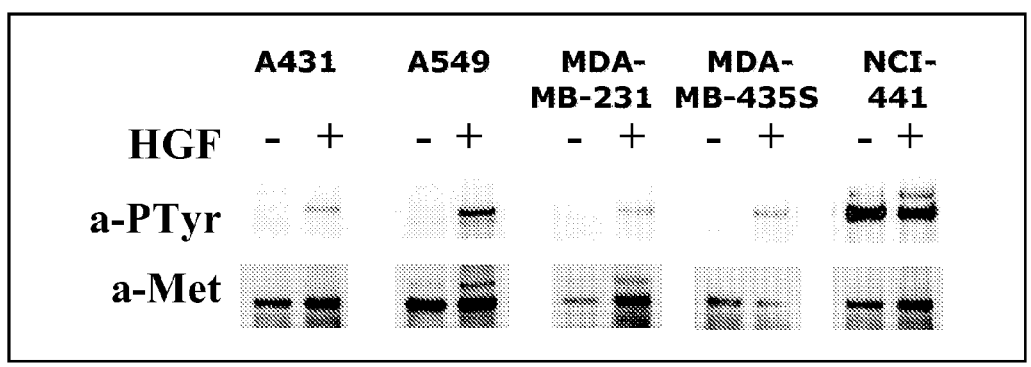
FIG. 21 shows HGF induction (20 ng/ml, Calbiochem) of Met phosphorylation in different human cell lines: A431, A549, MDA-MB-231 and MDA-MB-435S, NCI-H441 cells show constitutive Met phosphorylation.

FIG. 21 shows that HGF (Calbiochem) at the concentration of 20 ng/ml stimulated phosphorylation of Met in A431, A549, MDA-MB-231 and MDA-MB-435S cell lines. NCI-H441 cell line shows constitutive Met phosphorylation. Met phosphorylation was detected by immunoblotting with anti-Phospho-Tyrosine antibody after immunoprecipitation of Met. Met protein was detected using anti-Met antibody on the same membrane after stripping; results indicate the presence of Met at similar levels in the different lanes.

Example 5

Effect of Met-877 on HGF-Induced Tyrosine Phosphorylation of Met

In order to evaluate the effect of Met-877 variant on the levels of phosphorylated Met following induction with HGF, several human cell lines were employed. Cells were incubated with Met-877 prior to HGF treatment. Cells were lysed, and immunoprecipitation of Met was followed by immunoblotting with anti-phospho-Tyr Ab. Blots were reprobed with a general anti-Met antibody, and phosphorylation levels were normalized to total Met protein levels.

Cell Treatments and Lysis:

The following cell treatment and lysis protocols were applied. Cells were seeded in 6-well plates at 250,000 cells/well, in 2 ml DMEM+10% FCS. After 24 hours, cells were washed with 1 ml DMEM (without FCS), and the medium was changed to 2 ml DMEM (without FCS). The Cells were serum starved for 3 days. Each pair of plates was processed separately. Met-877 at 100 µg/ml and equivalent Mock were added to cells for 1 h, at 37° C. (two wells per treatment). HGF (R&D or Calbiochem) was added at 10 ng/ml for 10 min, followed by washing the cells twice with 2 ml ice-cold PBS. Then, 200 µl of lysis buffer (see below) were added to each well, and the cells were scraped with a rubber policeman. Duplicate lysates were combined in the same 1.5 ml tube and incubated on ice for 30 min, swirling occasionally. The tubes were centrifuged 10 min at 14,000 rpm, 4° C. and the supernatants of cleared lysates were transferred to new tubes for immunoprecipitation (see below). 20 ul of lysate from each cell line were kept for Western blot analysis and stored at −70° C.

The following sources of HGF were used: HGF from R&D (Cat. No. 294-HGN, Lot. QF025022) was prepared from powder to a final concentration of 5 µg/ml, stored at −70° C. HGF from Calbiochem, Cat. No. 375228, was prepared to a final concentration of 5 µg/ml, and stored at −70° C.

Lysis buffer contained 50 mM Tris pH 7.4, 1% NP-40, 2 mM EDTA, and 100 mM NaCl). Protease and phosphatase inhibitors were added just before use: Complete protease inhibitor cocktail, Cat No 1-873-580-001 Lot 11422600 Exp October 2006. Tablet was dissolved in 500 ul of PBS, stored at −20° C. For use, added 20 µl/ml of lysis buffer. Phosphatase inhibitor cocktail 1 (P-2850, Lot 064K4067) and cocktail 2 (P-5726, Lot. 064K4065) (Sigma)×100—Both added at 10 µl/ml.

Immunoprecipitation with Anti-Met Ab:

Immunoprecipitation with anti-Met Ab was carried out using agarose beads conjugated with anti-Met rabbit Ab (C-28) (SC-161, Santa Cruz). For each IP reaction, 20 µl of slurry (5 µl of beads) were taken. The combined volume of slurry (20 µl×number of IP reactions) was washed ×3 with 1 ml lysis buffer. During each wash, beads were centrifuged 2 min at 2000 rpm, 4° C. After final wash, beads were resuspended in lysis buffer to obtain again 20 µl×number of IP reactions. 20 µl of beads slurry were added to each tube with 400 µl cell lysate in 1.5 ml tubes, rotated for 2 hr at RT, following precipitation of the beads at 2000 rpm, for 2 min, RT. Then 300 µl from 400 µl of the supernatant were taken out carefully, and the beads were washed twice with 500 µl of lysis buffer. About 40 µl were left in the tube, and 20 µl of ×4 sample buffer (containing 10% DTT 1 M) were added to the beads, boiled for 5 minutes and stored at −70° C.

Immunoblot Analysis:

Immunoprecipitation of Met was followed by immunoblotting with anti-phospho-Tyr Ab. After stripping, the same membrane was tested again with anti-Met Ab.

The tubes containing beads with immunoprecipitated Met were spun down before loading on the gel. 25 ul of each sample were run on 10-wells 4-12% Bis-Tris gel (Invitrogen) in MOPS buffer, at 130V for ~2.5 h. Running buffer (Invitrogen, NuPAGE MES SDS running buffer, Cat. No. NP0002) was used according to manufacturer's recommendations. PVDF membrane was used for transfer. The PVDF membrane was pre-wet in 100% methanol, washed in DDW and then in transfer buffer. The transfer was carried out at 30V for 1.5 h. Transfer buffer (Invitrogen, NuPAGE transfer buffer, Cat. No. NP0006-1) was used according to manufacturer's recommendations. After the transfer, the membrane was washed in water and then in 100% methanol, air dried, and stored at RT. Before blocking, the PVDF membrane was pre-wet in 100% methanol, washed in DDW and then in PBS-T (PBS+0.1% Tween). Blocking was carried out for 1 h at RT in Blocking solution: PBS-T containing 1:10 dilution of Tnuva 1% "Amid" milk. The membrane was rinsed twice, and washed three times for 5 min with PBS-T. Primary Ab incubation was carried out with mouse anti-phospho-Tyr 4G10 mAb (Upstate, Cat No. 05-321, Lot. 28818) at 1:1000 dilution in 20 ml PBS-T+3% BSA, for 1 h at RT, followed by rinsing and washing with PBS-T as above. Secondary Ab incubation was carried out with goat anti-mouse Ab (Jackson ImmunoResearch, Cat. No. 115-035-146, Lot. 63343), used at 1:50,000 in 50 ml Blocking solution (see above) for 1 h at RT, followed by rinsing and washing with PBS-T as above. ECL was carried out with SuperSignal West Pico Chemiluminiscent (Pierce, cat #34080, Lot FD69582). Equal volumes of each solution were mixed, the blot was immersed in the mixture for 5 min and exposed to film. For stripping, membrane was incubated in Ponceau S solution for 5 min, rinsed twiced in water, followed by three times washes for 5 min in DDW, and then in PBS-T at RT O.N. Blocking was carried out for 1 h RT in Blocking solution, followed by rinsing and washing with PBS-T as above. Primary Ab incubation was carried out with rabbit anti-Met Ab (C-12, Santa Cruz, SC-10, Lot. J2504) at 1:1000 dilution in 20 ml PBS-T+1% BSA, for 1 h at RT, followed by rinsing twice, and washing three times for 5 min with PBS-T. Secondary Ab incubation was carried out with anti-rabbit (Jackson ImmunoResearch, Cat. No. 111-035-144, Lot 55285) was used at 1:50,000 dilution in 50 ml of Blocking solution, for 1 h at RT, followed by rinsing and washing as above. SuperSignal West Pico Chemiluminiscent was used for detection of HRP (Pierce, cat # 34080, Lot FD69582). Equal volumes of each solution were mixed, the blot was immersed solution for 5 min and exposed to film. Autoradiograms were scanned and densitometry was carried out using ImageJ 1.33 software.

Results

The influence of Met-877 on HGF-induced Met phosphorylation was tested as described above using A431 (epidermoid carcinoma) or A549 (non-small cell lung carcinoma) cell lines. The A431 or A549 cells were treated with 10 ng/ml HGF (R&D) for 10 min, in the presence or absence of 100 µg/ml Met-877, as described above. The results are presented in FIG. 22. Immunoprecipitation of Met was followed by immunoblotting with anti-Ptyr mAb. After stripping, the same membrane was immunoblotted with anti-Met Ab. UT refers to untreated cells. FIG. 22A shows the autoradiograms, while FIG. 22B demonstrates the densitometry results of the scanned autoradiograms. As can be seen from FIG. 22, Met-877 inhibited HGF-induction of Met-phosphorylation by about 70%.

Figure 22C:
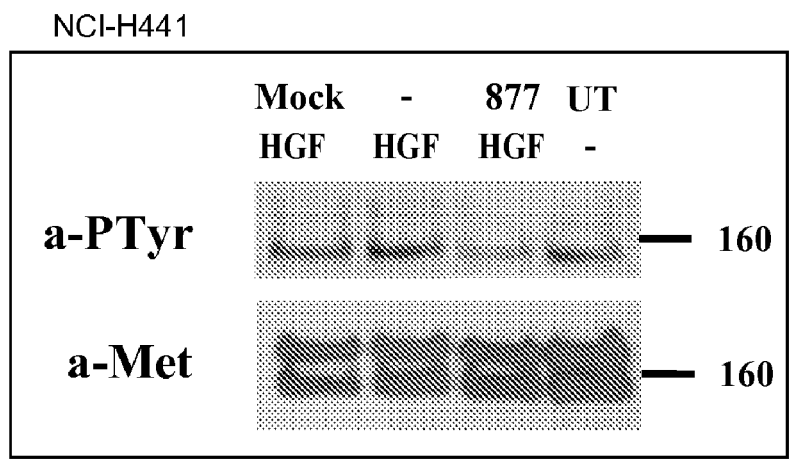
FIGS. 22C-22D demonstrate the influence of Met-877 on HGF induced Met phosphorylation, using NCI-H441 cells (non-small cell lung carcinoma) cells, treated with 10 ng/ml HGF (Calbiochem), in the presence or absence of 100 μg/ml CgenM3-877. UT=untreated cells. Cells were also exposed to the appropriate Mock preparation in the presence of HGF. Immunoprecipitation of Met was followed by immunoblotting with anti-Ptyr Ab. After stripping, the same membrane was tested again with anti-Met Ab.
Figure 22D:
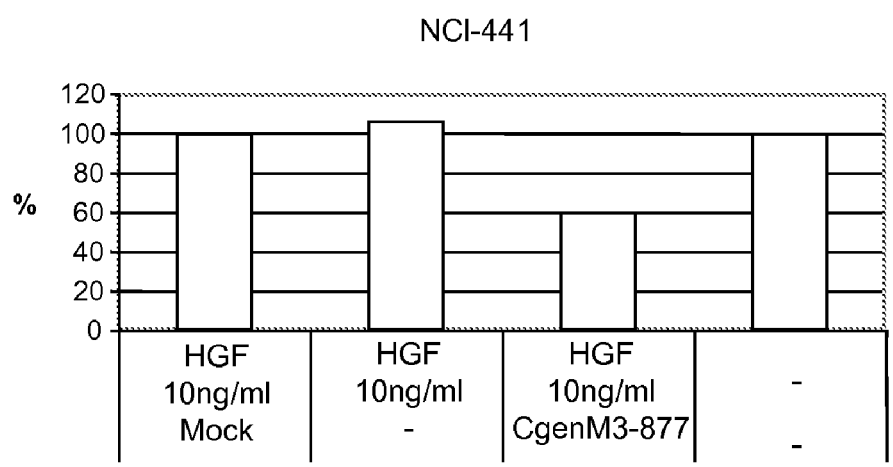

The influence of Met-877 on HGF-induced Met phosphorylation was further tested using NCI-H441 cells (non-small cell lung carcinoma), that were treated with 10 ng/ml HGF (Calbiochem), in the presence or absence of 100 µg/ml Met-877. The results are presented in FIGS. 22C and 22D. Cells were also exposed to the appropriate Mock preparation (described above) in the presence of HGF. immunoprecipitation of Met was followed by immunoblotting with anti-Ptyr Ab. After stripping, the same membrane was tested again with anti-Met Ab. UT refers to untreated cells. FIG. 22C shows the autoradiogram, while FIG. 22D demonstrates the densitometry results of the scanned autoradiogram. In agreement with the literature, this cell line contains constitutive levels of phosphorylated Met, which are not significantly increased upon exposure to HGF. Under these conditions, Met-877 inhibited Met-phosphorylation by about 40%.

Example 6

Effect of Met-Variants on HGF-Induced Phosphorylation of Specific Met Tyrosine Residues Two human cell lines, A549 and MDA-MB-231, were used to assess the inhibitory activity of our Met variants on HGF-induced phosphorylation of three specific tyrosines of Met (Y1230, Y1234, Y1235) which are located within the tyrosine kinase domain, and are the known targets of Met autophosphorylation upon its activation (Ma et al, 2003, Cancer & Metastasis Rev. 22: 309-325). Cells were serum starved, and Met splice variants were added prior to exposure of cells to HGF induction. A known antagonistic Fab mAb (5D5) was added in a similar manner as positive control. The cells were lysed and the phosphorylation levels of Met were determined by immunoblotting with an antibody against the specific phospho-tyrosine residues mentioned above. Blots were reprobed with a general anti-Met antibody, and the phosphorylation levels were normalized to total Met protein levels.

5D5 Fab Preparation:

5D5 Fab fragments were prepared by papain digestion of mAb purified from ascites fluid. BALB/c mice were injected with 5D5.11.6 hybridoma cells purchased from ATCC (ATCC number: HB-11895). Ascites fluid was collected and antibodies were purified using Protein A. For the generation of Fab fragments, the purified antibody was digested with papain. After dialysis, 50% papain slurry (1 ml papain coupled gel=250 µg papain enzyme) was applied into a gravity-flow column, such that the Enzyme:Protein ratio was of 1:20 (w/w) (ie: For 2.5-3.5 mg/ml antibody use 40 µg papain). Digestion was carried out overnight at 37° C. on a roller, in the presence of 20 mM Cystein-HCl.

The resulting Fab fragments were purified by anion exchange chromatography using a column of Q sepharose FF. The unbound fraction containing the Fab fragments was concentrated 50 fold and further purified by size exclusion chromatography (SEC) on HiLoad 16/60 superdex 200 prep grade column (GE healthcare, Cat# 17-1069-01). The eluted peak was pooled and concentrated 11.2 fold by a stir-cell.

The final product was analyzed for protein concentration using the Bradford protein assay with BSA standard (Bio-Rad, Cat# 500-0006) and by measurement of absorbance at 280 nm wavelength. The resulting 5D5 Fab fragments were at a concentration of approximately 200 µg/ml.

Cell Treatments and Lysis:

The following human cell lines were used: A549 (Non-Small Cell Lung Carcinoma, ATCC Cat. No. CC1-185) and MDA-MB-231 (breast carcinoma, ATCC Cat. No. HTB-26). Phosphorylation of Met in these cells lines is inducible by HGF. Cells were seeded in 2 ml growth medium (containing 10% FBS, Fetal Bovine Serum, Heat Inactivated, Biological Industries, Cat. No. 04-121-1A) at 300,000 cells/well in 6-well plates. After 24 hrs the cells were washed with 1 ml serum free medium (0% FBS) and grown for 3 days in 2 ml serum free medium. At the day of stimulation, medium was discarded and Met splice-variants, or mock were added to the cells at 3-1000 nM in 250 µl serum free medium, and plates were incubated at 37° C. for 1 hr. As a positive control, 10 nM of a known antagonistic Fab mAb (5D5) was similarly added to the cells. Subsequently, 10 ng/ml HGF (R&D, Cat. No. 294-HGN) were added for 10 min (from a working stock of 10 µg/ml in 0.1% BSA/PBS). The cells were washed twice with 2 ml ice-cold PBS (Biological Industries, Cat. No. 02-023-5A) and 200 µl of lysis buffer were added to each well: 50 mM Tris pH 7.4, 1% NP-40, 2 mM EDTA, 100 mM NaCl, containing complete protease inhibitor cocktail (Roche, 1-873-580-001), and phosphatase inhibitor cocktails 1 and 2 (Sigma, P-2850 and P-5726). Cells were scraped with a rubber policeman and transferred to 1.5 ml tubes. Lysates were incubated on ice for 30 min with occasional vortex. Lysates were centrifuged at 4° C. for 10 min at 14,000 rpm, and the sup was transferred to new tubes.

Immunoblot Analysis:

Phosphorylation of Met was analyzed by immunoblotting with an antibody specific for phospho-Tyr Met residues. After stripping, the same membrane was probed again with anti-Met Ab.

Lysate samples were separated on 4-12% Bis-Tris gels (Invitrogen) in NuPAGE MOPS running (Invitrogen, NP0001). Proteins were transferred to nitrocellulose membranes using NuPAGE transfer buffer (Invitrogen, NP0006). After transfer, blots were stained with Ponceau S solution (Sigma, Cat. No. P-7170), and washed twice with TBS-T 0.1% (TBS with 0.1% Tween-20). Blocking was carried out at RT for 1 hr with 5% BSA (Sigma, Cat. No. A-3059) in TBS-T 0.1%. Anti-phospho c-Met [pYpYpY1230/4/5], rabbit polyclonal Ab (Biosource, Cat. No. 44-888G) was added at 1:1000 in TBS-T 0.1% with 1% BSA, and incubated for 2 hrs at RT. Blots were washed ×3 in TBS-T 0.1%, and secondary Ab, peroxidase-conjugated goat anti-rabbit IgG (Jackson ImmunoResearch, 111-035-144) was added in blocking solution at 1:25,000, for 1 hr at RT. Blots were washed ×3 in TBS-T 0.1% and SuperSignal West Pico Chemiluminescent (Pierce, Cat. No. 34080) was used for detection of HRP. Equal volumes of each solution were mixed, the blot was immersed in the solution for 5 min and exposed to film.

For reprobing with anti-Met Ab, the blot was stripped with stripping buffer (100 mM β-mercaptoethanol, 2% SDS, 62.5 mM Tris-HCl pH6.7) for 15 min at 50° C., and washed ×3 in PBS-T 0.05% (PBS with 0.05% Tween-20). Complete stripping was determined by re-blocking, followed by incubation with secondary antibody and detection of HRP. Blocking was carried out at RT for 1 hr in 10% Tnuva milk (1% fat, Amid) in PBS-T 0.05%. Blots were washed ×3 in PBS-T 0.05% prior to incubation with 1:1000 anti-Met Ab (rabbit polyclonal Ab, C-12, Santa Cruz Cat. No. SC-10) at RT for 1 hr in 1% BSA, PBS-T 0.05%. Blots were washed as above, and secondary Ab, goat-anti-rabbit (see above) was added at 1:25,000 in blocking solution, for 1 hr at RT. Blots were washed again, and HRP detection was carried out with SuperSignal West Pico Chemiluminiscent as described above. Autoradiograms were scanned and levels of phosphorylated Met were quantified by densitometry using ImageJ 1.36b software, and normalized to levels of Met expression.

Results

Figure 23A:
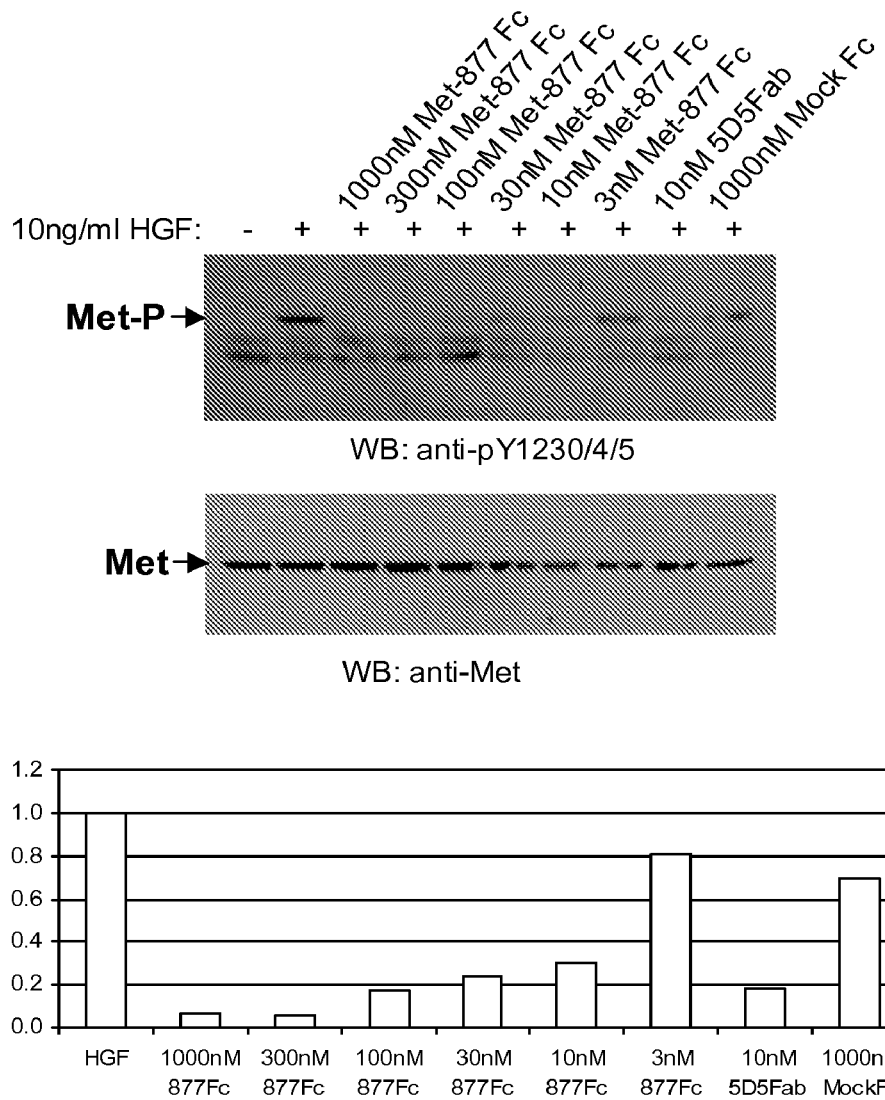
Figure 23B:
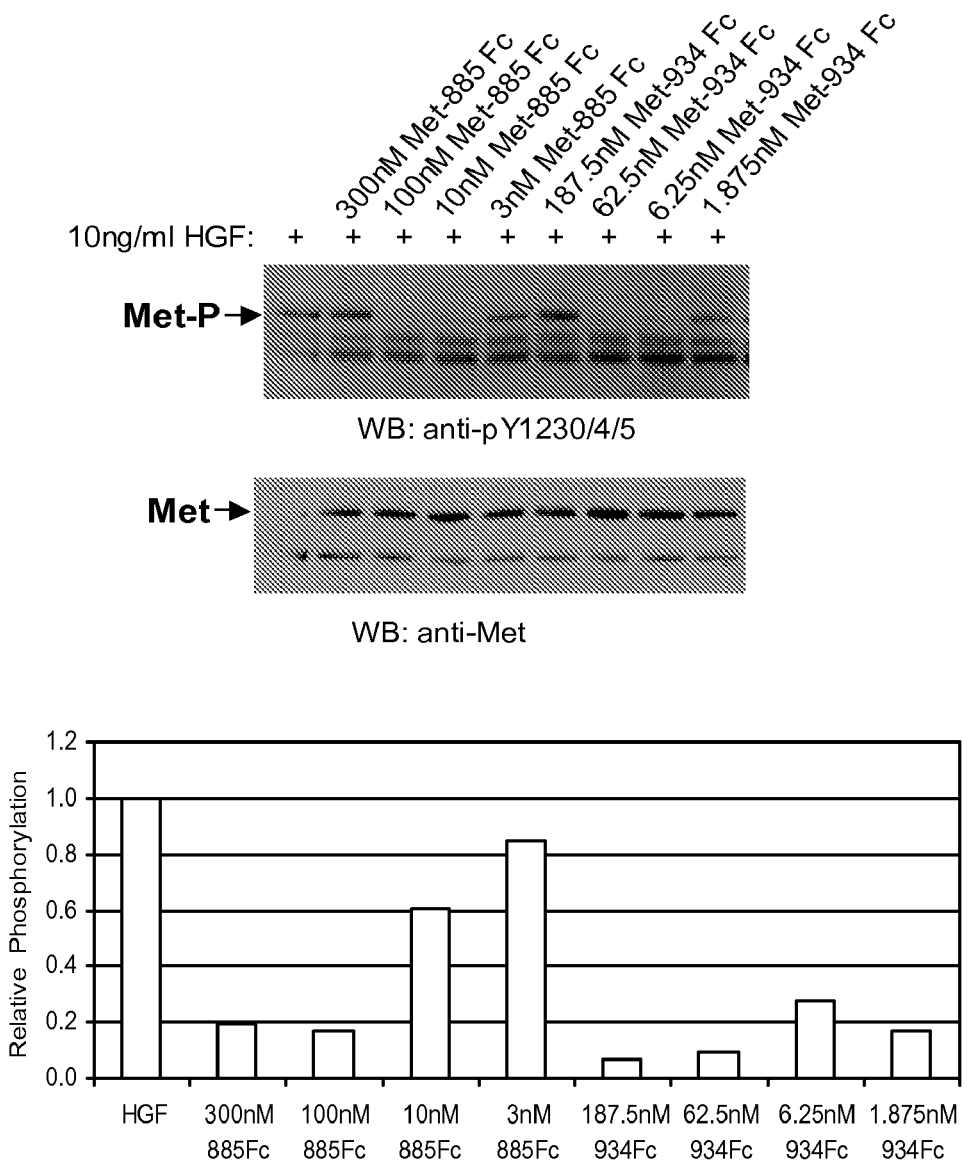

The influence of three variants of Met (877, 885 and 934, all fused to Fc; SEQ ID NOS: 79, 77 and 68, respectively) on HGF-induced phosphorylation of Y1230/4/5 was tested with a mAb specific to these phosphorylated tyrosine residues, as described above, using the A549 (Non-Small Cell Lung Carcinoma) and MDA-MB-231 (breast carcinoma) cell lines. Cells were exposed to 10 ng/ml HGF for 10 min, in the presence or absence of various doses of Met-inhibitory variants, as described above. Immunoblot analysis for specific phospho-tyrosines was carried out, and following stripping, the same membrane was immunoblotted with anti-Met Ab. The results are presented in FIG. 23. As shown in the autoradiogram and its densitometry evaluation in FIG. 23A, Met-877-Fc (SEQ ID NO:79) strongly inhibited the HGF-induced Met-phosphorylation of A549 cells, at doses equal or higher than 10 nM. The level of inhibition was similar to that exhibited by 5D5 Fab, a known antagonistic anti-Met mAb (Kong-Beltran et al, 2004, Cancer Cell 6: 75-84). UT refers to untreated cells. The negative control, Mock-Fc preparation, did not have a significant effect on the level of HGF-induced Met phosphorylation. The autoradiogram and densitometry evaluation shown in FIG. 23B, indicate a strong inhibitory activity of two other Met variants, Met-885-Fc (SEQ ID NO:77) and Met-934-Fc (SEQ ID NO:68), on HGF-induced Met phosphorylation in A549 cells. FIGS. 23C and 23D show similar results obtained with MDA-MB-231 cells, after treatment with Met-877-Fc (SEQ ID NO:79), 885-Fc (SEQ ID NO:77) and 934-Fc (SEQ ID NO:68). In this cell line, however, also the lowest dose of 3 nM seems to have a significant inhibitory effect of >60%. The conclusions from these series of experiments are as follows: all three Met variants inhibit >90% of HGF-induced Met-phosphorylation in two different human cell lines, upon prior exposure to doses higher than 3-10 nM of inhibitory protein.

Example 7

Effect of Met-Variants on HGF-Induced Cell Scattering

The aim of this study was to assess the inhibitory activity of our Met variants in using an in vitro functional assay-cell scattering, which is dependent on HGF signaling through Met.

Description of Cell Scattering Assay:

Two cell lines were used to evaluate the inhibitory effect of Met variants on HGF-induced scattering: MDCK-II cells (Madin-Darby canine kidney, ECACC, Cat. No. 00062107) or HT115 cells (Human colon carcinoma, ECACC, Cat. No. 85061104). Cells were seeded in 96-well plates at $1.5 \times 10^3$ cells (MDCK) or $4 \times 10^3$ cells (HT115) per well. Cells were grown at 37° C. in DMEM+5% FBS (for MDCK) or DMEM+15% FBS (for HT115). DMEM and FBS (Heat Inactivated) were purchased from Biological Industries, Cat. No. 01-055-1A, and 04-121-1A, respectively. After 24 hrs, HGF (R&D, Cat. No. 294-HGN) and Met splice-variants were added at various concentrations. All samples were tested in triplicates, at a final volume of 200 µl/well. At the day of induction medium was removed and 100 µl assay medium containing 1 up to 100 ng/ml HGF final concentration (working stock of 10 µg/ml in PBS+1% BSA) was added to all wells (except untreated control which received medium without HGF). Met splice-variants were diluted in assay medium and used at 1-100 µg/ml final concentrations in 100 µl assay medium. Solutions were prepared at 2× concentration, and mixed in wells at 1:1 with HGF. As controls served cells incubated with medium only, or with HGF without any inhibitors. In addition, a mock protein preparation was used as negative control. The cells were examined under microscope after 48 hrs for evaluation of cell clustering and scattering. This was evaluated independently by 2 different people in the lab, in a blinded manner. A score of 1 to 5 was given to evaluate minimal up to maximal scattering activity, respectively.

Results

Figure 24:
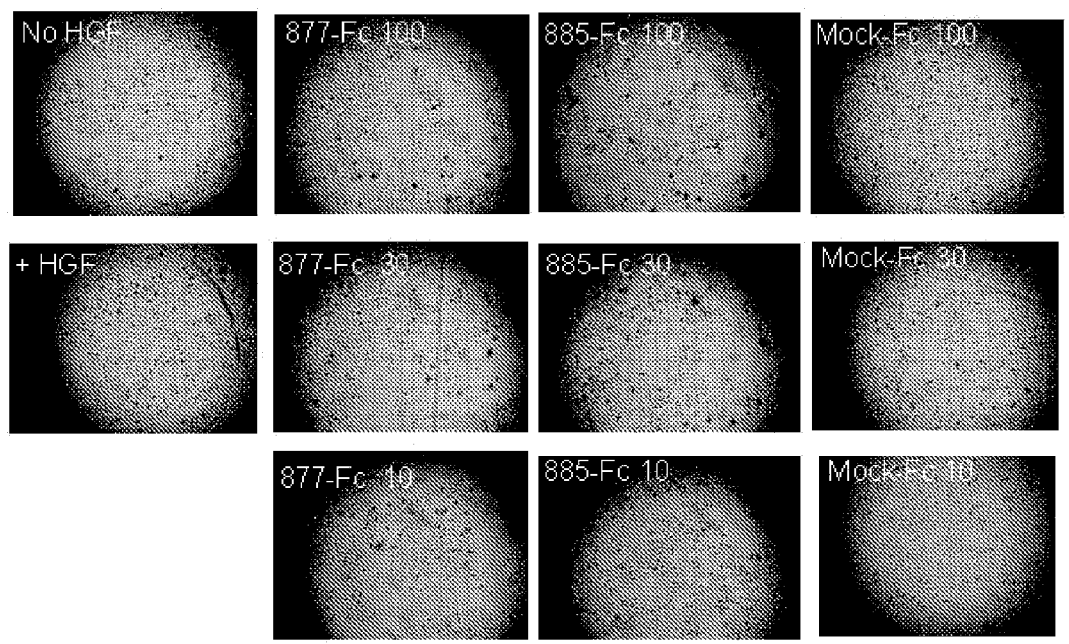
FIG. 24 presents the results of a representative scattering assay using MDCK II cells, demonstrating that Met-877-Fc (SEQ ID NO:79) and Met-885-Fc (SEQ ID NO:77) strongly inhibit HGF-induced scattering, while a mock Fc preparation has no effect.

FIG. 24 shows an example of a scattering assay carried out with MDCK cells. In this case, the cells were seeded in the absence or presence of 50 ng/ml HGF (left panels as indicated), or in the presence of HGF and 100, 30 or 10 µg/ml of Met877-Fc (SEQ ID NO:79) or Met885-Fc (SEQ ID NO:77) (middle panels as indicated), or equivalent amounts of mock protein preparation (right panels). Cell scattering was evaluated under the microscope as described above.

Table 31 summarizes the results obtained for all 3 variants (877 was used in two forms-fused or non-fused to Fc) in the two types of cell lines. As shown in the table, the lowest HGF concentration that still gave maximum cell scattering was ~5-7 ng/ml in both cell lines. At that concentration, the amount of inhibitory protein that gave roughly 50% inhibition of scattering was between 0.1-1 µg/ml for each of the variants, in both types of cell lines. This assay is not quantitative enough to provide accurate IC50 values.

TABLE 31

| Inhibitory protein | Concentration | HGF concent. | Cells | Score |
|---|---|---|---|---|
| None | — | — | MDCK | 1 |
| None | — | — | HT115 | 1 |
| None | — | 5-100 ng/ml | MDCK | 5 |
| None | — | 3 ng/ml | MDCK | 3-4 |
| None | — | 1 ng/ml | MDCK | 1-2 |
| None | — | 7-100 ng/ml | HT115 | 4-5 |
| None | — | 3-5 ng/ml | HT115 | 3-4 |
| None | — | 1 ng/ml | HT115 | 1-2 |
| Met 877 | 100 µg/ml | 50 ng/ml | MDCK | 3 |
|  | 30 µg/ml | 50 ng/ml | MDCK | 4 |
|  | 10 µg/ml | 50 ng/ml | MDCK | 4-5 |
|  | 10 µg/ml | 5 ng/ml | MDCK | 1-2 |
|  | 5 µg/ml | 5 ng/ml | MDCK | 2-3 |
|  | 1 µg/ml | 5 ng/ml | MDCK | 3-4 |
|  | 0.1 µg/ml | 5 ng/ml | MDCK | 5 |
|  | 100 µg/ml | 50 ng/ml | HT115 | 1 |
|  | 30 µg/ml | 50 ng/ml | HT115 | 1-2 |
|  | 10 µg/ml | 50 ng/ml | HT115 | 3 |
|  | 10 µg/ml | 7 ng/ml | HT115 | 1 |
|  | 5 µg/ml | 7 ng/ml | HT115 | 1 |
|  | 1 µg/ml | 7 ng/ml | HT115 | 1 |
|  | 0.1 µg/ml | 7 ng/ml | HT115 | 3-4 |
| Met 877-Fc | 100 µg/ml | 100 ng/ml | MDCK | 1 |
|  | 30 µg/ml | 100 ng/ml | MDCK | 2 |
|  | 10 µg/ml | 100 ng/ml | MDCK | 4-5 |
|  | 100 µg/ml | 50 ng/ml | MDCK | 1-2 |
|  | 30 µg/ml | 50 ng/ml | MDCK | 2-3 |
|  | 10 µg/ml | 50 ng/ml | MDCK | 3-4 |
|  | 30 µg/ml | 30 ng/ml | MDCK | 1 |
|  | 10 µg/ml | 30 ng/ml | MDCK | 2 |
|  | 3 µg/ml | 30 ng/ml | MDCK | 2-3 |
|  | 30 µg/ml | 10 ng/ml | MDCK | 1 |
|  | 10 µg/ml | 10 ng/ml | MDCK | 1 |
|  | 10 µg/ml | 10 ng/ml | MDCK | 1 |
|  | 5 µg/ml | 10 ng/ml | MDCK | 2 |
|  | 3 µg/ml | 10 ng/ml | MDCK | 1-2 |
|  | 1 µg/ml | 10 ng/ml | MDCK | 3 |
|  | 0.1 µg/ml | 10 ng/ml | MDCK | 4-5 |
|  | 10 µg/ml | 7 ng/ml | MDCK | 1 |
|  | 5 µg/ml | 7 ng/ml | MDCK | 1-2 |
|  | 1 µg/ml | 7 ng/ml | MDCK | 3 |
|  | 0.1 µg/ml | 7 ng/ml | MDCK | 5 |
|  | 10 µg/ml | 5 ng/ml | MDCK | 1 |
|  | 5 µg/ml | 5 ng/ml | MDCK | 1-2 |
|  | 1 µg/ml | 5 ng/ml | MDCK | 3 |
|  | 0.1 µg/ml | 5 ng/ml | MDCK | 4-5 |
|  | 10 µg/ml | 3 ng/ml | MDCK | 1-2 |
|  | 1 µg/ml | 3 ng/ml | MDCK | 1-2 |
|  | 0.1 µg/ml | 3 ng/ml | MDCK | 2-3 |
|  | 10 µg/ml | 1 ng/ml | MDCK | 1 |
|  | 1 µg/ml | 1 ng/ml | MDCK | 1 |
|  | 0.1 µg/ml | 1 ng/ml | MDCK | 1-2 |
|  | 100 µg/ml | 100 ng/ml | HT115 | 1-2 |
|  | 100 µg/ml | 50 ng/ml | HT115 | 1 |
|  | 30 µg/ml | 50 ng/ml | HT115 | 1-2 |
|  | 10 µg/ml | 50 ng/ml | HT115 | 2 |
|  | 100 µg/ml | 30 ng/ml | HT115 | 1-2 |
|  | 30 µg/ml | 30 ng/ml | HT115 | 1-2 |
|  | 10 µg/ml | 30 ng/ml | HT115 | 1-2 |
|  | 3 µg/ml | 30 ng/ml | HT115 | 1-2 |
|  | 30 µg/ml | 10 ng/ml | HT115 | 1-2 |
|  | 10 µg/ml | 10 ng/ml | HT115 | 1-2 |
|  | 5 µg/ml | 10 ng/ml | HT115 | 1-2 |
|  | 3 µg/ml | 10 ng/ml | HT115 | 1-2 |
|  | 1 µg/ml | 10 ng/ml | HT115 | 1-2 |
|  | 0.1 µg/ml | 10 ng/ml | HT115 | 4-5 |
|  | 10 µg/ml | 7 ng/ml | HT115 | 1 |
|  | 5 µg/ml | 7 ng/ml | HT115 | 1 |
|  | 1 µg/ml | 7 ng/ml | HT115 | 1-2 |
|  | 0.1 µg/ml | 7 ng/ml | HT115 | 3-4 |
|  | 10 µg/ml | 5 ng/ml | HT115 | 1 |
|  | 5 µg/ml | 5 ng/ml | HT115 | 1 |
|  | 1 µg/ml | 5 ng/ml | HT115 | 1-2 |
|  | 0.1 µg/ml | 5 ng/ml | HT115 | 3 |
|  | 10 µg/ml | 3 ng/ml | HT115 | 1 |
|  | 1 µg/ml | 3 ng/ml | HT115 | 1-2 |
|  | 0.1 µg/ml | 3 ng/ml | HT115 | 2 |
|  | 10 µg/ml | 1 ng/ml | HT115 | 1 |
|  | 1 µg/ml | 1 ng/ml | HT115 | 1-2 |
|  | 0.1 µg/ml | 1 ng/ml | HT115 | 1-2 |
| Met 934-Fc | 100 µg/ml | 100 ng/ml | MDCK | 1 |
|  | 30 µg/ml | 100 ng/ml | MDCK | 1-2 |
|  | 10 µg/ml | 100 ng/ml | MDCK | 5 |
|  | 100 µg/ml | 50 ng/ml | MDCK | 1+ |
|  | 30 µg/ml | 50 ng/ml | MDCK | 2 |
|  | 10 µg/ml | 50 ng/ml | MDCK | 3 |
| Met 885-Fc | 100 µg/ml | 50 ng/ml | MDCK | 1-2 |
|  | 30 µg/ml | 50 ng/ml | MDCK | 2-3 |
|  | 10 µg/ml | 50 ng/ml | MDCK | 3-4 |
|  | 10 µg/ml | 5 ng/ml | MDCK | 1-2 |
|  | 5 µg/ml | 5 ng/ml | MDCK | 2 |
|  | 1 µg/ml | 5 ng/ml | MDCK | 2 |
|  | 0.1 µg/ml | 5 ng/ml | MDCK | 3-4 |
|  | 100 µg/ml | 50 ng/ml | HT115 | 1-2 |
|  | 30 µg/ml | 50 ng/ml | HT115 | 2 |
|  | 10 µg/ml | 50 ng/ml | HT115 | 2-3 |
|  | 10 µg/ml | 7 ng/ml | HT115 | 1 |
|  | 5 µg/ml | 7 ng/ml | HT115 | 1 |
|  | 1 µg/ml | 7 ng/ml | HT115 | 1 |
|  | 0.1 µg/ml | 7 ng/ml | HT115 | 2-3 |

Example 8

Effect of Met-877 on HGF-Induced Invasion of DA3 Cells

Inhibitory activity of Met-877 on HGF-induced cell invasion was demonstrated using matrigel-coated Boyden chambers and DA3 cells, derived from a mouse mammary carcinoma.

Description of Invasion Assay:

DA3 invasion assays were performed in 96-well chemotaxis Boyden chambers (NeuroProbe, Maryland). Lower and upper wells were separated by Nucleopore filters (5 µm pore size) coated with Matrigel (3.6 µg/mm$^2$, BD Biosciences). To test the inhibition of HGF-induced cell invasion by the Met-variants according to the present invention, the cells were treated with HGF in combination with different concentrations of Met-variants or Mock. HGF (100 ng/ml), in the absence or presence of Met-variants (at 10, 30 or 100 µg/ml), diluted in 30 µl DMEM+1 mg/ml BSA, was placed in the lower wells. Mock was also tested at equivalent amounts to the above variant. All samples were tested in triplicates. DA3 cells (4×10$^4$) in DMEM were placed in the upper wells, and allowed to invade to lower wells by chemotaxis during a 48-hour period. Non-invading cells remaining on the upper surface were removed with a cotton swab. Invading cells that migrated to the lower surface of the filter were fixed with cold methanol and stained with Giemsa. The stained filter was scanned and the area occupied by stained cells was analyzed by Photoshop.

Figure 25E:
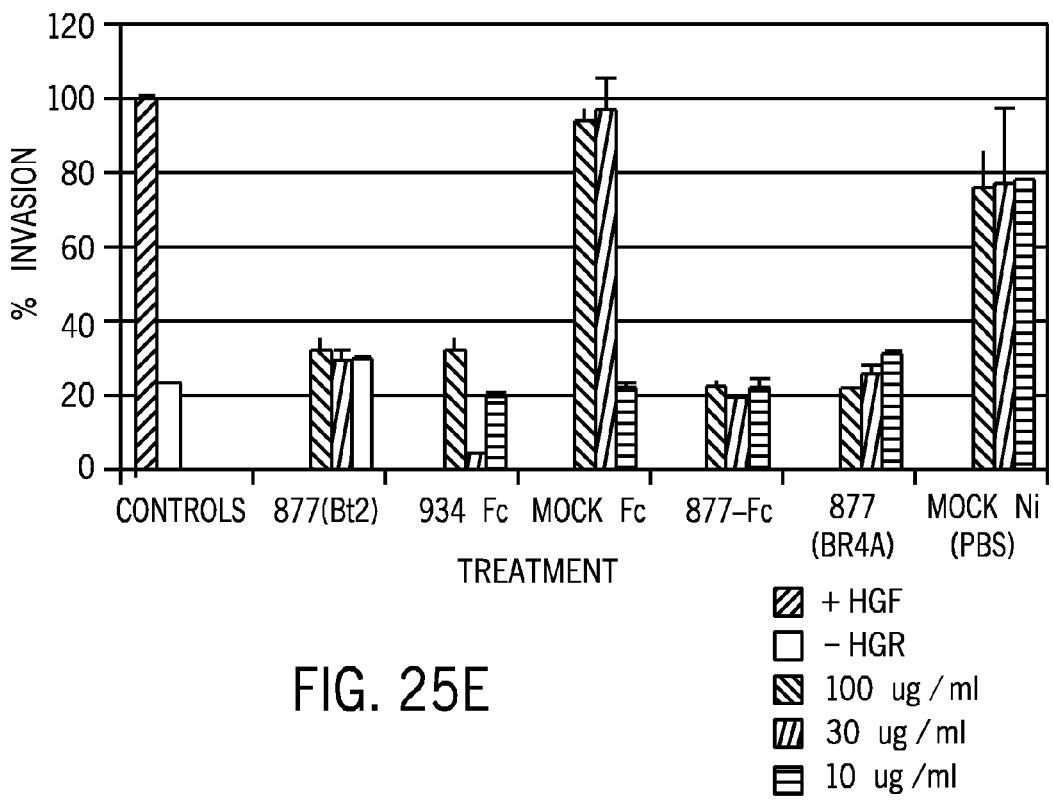
Figure 25F:
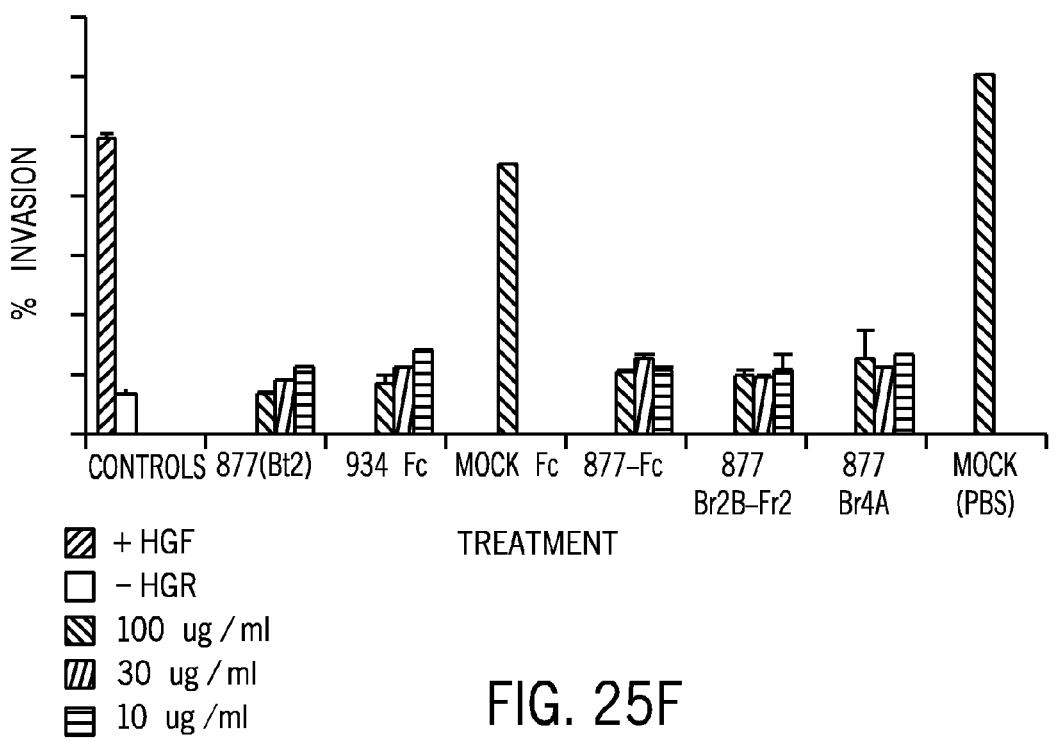
Figure 25G:
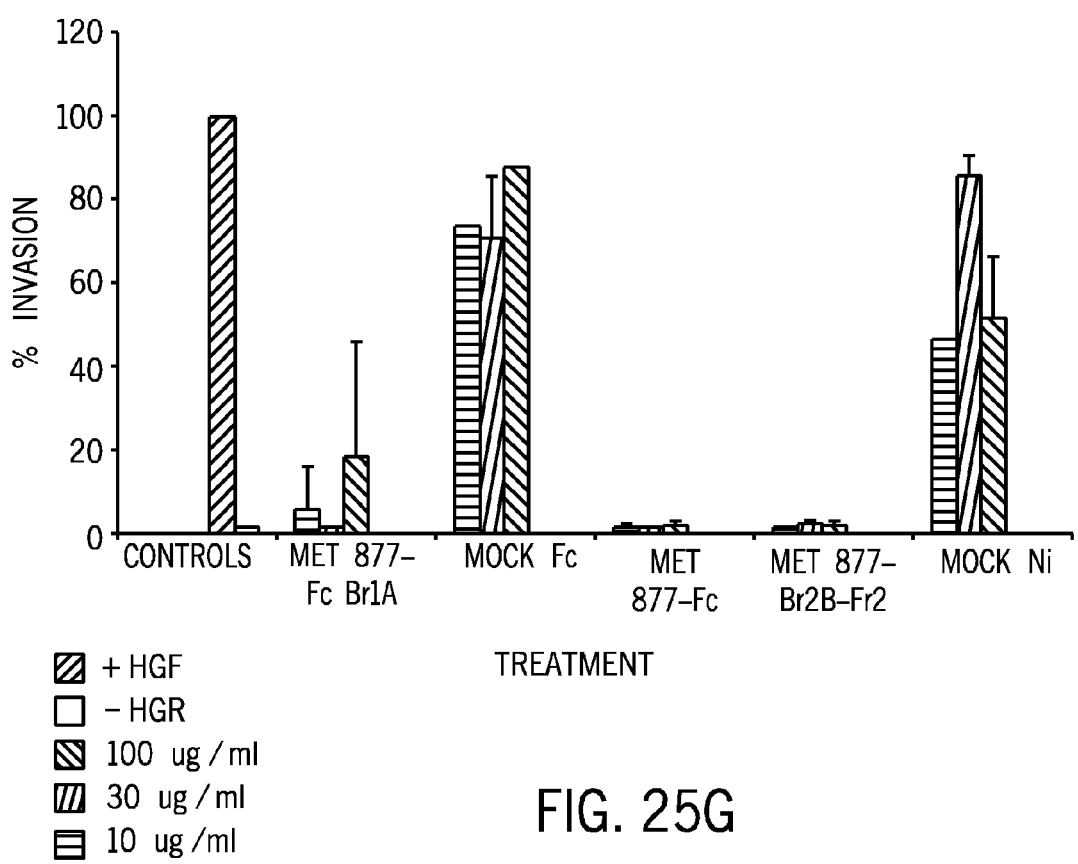

Results of Invasion Assay:

FIGS. 25A and 25B show the layout of an example invasion assay and its stained filter, respectively. Results of a total of 5 experiments are summarized in FIG. 25C through 25G. As shown in these figures, the DA3 cells migrated through the matrigel-coated filter in response to HGF (defined as 100% migration), while very low spontaneous migration was detected in the absence of HGF. In addition, FIGS. 25A through 25G, indicate that Met-variants strongly inhibited HGF-induced cell invasion, at all doses, while the various Mock protein preparations did not have a significant effect.

The results of the invasion assays, together with those of the scattering assays, shown in Example 7, indicate a strong inhibitory activity of all Met-variants on HGF-induced Met activity leading to cell motility and invasion, and suggest an anti-tumorigenic and anti-metastatic activity of these proteins in Met-dependent tumorigenic pathways.

Example 9

Effect of Met-Variants on HGF-Induced Urokinase Upregulation

HGF stimulation in a variety of cell lines expressing Met induces the expression of the serine protease urokinase (uPA, urokinase-type plasminogen activator) and its receptor (uPAR), resulting in an increase of uPA at the cell surface. Urokinase converts plasminogen into plasmin, a serine protease with broad substrate specificity toward component of the extracellular matrix. This activity facilitates cell invasion, tumor progression and metastasis. Analysis of urokinase activity in response to HGF induction, provides a functional and quantitative assay to determine the effect of various inhibitors of the HGF/Met-mediated signaling pathway (Webb et al, Cancer Research, Vol. 60, p. 342-349, 2000), and can enable the assessment of the potency of our Met-variants.

Urokinase Assay:

Urokinase activity was tested indirectly by measuring plasmin activity, upon addition of human plasminogen and a specific plasmin chromophore (Webb et al, 2000, Cancer Res. 60: 342-349). MDCK II cells were exposed to HGF in the presence or absence of Met splice-variants and examined for plasmin activity after 24 hrs. Percent inhibition was calculated relative to HGF-stimulated cells in the absence of inhibitor, after subtraction of background plasmin activity of unstimulated control cells.

MDCK-II cells (Madin-Darby canine kidney, ECACC, Cat. No. 00062107) were seeded at $1.5 \times 10^3$ cells per well in 96-well plates, with DMEM+10% FBS (Fetal bovine serum, Heat Inactivated, Biological Industries, Cat. No. 04-121-1A), at a final volume of 200 μl/well. Cells were incubated at 37° C. for 24 hrs prior to induction. On the day of induction, medium was removed and 100 μl assay medium containing HGF (R&D, Cat. No. 294-HGN) at a final concentration of 10 ng/ml (stock 10 μg/ml in PBS+1% BSA) was added to all wells (except the untreated control which received medium without HGF). Met splice-variants were diluted in assay medium and used at 1 to 300 nM final concentrations in 100 μl assay medium. Solutions were prepared at 2× concentration, and mixed in wells at 1:1 with HGF. All samples were tested in triplicates. Wells were washed twice with DMEM without phenol red (Gibco, Cat. No. 31053-028) and 200 μl of reaction buffer [50% (v/v) 0.05 units/ml plasminogen (Roche, Cat. No. 10874477001) in DMEM without phenol red, 40% (v/v) 50 mM Tris buffer pH8.2, and 10% (v/v) 3 mM Chromozyme PL (Roche, Cat. No. 10378461001) in 100 mM glycine solution] were added to each well. The plate was incubated at 37° C., for 4 hrs, and absorbance was measured at a single wavelength of 405 nm. Background Plasmin activity of unstimulated control cells was subtracted. Percent inhibition was calculated relative to HGF-stimulated cells in the absence of inhibitors.

Figure 26A:
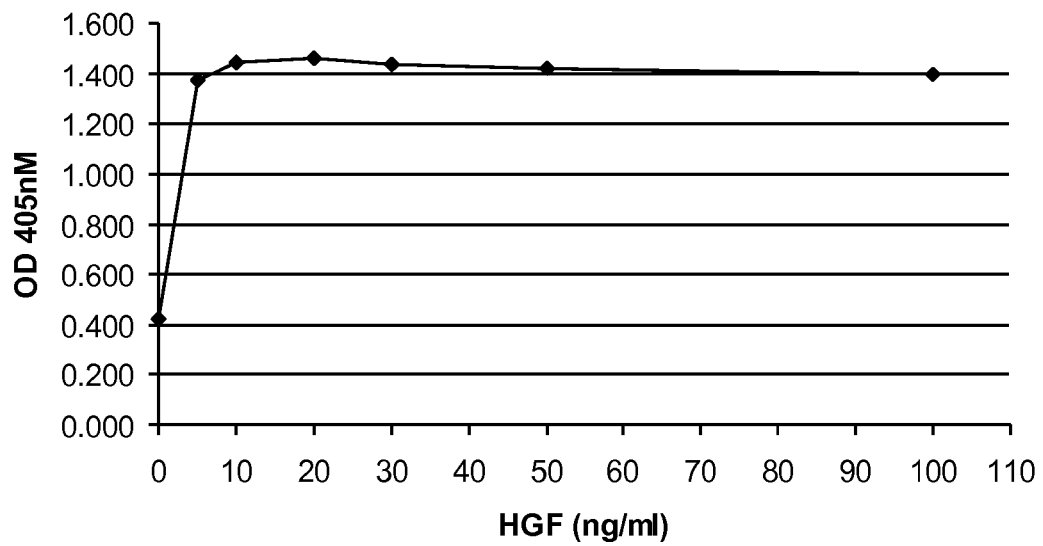
FIGS. 26A-26D show the influence of Met-variants on HGF-induced urokinase upregulation in MDCK II cells. Urokinase activity is evaluated indirectly by measuring plasmin activity, upon addition of plasminogen (a substrate of urokinase which is converted into plasmin) and a specific plasmin chromophore.
Figure 26B:
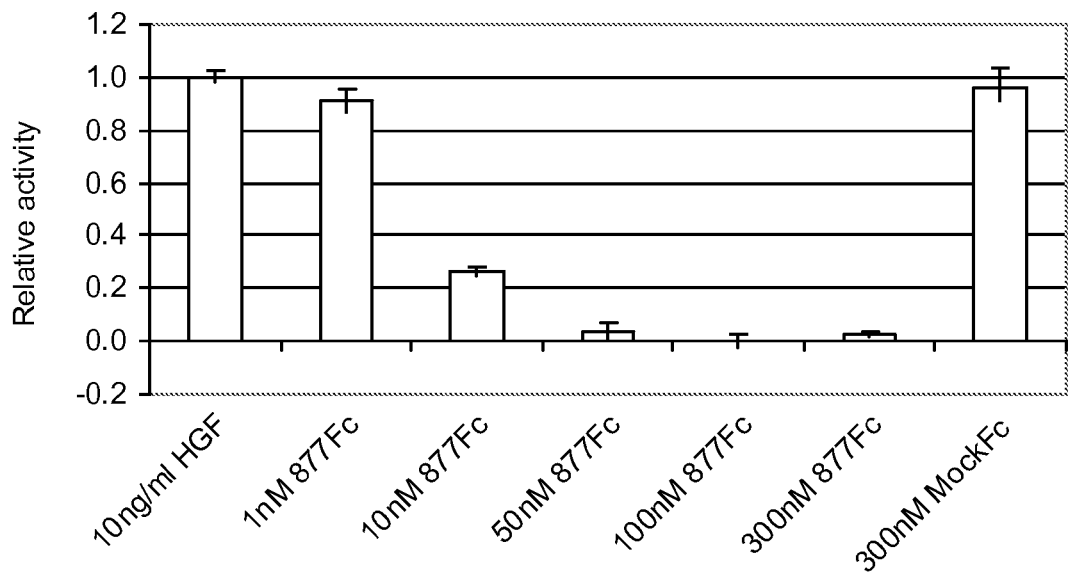
Figure 26C:
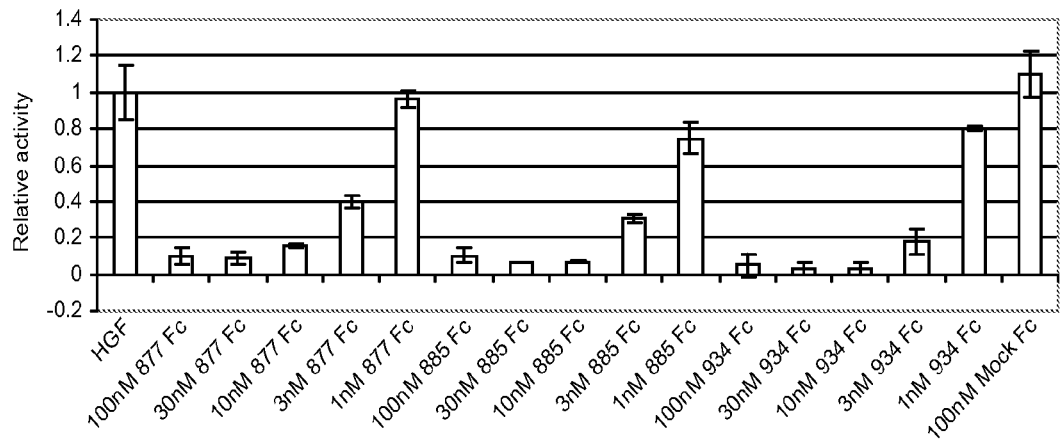
Figure 26D:
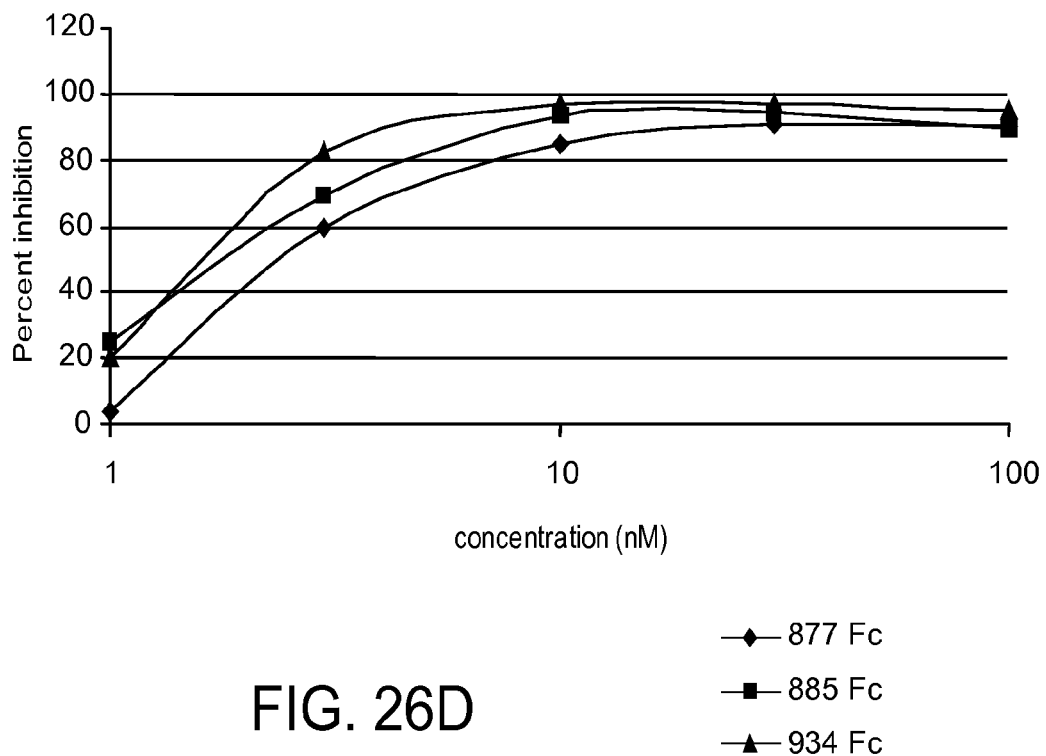

Results:

FIG. 26A shows the upregulation of urokinase (measured as plasmin activity) upon induction of MDCK II cells with various HGF concentrations (5-100 ng/ml). An HGF dose of 10 ng/ml was chosen to test the inhibitory activity of our Met variants on urokinase upregulation. FIG. 26B shows that Met-877-Fc exhibits strong inhibition of HGF-induced urokinase upregulation (~80% inhibition with 10 nM, and >95% inhibition with doses equal or bigger than 50 nM) FIG. 26C shows similar results in another experiment carried out with Met-877-Fc (SEQ ID NO:79), Met-885-Fc (SEQ ID NO:77) and Met-934-Fc (SEQ ID NO:68). As shown in FIG. 26D, very weak inhibition was observed with 1 nM, and about 60-80% inhibition with 3 nM of Met variants. With doses higher than 10 nM, all variants exhibited a strong inhibition which was higher than 90-95%. In both experiments, the Mock-Fc preparation had no effect.

Example 10

Effect of Met Variants on Cell Proliferation

The effect of Met variants on the HGF-induced proliferation of AsPC-1 (pancreatic adenocarcinoma, ATCC Cat. No. CRL-1682) and H441 cells (Non-small cell lung carcinoma, ATCC Cat. No. HTB-174) was tested using two types of proliferation assays: MTT assay and/or BrdU incorporation.

Description of MTT and BrdU Proliferation Assays:

Cells were seeded in 96-well microtiter plates at a concentration of 10,000 cells/well in a final volume of 200 μl RPMI-1640+10% FBS (Fetal bovine serum, Heat Inactivated, Biological Industries, Cat. No. 04-121-1A). On the next day, cells were rinsed and supplemented with 100 μl of RPMI-1640+ 0.1% FBS for additional 48 hrs. After serum starvation, cells were treated with different concentrations of Met-877-Fc (SEQ ID NO:79) or 885-Fc (SEQ ID NO:77), or with a mock preparation. One hour later HGF (R&D, Cat. No. 294-HGN) was added at concentrations of 10, 25 or 50 ng/ml. For the BrdU incorporation assay, BrdU was added on the same day to each well at a final concentration of 10 μM. Following incubation overnight, BrdU ELISA assay was performed according to the manufacturer instructions (Cell proliferation ELISA, Roche, Cat. No. 11 647 229 001). For the MTT assay, 24 hrs after the addition of HGF, 10 μl of MTT (5 mg/ml stock solution; Sigma, Thiazolyl blue, Cat. M-5655) were added to each well. After 4 hrs the medium was removed and 100 μl of DMSO (Sigma, Cat. No. D-8779) were added to each well for 2 hrs. Optical density was measured using an ELISA reader set to 490 nm.

Figure 27A:
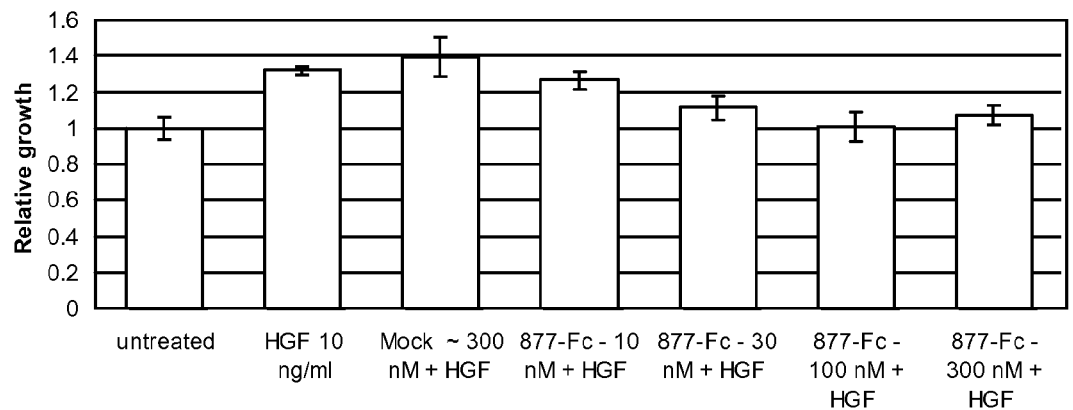
FIGS. 27A-27F show the influence of Met variants on HGF-induced cell proliferation of two cell lines: H441 (non-small cell lung cancer) and AsPC-1 (human pancreatic carcinoma).
Figure 27B:
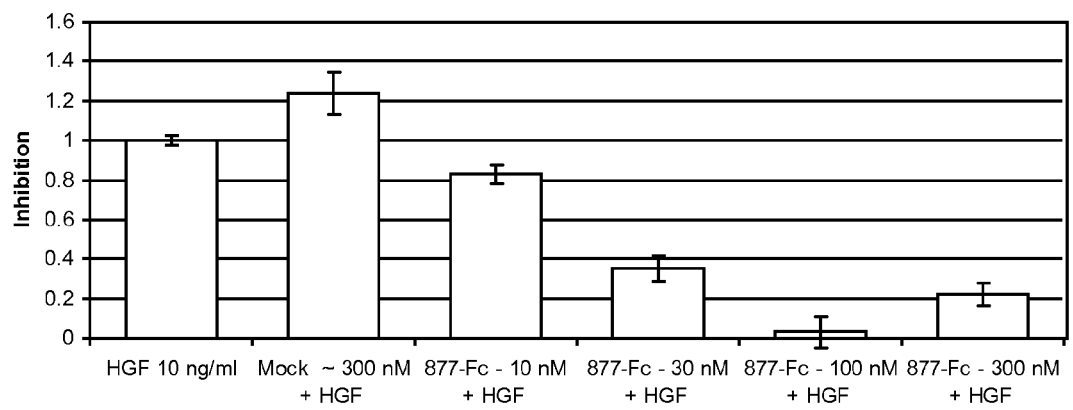
Figure 27C:
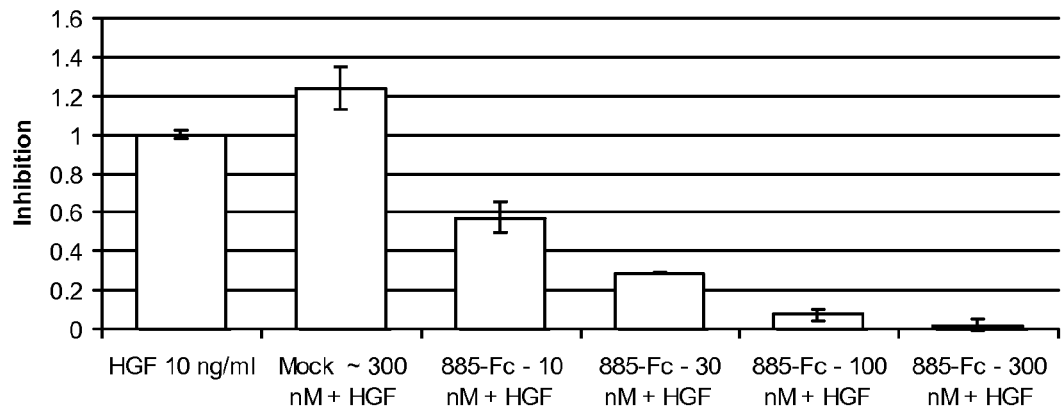
Figure 27D:
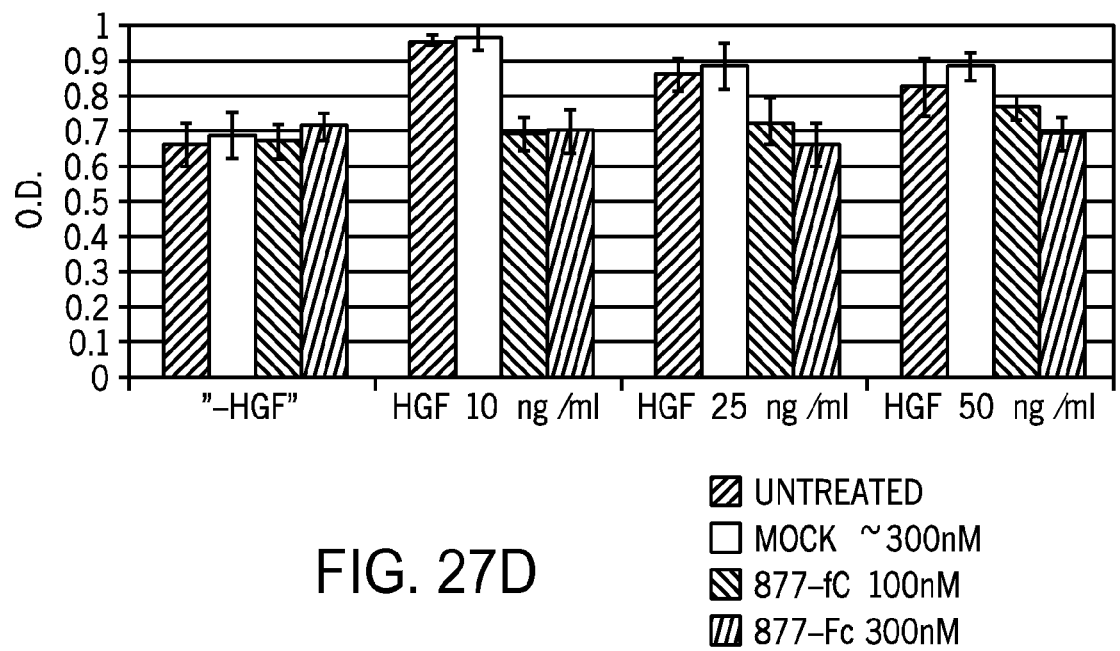

Results:

The results of the proliferation assays described above are shown in FIG. 27. As can be seen in FIG. 27A, Met-877-Fc (SEQ ID NO:79) inhibits the HGF-induction of H441 cell proliferation, as measured by BrdU incorporation. These results are depicted more clearly in FIG. 27B, in which the induction of BrdU incorporation by 10 ng/ml HGF is defined as 1.0. The histograms in FIG. 27B indicate a strong inhibition of HGF-induced proliferation by Met-877-Fc (SEQ ID NO:79), at doses higher than 30 nM. Similar inhibition of HGF-induced H441 proliferation is obtained with Met-885-Fc (SEQ ID NO:77) (FIG. 27C).

Figure 27E:
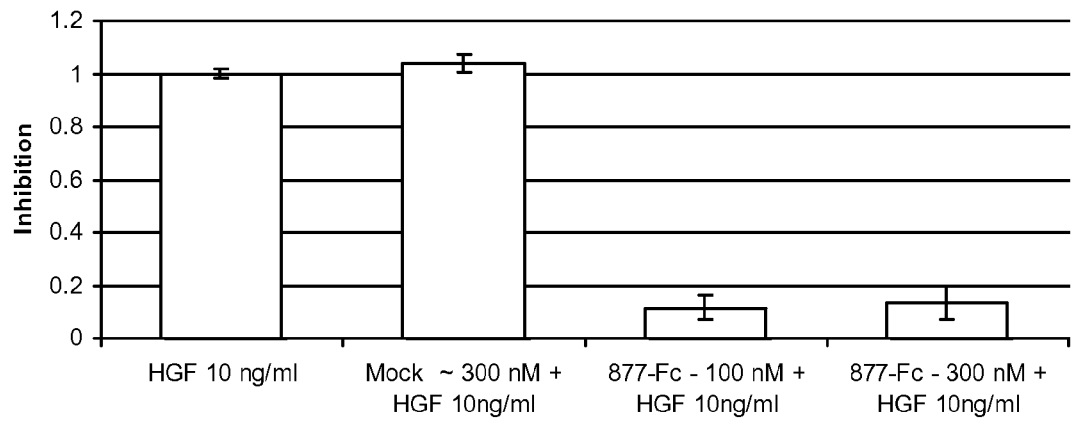
Figure 27F:
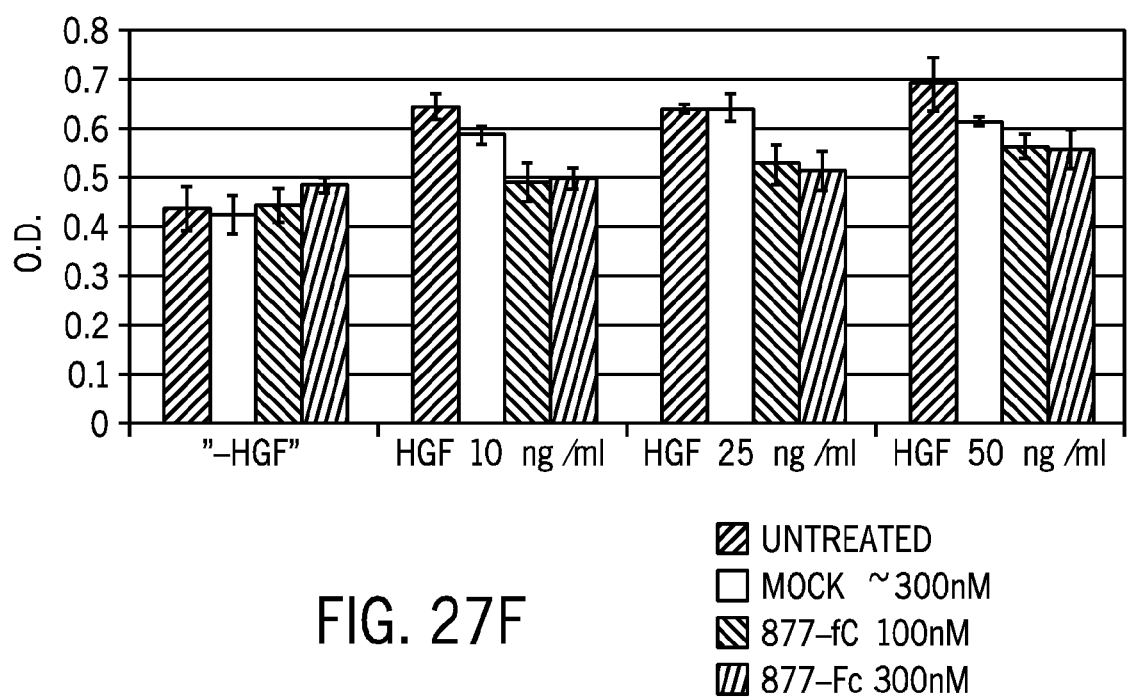

HGF-induction of AsPC-1 cells is also inhibited by Met-877-Fc, as measured by BrdU incorporation (FIG. 27D) or MTT assay (FIG. 27F). In this experiment, 3 different doses of HGF were employed. Testing BrdU incorporation, the best induction of proliferation is obtained with 10 ng/ml HGF, and at this dose, 877-Fc (at 100 and 300 nM) exhibited ~90% inhibition of HGF-induced proliferation (FIG. 27E).

Conclusions:

The strong inhibitory effect of Met variants on a variety of HGF-induced cellular functions, such as proliferation, scattering, invasion, urokinase upregulation and Met phosphorylation (presented in Examples 4 through 10, above) point to the strong anti-Met antagonistic capacity of these proteins, inhibiting diverse functional outcomes of Met activation in different cell types.

Example 11

Effect of Met Variants on Growth of Subcutaneous Xenografts in Nude Mice

In order to evaluate the in vivo activity of our Met variants, we tested their influence in subcutaneous xenograft models. Three human cell lines (U87, H441 and AsPC-1) were chosen, based on their in vitro response to our Met variants (see Example 10, above), and on their previously published sensitivity to various HGF/Met antagonists: The in vivo growth of the human glioblastoma cell line U87 MG, was previously shown to be inhibited by various antagonists of the HGF-Met pathway, such as anti-HGF mAbs (Kim et al, 2006, Clin. Cancer Res. 12: 1292-1298; Burgess et al 2006, Cancer Res. 66: 1721-1729), anti-Met ribozyme (Abounader et al 2002, FASEB J. 16: 108-110; Lal et al 2005, Clin. Cancer Res. 11: 4479-4486) or a known HGF competitive antagonist, NK4 (Brockman et al 2003, Clin. Cancer Res. 9: 4578-4585). The in vivo growth of the human pancreatic adenocarcinoma AsPC-1 cell line was shown to be inhibited by NK4 (Saimura et al 2002, Cancer Gene Therapy 9: 799-806). Its growth in vitro was also inhibited by anti-Met siRNA (Jagadeeswaran et al, 20006, Proc. Amer. Assoc. Cancer Res. 47: Abst # 3029). The in vitro growth of the human NSCLC cell line H441 was shown to be inhibited by several small molecule inhibitors of met (Christensen et al 2003, Cancer Res. 63: 7345-7355; Ma et al 2005, Clin. Cancer Res. 11: 2312-2319).

Description of Xenograft Study:

For each cell line, eight BALB/c athymic nude mice were injected subcutaneously with $5 \times 10^6$ cells in the flank. On the same day of cell inoculation, the mice were injected intraperitoneally with 100 or 20 ug of Met-877-Fc, 885-Fc or 934-Fc, or PBS as negative control, followed by repeated injections of the same agent three times a week for a total of about 3-4 weeks. Tumor volumes are determined by caliper measurements every 3-4 days. After 3 to 5 weeks, tumors were excised, weighed and measured. Frozen tumor sections are prepared and immunohistochemistry is carried out for PCNA or Ki67 staining of cell proliferation, CD31 or laminin staining of vascularization, and TUNEL or cleaved caspase-3 staining of apoptotic cells. Tumor-associated microvessel density, and tumor cell proliferation or apoptosis are quantified using image software analysis.

Example 12

Effect of Met Variants on Regression of Established Subcutaneous Xenografts in Nude Mice In order to analyze the effect of Met variants on inducing regression of established xenografts, the treatment with Met variants begins only after tumor establishment (when tumors reach a volume of about 100 mm$^3$). The continuation of treatment and analysis are carried out as described above for Example 11.

Example 13

Effect of Met Variants on Regression of Orthotopic Xenografts in Nude Mice

It is important to analyze the ability of Met variants to induce regression of established orthotopic xenografts, such as glioblastoma or pancreatic cancers. Such studies would shed light on the efficacy of systemic treatment with Met variants and their ability to cross the highly permeable tumor vasculature.

Glioblastoma is a particularly promising application for antagonistic Met variants, since those tumors commonly express HGF and Met, and have been successfully targeted in xenograft models with a variety of anti-Met agents (mAbs (Kim et al, 2006, Clin. Cancer Res. 12: 1292-1298; Burgess et al 2006, Cancer Res. 66: 1721-1729; Abounader et al 2002, FASEB J. 16: 108-110; Lal et al 2005, Clin. Cancer Res. 11: 4479-4486; Brockman et al 2003, Clin. Cancer Res. 9: 4578-4585; and others). Previous publications show that systemic administration of an anti-HGF mAb can be efficacious against intracranial as well as subcutaneous glioblastoma xenografts, and can induce regression of both types of xenografted tumors even in the setting of large pretreatment tumor burden. In addition, such treatment can substantially prolong survival of mice bearing natural human glioblastoma tumors in their brain (Kim et al, 2006, Clin. Cancer Res. 12: 1292-1298). These results indicate that the blood-brain and blood-tumor barriers do not seem to impede protein therapeutics that antagonize the HGF-Met pathway.

The following intracreaneal orthotopic glioblastoma xenograft model will be used: Human glioblastoma cells, such as U87 GM, at $1.5 \times 10^6$ are implanted within the caudate/putamen of anesthetized nude mice, and 4 days later treatment begins by intraperitoneal administration of Met variants at two doses (i.e. 20 and 100 ug) at a frequency of 3× per week. Animals are sacrificed on postimplantation day 18 and brains are removed for histologic studies. Efficacy can also be tested after more stringent conditions, where initiation of treatment is delayed until day 18. A subset of mice are sacrificed immediately before starting therapy, and the rest are sacrificed 14 days after initiation of treatment. Tumor volumes are quantified by measuring tumor cross-sectional areas of H&E stained brain sections using computer-assisted image analysis. Detailed analysis of histologic sections of intracranial tumors is carried out to investigate the potential mechanisms of the antitumor effects of Met variants: anti-Ki67 or anti-PCNA staining to detect tumor cell proliferation; anti-laminin or anti-CD31 staining to detect angiogenesis and vessel density); and TUNEL or activated caspase-3 staining to detect apoptotic cells. Tumor-associated microvessel density, and tumor cell proliferation or apoptosis are quantified using image software analysis An orthotopic human pancreatic xenograft model is also employed. Human pancreatic cells, such as AsPC-1 or SUIT-2, known to be sensitive to anti-Met agents (Saimura et al 2002, Cancer Gene Therapy 9: 799-806; Tomioka et al 2001, Cancer Res. 61: 7518-7524) are implanted surgically, at $1.5 \times 10^6$ cells, into the body of the pancreas of athymic nude mice. Treatment with antagonistic Met variants are initiated intraperitoneally 7 days after tumor cell implantation, and are continued at 3× week for additional 3 weeks. Analysis of tumor volumes and histology are carried out as described above.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

SEQUENCE LISTING

<160> NUMBER OF SEQ ID NOS: 83

<210> SEQ ID NO 1
<211> LENGTH: 4232
<212> TYPE: DNA
<213> ORGANISM: Homo sapiens

<400> SEQUENCE: 1

```
gaattccgcc ctcgccgccc gcggcgcccc gagcgctttg tgagcagatg cggagccgag      60
tggagggcgc gagccagatg cggggcgaca gctgacttgc tgagaggagg cggggaggcg     120
cggagcgcgc gtgtggtcct tgcgccgctg acttctccac tggttcctgg gcaccgaaag     180
ataaacctct cataatgaag gcccccgctg tgcttgcacc tggcatcctc gtgctcctgt     240
ttaccttggt gcagaggagc aatggggagt gtaaagaggc actagcaaag tccgagatga     300
atgtgaatat gaagtatcag cttcccaact tcaccgcgga aacacccatc cagaatgtca     360
ttctacatga gcatcacatt ttccttggtg ccactaacta catttatgtt ttaaatgagg     420
aagaccttca gaaggttgct gagtacaaga ctgggcctgt gctggaacac ccagattgtt     480
tcccatgtca ggactgcagc agcaaagcca atttatcagg aggtgtttgg aaagataaca     540
tcaacatggc tctagttgtc gacacctact atgatgatca actcattagc tgtggcagcg     600
tcaacagagg gacctgccag cgacatgtct ttccccacaa tcatactgct gacatacagt     660
cggaggttca ctgcatattc tccccacaga tagaagagcc cagccagtgt cctgactgtg     720
tggtgagcgc cctgggagcc aaagtccttt catctgtaaa ggaccggttc atcaacttct     780
ttgtaggcaa taccataaat tcttcttatt tcccagatca tccattgcat tcgatatcag     840
tgagaaggct aaaggaaacg aaagatggtt ttatgttttt gacggaccag tcctacattg     900
atgttttacc tgagttcaga gattcttacc ccattaagta tgtccatgcc tttgaaagca     960
acaattttat ttacttcttg acggtccaaa gggaaactct agatgctcag acttttcaca    1020
caagaataat caggttctgt tccataaact ctggattgca ttcctacatg gaaatgcctc    1080
tggagtgtat tctcacagaa aagagaaaaa agagatccac aaagaaggaa gtgtttaata    1140
tacttcaggc tgcgtatgtc agcaagcctg ggcccagct  tgctagacaa ataggagcca    1200
gcctgaatga tgacattctt ttcggggtgt tcgcacaaag caagccagat tctgccgaac    1260
caatggatcg atctgccatg tgtgcattcc ctatcaaata tgtcaacgac ttcttcaaca    1320
agatcgtcaa caaaaacaat gtgagatgtc tccagcattt ttacggaccc aatcatgagc    1380
actgctttaa taggacactt ctgagaaatt catcaggctg tgaagcgcgc cgtgatgaat    1440
atcgaacaga gtttaccaca gctttgcagc gcgttgactt attcatgggt caattcagcg    1500
```

```
aagtcctctt aacatctata tccaccttca ttaaaggaga cctcaccata gctaatcttg   1560
ggacatcaga gggtcgcttc atgcagtggt cctttggcgt gctcctctgg gagctgatga   1620
caagaggagc cccaccttat cctgatgtaa acacctttga tataactgtt tacttgttgc   1680
aagggagaag actcctacaa cccgaatact gcccagaccc cttatatgaa gtaatgctaa   1740
aatgctggca ccctaaagcc gaaatgcgcc catccttttc tgaactggtg tcccggatat   1800
cagcaatctt ctctactttc attggggagc actatgtcca tgtgaacgct acttatgtga   1860
acgtaaaatg tgtcgctcca tatccttctc tgttgtcatc agaagataac gctgatgatg   1920
aggtggacac acgaccagcc tccttctggg agacatcata gtgctagtac tatgtcaaag   1980
caacagtcca cactttgtcc aatggttttt tcactgcctg acctttaaaa ggccatcgat   2040
attctttgct cttgccaaaa ttgcactatt ataggacttg tattgttatt taaattactg   2100
gattctaagg aatttcttat ctgacagagc atcagaacca gaggcttggt cccacaggcc   2160
acggaccaat ggcctgcagc cgtgacaaca ctcctgtcat attggagtcc aaaacttgaa   2220
ttctgggttg aatttttttaa aaatcaggta ccacttgatt tcatatggga aattgaagca   2280
ggaaatattg agggcttctt gatcacagaa aactcagaag atagtaat gctcaggaca   2340 ggagcggcag ccccagaaca ggccactcat ttagaattct agtgtttcaa aacacttttg   2400
tgtgttgtat ggtcaataac attttttcatt actgatggtg tcattcaccc attaggtaaa   2460
cattcccttt taaatgtttg tttgttttt gagacaggat ctcactctgt tgccagggct   2520
gtagtgcagt ggtgtgatca tagctcactg caacctccac ctcccaggct caagcctccc   2580
gaatagctgg gactacaggc gcacaccacc atccccggct aattttttgta ttttttgtag   2640 agacggggtt ttgccatgtt gccaaggctg gtttcaaact cctggactca agaaatccac   2700
ccacctcagc ctcccaaagt gctaggatta caggcatgag ccactgcgcc cagcccttat   2760
aaatttttgt atagacattc ctttggttgg aagaatattt ataggcaata cagtcaaagt   2820
ttcaaaatag catcacacaa aacatgttta taatgaaca ggatgtaatg tacatagatg   2880
acattaagaa aatttgtatg aaataattta gtcatcatga atatttagt tgtcatataa   2940 aaacccactg tttgagaatg atgctactct gatctaatga atgtgaacat gtagatgttt   3000
tgtgtgtatt ttttttaaatg aaaactcaaa ataagacaag taatttgttg ataaatatttt   3060 ttaaagataa ctcagcatgt tgtaaagca ggatacattt tactaaaagg ttcattggtt   3120
ccaatcacag ctcataggta gagcaaagaa agggtggatg gattgaaaag attagcctct   3180
gtctcggtgg caggttccca cctcgcaagc aattggaaac aaaacttttg gggagtttta   3240
ttttgcatta gggtgtgttt tatgttaagc aaaacatact ttagaagcaa atgaaaaagg   3300
caattgaaaa tcccagctat ttcacctaga tggaatagcc accctgagca gaactttgtg   3360
atgcttcatt ctgtggaatt ttgtgcttac tactgtatag tgcatgtggt gtaggttact   3420
ctaactggtt ttgtcgacgt aaacatttaa agtgttatat ttttttataaa aatgtttatt   3480 tttaatgata tgagaaaaat tttgttaggc cacaaaaaca ctgcactgtg aacattttag   3540
aaaaggtatg tcagactggg attaatgaca gcatgatttt caatgactgt aaattgcgat   3600
aaggaaatgt actgattgcc aatacacccc accctcatta catcatcagg acttgaagcc   3660
aagggttaac ccagcaagct acaaagaggg tgtgtcacac tgaaactcaa tagttgagtt   3720
tggctgttgt tgcaggaaaa tgattataac taaaagctct ctgatagtgc agagacttac   3780
cagaagacac aaggaattgt actgaagagc tattacaatc caaatattgc cgtttcataa   3840
atgtaataag taatactaat tcacagagta ttgtaaatgg tggatgacaa aagaaaatct   3900
```

| | |
|---|---|
| gctctgtgga aagaaagaac tgtctctacc agggtcaaga gcatgaacgc atcaatagaa | 3960 |
| agaactcggg gaaacatccc atcaacagga ctacacactt gtatatacat tcttgagaac | 4020 |
| actgcaatgt gaaaatcacg tttgctattt ataaacttgt ccttagatta atgtgtctgg | 4080 |
| acagattgtg ggagtaagtg attcttctaa gaattagata cttgtcactg cctatacctg | 4140 |
| cagctgaact gaatggtact tcgtatgtta atagttgttc tgataaatca tgcaattaaa | 4200 |
| gtaaagtgat gcaacatctt gtaaaaaaaa ag | 4232 |

<210> SEQ ID NO 2
<211> LENGTH: 3042
<212> TYPE: DNA
<213> ORGANISM: Homo sapiens

<400> SEQUENCE: 2

| | |
|---|---|
| gaattccgcc ctcgccgccc gcggcgcccc gagcgctttg tgagcagatg cggagccgag | 60 |
| tggagggcgc gagccagatg cggggcgaca gctgacttgc tgagaggagg cggggaggcg | 120 |
| cggagcgcgc gtgtggtcct tgcgccgctg acttctccac tggttcctgg caccgaaag | 180 |
| ataaacctct cataatgaag gcccccgctg tgcttgcacc tggcatcctc gtgctcctgt | 240 |
| ttaccttggt gcagaggagc aatggggagt gtaaagaggc actagcaaag tccgagatga | 300 |
| atgtgaatat gaagtatcag cttcccaact tcaccgcgga aacacccatc cagaatgtca | 360 |
| ttctacatga gcatcacatt ttccttggtg ccactaacta catttatgtt ttaaatgagg | 420 |
| aagaccttca gaaggttgct gagtacaaga ctgggcctgt gctggaacac ccagattgtt | 480 |
| tcccatgtca ggactgcagc agcaaagcca atttatcagg aggtgtttgg aaagataaca | 540 |
| tcaacatggc tctagttgtc gacacctact atgatgatca actcattagc tgtggcagcg | 600 |
| tcaacagagg gacctgccag cgacatgtct ttccccacaa tcatactgct gacatacagt | 660 |
| cggaggttca ctgcatattc tccccacaga tagaagagcc cagccagtgt cctgactgtg | 720 |
| tggtgagcgc cctgggagcc aaagtccttt catctgtaaa ggaccggttc atcaacttct | 780 |
| ttgtaggcaa taccataaat tcttcttatt tcccagatca tccattgcat tcgatatcag | 840 |
| tgagaaggct aaaggaaacg aaagatggtt ttatgttttt gacggaccag tcctacattg | 900 |
| atgttttacc tgagttcaga gattcttacc ccattaagta tgtccatgcc tttgaaagca | 960 |
| acaattttat ttacttcttg acggtccaaa gggaaactct agatgctcag acttttcaca | 1020 |
| caagaataat caggttctgt tccataaact ctggattgca ttcctacatg gaaatgcctc | 1080 |
| tggagtgtat tctcacagaa aagagaaaaa agagatccac aaagaaggaa gtgtttaata | 1140 |
| tacttcaggc tgcgtatgtc agcaagcctg ggcccagct tgctagacaa ataggagcca | 1200 |
| gcctgaatga tgacattctt ttcggggtgt tcgcacaaag caagccagat tctgccgaac | 1260 |
| caatggatcg atctgccatg tgtgcattcc ctatcaaata tgtcaacgac ttcttcaaca | 1320 |
| agatcgtcaa caaaaacaat gtgagatgtc tccagcattt ttacggaccc aatcatgagc | 1380 |
| actgctttaa taggacactt ctgagaaatt catcaggctg tgaagcgcgc cgtgatgaat | 1440 |
| atcgaacaga gtttaccaca gctttgcagc gcgttgactt attcatgggt caattcagcg | 1500 |
| aagtcctctt aacatctata tccaccttca ttaaaggaga cctcaccata gctaatcttg | 1560 |
| ggacatcaga gggtcgcttc atgcaggttg tggtttctcg atcaggacca tcaaccoctc | 1620 |
| atgtgaattt tctcctggac tcccatccag tgtctccaga agtgattgtg gagcatacat | 1680 |
| taaaccaaaa tggctacaca ctggttatca ctgggaagaa gatcacgaag atcccattga | 1740 |

```
atggcttggg ctgcagacat ttccagtcct gcagtcaatg cctctctgcc ccacccttg     1800 ttcagtgtgg ctggtgccac gacaaatgtg tgcgatcgga ggaatgcctg agcgggacat    1860
ggactcaaca gatctgtctg cctgcaatct acaaggtttt cccaaatagt gcaccccttg    1920
aaggagggac aaggctgacc atatgtggct gggactttgg atttcggagg aataataaat    1980
ttgatttaaa gaaaactaga gttctccttg gaaatgagag ctgcaccttg actttaagtg    2040
agagcacgat gaatacattg aaatgcacag ttggtcctgc catgaataag catttcaata    2100
tgtccataat tatttcaaat ggccacggga caacacaata cagtacattc tcctatgtgg    2160
atcctgtaat aacaagtatt tcgccgaaat acggtcctat ggctggtggc actttactta    2220 cttaactgg aaattaccta aacagtggga attctagaca catttcaatt ggtggaaaaa     2280
catgtacttt aaaaagtgtg tcaaacagta ttcttgaatg ttatacccca gcccaaacca    2340
tttcaactga gtttgctgtt aaattgaaaa ttgacttagc caaccgagag acaagcatct    2400
tcagttaccg tgaagatccc attgtctatg aaattcatcc aaccaaatct tttattagtg    2460
gtgggagcac aataacaggt gttgggaaaa acctgaattc agttagtgtc ccgagaatgg    2520
tcataaatgt gcatgaagca ggaaggaact ttacagtggc atgtcaacat cgctctaatt    2580
cagagataat ctgttgtacc actccttccc tgcaacagct gaatctgcaa ctccccctga    2640
aaaccaaagc ttttttcatg ttagatggga tcctttccaa atactttgat ctcatttatg    2700
tacataatcc tgtgtttaag ccttttgaaa agccagtgat gatctcaatg ggcaatgaaa    2760
atgtactgga aattaaggga aatgatattg accctgaagc agttaaaggt gaagtgttaa    2820
aagttggaaa taagagctgt gagaatatac acttacattc tgaagccgtt ttatgcacgg    2880
tccccaatga cctgctgaaa ttgaacagcg agctaaatat agaggtggga ttcctgcatt    2940
cctctcatga tgtaaataag gaagccagtg taattatgtt attctcaggc ttaaaataaa    3000
tcattaaagc tcatttatgt gtgggttttg gctcatcaac tc                      3042
```

<210> SEQ ID NO 3
<211> LENGTH: 2840
<212> TYPE: DNA
<213> ORGANISM: Homo sapiens

<400> SEQUENCE: 3

```
gaattccgcc ctcgccgccc gcggcgcccc gagcgctttg tgagcagatg cggagccgag     60
tggagggcgc gagccagatg cggggcgaca gctgacttgc tgagaggagg cggggaggcg    120
cggagcgcgc gtgtggtcct tgcgccgctg acttctccac tggttcctgg gcaccgaaag    180
ataaacctct cataatgaag gccccgctg tgcttgcacc tggcatcctc gtgctcctgt     240
ttaccttggt gcagaggagc aatggggagt gtaaagaggc actagcaaag tccgagatga    300
atgtgaatat gaagtatcag cttcccaact tcaccgcgga aacacccatc cagaatgtca    360
ttctacatga gcatcacatt ttccttggtg ccactaacta catttatgtt ttaaatgagg    420
aagaccttca gaaggttgct gagtacaaga ctgggcctgt gctggaacac ccagattgtt    480
tcccatgtca ggactgcagc agcaaagcca atttatcagg aggtgtttgg aaagataaca    540
tcaacatggc tctagttgtc gacacctact atgatgatca actcattagc tgtggcagcg    600
tcaacagagg gacctgccag cgacatgtct tccccacaa tcatactgct gacatacagt     660
cggaggttca ctgcatattc tccccacaga tagaagagcc cagccagtgt cctgactgtg    720
tggtgagcgc cctgggagcc aaagtccttt catctgtaaa ggaccggttc atcaacttct    780
ttgtaggcaa taccataaat tcttcttatt tcccagatca tccattgcat tcgatatcag    840
```

```
tgagaaggct aaaggaaacg aaagatggtt ttatgttttt gacggaccag tcctacattg    900
atgttttacc tgagttcaga gattcttacc ccattaagta tgtccatgcc tttgaaagca    960
acaattttat ttacttcttg acggtccaaa gggaaactct agatgctcag acttttcaca   1020
caagaataat caggttctgt tccataaact ctggattgca ttcctacatg gaaatgcctc   1080
tggagtgtat tctcacagaa aagagaaaaa agagatccac aaagaaggaa gtgtttaata   1140
tacttcaggc tgcgtatgtc agcaagcctg ggcccagct tgctagacaa ataggagcca    1200
gcctgaatga tgacattctt ttcggggtgt cgcacaaag caagccagat tctgccgaac    1260
caatggatcg atctgccatg tgtgcattcc ctatcaaata tgtcaacgac ttcttcaaca   1320
agatcgtcaa caaaaacaat gtgagatgtc tccagcattt ttacggaccc aatcatgagc   1380
actgctttaa taggacactt ctgagaaatt catcaggctg tgaagcgcgc cgtgatgaat   1440
atcgaacaga gtttaccaca gctttgcagc gcgttgactt attcatgggt caattcagcg   1500
aagtcctctt aacatctata tccaccttca ttaaaggaga cctcaccata gctaatcttg   1560
ggacatcaga gggtcgcttc atgcaggttg tggtttctcg atcaggacca tcaacccctc   1620
atgtgaattt tctcctggac tcccatccag tgtctccaga agtgattgtg gagcatacat   1680
taaaccaaaa tggctacaca ctggttatca ctgggaagaa gatcacgaag atcccattga   1740
atggcttggg ctgcagacat ttccagtcct gcagtcaatg cctctctgcc ccacccttg    1800
ttcagtgtgg ctggtgccac gacaaatgtg tgcgatcgga ggaatgcctg agcgggacat   1860
ggactcaaca gatctgtctg cctgcaatct acaaggtttt cccaaatagt gcaccccttg   1920
aaggagggac aaggctgacc atatgtggct gggactttgg atttcggagg aataataaat   1980
ttgatttaaa gaaaactaga gttctccttg gaaatgagag ctgcaccttg actttaagtg   2040
agagcacgat gaatacattg aaatgcacag ttggtcctgc catgaataag catttcaata   2100
tgtccataat tatttcaaat ggccacggga caacacaata cagtacattc tcctatgtgg   2160
atcctgtaat aacaagtatt tcgccgaaat acggtcctat ggctggtggc acttttactta  2220
cttaactgg aaattaccta aacagtggga attctagaca catttcaatt ggtgaaaaa    2280
catgtacttt aaaaagtgtg tcaaacagta ttcttgaatg ttataccca gcccaaacca    2340
tttcaactga gtttgctgtt aaattgaaaa ttgacttagc caaccgagag acaagcatct   2400
tcagttaccg tgaagatccc attgtctatg aaattcatcc aaccaaatct tttattagtg   2460
gtgggagcac aataacaggt gttgggaaaa acctgaattc agttagtgtc ccgagaatgg   2520
tcataaatgt gcatgaagca ggaaggaact ttacagtggc atgtcaacat cgctctaatt   2580
cagagataat ctgttgtacc actccttccc tgcaacagct gaatctgcaa ctcccctga    2640
aaaccaaagc cttttttcatg ttagatggga tcctttccaa atactttgat ctcatttatg   2700
tacataatcc tgtgtttaag cctttttgaaa agccagtgat gatctcaatg ggcaatgaaa   2760
atgtactgga aattaaggta agaaatgctt taaacactgt cttaaatcat cagctcaaac   2820
ttaattgact tcatagctat                                                2840
```

<210> SEQ ID NO 4
<211> LENGTH: 180
<212> TYPE: DNA
<213> ORGANISM: Artificial Organism
<220> FEATURE:
<223> OTHER INFORMATION: Synthetic oligonucleotide

<400> SEQUENCE: 4

```
gaattccgcc ctcgccgccc gcggcgcccc gagcgctttg tgagcagatg cggagccgag      60
tggagggcgc gagccagatg cggggcgaca gctgacttgc tgagaggagg cggggaggcg     120
cggagcgcgc gtgtggtcct tgcgccgctg acttctccac tggttcctgg gcaccgaaag     180

<210> SEQ ID NO 5
<211> LENGTH: 1214
<212> TYPE: DNA
<213> ORGANISM: Artificial Organism
<220> FEATURE:
<223> OTHER INFORMATION: Synthetic oligonucleotide

<400> SEQUENCE: 5
ataaacctct cataatgaag gccccgctg tgcttgcacc tggcatcctc gtgctcctgt      60
ttaccttggt gcagaggagc aatggggagt gtaaagaggc actagcaaag tccgagatga    120
atgtgaatat gaagtatcag cttcccaact tcaccgcgga acacccatc cagaatgtca    180 ttctacatga gcatcacatt ttccttggtg ccactaacta catttatgtt ttaaatgagg    240
aagaccttca gaaggttgct gagtacaaga ctgggcctgt gctggaacac ccagattgtt    300
tcccatgtca ggactgcagc agcaaagcca atttatcagg aggtgtttgg aaagataaca    360
tcaacatggc tctagttgtc gacacctact atgatgatca actcattagc tgtggcagcg    420
tcaacagagg gacctgccag cgacatgtct tccccacaa tcatactgct gacatacagt    480
cggaggttca ctgcatattc tccccacaga tagaagagcc cagccagtgt cctgactgtg    540
tggtgagcgc cctgggagcc aaagtccttt catctgtaaa ggaccggttc atcaacttct    600
ttgtaggcaa taccataaat tcttcttatt tcccagatca tccattgcat tcgatatcag    660
tgagaaggct aaaggaaacg aaagatggtt ttatgttttt gacggaccag tcctacattg    720 atgtttttacc tgagttcaga gattcttacc ccattaagta tgtccatgcc tttgaaagca    780
acaattttat ttacttcttg acggtccaaa gggaaactct agatgctcag acttttcaca    840
caagaataat caggttctgt tccataaact ctggattgca ttcctacatg gaaatgcctc    900
tggagtgtat tctcacagaa aagagaaaaa agagatccac aaagaaggaa gtgtttaata    960
tacttcaggc tgcgtatgtc agcaagcctg gggccagct tgctagacaa ataggagcca   1020
gcctgaatga tgacattctt ttcggggtgt tcgcacaaag caagccagat tctgccgaac   1080
caatggatcg atctgccatg tgtgcattcc ctatcaaata tgtcaacgac ttcttcaaca   1140
agatcgtcaa caaaaacaat gtgagatgtc tccagcattt ttacggaccc aatcatgagc   1200
actgctttaa tagg                                                    1214

<210> SEQ ID NO 6
<211> LENGTH: 192
<212> TYPE: DNA
<213> ORGANISM: Artificial Organism
<220> FEATURE:
<223> OTHER INFORMATION: Synthetic oligonucleotide

<400> SEQUENCE: 6
acacttctga gaaattcatc aggctgtgaa gcgcgccgtg atgaatatcg aacagagttt      60
accacagctt tgcagcgcgt tgacttattc atgggtcaat tcagcgaagt cctcttaaca    120
tctatatcca ccttcattaa aggagaccctc accatagcta atcttgggac atcagagggt    180
cgcttcatgc ag                                                       192

<210> SEQ ID NO 7
<211> LENGTH: 135
```

```
<212> TYPE: DNA
<213> ORGANISM: Artificial Organism
<220> FEATURE:
<223> OTHER INFORMATION: Synthetic oligonucleotide

<400> SEQUENCE: 7
gttgtggttt ctcgatcagg accatcaacc cctcatgtga attttctcct ggactcccat        60
ccagtgtctc cagaagtgat tgtggagcat acattaaacc aaaatggcta cacactggtt       120
atcactggga agaag                                                         135

<210> SEQ ID NO 8
<211> LENGTH: 161
<212> TYPE: DNA
<213> ORGANISM: Artificial Organism
<220> FEATURE:
<223> OTHER INFORMATION: Synthetic oligonucleotide

<400> SEQUENCE: 8
gttttcccaa atagtgcacc ccttgaagga gggacaaggc tgaccatatg tggctgggac        60
tttggatttc ggaggaataa taaatttgat ttaaagaaaa ctagagttct ccttggaaat       120
gagagctgca ccttgacttt aagtgagagc acgatgaata c                           161

<210> SEQ ID NO 9
<211> LENGTH: 137
<212> TYPE: DNA
<213> ORGANISM: Artificial Organism
<220> FEATURE:
<223> OTHER INFORMATION: Synthetic oligonucleotide

<400> SEQUENCE: 9
gatcctgtaa taacaagtat ttcgccgaaa tacggtccta tggctggtgg cactttactt        60
actttaactg gaaattacct aaacagtggg aattctagac acatttcaat tggtggaaaa       120
acatgtactt taaaaag                                                       137

<210> SEQ ID NO 10
<211> LENGTH: 162
<212> TYPE: DNA
<213> ORGANISM: Artificial Organism
<220> FEATURE:
<223> OTHER INFORMATION: Synthetic oligonucleotide

<400> SEQUENCE: 10
tgtgtcaaac agtattcttg aatgttatac cccagcccaa accatttcaa ctgagtttgc        60
tgttaaattg aaaattgact tagccaaccg agagacaagc atcttcagtt accgtgaaga       120
tcccattgtc tatgaaattc atccaaccaa atctttttat t ag                         162

<210> SEQ ID NO 11
<211> LENGTH: 219
<212> TYPE: DNA
<213> ORGANISM: Artificial Organism
<220> FEATURE:
<223> OTHER INFORMATION: Synthetic oligonucleotide

<400> SEQUENCE: 11
gcatgtcaac atcgctctaa ttcagagata atctgttgta ccactccttc cctgcaacag        60
ctgaatctgc aactccccct gaaaaccaaa gccttttca tgttagatgg gatcctttcc       120
aaatactttg atctcattta tgtacataat cctgtgttta gccttttga aaagccagtg       180 atgatctcaa tgggcaatga aaatgtactg gaaattaag                              219
```

<210> SEQ ID NO 12
<211> LENGTH: 147
<212> TYPE: DNA
<213> ORGANISM: Artificial Organism
<220> FEATURE:
<223> OTHER INFORMATION: Synthetic oligonucleotide

<400> SEQUENCE: 12
ggaaatgata ttgaccctga agcagttaaa ggtgaagtgt taaaagttgg aaataagagc    60
tgtgagaata tacacttaca ttctgaagcc gttttatgca cggtccccaa tgacctgctg   120
aaattgaaca gcgagctaaa tatagag                                       147

<210> SEQ ID NO 13
<211> LENGTH: 328
<212> TYPE: DNA
<213> ORGANISM: Artificial Organism
<220> FEATURE:
<223> OTHER INFORMATION: Synthetic oligonucleotide

<400> SEQUENCE: 13
atatgaagta atgctaaaat gctggcaccc taaagccgaa atgcgcccat cctttctga    60 actggtgtcc cggatatcag caatcttctc tactttcatt ggggagcact atgtccatgt   120
gaacgctact tatgtgaacg taaaatgtgt cgctccatat ccttctctgt tgtcatcaga   180
agataacgct gatgatgagg tggacacacg accagcctcc ttctgggaga catcatagtg   240
ctagtactat gtcaaagcaa cagtccacac tttgtccaat ggtttttttca ctgcctgacc   300 tttaaaaggc catcgatatt ctttgctc                                      328

<210> SEQ ID NO 14
<211> LENGTH: 135
<212> TYPE: DNA
<213> ORGANISM: Artificial Organism
<220> FEATURE:
<223> OTHER INFORMATION: Synthetic oligonucleotide

<400> SEQUENCE: 14
gacttgtatt gttatttaaa ttactggatt ctaaggaatt tcttatctga cagagcatca    60
gaaccagagg cttggtccca caggccacgg accaatggcc tgcagccgtg acaacactcc   120
tgtcatattg gagtc                                                    135

<210> SEQ ID NO 15
<211> LENGTH: 123
<212> TYPE: DNA
<213> ORGANISM: Artificial Organism
<220> FEATURE:
<223> OTHER INFORMATION: Synthetic oligonucleotide

<400> SEQUENCE: 15
caaaacttga attctgggtt gaatttttta aaaatcaggt accacttgat ttcatatggg    60
aaattgaagc aggaaatatt gagggcttct tgatcacaga aaactcagaa gagatagtaa   120
tgc                                                                 123

<210> SEQ ID NO 16
<211> LENGTH: 266
<212> TYPE: DNA
<213> ORGANISM: Artificial Organism
<220> FEATURE:
<223> OTHER INFORMATION: Synthetic oligonucleotide

<400> SEQUENCE: 16

```
tcaggacagg agcggcagcc ccagaacagg ccactcattt agaattctag tgtttcaaaa      60
cacttttgtg tgttgtatgg tcaataacat ttttcattac tgatggtgtc attcacccat     120
taggtaaaca ttcccttta aatgtttgtt tgttttttga dacaggatct cactctgttg      180
ccagggctgt agtgcagtgg tgtgatcata gctcactgca acctccacct cccaggctca     240
agcctcccga atagctggga ctacag                                          266

<210> SEQ ID NO 17
<211> LENGTH: 271
<212> TYPE: DNA
<213> ORGANISM: Artificial Organism
<220> FEATURE:
<223> OTHER INFORMATION: Synthetic oligonucleotide

<400> SEQUENCE: 17
gcgcacacca ccatccccgg ctaatttttg tatttttgt agagacgggg ttttgccatg       60
ttgccaaggc tggtttcaaa ctcctggact caagaaatcc acccacctca gcctcccaaa     120
gtgctaggat tacaggcatg agccactgcg cccagccctt ataaattttt gtatagacat     180
tcctttggtt ggaagaatat ttataggcaa tacagtcaaa gtttcaaaat agcatcacac     240
aaaacatgtt tataaatgaa caggatgtaa t                                    271

<210> SEQ ID NO 18
<211> LENGTH: 1031
<212> TYPE: DNA
<213> ORGANISM: Artificial Organism
<220> FEATURE:
<223> OTHER INFORMATION: Synthetic oligonucleotide

<400> SEQUENCE: 18
tctgatctaa tgaatgtgaa catgtagatg ttttgtgtgt attttttaa atgaaaactc       60 aaaataagac aagtaatttg ttgataaata ttttaaaga taactcagca tgtttgtaaa     120
gcaggataca ttttactaaa aggttcattg gttccaatca cagctcatag gtagagcaaa     180
gaaagggtgg atggattgaa aagattagcc tctgtctcgg tggcaggttc ccacctcgca     240
agcaattgga aacaaaactt tggggagtt ttattttgca ttagggtgtg ttttatgtta     300
agcaaaacat actttagaag caaatgaaaa aggcaattga aaatcccagc tatttcacct     360
agatggaata gccacccctga gcagaacttt gtgatgcttc attctgtgga attttgtgct     420
tactactgta tagtgcatgt ggtgtaggtt actctaactg gttttgtcga cgtaaacatt     480
taaagtgtta tattttttat aaaaatgttt attttaatg atatgagaaa attttgtta     540 ggccacaaaa acactgcact gtgaacattt tagaaaaggt atgtcagact gggattaatg     600
acagcatgat tttcaatgac tgtaaattgc gataaggaaa tgtactgatt gccaatacac     660 cccacccctca ttcatcatc aggacttgaa gccaagggtt aacccagcaa gctacaaaga     720
gggtgtgtca cactgaaact caatagttga gtttggctgt tgttgcagga aaatgattat     780
aactaaaagc tctctgatag tgcagagact taccagaaga cacaaggaat tgtactgaag     840
agctattaca atccaaatat tgccgtttca taaatgtaat aagtaatact aattcacaga     900
gtattgtaaa tggtggatga caaaagaaaa tctgctctgt ggaaagaaag aactgtctct     960
accagggtca agagcatgaa cgcatcaata gaaagaactc ggggaaacat cccatcaaca    1020
ggactacaca c                                                         1031

<210> SEQ ID NO 19
```

<211> LENGTH: 141
<212> TYPE: DNA
<213> ORGANISM: Artificial Organism
<220> FEATURE:
<223> OTHER INFORMATION: Synthetic oligonucleotide

<400> SEQUENCE: 19
gagtaagtga ttcttctaag aattagatac ttgtcactgc ctatacctgc agctgaactg    60
aatggtactt cgtatgttaa tagttgttct gataaatcat gcaattaaag taaagtgatg   120
caacatcttg taaaaaaaaa g                                             141

<210> SEQ ID NO 20
<211> LENGTH: 84
<212> TYPE: DNA
<213> ORGANISM: Artificial Organism
<220> FEATURE:
<223> OTHER INFORMATION: Synthetic oligonucleotide

<400> SEQUENCE: 20
atcacgaaga tcccattgaa tggcttgggc tgcagacatt tccagtcctg cagtcaatgc    60
ctctctgccc caccctttgt tcag                                           84

<210> SEQ ID NO 21
<211> LENGTH: 90
<212> TYPE: DNA
<213> ORGANISM: Artificial Organism
<220> FEATURE:
<223> OTHER INFORMATION: Synthetic oligonucleotide

<400> SEQUENCE: 21
tgtggctggt gccacgacaa atgtgtgcga tcggaggaat gcctgagcgg gacatggact    60
caacagatct gtctgcctgc aatctacaag                                     90

<210> SEQ ID NO 22
<211> LENGTH: 103
<212> TYPE: DNA
<213> ORGANISM: Artificial Organism
<220> FEATURE:
<223> OTHER INFORMATION: Synthetic oligonucleotide

<400> SEQUENCE: 22
attgaaatgc acagttggtc ctgccatgaa taagcatttc aatatgtcca taattatttc    60
aaatggccac gggacaacac aatacagtac attctcctat gtg                     103

<210> SEQ ID NO 23
<211> LENGTH: 100
<212> TYPE: DNA
<213> ORGANISM: Artificial Organism
<220> FEATURE:
<223> OTHER INFORMATION: Synthetic oligonucleotide

<400> SEQUENCE: 23
tggtgggagc acaataacag gtgttggaa aaacctgaat tcagttagtg tcccgagaat     60
ggtcataaat gtgcatgaag caggaaggaa ctttacagtg                         100

<210> SEQ ID NO 24
<211> LENGTH: 63
<212> TYPE: DNA
<213> ORGANISM: Artificial Organism
<220> FEATURE:
<223> OTHER INFORMATION: Synthetic oligonucleotide

<400> SEQUENCE: 24

```
gtaagaaatg ctttaaacac tgtcttaaat catcagctca aacttaattg acttcatagc    60
tat                                                                 63

<210> SEQ ID NO 25
<211> LENGTH: 118
<212> TYPE: DNA
<213> ORGANISM: Artificial Organism
<220> FEATURE:
<223> OTHER INFORMATION: Synthetic oligonucleotide

<400> SEQUENCE: 25
gtgggattcc tgcattcctc tcatgatgta aataaggaag ccagtgtaat tatgttattc    60
tcaggcttaa aataaatcat taaagctcat ttatgtgtgg gttttggctc atcaactc     118

<210> SEQ ID NO 26
<211> LENGTH: 27
<212> TYPE: DNA
<213> ORGANISM: Artificial Organism
<220> FEATURE:
<223> OTHER INFORMATION: Synthetic oligonucleotide

<400> SEQUENCE: 26
tggtcctttg gcgtgctcct ctgggag                                       27

<210> SEQ ID NO 27
<211> LENGTH: 28
<212> TYPE: DNA
<213> ORGANISM: Artificial Organism
<220> FEATURE:
<223> OTHER INFORMATION: Synthetic oligonucleotide

<400> SEQUENCE: 27
ctgatgacaa gaggagcccc accttatc                                      28

<210> SEQ ID NO 28
<211> LENGTH: 43
<212> TYPE: DNA
<213> ORGANISM: Artificial Organism
<220> FEATURE:
<223> OTHER INFORMATION: Synthetic oligonucleotide

<400> SEQUENCE: 28
ctgatgtaaa cacctttgat ataactgttt acttgttgca agg                     43

<210> SEQ ID NO 29
<211> LENGTH: 39
<212> TYPE: DNA
<213> ORGANISM: Artificial Organism
<220> FEATURE:
<223> OTHER INFORMATION: Synthetic oligonucleotide

<400> SEQUENCE: 29
gagaagactc ctacaacccg aatactgccc agaccccctt                         39

<210> SEQ ID NO 30
<211> LENGTH: 9
<212> TYPE: DNA
<213> ORGANISM: Artificial Organism
<220> FEATURE:
<223> OTHER INFORMATION: Synthetic oligonucleotide

<400> SEQUENCE: 30 ttgccaaaa                                                           9
```

-continued

<210> SEQ ID NO 31
<211> LENGTH: 14
<212> TYPE: DNA
<213> ORGANISM: Artificial Organism
<220> FEATURE:
<223> OTHER INFORMATION: Synthetic oligonucleotide

<400> SEQUENCE: 31
ttgcactatt atag                                                      14

<210> SEQ ID NO 32
<211> LENGTH: 98
<212> TYPE: DNA
<213> ORGANISM: Artificial Organism
<220> FEATURE:
<223> OTHER INFORMATION: Synthetic oligonucleotide

<400> SEQUENCE: 32
gtacatagat gacattaaga aaatttgtat gaaataattt agtcatcatg aaatatttag    60
ttgtcatata aaacccact gtttgagaat gatgctac                             98

<210> SEQ ID NO 33
<211> LENGTH: 93
<212> TYPE: DNA
<213> ORGANISM: Artificial Organism
<220> FEATURE:
<223> OTHER INFORMATION: Synthetic oligonucleotide

<400> SEQUENCE: 33
ttgtatatac attcttgaga acactgcaat gtgaaaatca cgtttgctat ttataaactt    60
gtccttagat taatgtgtct ggacagattg tgg                                 93

<210> SEQ ID NO 34
<211> LENGTH: 1390
<212> TYPE: PRT
<213> ORGANISM: Homo sapiens

<400> SEQUENCE: 34

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val

-continued

```
            165                 170                 175
Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
            195                 200                 205

His Pro Leu His Ser Ile Ser Val Arg Arg Leu Lys Glu Thr Lys Asp
            210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
                260                 265                 270

Thr Phe His Thr Arg Ile Ile Arg Phe Cys Ser Ile Asn Ser Gly Leu
            275                 280                 285

His Ser Tyr Met Glu Met Pro Leu Glu Cys Ile Leu Thr Glu Lys Arg
            290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
            355                 360                 365

Tyr Val Asn Asp Phe Phe Asn Lys Ile Val Asn Lys Asn Asn Val Arg
            370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
            435                 440                 445

Asp Leu Thr Ile Ala Asn Leu Gly Thr Ser Glu Gly Arg Phe Met Gln
            450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590
```

-continued

```
Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
        610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                    645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
        690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                    725                 730                 735

Ser Tyr Arg Glu Asp Pro Ile Val Tyr Glu Ile His Pro Thr Lys Ser
                740                 745                 750

Phe Ile Ser Gly Gly Ser Thr Ile Thr Gly Val Gly Lys Asn Leu Asn
            755                 760                 765

Ser Val Ser Val Pro Arg Met Val Ile Asn Val His Glu Ala Gly Arg
        770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                    805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Lys Pro Phe Glu Lys Pro Val
            835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                    885                 890                 895

Pro Asn Asp Leu Leu Lys Leu Asn Ser Glu Leu Asn Ile Glu Trp Lys
                900                 905                 910

Gln Ala Ile Ser Ser Thr Val Leu Gly Lys Val Ile Val Gln Pro Asp
            915                 920                 925

Gln Asn Phe Thr Gly Leu Ile Ala Gly Val Val Ser Ile Ser Thr Ala
        930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                    965                 970                 975

Thr Pro His Leu Asp Arg Leu Val Ser Ala Arg Ser Val Ser Pro Thr
                980                 985                 990

Thr Glu Met Val Ser Asn Glu Ser  Val Asp Tyr Arg Ala  Thr Phe Pro
            995                 1000                 1005
```

-continued

```
Glu Asp Gln Phe Pro Asn Ser Ser Gln Asn Gly Ser Cys Arg Gln
1010                1015                1020

Val Gln Tyr Pro Leu Thr Asp Met Ser Pro Ile Leu Thr Ser Gly
1025                1030                1035

Asp Ser Asp Ile Ser Ser Pro Leu Leu Gln Asn Thr Val His Ile
1040                1045                1050

Asp Leu Ser Ala Leu Asn Pro Glu Leu Val Gln Ala Val Gln His
1055                1060                1065

Val Val Ile Gly Pro Ser Ser Leu Ile Val His Phe Asn Glu Val
1070                1075                1080

Ile Gly Arg Gly His Phe Gly Cys Val Tyr His Gly Thr Leu Leu
1085                1090                1095

Asp Asn Asp Gly Lys Lys Ile His Cys Ala Val Lys Ser Leu Asn
1100                1105                1110

Arg Ile Thr Asp Ile Gly Glu Val Ser Gln Phe Leu Thr Glu Gly
1115                1120                1125

Ile Ile Met Lys Asp Phe Ser His Pro Asn Val Leu Ser Leu Leu
1130                1135                1140

Gly Ile Cys Leu Arg Ser Glu Gly Ser Pro Leu Val Val Leu Pro
1145                1150                1155

Tyr Met Lys His Gly Asp Leu Arg Asn Phe Ile Arg Asn Glu Thr
1160                1165                1170

His Asn Pro Thr Val Lys Asp Leu Ile Gly Phe Gly Leu Gln Val
1175                1180                1185

Ala Lys Gly Met Lys Tyr Leu Ala Ser Lys Lys Phe Val His Arg
1190                1195                1200

Asp Leu Ala Ala Arg Asn Cys Met Leu Asp Glu Lys Phe Thr Val
1205                1210                1215

Lys Val Ala Asp Phe Gly Leu Ala Arg Asp Met Tyr Asp Lys Glu
1220                1225                1230

Tyr Tyr Ser Val His Asn Lys Thr Gly Ala Lys Leu Pro Val Lys
1235                1240                1245

Trp Met Ala Leu Glu Ser Leu Gln Thr Gln Lys Phe Thr Thr Lys
1250                1255                1260

Ser Asp Val Trp Ser Phe Gly Val Val Leu Trp Glu Leu Met Thr
1265                1270                1275

Arg Gly Ala Pro Pro Tyr Pro Asp Val Asn Thr Phe Asp Ile Thr
1280                1285                1290

Val Tyr Leu Leu Gln Gly Arg Arg Leu Leu Gln Pro Glu Tyr Cys
1295                1300                1305

Pro Asp Pro Leu Tyr Glu Val Met Leu Lys Cys Trp His Pro Lys
1310                1315                1320

Ala Glu Met Arg Pro Ser Phe Ser Glu Leu Val Ser Arg Ile Ser
1325                1330                1335

Ala Ile Phe Ser Thr Phe Ile Gly Glu His Tyr Val His Val Asn
1340                1345                1350

Ala Thr Tyr Val Asn Val Lys Cys Val Ala Pro Tyr Pro Ser Leu
1355                1360                1365

Leu Ser Ser Glu Asp Asn Ala Asp Asp Glu Val Asp Thr Arg Pro
1370                1375                1380

Ala Ser Phe Trp Glu Thr Ser
1385                1390
```

```
<210> SEQ ID NO 35
<211> LENGTH: 1390
<212> TYPE: PRT
<213> ORGANISM: Homo sapiens

<400> SEQUENCE: 35
```

| | | | | | | | | | | | | | | |
|---|---|---|---|---|---|---|---|---|---|---|---|---|---|---|
| Met | Lys | Ala | Pro | Ala | Val | Leu | Ala | Pro | Gly | Ile | Leu | Val | Leu | Phe |
| 1 | | | | 5 | | | | | 10 | | | | | 15 |
| Thr | Leu | Val | Gln | Arg | Ser | Asn | Gly | Glu | Cys | Lys | Glu | Ala | Leu | Ala | Lys |
| | | | 20 | | | | | 25 | | | | | 30 | | |
| Ser | Glu | Met | Asn | Val | Asn | Met | Lys | Tyr | Gln | Leu | Pro | Asn | Phe | Thr | Ala |
| | | 35 | | | | | 40 | | | | | 45 | | | |
| Glu | Thr | Pro | Ile | Gln | Asn | Val | Ile | Leu | His | Glu | His | His | Ile | Phe | Leu |
| | 50 | | | | | 55 | | | | | 60 | | | | |
| Gly | Ala | Thr | Asn | Tyr | Ile | Tyr | Val | Leu | Asn | Glu | Glu | Asp | Leu | Gln | Lys |
| 65 | | | | | 70 | | | | | 75 | | | | | 80 |
| Val | Ala | Glu | Tyr | Lys | Thr | Gly | Pro | Val | Leu | Glu | His | Pro | Asp | Cys | Phe |
| | | | | 85 | | | | | 90 | | | | | 95 | |
| Pro | Cys | Gln | Asp | Cys | Ser | Ser | Lys | Ala | Asn | Leu | Ser | Gly | Gly | Val | Trp |
| | | | 100 | | | | | 105 | | | | | 110 | | |
| Lys | Asp | Asn | Ile | Asn | Met | Ala | Leu | Val | Val | Asp | Thr | Tyr | Tyr | Asp | Asp |
| | | 115 | | | | | 120 | | | | | 125 | | | |
| Gln | Leu | Ile | Ser | Cys | Gly | Ser | Val | Asn | Arg | Gly | Thr | Cys | Gln | Arg | His |
| | 130 | | | | | 135 | | | | | 140 | | | | |
| Val | Phe | Pro | His | Asn | His | Thr | Ala | Asp | Ile | Gln | Ser | Glu | Val | His | Cys |
| 145 | | | | | 150 | | | | | 155 | | | | | 160 |
| Ile | Phe | Ser | Pro | Gln | Ile | Glu | Glu | Pro | Ser | Gln | Cys | Pro | Asp | Cys | Val |
| | | | | 165 | | | | | 170 | | | | | 175 | |
| Val | Ser | Ala | Leu | Gly | Ala | Lys | Val | Leu | Ser | Ser | Val | Lys | Asp | Arg | Phe |
| | | | 180 | | | | | 185 | | | | | 190 | | |
| Ile | Asn | Phe | Phe | Val | Gly | Asn | Thr | Ile | Asn | Ser | Ser | Tyr | Phe | Pro | Asp |
| | | 195 | | | | | 200 | | | | | 205 | | | |
| His | Pro | Leu | His | Ser | Ile | Ser | Val | Arg | Arg | Leu | Lys | Glu | Thr | Lys | Asp |
| | 210 | | | | | 215 | | | | | 220 | | | | |
| Gly | Phe | Met | Phe | Leu | Thr | Asp | Gln | Ser | Tyr | Ile | Asp | Val | Leu | Pro | Glu |
| 225 | | | | | 230 | | | | | 235 | | | | | 240 |
| Phe | Arg | Asp | Ser | Tyr | Pro | Ile | Lys | Tyr | Val | His | Ala | Phe | Glu | Ser | Asn |
| | | | | 245 | | | | | 250 | | | | | 255 | |
| Asn | Phe | Ile | Tyr | Phe | Leu | Thr | Val | Gln | Arg | Glu | Thr | Leu | Asp | Ala | Gln |
| | | | 260 | | | | | 265 | | | | | 270 | | |
| Thr | Phe | His | Thr | Arg | Ile | Ile | Arg | Phe | Cys | Ser | Ile | Asn | Ser | Gly | Leu |
| | | 275 | | | | | 280 | | | | | 285 | | | |
| His | Ser | Tyr | Met | Glu | Met | Pro | Leu | Glu | Cys | Ile | Leu | Thr | Glu | Lys | Arg |
| | 290 | | | | | 295 | | | | | 300 | | | | |
| Lys | Lys | Arg | Ser | Thr | Lys | Lys | Glu | Val | Phe | Asn | Ile | Leu | Gln | Ala | Ala |
| 305 | | | | | 310 | | | | | 315 | | | | | 320 |
| Tyr | Val | Ser | Lys | Pro | Gly | Ala | Gln | Leu | Ala | Arg | Gln | Ile | Gly | Ala | Ser |
| | | | | 325 | | | | | 330 | | | | | 335 | |
| Leu | Asn | Asp | Asp | Ile | Leu | Phe | Gly | Val | Phe | Ala | Gln | Ser | Lys | Pro | Asp |
| | | | 340 | | | | | 345 | | | | | 350 | | |
| Ser | Ala | Glu | Pro | Met | Asp | Arg | Ser | Ala | Met | Cys | Ala | Phe | Pro | Ile | Lys |
| | | 355 | | | | | 360 | | | | | 365 | | | |
| Tyr | Val | Asn | Asp | Phe | Phe | Asn | Lys | Ile | Val | Asn | Lys | Asn | Asn | Val | Arg |
| | 370 | | | | | 375 | | | | | 380 | | | | |

```
                -continued

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
            405                 410                 415

Arg Thr Glu Phe Thr Thr Ala Leu Gln Arg Val Asp Leu Phe Met Gly
        420                 425                 430

Gln Phe Ser Glu Val Leu Leu Thr Ser Ile Ser Thr Phe Ile Lys Gly
    435                 440                 445

Asp Leu Thr Ile Ala Asn Leu Gly Thr Ser Glu Gly Arg Phe Met Gln
450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
```

-continued

```
              805                 810                 815
Thr Lys Ala Phe Phe Met Leu Asp Gly Ile Leu Ser Lys Tyr Phe Asp
            820                 825                 830
Leu Ile Tyr Val His Asn Pro Val Phe Lys Pro Phe Glu Lys Pro Val
            835                 840                 845
Met Ile Ser Met Gly Asn Glu Asn Val Leu Glu Ile Lys Gly Asn Asp
            850                 855                 860
Ile Asp Pro Glu Ala Val Lys Gly Glu Val Leu Lys Val Gly Asn Lys
865                 870                 875                 880
Ser Cys Glu Asn Ile His Leu His Ser Glu Ala Val Leu Cys Thr Val
                885                 890                 895
Pro Asn Asp Leu Leu Lys Leu Asn Ser Glu Leu Asn Ile Glu Trp Lys
                900                 905                 910
Gln Ala Ile Ser Ser Thr Val Leu Gly Lys Val Ile Val Gln Pro Asp
                915                 920                 925
Gln Asn Phe Thr Gly Leu Ile Ala Gly Val Val Ser Ile Ser Thr Ala
                930                 935                 940
Leu Leu Leu Leu Leu Gly Phe Phe Leu Trp Leu Lys Lys Arg Lys Gln
945                 950                 955                 960
Ile Lys Asp Leu Gly Ser Glu Leu Val Arg Tyr Asp Ala Arg Val His
                965                 970                 975
Thr Pro His Leu Asp Arg Leu Val Ser Ala Arg Ser Val Ser Pro Thr
                980                 985                 990
Thr Glu Met Val Ser Asn Glu Ser  Val Asp Tyr Arg Ala  Thr Phe Pro
                995                 1000                1005
Glu Asp  Gln Phe Pro Asn Ser  Ser Gln Asn Gly Ser  Cys Arg Gln
    1010                1015                1020
Val Gln  Tyr Pro Leu Thr Asp  Met Ser Pro Ile Leu  Thr Ser Gly
    1025                1030                1035
Asp Ser  Asp Ile Ser Ser Pro  Leu Leu Gln Asn Thr  Val His Ile
    1040                1045                1050
Asp Leu  Ser Ala Leu Asn Pro  Glu Leu Val Gln Ala  Val Gln His
    1055                1060                1065
Val Val  Ile Gly Pro Ser Ser  Leu Ile Val His Phe  Asn Glu Val
    1070                1075                1080
Ile Gly  Arg Gly His Phe Gly  Cys Val Tyr His Gly  Thr Leu Leu
    1085                1090                1095
Asp Asn  Asp Gly Lys Lys Ile  His Cys Ala Val Lys  Ser Leu Asn
    1100                1105                1110
Arg Ile  Thr Asp Ile Gly Glu  Val Ser Gln Phe Leu  Thr Glu Gly
    1115                1120                1125
Ile Ile  Met Lys Asp Phe Ser  His Pro Asn Val Leu  Ser Leu Leu
    1130                1135                1140
Gly Ile  Cys Leu Arg Ser Glu  Gly Ser Pro Leu Val  Val Leu Pro
    1145                1150                1155
Tyr Met  Lys His Gly Asp Leu  Arg Asn Phe Ile Arg  Asn Glu Thr
    1160                1165                1170
His Asn  Pro Thr Val Lys Asp  Leu Ile Gly Phe Gly  Leu Gln Val
    1175                1180                1185
Ala Lys  Gly Met Lys Tyr Leu  Ala Ser Lys Lys Phe  Val His Arg
    1190                1195                1200
Asp Leu  Ala Ala Arg Asn Cys  Met Leu Asp Glu Lys  Phe Thr Val
    1205                1210                1215
```

-continued

```
Lys Val Ala Asp Phe Gly Leu Ala Arg Asp Met Tyr Asp Lys Glu
    1220                1225                1230

Tyr Tyr Ser Val His Asn Lys Thr Gly Ala Lys Leu Pro Val Lys
    1235                1240                1245

Trp Met Ala Leu Glu Ser Leu Gln Thr Gln Lys Phe Thr Thr Lys
    1250                1255                1260

Ser Asp Val Trp Ser Phe Gly Val Leu Leu Trp Glu Leu Met Thr
    1265                1270                1275

Arg Gly Ala Pro Pro Tyr Pro Asp Val Asn Thr Phe Asp Ile Thr
    1280                1285                1290

Val Tyr Leu Leu Gln Gly Arg Arg Leu Leu Gln Pro Glu Tyr Cys
    1295                1300                1305

Pro Asp Pro Leu Tyr Glu Val Met Leu Lys Cys Trp His Pro Lys
    1310                1315                1320

Ala Glu Met Arg Pro Ser Phe Ser Glu Leu Val Ser Arg Ile Ser
    1325                1330                1335

Ala Ile Phe Ser Thr Phe Ile Gly Glu His Tyr Val His Val Asn
    1340                1345                1350

Ala Thr Tyr Val Asn Val Lys Cys Val Ala Pro Tyr Pro Ser Leu
    1355                1360                1365

Leu Ser Ser Glu Asp Asn Ala Asp Asp Glu Val Asp Thr Arg Pro
    1370                1375                1380

Ala Ser Phe Trp Glu Thr Ser
    1385                1390

<210> SEQ ID NO 36
<211> LENGTH: 588
<212> TYPE: PRT
<213> ORGANISM: Homo sapiens

<400> SEQUENCE: 36

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
                20                  25                  30

Ser Glu Met Asn Val Asn Met Lys Tyr Gln Leu Pro Asn Phe Thr Ala
            35                  40                  45

Glu Thr Pro Ile Gln Asn Val Ile Leu His Glu His Ile Phe Leu
        50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
```

-continued

```
             180                 185                 190
Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Trp Ser Phe Gly Val Leu Leu Trp Glu Leu Met Thr Arg Gly Ala Pro
465                 470                 475                 480

Pro Tyr Pro Asp Val Asn Thr Phe Asp Ile Thr Val Tyr Leu Leu Gln
                485                 490                 495

Gly Arg Arg Leu Leu Gln Pro Glu Tyr Cys Pro Asp Pro Leu Tyr Glu
            500                 505                 510

Val Met Leu Lys Cys Trp His Pro Lys Ala Glu Met Arg Pro Ser Phe
        515                 520                 525

Ser Glu Leu Val Ser Arg Ile Ser Ala Ile Phe Ser Thr Phe Ile Gly
    530                 535                 540

Glu His Tyr Val His Val Asn Ala Thr Tyr Val Asn Val Lys Cys Val
545                 550                 555                 560

Ala Pro Tyr Pro Ser Leu Leu Ser Ser Glu Asp Asn Ala Asp Asp Glu
                565                 570                 575

Val Asp Thr Arg Pro Ala Ser Phe Trp Glu Thr Ser
            580                 585

<210> SEQ ID NO 37
```

<211> LENGTH: 877
<212> TYPE: PRT
<213> ORGANISM: Homo sapiens

<400> SEQUENCE: 37

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
```

```
385                 390                 395                 400
Thr Leu Leu Arg Asn Ser Ser Gly Cys Glu Ala Arg Arg Asp Glu Tyr
                405                 410                 415
Arg Thr Glu Phe Thr Thr Ala Leu Gln Arg Val Asp Leu Phe Met Gly
                420                 425                 430
Gln Phe Ser Glu Val Leu Leu Thr Ser Ile Ser Thr Phe Ile Lys Gly
                435                 440                 445
Asp Leu Thr Ile Ala Asn Leu Gly Thr Ser Glu Gly Arg Phe Met Gln
                450                 455                 460
Val Val Val Ser Arg Ser Gly Pro Ser Thr Pro His Val Asn Phe Leu
465                 470                 475                 480
Leu Asp Ser His Pro Val Ser Pro Glu Val Ile Val Glu His Thr Leu
                485                 490                 495
Asn Gln Asn Gly Tyr Thr Leu Val Ile Thr Gly Lys Lys Ile Thr Lys
                500                 505                 510
Ile Pro Leu Asn Gly Leu Gly Cys Arg His Phe Gln Ser Cys Ser Gln
                515                 520                 525
Cys Leu Ser Ala Pro Pro Phe Val Gln Cys Gly Trp Cys His Asp Lys
                530                 535                 540
Cys Val Arg Ser Glu Glu Cys Leu Ser Gly Thr Trp Thr Gln Gln Ile
545                 550                 555                 560
Cys Leu Pro Ala Ile Tyr Lys Val Phe Pro Asn Ser Ala Pro Leu Glu
                565                 570                 575
Gly Gly Thr Arg Leu Thr Ile Cys Gly Trp Asp Phe Gly Phe Arg Arg
                580                 585                 590
Asn Asn Lys Phe Asp Leu Lys Lys Thr Arg Val Leu Leu Gly Asn Glu
                595                 600                 605
Ser Cys Thr Leu Thr Leu Ser Glu Ser Thr Met Asn Thr Leu Lys Cys
                610                 615                 620
Thr Val Gly Pro Ala Met Asn Lys His Phe Asn Met Ser Ile Ile Ile
625                 630                 635                 640
Ser Asn Gly His Gly Thr Thr Gln Tyr Ser Thr Phe Ser Tyr Val Asp
                645                 650                 655
Pro Val Ile Thr Ser Ile Ser Pro Lys Tyr Gly Pro Met Ala Gly Gly
                660                 665                 670
Thr Leu Leu Thr Leu Thr Gly Asn Tyr Leu Asn Ser Gly Asn Ser Arg
                675                 680                 685
His Ile Ser Ile Gly Gly Lys Thr Cys Thr Leu Lys Ser Val Ser Asn
                690                 695                 700
Ser Ile Leu Glu Cys Tyr Thr Pro Ala Gln Thr Ile Ser Thr Glu Phe
705                 710                 715                 720
Ala Val Lys Leu Lys Ile Asp Leu Ala Asn Arg Glu Thr Ser Ile Phe
                725                 730                 735
Ser Tyr Arg Glu Asp Pro Ile Val Tyr Glu Ile His Pro Thr Lys Ser
                740                 745                 750
Phe Ile Ser Gly Gly Ser Thr Ile Thr Gly Val Gly Lys Asn Leu Asn
                755                 760                 765
Ser Val Ser Val Pro Arg Met Val Ile Asn Val His Glu Ala Gly Arg
                770                 775                 780
Asn Phe Thr Val Ala Cys Gln His Arg Ser Asn Ser Glu Ile Ile Cys
785                 790                 795                 800
Cys Thr Thr Pro Ser Leu Gln Gln Leu Asn Leu Gln Leu Pro Leu Lys
                805                 810                 815
```

```
Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845

Met Ile Ser Met Gly Asn Glu Asn Val Leu Glu Ile Lys Val Arg Asn
    850                 855                 860

Ala Leu Asn Thr Val Leu Asn His Gln Leu Lys Leu Asn
865                 870                 875

<210> SEQ ID NO 38
<211> LENGTH: 934
<212> TYPE: PRT
<213> ORGANISM: Homo sapiens

<400> SEQUENCE: 38

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
```

```
            305                 310                 315                 320
Tyr Val Ser Lys Pro Gly Ala Gln Leu Ala Arg Gln Ile Gly Ala Ser
                325                 330                 335
Leu Asn Asp Asp Ile Leu Phe Gly Val Phe Ala Gln Ser Lys Pro Asp
                340                 345                 350
Ser Ala Glu Pro Met Asp Arg Ser Ala Met Cys Ala Phe Pro Ile Lys
                355                 360                 365
Tyr Val Asn Asp Phe Phe Asn Lys Ile Val Asn Lys Asn Asn Val Arg
                370                 375                 380
Cys Leu Gln His Phe Tyr Gly Pro Asn His Glu His Cys Phe Asn Arg
385                 390                 395                 400
Thr Leu Leu Arg Asn Ser Ser Gly Cys Glu Ala Arg Arg Asp Glu Tyr
                405                 410                 415
Arg Thr Glu Phe Thr Thr Ala Leu Gln Arg Val Asp Leu Phe Met Gly
                420                 425                 430
Gln Phe Ser Glu Val Leu Leu Thr Ser Ile Ser Thr Phe Ile Lys Gly
                435                 440                 445
Asp Leu Thr Ile Ala Asn Leu Gly Thr Ser Glu Gly Arg Phe Met Gln
                450                 455                 460
Val Val Val Ser Arg Ser Gly Pro Ser Thr Pro His Val Asn Phe Leu
465                 470                 475                 480
Leu Asp Ser His Pro Val Ser Pro Glu Val Ile Val Glu His Thr Leu
                485                 490                 495
Asn Gln Asn Gly Tyr Thr Leu Val Ile Thr Gly Lys Lys Ile Thr Lys
                500                 505                 510
Ile Pro Leu Asn Gly Leu Gly Cys Arg His Phe Gln Ser Cys Ser Gln
                515                 520                 525
Cys Leu Ser Ala Pro Pro Phe Val Gln Cys Gly Trp Cys His Asp Lys
                530                 535                 540
Cys Val Arg Ser Glu Glu Cys Leu Ser Gly Thr Trp Thr Gln Gln Ile
545                 550                 555                 560
Cys Leu Pro Ala Ile Tyr Lys Val Phe Pro Asn Ser Ala Pro Leu Glu
                565                 570                 575
Gly Gly Thr Arg Leu Thr Ile Cys Gly Trp Asp Phe Gly Phe Arg Arg
                580                 585                 590
Asn Asn Lys Phe Asp Leu Lys Lys Thr Arg Val Leu Leu Gly Asn Glu
                595                 600                 605
Ser Cys Thr Leu Thr Leu Ser Glu Ser Thr Met Asn Thr Leu Lys Cys
                610                 615                 620
Thr Val Gly Pro Ala Met Asn Lys His Phe Asn Met Ser Ile Ile Ile
625                 630                 635                 640
Ser Asn Gly His Gly Thr Thr Gln Tyr Ser Thr Phe Ser Tyr Val Asp
                645                 650                 655
Pro Val Ile Thr Ser Ile Ser Pro Lys Tyr Gly Pro Met Ala Gly Gly
                660                 665                 670
Thr Leu Leu Thr Leu Thr Gly Asn Tyr Leu Asn Ser Gly Asn Ser Arg
                675                 680                 685
His Ile Ser Ile Gly Gly Lys Thr Cys Thr Leu Lys Ser Val Ser Asn
                690                 695                 700
Ser Ile Leu Glu Cys Tyr Thr Pro Ala Gln Thr Ile Ser Thr Glu Phe
705                 710                 715                 720
Ala Val Lys Leu Lys Ile Asp Leu Ala Asn Arg Glu Thr Ser Ile Phe
                725                 730                 735
```

-continued

Ser Tyr Arg Glu Asp Pro Ile Val Tyr Glu Ile His Pro Thr Lys Ser
                740                 745                 750

Phe Ile Ser Gly Gly Ser Thr Ile Thr Gly Val Gly Lys Asn Leu Asn
            755                 760                 765

Ser Val Ser Val Pro Arg Met Val Ile Asn Val His Glu Ala Gly Arg
        770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845

Met Ile Ser Met Gly Asn Glu Asn Val Leu Glu Ile Lys Gly Asn Asp
        850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Val Gly
            900                 905                 910

Phe Leu His Ser Ser His Asp Val Asn Lys Glu Ala Ser Val Ile Met
        915                 920                 925

Leu Phe Ser Gly Leu Lys
    930

<210> SEQ ID NO 39
<211> LENGTH: 567
<212> TYPE: PRT
<213> ORGANISM: Homo sapiens

<400> SEQUENCE: 39

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val

```
                165                 170                 175
Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
            195                 200                 205

His Pro Leu His Ser Ile Ser Val Arg Arg Leu Lys Glu Thr Lys Asp
            210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
            245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
            275                 280                 285

His Ser Tyr Met Glu Met Pro Leu Glu Cys Ile Leu Thr Glu Lys Arg
            290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
            325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
            355                 360                 365

Tyr Val Asn Asp Phe Phe Asn Lys Ile Val Asn Lys Asn Asn Val Arg
            370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
            405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
            435                 440                 445

Asp Leu Thr Ile Ala Asn Leu Gly Thr Ser Glu Gly Arg Phe Met Gln
            450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
            485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
545                 550                 555                 560

Cys Leu Pro Ala Ile Tyr Lys
            565

<210> SEQ ID NO 40
```

<211> LENGTH: 877
<212> TYPE: PRT
<213> ORGANISM: Homo sapiens

<400> SEQUENCE: 40

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro Arg Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Thr Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Pro Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
```

-continued

```
            385                 390                 395                 400
Thr Leu Leu Arg Asn Ser Ser Gly Cys Glu Ala Arg Arg Asp Glu Tyr
                    405                 410                 415
Arg Thr Glu Phe Thr Thr Ala Leu Gln Arg Val Asp Leu Phe Met Gly
                420                 425                 430
Gln Phe Ser Glu Val Leu Leu Thr Ser Ile Ser Thr Phe Ile Lys Gly
            435                 440                 445
Asp Leu Thr Ile Ala Asn Leu Gly Thr Ser Glu Gly Arg Phe Met Gln
        450                 455                 460
Val Val Val Ser Arg Ser Gly Pro Ser Thr Pro His Val Asn Phe Leu
465                 470                 475                 480
Leu Asp Ser His Pro Val Ser Pro Glu Val Ile Val Glu His Thr Leu
                485                 490                 495
Asn Gln Asn Gly Tyr Thr Leu Val Ile Thr Gly Lys Lys Ile Thr Lys
                500                 505                 510
Ile Pro Leu Asn Gly Leu Gly Cys Arg His Phe Gln Ser Cys Ser Gln
            515                 520                 525
Cys Leu Ser Ala Pro Pro Phe Val Gln Cys Gly Trp Cys His Asp Lys
        530                 535                 540
Cys Val Arg Ser Glu Glu Cys Leu Ser Gly Thr Trp Thr Gln Gln Ile
545                 550                 555                 560
Cys Leu Pro Ala Ile Tyr Lys Val Phe Pro Asn Ser Ala Pro Leu Glu
                565                 570                 575
Gly Gly Thr Arg Leu Thr Ile Cys Gly Trp Asp Phe Gly Phe Arg Arg
                580                 585                 590
Asn Asn Lys Phe Asp Leu Lys Lys Thr Arg Val Leu Leu Gly Asn Glu
            595                 600                 605
Ser Cys Thr Leu Thr Leu Ser Glu Ser Thr Met Asn Thr Leu Lys Cys
        610                 615                 620
Thr Val Gly Pro Ala Met Asn Lys His Phe Asn Met Ser Ile Ile Ile
625                 630                 635                 640
Ser Asn Gly His Gly Thr Thr Gln Tyr Ser Thr Phe Ser Tyr Val Asp
                645                 650                 655
Pro Val Ile Thr Ser Ile Ser Pro Lys Tyr Gly Pro Met Ala Gly Gly
                660                 665                 670
Thr Leu Leu Thr Leu Thr Gly Asn Tyr Leu Asn Ser Gly Asn Ser Arg
            675                 680                 685
His Ile Ser Ile Gly Gly Lys Thr Cys Thr Leu Lys Ser Val Ser Asn
        690                 695                 700
Ser Ile Leu Glu Cys Tyr Thr Pro Ala Gln Thr Ile Ser Thr Glu Phe
705                 710                 715                 720
Ala Val Lys Leu Lys Ile Asp Leu Ala Asn Arg Glu Thr Ser Ile Phe
                725                 730                 735
Ser Tyr Arg Glu Asp Pro Ile Val Tyr Glu Ile His Pro Thr Lys Ser
                740                 745                 750
Phe Ile Ser Gly Gly Ser Thr Ile Thr Gly Val Gly Lys Asn Leu Asn
            755                 760                 765
Ser Val Ser Val Pro Arg Met Val Ile Asn Val His Glu Ala Gly Arg
        770                 775                 780
Asn Phe Thr Val Ala Cys Gln His Arg Ser Asn Ser Glu Ile Ile Cys
785                 790                 795                 800
Cys Thr Thr Pro Ser Leu Gln Gln Leu Asn Leu Gln Leu Pro Leu Lys
                805                 810                 815
```

```
Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845

Met Ile Ser Met Gly Asn Glu Asn Val Leu Glu Ile Lys Val Arg Asn
    850                 855                 860

Ala Leu Asn Thr Val Leu Asn His Gln Leu Lys Leu Asn
865                 870                 875

<210> SEQ ID NO 41
<211> LENGTH: 20
<212> TYPE: DNA
<213> ORGANISM: Homo sapiens

<400> SEQUENCE: 41
ctgggcaccg aaagataaac                                              20

<210> SEQ ID NO 42
<211> LENGTH: 20
<212> TYPE: DNA
<213> ORGANISM: Homo sapiens

<400> SEQUENCE: 42
gttgatgagc aaaacccac                                               20

<210> SEQ ID NO 43
<211> LENGTH: 20
<212> TYPE: DNA
<213> ORGANISM: Homo sapiens

<400> SEQUENCE: 43
ccagcccaaa ccatttcaac                                              20

<210> SEQ ID NO 44
<211> LENGTH: 33
<212> TYPE: DNA
<213> ORGANISM: Homo sapiens

<400> SEQUENCE: 44
gcggatccag ctatgaagtc aattaagttt gag                               33

<210> SEQ ID NO 45
<211> LENGTH: 519
<212> TYPE: DNA
<213> ORGANISM: Homo sapiens

<400> SEQUENCE: 45
ccagcccaaa ccatttcaac tgagtttgct gttaaattga aaattgactt agccaaccga    60
gagacaagca tcttcagtta ccgtgaagat cccattgtct atgaaattca tccaaccaaa   120
tcttttatta gtggtgggag cacaataaca ggtgttggga aaaacctgaa ttcagttagt   180
gtcccgagaa tggtcataaa tgtgcatgaa gcaggaagga actttacagt ggcatgtcaa   240
catcgctcta attcagagat aatctgttgt accactcctt ccctgcaaca gctgaatctg   300
caactccccc tgaaaaccaa agccttttc atgttagatg ggatcctttc caaatacttt   360
gatctcattt atgtacataa tcctgtgttt aagccttttg aaaagccagt gatgatctca   420
atgggcaatg aaaatgtact ggaaattaag gtaagaaatg ctttaaacac tgtcttaaat   480
catcagctca aacttaattg acttcatagc tggatccgc                          519
```

<210> SEQ ID NO 46
<211> LENGTH: 2723
<212> TYPE: DNA
<213> ORGANISM: Homo sapiens

<400> SEQUENCE: 46

| | | | | | |
|---|---|---|---|---|---|
| gaattcgcca | ccatgaaggc | ccctgccgtg | ctggcccctg | gcatcctggt | gctgctgttc |    60 |
| accctggtgc | agagaagcaa | cggcgagtgt | aaggaggccc | tggccaagag | cgagatgaac |   120 |
| gtgaacatga | agtaccagct | gcccaacttc | accgccgaga | cacccatcca | gaacgtgatc |   180 |
| ctgcacgagc | accacatctt | cctgggcgcc | accaactaca | tctacgtgct | gaacgaggag |   240 |
| gacctgcaga | aggtggccga | gtacaagacc | ggccctgtgc | tggagcaccc | tgactgcttc |   300 |
| ccttgccagg | actgtagcag | caaggccaac | ctgagcggcg | agtgtggaa | ggacaacatc |   360 |
| aacatggccc | tggtggtgga | cacctactac | gacgaccagc | tgatcagctg | tggcagcgtg |   420 |
| aatagaggca | cctgccagag | acacgtgttc | ccccacaacc | acaccgccga | tatccagagc |   480 |
| gaggtgcact | gcatcttcag | ccccagatc | gaggagccca | gccagtgccc | cgactgtgtg |   540 |
| gtgtccgccc | tggagccaa | ggtgctgtcc | agcgtgaagg | accggttcat | caatttcttt |   600 |
| gtgggcaaca | ccatcaacag | cagctacttc | cccgatcacc | ccctgcacag | catctctgtg |   660 |
| aggcggctga | aggagacaaa | ggacggcttc | atgttcctga | ccgaccagag | ctacatcgat |   720 |
| gtgctgcccg | agttcagaga | cagctacccc | atcaagtacg | tgcacgcctt | cgagagcaac |   780 |
| aacttcatct | actttctgac | cgtgcagcgg | gagacactgg | acgcccagac | cttccacacc |   840 |
| cggatcatcc | ggttctgctc | catcaatagc | ggcctgcaca | gctacatgga | gatgcccctg |   900 |
| gagtgtatcc | tgaccgagaa | gcggaagaag | cggtccacca | agaaggaggt | gttcaacatc |   960 |
| ctgcaggccg | cctacgtgtc | caagcctggc | gcccagctgg | ccagacagat | cggcgccagc |  1020 |
| ctgaacgacg | atatcctgtt | cggcgtgttc | gcccagagca | agcccgacag | cgccgagccc |  1080 |
| atggatagaa | gcgccatgtg | tgccttccct | atcaagtatg | tgaacgactt | cttcaacaag |  1140 |
| atcgtgaaca | gaacaatgt | gagatgcctg | cagcacttct | acggccccaa | tcacgagcac |  1200 |
| tgcttcaacc | ggaccctgct | gagaaacagc | agcggctgtg | aggccaggag | ggacgagtac |  1260 |
| aggaccgagt | tcaccaccgc | cctgcagcgc | gtggatctgt | tcatgggcca | gttcagcgag |  1320 |
| gtgctgctga | ccagcatcag | caccttcatc | aagggagacc | tgaccatcgc | caacctgggc |  1380 |
| accagcgagg | gcagattcat | gcaggtggtg | gtgtccagaa | gcggcccag | cacccctcac |  1440 |
| gtgaacttcc | tgctggacag | ccaccctgtg | agccccgagg | tgatcgtgga | gcacaccctg |  1500 |
| aaccagaacg | gctacacccct | ggtgatcacc | ggcaagaaga | tcaccaagat | cccccctgaac |  1560 |
| ggcctgggct | gtagacactt | ccagagctgc | tcccagtgcc | tgagcgcccc | tcccttcgtg |  1620 |
| cagtgcggct | ggtgccacga | caagtgtgtg | aggagcgagg | agtgtctgag | cggcacctgg |  1680 |
| acccagcaga | tctgcctgcc | cgccatctac | aaggtgttcc | ccaacagcgc | ccctctggag |  1740 |
| ggcggcacca | gactgaccat | ctgtggctgg | gacttcggct | tccggcggaa | caacaagttc |  1800 |
| gacctgaaga | aaaccagggt | gctgctgggc | aatgagagct | gtaccctgac | cctgagcgag |  1860 |
| agcaccatga | cacccctgaa | gtgcacagtg | ggccctgcca | tgaacaagca | cttcaacatg |  1920 |
| agcatcatca | tcagcaacgg | ccacggcacc | acccagtaca | gcaccttctc | ctacgtggac |  1980 |
| cccgtgatca | caagcatcag | ccccaagtac | ggccctatgg | ccggaggaac | cctgctgacc |  2040 |
| ctgaccggca | actacctgaa | cagcggcaac | agccggcaca | tcagcatcgg | cggcaagaca |  2100 |
| tgtaccctga | agagcgtgtc | caacagcatc | ctggagtgct | acacccctgc | ccagaccatc |  2160 |

-continued

```
agcaccgagt tcgccgtgaa gctgaagatc gacctggcca accgggagac atccatcttc    2220
agctaccggg aggaccctat cgtgtacgag atccacccca ccaagagctt catcagcggc    2280
ggcagcacca tcaccggagt gggcaagaac ctgaactctg tgagcgtgcc ccggatggtg    2340
atcaacgtgc acgaggccgg cagaaacttc accgtggcct gccagcacag aagcaactcc    2400
gagatcatct gctgtaccac ccctagcctg cagcagctga acctgcagct gcccctgaaa    2460
accaaggcct tcttcatgct ggacggcatc ctgagcaagt acttcgacct gatctatgta    2520
cacaaccccg tgttcaagcc cttcgagaag cccgtgatga tcagcatggg caacgagaac    2580
gtgctggaga tcaaggtgag gaacgccctg aacaccgtgc tgaatcacca gctgaagctg    2640 aaccctgga gccaccctca gttcgagaaa accggccacc atcaccacca tcatcaccac    2700
ggcggccagt gataagcggc cgc                                            2723
```

<210> SEQ ID NO 47
<211> LENGTH: 899
<212> TYPE: PRT
<213> ORGANISM: Homo sapiens

<400> SEQUENCE: 47

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270
```

-continued

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
        290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Val Arg
        370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
        420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
        450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
        500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
        530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
        580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
        610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
                755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Lys Pro Phe Glu Lys Pro Val
            835                 840                 845

Met Ile Ser Met Gly Asn Glu Asn Val Leu Glu Ile Lys Val Arg Asn
850                 855                 860

Ala Leu Asn Thr Val Leu Asn His Gln Leu Lys Leu Asn Pro Trp Ser
865                 870                 875                 880

His Pro Gln Phe Glu Lys Thr Gly His His His His His His His His
                885                 890                 895

Gly Gly Gln

<210> SEQ ID NO 48
<211> LENGTH: 2888
<212> TYPE: DNA
<213> ORGANISM: Homo sapiens

<400> SEQUENCE: 48

```
gccctcgccg cccgcggcgc cccgagcgct ttgtgagcag atgcggagcc gagtggaggg    60
cgcgagccag atgcggggcg acagctgact tgctgagagg aggcggggag gcgcggagcg   120
cgcgtgtggt ccttgcgccg ctgacttctc cactggttcc tgggcaccga aagataaacc   180
tctcataatg aaggccccg ctgtgcttgc acctggcatc ctcgtgctcc tgtttacctt   240
ggtgcagagg agcaatgggg agtgtaaaga ggcactagca aagtccgaga tgaatgtgaa   300
tatgaagtat cagcttccca acttcaccgc ggaaacaccc atccagaatg tcattctaca   360
tgagcatcac attttccttg gtgccactaa ctacatttat gttttaaatg aggaagacct   420
tcagaaggtt gctgagtaca agactgggcc tgtgctggaa cacccagatt gtttcccatg   480
tcaggactgc agcagcaaag ccaatttatc aggaggtgtt tggaaagata acatcaacat   540
ggctctagtt gtcgacacct actatgatga tcaactcatt agctgtggca gcgtcaacag   600
agggacctgc cagcgacatg tctttccca caatcatact gctgacatac agtcggaggt   660
tcactgcata ttctcccac agatagaaga gcccagccag tgtcctgact gtgtggtgag   720
cgccctggga gccaaagtcc tttcatctgt aaaggaccgg ttcatcaact tctttgtagg   780
caataccata aattcttctt atttcccaga tcatccattg cattcgatat cagtgagaag   840
gctaaaggaa acgaaagatg gttttatgtt tttgacggac cagtcctaca ttgatgtttt   900
```

```
acctgagttc agagattctt accccattaa gtatgtccat gcctttgaaa gcaacaattt      960
tatttacttc ttgacggtcc aaagggaaac tctagatgct cagactttc acacaagaat     1020
aatcaggttc tgttccataa actctggatt gcattcctac atggaaatgc ctctggagtg     1080
tattctcaca gaaagagaa aaagagatc cacaaagaag gaagtgttta atatacttca      1140
ggctgcgtat gtcagcaagc ctggggccca gcttgctaga caaataggag ccagcctgaa     1200
tgatgacatt cttttcgggg tgttcgcaca aagcaagcca gattctgccg aaccaatgga    1260
tcgatctgcc atgtgtgcat tccctatcaa atatgtcaac gacttcttca acaagatcgt    1320
caacaaaaac aatgtgagat gtctccagca tttttacgga cccaatcatg agcactgctt    1380
taataggaca cttctgagaa attcatcagg ctgtgaagcg cgccgtgatg aatatcgaac    1440
agagtttacc acagctttgc agcgcgttga cttattcatg ggtcaattca gcgaagtcct    1500
cttaacatct atatccacct tcattaaagg agacctcacc atagctaatc ttgggacatc    1560
agagggtcgc ttcatgcagg ttgtggtttc tcgatcagga ccatcaaccc ctcatgtgaa    1620
ttttctcctg gactcccatc cagtgtctcc agaagtgatt gtggagcata cattaaacca    1680
aaatggctac acactggtta tcactgggaa gaagatcacg aagatcccat tgaatggctt    1740
gggctgcaga catttccagt cctgcagtca atgcctctct gccccaccct tgttcagtg    1800
tggctggtgc cacgacaaat gtgtgcgatc ggaggaatgc ctgagcggga catggactca    1860
acagatctgt ctgcctgcaa tctacaaggt ttcccaaat agtgcacccc ttgaaggagg    1920
gacaaggctg accatatgtg gctgggactt tggatttcgg aggaataata aatttgattt    1980
aaagaaaact agagttctcc ttggaaatga gagctgcacc ttgactttaa gtgagagcac    2040
gatgaataca ttgaaatgca cagttggtcc tgccatgaat aagcattca atatgtccat    2100
aattatttca aatggccacg ggacaacaca atacagtaca ttctcctatg tggatcctgt    2160
aataacaagt atttcgccga atacggtcc tatggctggt ggcactttac ttacttaac    2220
tggaaattac ctaaacagtg ggaattctag acacatttca attggtggaa aaacatgtac    2280
tttaaaaagt gtgtcaaaca gtattcttga atgttatacc ccagcccaaa ccatttcaac    2340
tgagtttgct gttaaattga aaattgactt agccaaccga gagacaagca tcttcagtta    2400
ccgtgaagat cccattgtct atgaaattca tccaaccaaa tcttttatta gtggtgggag    2460
cacaataaca ggtgttggga aaaacctgaa ttcagttagt gtcccgagaa tggtcataaa    2520
tgtgcatgaa gcaggaagga actttacagt ggcatgtcaa catcgctcta attcagagat    2580
aatctgttgt accactcctt ccctgcaaca gctgaatctg caactccccc tgaaaaccaa    2640
agccttttc atgttagatg ggatcctttc caaatacttt gatctcattt atgtacataa    2700
tcctgtgttt aagcctttg aaaagccagt gatgatctca atgggcaatg aaaatgtact    2760
ggaaattaag gtgggattcc tgcattcctc tcatgatgta aataaggaag ccagtgtaat    2820
tatgttattc tcaggcttaa aataaatcat taaagctcat ttatgtgtgg gttttggctc    2880
atcaactc                                                              2888

<210> SEQ ID NO 49
<211> LENGTH: 1214
<212> TYPE: DNA
<213> ORGANISM: Homo sapiens

<400> SEQUENCE: 49
ataaacctct cataatgaag gcccccgctg tgcttgcacc tggcatcctc gtgctcctgt       60
ttaccttggt gcagaggagc aatggggagt gtaaagaggc actagcaaag tccgagatga      120
```

```
atgtgaatat gaagtatcag cttcccaact tcaccgcgga aacacccatc cagaatgtca     180
ttctacatga gcatcacatt ttccttggtg ccactaacta catttatgtt ttaaatgagg     240
aagaccttca gaaggttgct gagtacaaga ctgggcctgt gctggaacac ccagattgtt     300
tcccatgtca ggactgcagc agcaaagcca atttatcagg aggtgtttgg aaagataaca     360
tcaacatggc tctagttgtc gacacctact atgatgatca actcattagc tgtggcagcg     420
tcaacagagg gacctgccag cgacatgtct ttccccacaa tcatactgct gacatacagt     480
cggaggttca ctgcatattc tccccacaga tagaagagcc cagccagtgt cctgactgtg     540
tggtgagcgc cctgggagcc aaagtccttt catctgtaaa ggaccggttc atcaacttct     600
ttgtaggcaa taccataaat tcttcttatt tcccagatca tccattgcat tcgatatcag     660
tgagaaggct aaaggaaacg aaagatggtt ttatgttttt gacggaccag tcctacattg     720
atgttttacc tgagttcaga gattcttacc ccattaagta tgtccatgcc tttgaaagca     780
acaattttat ttacttcttg acggtccaaa gggaaactct agatgctcag acttttcaca     840
caagaataat caggttctgt tccataaact ctggattgca ttcctacatg gaaatgcctc     900
tggagtgtat tctcacagaa aagagaaaaa agagatccac aaagaaggaa gtgtttaata     960
tacttcaggc tgcgtatgtc agcaagcctg gggcccagct tgctagacaa ataggagcca    1020
gcctgaatga tgacattctt ttcggggtgt tcgcacaaag caagccagat tctgccgaac    1080
caatggatcg atctgccatg tgtgcattcc ctatcaaata tgtcaacgac ttcttcaaca    1140
agatcgtcaa caaaaacaat gtgagatgtc tccagcattt ttacggaccc aatcatgagc    1200
actgctttaa tagg                                                      1214

<210> SEQ ID NO 50
<211> LENGTH: 192
<212> TYPE: DNA
<213> ORGANISM: Homo sapiens

<400> SEQUENCE: 50
acacttctga gaaattcatc aggctgtgaa gcgcgccgtg atgaatatcg aacagagttt      60
accacagctt tgcagcgcgt tgacttattc atgggtcaat tcagcgaagt cctcttaaca     120
tctatatcca ccttcattaa aggagacctc accatagcta atcttgggac atcagagggt     180
cgcttcatgc ag                                                         192

<210> SEQ ID NO 51
<211> LENGTH: 135
<212> TYPE: DNA
<213> ORGANISM: Homo sapiens

<400> SEQUENCE: 51
gttgtggttt ctcgatcagg accatcaacc cctcatgtga attttctcct ggactcccat      60
ccagtgtctc cagaagtgat tgtggagcat acattaaacc aaaatggcta cacactggtt     120
atcactggga agaag                                                      135

<210> SEQ ID NO 52
<211> LENGTH: 161
<212> TYPE: DNA
<213> ORGANISM: Homo sapiens

<400> SEQUENCE: 52
gttttcccaa atagtgcacc ccttgaagga gggacaaggc tgaccatatg tggctgggac      60
```

```
tttggatttc ggaggaataa taaatttgat ttaaagaaaa ctagagttct ccttggaaat      120
gagagctgca ccttgacttt aagtgagagc acgatgaata c                         161

<210> SEQ ID NO 53
<211> LENGTH: 137
<212> TYPE: DNA
<213> ORGANISM: Homo sapiens

<400> SEQUENCE: 53
gatcctgtaa taacaagtat ttcgccgaaa tacggtccta tggctggtgg cactttactt      60
actttaactg gaaattacct aaacagtggg aattctagac acatttcaat tggtggaaaa     120
acatgtactt taaaaag                                                    137

<210> SEQ ID NO 54
<211> LENGTH: 162
<212> TYPE: DNA
<213> ORGANISM: Homo sapiens

<400> SEQUENCE: 54
tgtgtcaaac agtattcttg aatgttatac cccagcccaa accatttcaa ctgagtttgc      60
tgttaaattg aaaattgact tagccaaccg agagacaagc atcttcagtt accgtgaaga     120
tcccattgtc tatgaaattc atccaaccaa atctttttatt ag                       162

<210> SEQ ID NO 55
<211> LENGTH: 219
<212> TYPE: DNA
<213> ORGANISM: Homo sapiens

<400> SEQUENCE: 55
gcatgtcaac atcgctctaa ttcagagata atctgttgta ccactccttc cctgcaacag      60
ctgaatctgc aactcccccct gaaaaccaaa gccttttttca tgttagatgg gatcctttcc    120
aaatactttg atctcatttta tgtacataat cctgtgttta agccttttga aaagccagtg    180
atgatctcaa tgggcaatga aaatgtactg gaaattaag                            219

<210> SEQ ID NO 56
<211> LENGTH: 89
<212> TYPE: DNA
<213> ORGANISM: Homo sapiens

<400> SEQUENCE: 56
gccctcgccg cccgcggcgc cccgagcgct tgtgagcag atgcggagcc gagtggaggg       60
cgcgagccag atgcggggcg acagctgac                                        89

<210> SEQ ID NO 57
<211> LENGTH: 56
<212> TYPE: DNA
<213> ORGANISM: Homo sapiens

<400> SEQUENCE: 57
ttgctgagag gaggcgggga ggcgcggagc gcgcgtgtgg tccttgcgcc gctgac          56

<210> SEQ ID NO 58
<211> LENGTH: 28
<212> TYPE: DNA
<213> ORGANISM: Homo sapiens

<400> SEQUENCE: 58
ttctccactg gttcctgggc accgaaag                                         28
```

<210> SEQ ID NO 59
<211> LENGTH: 84
<212> TYPE: DNA
<213> ORGANISM: Homo sapiens

<400> SEQUENCE: 59

```
atcacgaaga tcccattgaa tggcttgggc tgcagacatt ccagtcctg cagtcaatgc      60
ctctctgccc cacccttgt tcag                                             84
```

<210> SEQ ID NO 60
<211> LENGTH: 90
<212> TYPE: DNA
<213> ORGANISM: Homo sapiens

<400> SEQUENCE: 60

```
tgtggctggt gccacgacaa atgtgtgcga tcggaggaat gcctgagcgg gacatggact      60
caacagatct gtctgcctgc aatctacaag                                       90
```

<210> SEQ ID NO 61
<211> LENGTH: 103
<212> TYPE: DNA
<213> ORGANISM: Homo sapiens

<400> SEQUENCE: 61

```
attgaaatgc acagttggtc ctgccatgaa taagcatttc aatatgtcca taattatttc      60
aaatggccac gggacaacac aatacagtac attctcctat gtg                       103
```

<210> SEQ ID NO 62
<211> LENGTH: 100
<212> TYPE: DNA
<213> ORGANISM: Homo sapiens

<400> SEQUENCE: 62

```
tggtgggagc acaataacag gtgttgggaa aaacctgaat tcagttagtg tcccgagaat      60
ggtcataaat gtgcatgaag caggaaggaa ctttacagtg                           100
```

<210> SEQ ID NO 63
<211> LENGTH: 118
<212> TYPE: DNA
<213> ORGANISM: Homo sapiens

<400> SEQUENCE: 63

```
gtgggattcc tgcattcctc tcatgatgta aataaggaag ccagtgtaat tatgttattc      60
tcaggcttaa ataaatcat taagctcat ttatgtgtgg gttttggctc atcaactc        118
```

<210> SEQ ID NO 64
<211> LENGTH: 1390
<212> TYPE: PRT
<213> ORGANISM: Homo sapiens

<400> SEQUENCE: 64

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu

```
                50                  55                  60
Gly Ala Thr Asn Tyr Ile Tyr Val Leu Asn Glu Glu Asp Leu Gln Lys
 65                  70                  75                  80

Val Ala Glu Tyr Lys Thr Gly Pro Val Leu Glu His Pro Asp Cys Phe
                 85                  90                  95

Pro Cys Gln Asp Cys Ser Ser Lys Ala Asn Leu Ser Gly Gly Val Trp
                100                 105                 110

Lys Asp Asn Ile Asn Met Ala Leu Val Val Asp Thr Tyr Tyr Asp Asp
                115                 120                 125

Gln Leu Ile Ser Cys Gly Ser Val Asn Arg Gly Thr Cys Gln Arg His
130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
                180                 185                 190

Ile Asn Phe Phe Val Gly Asn Thr Ile Asn Ser Ser Tyr Phe Pro Asp
                195                 200                 205

His Pro Leu His Ser Ile Ser Val Arg Arg Leu Lys Glu Thr Lys Asp
210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
                260                 265                 270

Thr Phe His Thr Arg Ile Ile Arg Phe Cys Ser Ile Asn Ser Gly Leu
                275                 280                 285

His Ser Tyr Met Glu Met Pro Leu Glu Cys Ile Leu Thr Glu Lys Arg
                290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
                355                 360                 365

Tyr Val Asn Asp Phe Phe Asn Lys Ile Val Asn Lys Asn Asn Val Arg
                370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
                420                 425                 430

Gln Phe Ser Glu Val Leu Leu Thr Ser Ile Ser Thr Phe Ile Lys Gly
                435                 440                 445

Asp Leu Thr Ile Ala Asn Leu Gly Thr Ser Glu Gly Arg Phe Met Gln
                450                 455                 460

Val Val Val Ser Arg Ser Gly Pro Ser Thr Pro His Val Asn Phe Leu
465                 470                 475                 480
```

```
Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
            530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
            595                 600                 605

Ser Cys Thr Leu Thr Leu Ser Glu Ser Thr Met Asn Thr Leu Lys Cys
            610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
                690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750

Phe Ile Ser Gly Gly Ser Thr Ile Thr Gly Val Gly Lys Asn Leu Asn
                755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
                820                 825                 830

Leu Ile Tyr Val His Asn Pro Val Phe Lys Pro Phe Glu Lys Pro Val
                835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895
```

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
            915                 920                 925

Gln Asn Phe Thr Gly Leu Ile Ala Gly Val Val Ser Ile Ser Thr Ala
            930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
            965                 970                 975

Thr Pro His Leu Asp Arg Leu Val Ser Ala Arg Ser Val Ser Pro Thr
            980                 985                 990

Thr Glu Met Val Ser Asn Glu Ser Val Asp Tyr Arg Ala Thr Phe Pro
            995                 1000                1005

Glu Asp Gln Phe Pro Asn Ser Ser Gln Asn Gly Ser Cys Arg Gln
    1010                1015                1020

Val Gln Tyr Pro Leu Thr Asp Met Ser Pro Ile Leu Thr Ser Gly
    1025                1030                1035

Asp Ser Asp Ile Ser Ser Pro Leu Leu Gln Asn Thr Val His Ile
    1040                1045                1050

Asp Leu Ser Ala Leu Asn Pro Glu Leu Val Gln Ala Val Gln His
    1055                1060                1065

Val Val Ile Gly Pro Ser Ser Leu Ile Val His Phe Asn Glu Val
    1070                1075                1080

Ile Gly Arg Gly His Phe Gly Cys Val Tyr His Gly Thr Leu Leu
    1085                1090                1095

Asp Asn Asp Gly Lys Lys Ile His Cys Ala Val Lys Ser Leu Asn
    1100                1105                1110

Arg Ile Thr Asp Ile Gly Glu Val Ser Gln Phe Leu Thr Glu Gly
    1115                1120                1125

Ile Ile Met Lys Asp Phe Ser His Pro Asn Val Leu Ser Leu Leu
    1130                1135                1140

Gly Ile Cys Leu Arg Ser Glu Gly Ser Pro Leu Val Val Leu Pro
    1145                1150                1155

Tyr Met Lys His Gly Asp Leu Arg Asn Phe Ile Arg Asn Glu Thr
    1160                1165                1170

His Asn Pro Thr Val Lys Asp Leu Ile Gly Phe Gly Leu Gln Val
    1175                1180                1185

Ala Lys Gly Met Lys Tyr Leu Ala Ser Lys Lys Phe Val His Arg
    1190                1195                1200

Asp Leu Ala Ala Arg Asn Cys Met Leu Asp Glu Lys Phe Thr Val
    1205                1210                1215

Lys Val Ala Asp Phe Gly Leu Ala Arg Asp Met Tyr Asp Lys Glu
    1220                1225                1230

Tyr Tyr Ser Val His Asn Lys Thr Gly Ala Lys Leu Pro Val Lys
    1235                1240                1245

Trp Met Ala Leu Glu Ser Leu Gln Thr Gln Lys Phe Thr Thr Lys
    1250                1255                1260

Ser Asp Val Trp Ser Phe Gly Val Leu Leu Trp Glu Leu Met Thr
    1265                1270                1275

Arg Gly Ala Pro Pro Tyr Pro Asp Val Asn Thr Phe Asp Ile Thr
    1280                1285                1290

Val Tyr Leu Leu Gln Gly Arg Arg Leu Leu Gln Pro Glu Tyr Cys

-continued

```
           1295                1300                1305
Pro Asp Pro Leu Tyr Glu Val Met Leu Lys Cys Trp His Pro Lys
    1310                1315                1320

Ala Glu Met Arg Pro Ser Phe Ser Glu Leu Val Ser Arg Ile Ser
    1325                1330                1335

Ala Ile Phe Ser Thr Phe Ile Gly Glu His Tyr Val His Val Asn
    1340                1345                1350

Ala Thr Tyr Val Asn Val Lys Cys Val Ala Pro Tyr Pro Ser Leu
    1355                1360                1365

Leu Ser Ser Glu Asp Asn Ala Asp Asp Gly Val Asp Thr Arg Pro
    1370                1375                1380

Ala Ser Phe Trp Glu Thr Ser
    1385                1390

<210> SEQ ID NO 65
<211> LENGTH: 1408
<212> TYPE: PRT
<213> ORGANISM: Homo sapiens

<400> SEQUENCE: 65

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
                20                  25                  30

Ser Glu Met Asn Val Asn Met Lys Tyr Gln Leu Pro Asn Phe Thr Ala
            35                  40                  45

Glu Thr Pro Ile Gln Asn Val Ile Leu His Glu His His Ile Phe Leu
        50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270
```

-continued

```
Thr Phe His Thr Arg Ile Ile Arg Phe Cys Ser Ile Asn Ser Gly Leu
            275                 280                 285

His Ser Tyr Met Glu Met Pro Leu Glu Cys Ile Leu Thr Glu Lys Arg
        290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
```

-continued

```
            690                 695                 700
Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750

Phe Ile Ser Thr Trp Trp Lys Glu Pro Leu Asn Ile Val Ser Phe Leu
                755                 760                 765

Phe Cys Phe Ala Ser Gly Gly Ser Thr Ile Thr Gly Val Gly Lys Asn
770                 775                 780

Leu Asn Ser Val Ser Val Pro Arg Met Val Ile Asn Val His Glu Ala
785                 790                 795                 800

Gly Arg Asn Phe Thr Val Ala Cys Gln His Arg Ser Asn Ser Glu Ile
                805                 810                 815

Ile Cys Cys Thr Thr Pro Ser Leu Gln Gln Leu Asn Leu Gln Leu Pro
                820                 825                 830

Leu Lys Thr Lys Ala Phe Phe Met Leu Asp Gly Ile Leu Ser Lys Tyr
                835                 840                 845

Phe Asp Leu Ile Tyr Val His Asn Pro Val Phe Lys Pro Phe Glu Lys
    850                 855                 860

Pro Val Met Ile Ser Met Gly Asn Glu Asn Val Leu Glu Ile Lys Gly
865                 870                 875                 880

Asn Asp Ile Asp Pro Glu Ala Val Lys Gly Glu Val Leu Lys Val Gly
                885                 890                 895

Asn Lys Ser Cys Glu Asn Ile His Leu His Ser Glu Ala Val Leu Cys
                900                 905                 910

Thr Val Pro Asn Asp Leu Leu Lys Leu Asn Ser Glu Leu Asn Ile Glu
                915                 920                 925

Trp Lys Gln Ala Ile Ser Ser Thr Val Leu Gly Lys Val Ile Val Gln
    930                 935                 940

Pro Asp Gln Asn Phe Thr Gly Leu Ile Ala Gly Val Val Ser Ile Ser
945                 950                 955                 960

Thr Ala Leu Leu Leu Leu Leu Gly Phe Phe Leu Trp Leu Lys Lys Arg
                965                 970                 975

Lys Gln Ile Lys Asp Leu Gly Ser Glu Leu Val Arg Tyr Asp Ala Arg
                980                 985                 990

Val His Thr Pro His Leu Asp Arg  Leu Val Ser Ala Arg  Ser Val Ser
                995                1000                1005

Pro Thr Thr Glu Met Val Ser  Asn Glu Ser Val Asp  Tyr Arg Ala
    1010                1015                1020

Thr Phe Pro Glu Asp Gln Phe  Pro Asn Ser Ser Gln  Asn Gly Ser
    1025                1030                1035

Cys Arg Gln Val Gln Tyr Pro  Leu Thr Asp Met Ser  Pro Ile Leu
    1040                1045                1050

Thr Ser Gly Asp Ser Asp Ile  Ser Ser Pro Leu Leu  Gln Asn Thr
    1055                1060                1065

Val His Ile Asp Leu Ser Ala  Leu Asn Pro Glu Leu  Val Gln Ala
    1070                1075                1080

Val Gln His Val Val Ile Gly  Pro Ser Ser Leu Ile  Val His Phe
    1085                1090                1095

Asn Glu Val Ile Gly Arg Gly  His Phe Gly Cys Val  Tyr His Gly
    1100                1105                1110
```

```
Thr Leu Leu Asp Asn Asp Gly Lys Lys Ile His Cys Ala Val Lys
    1115                1120                1125

Ser Leu Asn Arg Ile Thr Asp Ile Gly Glu Val Ser Gln Phe Leu
    1130                1135                1140

Thr Glu Gly Ile Ile Met Lys Asp Phe Ser His Pro Asn Val Leu
    1145                1150                1155

Ser Leu Leu Gly Ile Cys Leu Arg Ser Glu Gly Ser Pro Leu Val
    1160                1165                1170

Val Leu Pro Tyr Met Lys His Gly Asp Leu Arg Asn Phe Ile Arg
    1175                1180                1185

Asn Glu Thr His Asn Pro Thr Val Lys Asp Leu Ile Gly Phe Gly
    1190                1195                1200

Leu Gln Val Ala Lys Gly Met Lys Tyr Leu Ala Ser Lys Lys Phe
    1205                1210                1215

Val His Arg Asp Leu Ala Ala Arg Asn Cys Met Leu Asp Glu Lys
    1220                1225                1230

Phe Thr Val Lys Val Ala Asp Phe Gly Leu Ala Arg Asp Met Tyr
    1235                1240                1245

Asp Lys Glu Tyr Tyr Ser Val His Asn Lys Thr Gly Ala Lys Leu
    1250                1255                1260

Pro Val Lys Trp Met Ala Leu Glu Ser Leu Gln Thr Gln Lys Phe
    1265                1270                1275

Thr Thr Lys Ser Asp Val Trp Ser Phe Gly Val Val Leu Trp Glu
    1280                1285                1290

Leu Met Thr Arg Gly Ala Pro Pro Tyr Pro Asp Val Asn Thr Phe
    1295                1300                1305

Asp Ile Thr Val Tyr Leu Leu Gln Gly Arg Arg Leu Leu Gln Pro
    1310                1315                1320

Glu Tyr Cys Pro Asp Pro Leu Tyr Glu Val Met Leu Lys Cys Trp
    1325                1330                1335

His Pro Lys Ala Glu Met Arg Pro Ser Phe Ser Glu Leu Val Ser
    1340                1345                1350

Arg Ile Ser Ala Ile Phe Ser Thr Phe Ile Gly Glu His Tyr Val
    1355                1360                1365

His Val Asn Ala Thr Tyr Val Asn Val Lys Cys Val Ala Pro Tyr
    1370                1375                1380

Pro Ser Leu Leu Ser Ser Glu Asp Asn Ala Asp Asp Glu Val Asp
    1385                1390                1395

Thr Arg Pro Ala Ser Phe Trp Glu Thr Ser
    1400                1405

<210> SEQ ID NO 66
<211> LENGTH: 885
<212> TYPE: PRT
<213> ORGANISM: Homo sapiens

<400> SEQUENCE: 66

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
```

```
                  50                  55                  60
Gly Ala Thr Asn Tyr Ile Tyr Val Leu Asn Glu Glu Asp Leu Gln Lys
 65                  70                  75                  80

Val Ala Glu Tyr Lys Thr Gly Pro Val Leu Glu His Pro Asp Cys Phe
                 85                  90                  95

Pro Cys Gln Asp Cys Ser Ser Lys Ala Asn Leu Ser Gly Gly Val Trp
                100                 105                 110

Lys Asp Asn Ile Asn Met Ala Leu Val Val Asp Thr Tyr Tyr Asp Asp
                115                 120                 125

Gln Leu Ile Ser Cys Gly Ser Val Asn Arg Gly Thr Cys Gln Arg His
130                 135                 140

Val Phe Pro His Asn His Thr Ala Asp Ile Gln Ser Glu Val His Cys
145                 150                 155                 160

Ile Phe Ser Pro Gln Ile Glu Pro Ser Gln Cys Pro Asp Cys Val
                165                 170                 175

Val Ser Ala Leu Gly Ala Lys Val Leu Ser Ser Val Lys Asp Arg Phe
                180                 185                 190

Ile Asn Phe Phe Val Gly Asn Thr Ile Asn Ser Ser Tyr Phe Pro Asp
                195                 200                 205

His Pro Leu His Ser Ile Ser Val Arg Arg Leu Lys Glu Thr Lys Asp
                210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
                260                 265                 270

Thr Phe His Thr Arg Ile Ile Arg Phe Cys Ser Ile Asn Ser Gly Leu
                275                 280                 285

His Ser Tyr Met Glu Met Pro Leu Glu Cys Ile Leu Thr Glu Lys Arg
                290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
                355                 360                 365

Tyr Val Asn Asp Phe Phe Asn Lys Ile Val Asn Lys Asn Asn Val Arg
                370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
                420                 425                 430

Gln Phe Ser Glu Val Leu Leu Thr Ser Ile Ser Thr Phe Ile Lys Gly
                435                 440                 445

Asp Leu Thr Ile Ala Asn Leu Gly Thr Ser Glu Gly Arg Phe Met Gln
                450                 455                 460

Val Val Val Ser Arg Ser Gly Pro Ser Thr Pro His Val Asn Phe Leu
465                 470                 475                 480
```

-continued

```
Leu Asp Ser His Pro Val Ser Pro Glu Val Ile Val Glu His Thr Leu
            485                 490                 495
Asn Gln Asn Gly Tyr Thr Leu Val Ile Thr Gly Lys Lys Ile Thr Lys
        500                 505                 510
Ile Pro Leu Asn Gly Leu Gly Cys Arg His Phe Gln Ser Cys Ser Gln
        515                 520                 525
Cys Leu Ser Ala Pro Pro Phe Val Gln Cys Gly Trp Cys His Asp Lys
    530                 535                 540
Cys Val Arg Ser Glu Glu Cys Leu Ser Gly Thr Trp Thr Gln Gln Ile
545                 550                 555                 560
Cys Leu Pro Ala Ile Tyr Lys Val Phe Pro Asn Ser Ala Pro Leu Glu
                565                 570                 575
Gly Gly Thr Arg Leu Thr Ile Cys Gly Trp Asp Phe Gly Phe Arg Arg
            580                 585                 590
Asn Asn Lys Phe Asp Leu Lys Lys Thr Arg Val Leu Leu Gly Asn Glu
        595                 600                 605
Ser Cys Thr Leu Thr Leu Ser Glu Ser Thr Met Asn Thr Leu Lys Cys
    610                 615                 620
Thr Val Gly Pro Ala Met Asn Lys His Phe Asn Met Ser Ile Ile Ile
625                 630                 635                 640
Ser Asn Gly His Gly Thr Thr Gln Tyr Ser Thr Phe Ser Tyr Val Asp
                645                 650                 655
Pro Val Ile Thr Ser Ile Ser Pro Lys Tyr Gly Pro Met Ala Gly Gly
            660                 665                 670
Thr Leu Leu Thr Leu Thr Gly Asn Tyr Leu Asn Ser Gly Asn Ser Arg
        675                 680                 685
His Ile Ser Ile Gly Gly Lys Thr Cys Thr Leu Lys Ser Val Ser Asn
    690                 695                 700
Ser Ile Leu Glu Cys Tyr Thr Pro Ala Gln Thr Ile Ser Thr Glu Phe
705                 710                 715                 720
Ala Val Lys Leu Lys Ile Asp Leu Ala Asn Arg Glu Thr Ser Ile Phe
                725                 730                 735
Ser Tyr Arg Glu Asp Pro Ile Val Tyr Glu Ile His Pro Thr Lys Ser
            740                 745                 750
Phe Ile Ser Gly Gly Ser Thr Ile Thr Gly Val Gly Lys Asn Leu Asn
        755                 760                 765
Ser Val Ser Val Pro Arg Met Val Ile Asn Val His Glu Ala Gly Arg
    770                 775                 780
Asn Phe Thr Val Ala Cys Gln His Arg Ser Asn Ser Glu Ile Ile Cys
785                 790                 795                 800
Cys Thr Thr Pro Ser Leu Gln Gln Leu Asn Leu Gln Leu Pro Leu Lys
                805                 810                 815
Thr Lys Ala Phe Phe Met Leu Asp Gly Ile Leu Ser Lys Tyr Phe Asp
            820                 825                 830
Leu Ile Tyr Val His Asn Pro Val Phe Lys Pro Phe Glu Lys Pro Val
        835                 840                 845
Met Ile Ser Met Gly Asn Glu Asn Val Leu Glu Ile Lys Val Gly Phe
    850                 855                 860
Leu His Ser Ser His Asp Val Asn Lys Glu Ala Ser Val Ile Met Leu
865                 870                 875                 880
Phe Ser Gly Leu Lys
                885
```

<210> SEQ ID NO 67
<211> LENGTH: 3527
<212> TYPE: DNA
<213> ORGANISM: Homo sapiens

<400> SEQUENCE: 67

```
gaattcgcca ccatgaaggc ccctgccgtg ctggcccctg gcatcctggt gctgctgttc      60
accctggtgc agagaagcaa cggcgagtgt aaggaggccc tggccaagag cgagatgaac     120
gtgaacatga agtaccagct gcccaacttc accgccgaga cacccatcca gaacgtgatc     180
ctgcacgagc accacatctt cctgggcgcc accaactaca tctacgtgct gaacgaggag     240
gacctgcaga aggtggccga gtacaagacc ggccctgtgc tggagcaccc tgactgcttc     300
ccttgccagg actgtagcag caaggccaac ctgagcggcg agtgtggaa ggacaacatc     360
aacatggccc tggtggtgga cacctactac gacgaccagc tgatcagctg tggcagcgtg     420
aatagaggca cctgccagag acacgtgttc ccccacaacc acaccgccga tatccagagc     480
gaggtgcact gcatcttcag cccccagatc gaggagccca gccagtgccc cgactgtgtg     540
gtgtccgccc tggagccaa ggtgctgtcc agcgtgaagg accggttcat caatttcttt     600
gtgggcaaca ccatcaacag cagctacttc cccgatcacc ccctgcacag catctctgtg     660
aggcggctga aggagacaaa ggacggcttc atgttcctga ccgaccagag ctacatcgat     720
gtgctgcccg agttcagaga cagctacccc atcaagtacg tgcacgcctt cgagagcaac     780
aacttcatct actttctgac cgtgcagcgg gagacactgg acgcccagac cttccacacc     840
cggatcatcc ggttctgctc catcaatagc ggcctgcaca gctacatgga gatgcccctg     900
gagtgtatcc tgaccgagaa gcggaagaag cggtccacca gaaggaggt gttcaacatc     960
ctgcaggccg cctacgtgtc caagcctggc gcccagctgg ccagacagat cggcgccagc    1020
ctgaacgacg atatcctgtt cggcgtgttc gcccagagca agcccgacag cgccgagccc    1080
atggatagaa gcgccatgtg tgccttccct atcaagtatg tgaacgactt cttcaacaag    1140
atcgtgaaca gaacaatgt gagatgcctg cagcacttct acggccccaa tcacgagcac    1200
tgcttcaacc ggaccctgct gagaaacagc agcggctgtg aggccaggag ggacgagtac    1260
aggaccgagt tcaccaccgc cctgcagcgc gtggatctgt tcatgggcca gttcagcgag    1320
gtgctgctga ccagcatcag caccttcatc aagggagacc tgaccatcgc caacctgggc    1380
accagcgagg gcagattcat gcaggtggtg gtgtccagaa gcggcccag caccccctcac    1440
gtgaacttcc tgctggacag ccaccctgtg agccccgagg tgatcgtgga gcacaccctg    1500
aaccagaacg gctacaccct ggtgatcacc ggcaagaaga tcaccaagat ccccctgaac    1560
ggcctgggct gtagacactt ccagagctgc tcccagtgcc tgagcgcccc tcccttcgtg    1620
cagtgcggct ggtgccacga caagtgtgtg aggagcgagg agtgtctgag cggcacctgg    1680
acccagcaga tctgcctgcc cgccatctac aaggtgttcc caacagcgc ccctctggag    1740
ggcggcacca gactgaccat ctgtggctgg gacttcggct ccggcggaa caacaagttc    1800
gacctgaaga aaaccagggt gctgctgggc aatgagagct gtaccctgac cctgagcgag    1860
agcaccatga cacccctgaa gtgcacagtg ggccctgcca tgaacaagca cttcaacatg    1920
agcatcatca tcagcaacgg ccacggcacc acccagtaca gcaccttctc ctacgtggac    1980
cccgtgatca caagcatcag ccccaagtac ggccctatgg ccggaggaac cctgctgacc    2040
ctgaccggca actacctgaa cagcggcaac agcggcaca tcagcatcgg cggcaagaca    2100
tgtacccctga agagcgtgtc caacagcatc ctggagtgct acacccctgc ccagaccatc    2160
```

```
agcaccgagt tcgccgtgaa gctgaagatc gacctggcca accgggagac atccatcttc    2220
agctaccggg aggaccctat cgtgtacgag atccacccca ccaagagctt catcagcggc    2280
ggcagcacca tcaccggagt gggcaagaac ctgaactctg tgagcgtgcc ccggatggtg    2340
atcaacgtgc acgaggccgg cagaaacttc accgtggcct gccagcacag aagcaactcc    2400
gagatcatct gctgtaccac ccctagcctg cagcagctga acctgcagct gcccctgaaa    2460
accaaggcct tcttcatgct ggacggcatc ctgagcaagt acttcgacct gatctatgta    2520
cacaaccccg tgttcaagcc cttcgagaag cccgtgatga tcagcatggg caacgagaac    2580
gtgctggaga tcaagggcaa cgacatcgat cctgaggccg tgaagggcga agtgctgaaa    2640
gtgggcaaca agagctgtga gaacatccac ctgcacagcg aggccgtgct gtgtaccgtg    2700
cccaacgacc tgctgaagct gaacagcgag ctgaacatcg aagtgggctt tctgcacagc    2760
agccacgacg tgaacaaaga ggccagcgtg atcatgctgt tcagcggcct gaagttcgaa    2820
cccaagagct gtgacaagac ccacacctgc ccccttgcc ctgcccctga gctgctgggc    2880
ggacccagcg tgttcctgtt ccctcccaag cctaaggaca ccctgatgat cagcagaacc    2940
cccgaggtga cctgtgtggt ggtggatgtg agccacgagg accctgaggt gaagttcaac    3000
tggtacgtgg acggcgtgga ggtgcacaat gccaagacca gcccaggga ggagcagtac    3060 aacagcacct accgggtggt gtccgtgctg accgtgctgc accaggattg gctgaacggc    3120
aaggaataca agtgtaaggt gtccaacaag gccctgcctg cccctatcga gaaaaccatc    3180
agcaaggcca agggccagcc tagggagccc caggtgtaca ccctgccccc tagcagagat    3240
gagctgacca agaatcaggt gtccctgacc tgcctggtga agggcttcta ccccagcgac    3300
atcgccgtgg agtgggagag caacggccag cccgagaaca actacaagac cacccccct    3360 gtgctggaca gcgatggcag cttcttcctg tacagcaagc tgaccgtgga taagagcaga    3420
tggcagcagg gcaacgtgtt cagctgctcc gtgatgcacg aggccctgca caatcactac    3480
acccagaaga gcctgagcct gtcccctggc aagtgatgag cggccgc               3527
```

<210> SEQ ID NO 68
<211> LENGTH: 1167
<212> TYPE: PRT
<213> ORGANISM: Homo sapiens

<400> SEQUENCE: 68

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125
```

```
Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
```

```
                                                -continued
545                 550                 555                 560
Cys Leu Pro Ala Ile Tyr Lys Val Phe Pro Asn Ser Ala Pro Leu Glu
                565                 570                 575
Gly Gly Thr Arg Leu Thr Ile Cys Gly Trp Asp Phe Gly Phe Arg Arg
                580                 585                 590
Asn Asn Lys Phe Asp Leu Lys Lys Thr Arg Val Leu Leu Gly Asn Glu
                595                 600                 605
Ser Cys Thr Leu Thr Leu Ser Glu Ser Thr Met Asn Thr Leu Lys Cys
                610                 615                 620
Thr Val Gly Pro Ala Met Asn Lys His Phe Asn Met Ser Ile Ile Ile
625                 630                 635                 640
Ser Asn Gly His Gly Thr Thr Gln Tyr Ser Thr Phe Ser Tyr Val Asp
                645                 650                 655
Pro Val Ile Thr Ser Ile Ser Pro Lys Tyr Gly Pro Met Ala Gly Gly
                660                 665                 670
Thr Leu Leu Thr Leu Thr Gly Asn Tyr Leu Asn Ser Gly Asn Ser Arg
                675                 680                 685
His Ile Ser Ile Gly Gly Lys Thr Cys Thr Leu Lys Ser Val Ser Asn
                690                 695                 700
Ser Ile Leu Glu Cys Tyr Thr Pro Ala Gln Thr Ile Ser Thr Glu Phe
705                 710                 715                 720
Ala Val Lys Leu Lys Ile Asp Leu Ala Asn Arg Glu Thr Ser Ile Phe
                725                 730                 735
Ser Tyr Arg Glu Asp Pro Ile Val Tyr Glu Ile His Pro Thr Lys Ser
                740                 745                 750
Phe Ile Ser Gly Gly Ser Thr Ile Thr Gly Val Gly Lys Asn Leu Asn
                755                 760                 765
Ser Val Ser Val Pro Arg Met Val Ile Asn Val His Glu Ala Gly Arg
                770                 775                 780
Asn Phe Thr Val Ala Cys Gln His Arg Ser Asn Ser Glu Ile Ile Cys
785                 790                 795                 800
Cys Thr Thr Pro Ser Leu Gln Gln Leu Asn Leu Gln Leu Pro Leu Lys
                805                 810                 815
Thr Lys Ala Phe Phe Met Leu Asp Gly Ile Leu Ser Lys Tyr Phe Asp
                820                 825                 830
Leu Ile Tyr Val His Asn Pro Val Phe Lys Pro Phe Glu Lys Pro Val
                835                 840                 845
Met Ile Ser Met Gly Asn Glu Asn Val Leu Glu Ile Lys Gly Asn Asp
850                 855                 860
Ile Asp Pro Glu Ala Val Lys Gly Glu Val Leu Lys Val Gly Asn Lys
865                 870                 875                 880
Ser Cys Glu Asn Ile His Leu His Ser Glu Ala Val Leu Cys Thr Val
                885                 890                 895
Pro Asn Asp Leu Leu Lys Leu Asn Ser Glu Leu Asn Ile Glu Val Gly
                900                 905                 910
Phe Leu His Ser Ser His Asp Val Asn Lys Glu Ala Ser Val Ile Met
                915                 920                 925
Leu Phe Ser Gly Leu Lys Phe Glu Pro Lys Ser Cys Asp Lys Thr His
                930                 935                 940
Thr Cys Pro Pro Cys Pro Ala Pro Glu Leu Leu Gly Gly Pro Ser Val
945                 950                 955                 960
Phe Leu Phe Pro Pro Lys Pro Lys Asp Thr Leu Met Ile Ser Arg Thr
                965                 970                 975
```

```
Pro Glu Val Thr Cys Val Val Asp Val Ser His Glu Asp Pro Glu
        980                 985                 990

Val Lys Phe Asn Trp Tyr Val Asp Gly Val Glu Val His Asn Ala Lys
    995                 1000                1005

Thr Lys Pro Arg Glu Glu Gln Tyr Asn Ser Thr Tyr Arg Val Val
    1010                1015                1020

Ser Val Leu Thr Val Leu His Gln Asp Trp Leu Asn Gly Lys Glu
    1025                1030                1035

Tyr Lys Cys Lys Val Ser Asn Lys Ala Leu Pro Ala Pro Ile Glu
    1040                1045                1050

Lys Thr Ile Ser Lys Ala Lys Gly Gln Pro Arg Glu Pro Gln Val
    1055                1060                1065

Tyr Thr Leu Pro Pro Ser Arg Asp Glu Leu Thr Lys Asn Gln Val
    1070                1075                1080

Ser Leu Thr Cys Leu Val Lys Gly Phe Tyr Pro Ser Asp Ile Ala
    1085                1090                1095

Val Glu Trp Glu Ser Asn Gly Gln Pro Glu Asn Asn Tyr Lys Thr
    1100                1105                1110

Thr Pro Pro Val Leu Asp Ser Asp Gly Ser Phe Phe Leu Tyr Ser
    1115                1120                1125

Lys Leu Thr Val Asp Lys Ser Arg Trp Gln Gln Gly Asn Val Phe
    1130                1135                1140

Ser Cys Ser Val Met His Glu Ala Leu His Asn His Tyr Thr Gln
    1145                1150                1155

Lys Ser Leu Ser Leu Ser Pro Gly Lys
    1160                1165

<210> SEQ ID NO 69
<211> LENGTH: 20
<212> TYPE: DNA
<213> ORGANISM: Homo sapiens

<400> SEQUENCE: 69
tggacggcat cctgagcaag                                                 20

<210> SEQ ID NO 70
<211> LENGTH: 42
<212> TYPE: DNA
<213> ORGANISM: Homo sapiens

<400> SEQUENCE: 70
gctgctgtgc agaaagccca ccttgatctc cagcacgttc tc                        42

<210> SEQ ID NO 71
<211> LENGTH: 40
<212> TYPE: DNA
<213> ORGANISM: Homo sapiens

<400> SEQUENCE: 71
ggcctctttg ttcacgtcgt ggctgctgtg cagaaagccc                           40

<210> SEQ ID NO 72
<211> LENGTH: 43
<212> TYPE: DNA
<213> ORGANISM: Homo sapiens

<400> SEQUENCE: 72
gctgaacagc atgatcacgc tggcctcttt gttcacgtcg tgg                       43
```

<210> SEQ ID NO 73
<211> LENGTH: 36
<212> TYPE: DNA
<213> ORGANISM: Homo sapiens

<400> SEQUENCE: 73
cgcttcgaac ttcaggccgc tgaacagcat gatcac                        36

<210> SEQ ID NO 74
<211> LENGTH: 2747
<212> TYPE: DNA
<213> ORGANISM: Homo sapiens

<400> SEQUENCE: 74
gaattcgcca ccatgaaggc ccctgccgtg ctggcccctg gcatcctggt gctgctgttc     60
accctggtgc agagaagcaa cggcgagtgt aaggaggccc tggccaagag cgagatgaac    120
gtgaacatga agtaccagct gcccaacttc accgccgaga cacccatcca gaacgtgatc    180
ctgcacgagc accacatctt cctgggcgcc accaactaca tctacgtgct gaacgaggag    240
gacctgcaga aggtggccga gtacaagacc ggccctgtgc tggagcaccc tgactgcttc    300
ccttgccagg actgtagcag caaggccaac ctgagcggcg agtgtggaa ggacaacatc    360
aacatggccc tggtggtgga cacctactac gacgaccagc tgatcagctg tggcagcgtg    420
aatagaggca cctgccagag acacgtgttc ccccacaacc acaccgccga tatccagagc    480
gaggtgcact gcatcttcag ccccccagatc gaggagccca ccagtgccc cgactgtgtg    540
gtgtccgccc tgggagccaa ggtgctgtcc agcgtgaagg accggttcat caatttcttt    600
gtgggcaaca ccatcaacag cagctacttc cccgatcacc ccctgcacag catctctgtg    660
aggcggctga aggagacaaa ggacggcttc atgttcctga ccgaccagag ctacatcgat    720
gtgctgcccg agttcagaga cagctacccc atcaagtacg tgcacgcctt cgagagcaac    780
aacttcatct actttctgac cgtgcagcgg agagactgg acgcccagac cttccacacc    840
cggatcatcc ggttctgctc catcaatagc ggcctgcaca gctacatgga gatgccctg    900
gagtgtatcc tgaccgagaa cggaagaag cggtccacca gaaggaggt gttcaacatc    960
ctgcaggccg cctacgtgtc caagcctggc gcccagctgg ccagacagat cggcgccagc   1020
ctgaacgacg atatcctgtt cggcgtgttc gcccagagca agcccgacag cgccgagccc   1080
atggatagaa gcgccatgtg tgccttccct atcaagtatg tgaacgactt cttcaacaag   1140
atcgtgaaca gaacaatgt gagatgcctg cagcacttct acggccccaa tcacgagcac   1200
tgcttcaacc ggaccctgct gagaaacagc agcggctgtg aggccaggag ggacgagtac   1260
aggaccgagt tcaccaccgc cctgcagcgc gtggatctgt tcatgggcca gttcagcgag   1320
gtgctgctga ccagcatcag caccttcatc aagggagacc tgaccatcgc caacctgggc   1380
accagcgagg gcagattcat gcaggtggtg gtgtccagaa gcggcccag caccctcac   1440
gtgaacttcc tgctggacag ccaccctgtg agccccgagg tgatcgtgga gcacaccctg   1500
aaccagaacg gctacaccct ggtgatcacc ggcaagaaga tcaccaagat ccccctgaac   1560
ggcctgggct gtagacactt ccagagctgc tcccagtgcc tgagcgcccc tcccttcgtg   1620
cagtgcggct ggtgccacga caagtgtgtg aggagcgagg agtgtctgag cggcacctgg   1680
acccagcaga tctgcctgcc cgccatctac aaggtgttcc ccaacagcgc ccctctggag   1740
ggcggcacca gactgaccat ctgtggctgg gacttcggct tccggcggaa caacaagttc   1800

-continued

```
gacctgaaga aaaccagggt gctgctgggc aatgagagct gtaccctgac cctgagcgag    1860
agcaccatga acaccctgaa gtgcacagtg ggccctgcca tgaacaagca cttcaacatg    1920
agcatcatca tcagcaacgg ccacggcacc acccagtaca gcaccttctc ctacgtggac    1980
cccgtgatca caagcatcag ccccaagtac ggccctatgg ccggaggaac cctgctgacc    2040
ctgaccggca actacctgaa cagcggcaac agcggcaca tcagcatcgg cggcaagaca    2100
tgtaccctga agagcgtgtc caacagcatc ctggagtgct acacccctgc ccagaccatc    2160
agcaccgagt cgccgtgaa gctgaagatc gacctggcca accgggagac atccatcttc    2220
agctaccggg aggaccctat cgtgtacgag atccaccccca ccaagagctt catcagcggc    2280
ggcagcacca tcaccggagt gggcaagaac ctgaactctg tgagcgtgcc ccggatggtg    2340
atcaacgtgc acgaggccgg cagaaacttc accgtggcct gccagcacag aagcaactcc    2400
gagatcatct gctgtaccac ccctagcctg cagcagctga acctgcagct gcccctgaaa    2460
accaaggcct tcttcatgct ggacggcatc ctgagcaagt acttcgacct gatctatgta    2520
cacaaccccg tgttcaagcc cttcgagaag cccgtgatga tcagcatggg caacgagaac    2580
gtgctggaga tcaaggtggg ctttctgcac agcagccacg acgtgaacaa agaggccagc    2640
gtgatcatgc tgttcagcgg cctgaagccc tggagccacc ctcagttcga gaaaaccggc    2700
caccatcacc accatcatca ccacggcggc cagtgataag cggccgc                  2747
```

<210> SEQ ID NO 75
<211> LENGTH: 907
<212> TYPE: PRT
<213> ORGANISM: Homo sapiens

<400> SEQUENCE: 75

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205
```

```
His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
```

```
                625                 630                 635                 640
Ser Asn Gly His Gly Thr Thr Gln Tyr Ser Thr Phe Ser Tyr Val Asp
                        645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
        690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
        755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
                785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845

Met Ile Ser Met Gly Asn Glu Asn Val Leu Glu Ile Lys Val Gly Phe
    850                 855                 860

Leu His Ser Ser His Asp Val Asn Lys Glu Ala Ser Val Ile Met Leu
865                 870                 875                 880

Phe Ser Gly Leu Lys Pro Trp Ser His Pro Gln Phe Glu Lys Thr Gly
                885                 890                 895

His His His His His His His Gly Gly Gln
                900                 905

<210> SEQ ID NO 76
<211> LENGTH: 3380
<212> TYPE: DNA
<213> ORGANISM: Homo sapiens

<400> SEQUENCE: 76
gaattcgcca ccatgaaggc ccctgccgtg ctggccctg gcatcctggt gctgctgttc      60
accctggtgc agagaagcaa cggcgagtgt aaggaggccc tggccaagag cgagatgaac     120
gtgaacatga agtaccagct gcccaacttc accgccgaga cacccatcca gaacgtgatc     180
ctgcacgagc accacatctt cctgggcgcc accaactaca tctacgtgct gaacgaggag     240
gacctgcaga aggtggccga gtacaagacc ggccctgtgc tggagcaccc tgactgcttc     300
ccttgccagg actgtagcag caaggccaac ctgagcggcg agtgtggaa ggacaacatc     360 aacatggccc tggtggtgga cacctactac gacgaccagc tgatcagctg tggcagcgtg     420
aatagaggca cctgccagag acacgtgttc cccacaaccc acaccgccga tatccagagc     480
gaggtgcact gcatcttcag cccccagatc gaggagccca gccagtgccc cgactgtgtg     540
```

```
gtgtccgccc tgggagccaa ggtgctgtcc agcgtgaagg accggttcat caatttcttt    600
gtgggcaaca ccatcaacag cagctacttc cccgatcacc ccctgcacag catctctgtg    660
aggcggctga aggagacaaa ggacggcttc atgttcctga ccgaccagag ctacatcgat    720
gtgctgcccg agttcagaga cagctacccc atcaagtacg tgcacgcctt cgagagcaac    780
aacttcatct actttctgac cgtgcagcgg gagacactgg acgccagac cttccacacc     840
cggatcatcc ggttctgctc catcaatagc ggcctgcaca gctacatgga gatgcccctg    900
gagtgtatcc tgaccgagaa gcggaagaag cggtccacca agaaggaggt gttcaacatc    960
ctgcaggccg cctacgtgtc caagcctggc gcccagctgg ccagacagat cggcgccagc   1020
ctgaacgacg atatcctgtt cggcgtgttc gcccagagca gcccgacag cgccgagccc    1080
atggatagaa gcgccatgtg tgccttccct atcaagtatg tgaacgactt cttcaacaag   1140
atcgtgaaca agaacaatgt gagatgcctg cagcacttct acggcccaa tcacgagcac    1200
tgcttcaacc ggaccctgct gagaaacagc agcggctgtg aggccaggag ggacgagtac   1260
aggaccgagt tcaccaccgc cctgcagcgc gtggatctgt tcatgggcca gttcagcgag   1320
gtgctgctga ccagcatcag caccttcatc aagggagacc tgaccatcgc caacctgggc   1380
accagcgagg gcagattcat gcaggtggtg gtgtccagaa gcggcccag cacccctcac    1440
gtgaacttcc tgctggacag ccaccctgtg agccccgagg tgatcgtgga gcacccctg    1500
aaccagaacg gctacaccct ggtgatcacc ggcaagaaga tcaccaagat ccccctgaac   1560
ggcctgggct gtagacactt ccagagctgc tcccagtgcc tgagcgcccc tcccttcgtg   1620
cagtgcggct ggtgccacga caagtgtgtg aggagcgagg agtgtctgag cggcacctgg   1680
acccagcaga tctgcctgcc cgccatctac aaggtgttcc caacagcgc ccctctggag    1740
ggcggcacca gactgaccat ctgtggctgg gacttcggct tccggcggaa caacaagttc   1800
gacctgaaga aaaccagggt gctgctgggc aatgagagct gtaccctgac cctgagcgag   1860
agcaccatga acaccctgaa gtgcacagtg ggccctgcca tgaacaagca cttcaacatg   1920
agcatcatca tcagcaacgg ccacggcacc acccagtaca gcaccttctc ctacgtggac   1980
cccgtgatca caagcatcag ccccaagtac ggccctatgg ccggaggaac cctgctgacc   2040
ctgaccggca actacctgaa cagcggcaac agcggcaca tcagcatcgg cggcaagaca    2100
tgtaccctga agagcgtgtc caacagcatc ctggagtgct acacccctgc ccagaccatc   2160
agcaccgagt tcgccgtgaa gctgaagatc gacctggcca accgggagac atccatcttc   2220
agctaccggg aggaccctat cgtgtacgag atccacccca ccaagagctt catcagcggc   2280
ggcagcacca tcaccggagt gggcaagaac ctgaactctg tgagcgtgcc ccggatggtg   2340
atcaacgtgc acgaggccgg cagaaacttc accgtggcct gccagcacag aagcaactcc   2400
gagatcatct gctgtaccac ccctagcctg cagcagctga acctgcagct gccccctgaaa  2460
accaaggcct tcttcatgct ggacggcatc ctgagcaagt acttcgacct gatctatgta   2520
cacaaccccg tgttcaagcc cttcgagaag cccgtgatga tcagcatggg caacgagaac   2580
gtgctggaga tcaaggtggg ctttctgcac agcagccacg acgtgaacaa agaggccagc   2640
gtgatcatgc tgttcagcgg cctgaagttc gaacccaaga ctgtgacaa gacccacacc   2700
tgccccccctt gccctgcccc tgagctgctg gcggaccca cgtgttcct gttccctccc   2760
aagcctaagg acaccctgat gatcagcaga acccccgagg tgacctgtgt ggtggtggat   2820
gtgagccacg aggaccctga ggtgaagttc aactggtacg tggacggcgt ggaggtgcac   2880
aatgccaaga ccaagcccag ggaggagcag tacaacagca cctaccgggt ggtgtccgtg   2940
```

-continued

```
ctgaccgtgc tgcaccagga ttggctgaac ggcaaggaat acaagtgtaa ggtgtccaac    3000
aaggccctgc ctgccccctat cgagaaaacc atcagcaagg ccaagggcca gcctagggag   3060
ccccaggtgt acaccctgcc ccctagcaga gatgagctga ccaagaatca ggtgtccctg    3120
acctgcctgg tgaagggctt ctaccccagc gacatcgccg tggagtggga gagcaacggc    3180
cagcccgaga caactacaa gaccaccccc cctgtgctgg acagcgatgg cagcttcttc     3240
ctgtacagca agctgaccgt ggataagagc agatggcagc agggcaacgt gttcagctgc    3300
tccgtgatgc acgaggccct gcacaatcac tacacccaga agagcctgag cctgtcccct   3360
ggcaagtgat gagcggccgc                                                 3380
```

<210> SEQ ID NO 77
<211> LENGTH: 1118
<212> TYPE: PRT
<213> ORGANISM: Homo sapiens

<400> SEQUENCE: 77

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285
```

-continued

```
His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
            355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
```

```
                705                 710                 715                 720
Ala Val Lys Leu Lys Ile Asp Leu Ala Asn Arg Glu Thr Ser Ile Phe
                    725                 730                 735
Ser Tyr Arg Glu Asp Pro Ile Val Tyr Glu Ile His Pro Thr Lys Ser
                    740                 745                 750
Phe Ile Ser Gly Gly Ser Thr Ile Thr Gly Val Gly Lys Asn Leu Asn
                    755                 760                 765
Ser Val Ser Val Pro Arg Met Val Ile Asn Val His Glu Ala Gly Arg
    770                 775                 780
Asn Phe Thr Val Ala Cys Gln His Arg Ser Asn Ser Glu Ile Ile Cys
785                 790                 795                 800
Cys Thr Thr Pro Ser Leu Gln Gln Leu Asn Leu Gln Leu Pro Leu Lys
                805                 810                 815
Thr Lys Ala Phe Phe Met Leu Asp Gly Ile Leu Ser Lys Tyr Phe Asp
                820                 825                 830
Leu Ile Tyr Val His Asn Pro Val Phe Lys Pro Phe Lys Pro Val
                835                 840                 845
Met Ile Ser Met Gly Asn Glu Asn Val Leu Glu Ile Lys Val Gly Phe
    850                 855                 860
Leu His Ser Ser His Asp Val Asn Lys Glu Ala Ser Val Ile Met Leu
865                 870                 875                 880
Phe Ser Gly Leu Lys Phe Glu Pro Lys Ser Cys Asp Lys Thr His Thr
                885                 890                 895
Cys Pro Pro Cys Pro Ala Pro Glu Leu Leu Gly Gly Pro Ser Val Phe
                900                 905                 910
Leu Phe Pro Pro Lys Pro Lys Asp Thr Leu Met Ile Ser Arg Thr Pro
                915                 920                 925
Glu Val Thr Cys Val Val Val Asp Val Ser His Glu Asp Pro Glu Val
    930                 935                 940
Lys Phe Asn Trp Tyr Val Asp Gly Val Glu Val His Asn Ala Lys Thr
945                 950                 955                 960
Lys Pro Arg Glu Glu Gln Tyr Asn Ser Thr Tyr Arg Val Val Ser Val
                965                 970                 975
Leu Thr Val Leu His Gln Asp Trp Leu Asn Gly Lys Glu Tyr Lys Cys
                980                 985                 990
Lys Val Ser Asn Lys Ala Leu Pro Ala Pro Ile Glu Lys Thr Ile Ser
                995                 1000                1005
Lys Ala Lys Gly Gln Pro Arg Glu Pro Gln Val Tyr Thr Leu Pro
    1010                1015                1020
Pro Ser Arg Asp Glu Leu Thr Lys Asn Gln Val Ser Leu Thr Cys
    1025                1030                1035
Leu Val Lys Gly Phe Tyr Pro Ser Asp Ile Ala Val Glu Trp Glu
    1040                1045                1050
Ser Asn Gly Gln Pro Glu Asn Asn Tyr Lys Thr Thr Pro Pro Val
    1055                1060                1065
Leu Asp Ser Asp Gly Ser Phe Phe Leu Tyr Ser Lys Leu Thr Val
    1070                1075                1080
Asp Lys Ser Arg Trp Gln Gln Gly Asn Val Phe Ser Cys Ser Val
    1085                1090                1095
Met His Glu Ala Leu His Asn His Tyr Thr Gln Lys Ser Leu Ser
    1100                1105                1110
Leu Ser Pro Gly Lys
    1115
```

<210> SEQ ID NO 78
<211> LENGTH: 3374
<212> TYPE: DNA
<213> ORGANISM: Homo sapiens

<400> SEQUENCE: 78

| | | | | | |
|---|---|---|---|---|---|
| gaattcgcca | ccatgaaggc | ccctgccgtg | ctggccctg | gcatcctggt | gctgctgttc | 60 |
| accctggtgc | agagaagcaa | cggcgagtgt | aaggaggccc | tggccaagag | cgagatgaac | 120 |
| gtgaacatga | agtaccagct | gcccaacttc | accgccgaga | cacccatcca | gaacgtgatc | 180 |
| ctgcacgagc | accacatctt | cctgggcgcc | accaactaca | tctacgtgct | gaacgaggag | 240 |
| gacctgcaga | aggtggccga | gtacaagacc | ggccctgtgc | tggagcaccc | tgactgcttc | 300 |
| ccttgccagg | actgtagcag | caaggccaac | ctgagcggcg | gagtgtggaa | ggacaacatc | 360 |
| aacatggccc | tggtggtgga | cacctactac | gacgaccagc | tgatcagctg | tggcagcgtg | 420 |
| aatagaggca | cctgccagag | acacgtgttc | ccccacaacc | acaccgccga | tatccagagc | 480 |
| gaggtgcact | gcatcttcag | cccccagatc | gaggagccca | gccagtgccc | cgactgtgtg | 540 |
| gtgtccgccc | tgggagccaa | ggtgctgtcc | agcgtgaagg | accggttcat | caatttcttt | 600 |
| gtgggcaaca | ccatcaacag | cagctacttc | cccgatcacc | ccctgcacag | catctctgtg | 660 |
| aggcggctga | aggagacaaa | ggacggcttc | atgttcctga | ccgaccagag | ctacatcgat | 720 |
| gtgctgcccg | agttcagaga | cagctacccc | atcaagtacg | tgcacgcctt | cgagagcaac | 780 |
| aacttcatct | actttctgac | cgtgcagcgg | gagacactgg | acgcccagac | cttccacacc | 840 |
| cggatcatcc | ggttctgctc | catcaatagc | ggcctgcaca | gctacatgga | gatgcccctg | 900 |
| gagtgtatcc | tgaccgagaa | gcggaagaag | cggtccacca | gaaggaggt | gttcaacatc | 960 |
| ctgcaggccg | cctacgtgtc | caagcctggc | gcccagctgg | ccagacagat | cggcgccagc | 1020 |
| ctgaacgacg | atatcctgtt | cggcgtgttc | gcccagagca | agcccgacag | cgccgagccc | 1080 |
| atggatagaa | gcgccatgtg | tgccttccct | atcaagtatg | tgaacgactt | cttcaacaag | 1140 |
| atcgtgaaca | gaacaatgt | gagatgcctg | cagcacttct | acggccccaa | tcacgagcac | 1200 |
| tgcttcaacc | ggaccctgct | gagaaacagc | agcggctgtg | aggccaggag | ggacgagtac | 1260 |
| aggaccgagt | tcaccaccgc | cctgcagcgc | gtggatctgt | tcatgggcca | gttcagcgag | 1320 |
| gtgctgctga | ccagcatcag | caccttcatc | aagggagacc | tgaccatcgc | caacctgggc | 1380 |
| accagcgagg | gcagattcat | gcaggtggtg | gtgtccagaa | gcggcccag | caccctcac | 1440 |
| gtgaacttcc | tgctggacag | ccaccctgtg | agccccgagg | tgatcgtgga | gcacaccctg | 1500 |
| aaccagaacg | gctacacccct | ggtgatcacc | ggcaagaaga | tcaccaagat | cccccctgaac | 1560 |
| ggcctgggct | gtagacactt | ccagagctgc | tcccagtgcc | tgagcgcccc | tcccttcgtg | 1620 |
| cagtgcggct | ggtgccacga | caagtgtgtg | aggagcgagg | agtgtctgag | cggcacctgg | 1680 |
| acccagcaga | tctgcctgcc | cgccatctac | aaggtgttcc | ccaacagcgc | ccctctggag | 1740 |
| ggcggcacca | gactgaccat | ctgtggctgg | gacttcggct | tccggcggaa | caacaagttc | 1800 |
| gacctgaaga | aaaccagggt | gctgctgggc | aatgagagct | gtaccctgac | cctgagcgag | 1860 |
| agcaccatga | cacccctgaa | gtgcacagtg | ggccctgcca | tgaacaagca | cttcaacatg | 1920 |
| agcatcatca | tcagcaacgg | ccacggcacc | acccagtaca | gcaccttctc | ctacgtggac | 1980 |
| cccgtgatca | caagcatcag | ccccaagtac | ggcctatgg | ccggaggaac | cctgctgacc | 2040 |
| ctgaccggca | actacctgaa | cagcggcaac | agccggcaca | tcagcatcgg | cggcaagaca | 2100 |

-continued

```
tgtaccctga agagcgtgtc aacagcatc ctggagtgct acaccctgc ccagaccatc      2160 agcaccgagt tcgccgtgaa gctgaagatc gacctggcca accgggagac atccatcttc      2220
agctaccggg aggaccctat cgtgtacgag atccacccca ccaagagctt catcagcggc      2280
ggcagcacca tcaccggagt gggcaagaac ctgaactctg tgagcgtgcc ccggatggtg      2340
atcaacgtgc acgaggccgg cagaaacttc accgtggcct gccagcacag aagcaactcc      2400
gagatcatct gctgtaccac ccctagcctg cagcagctga acctgcagct gcccctgaaa      2460
accaaggcct tcttcatgct ggacggcatc ctgagcaagt acttcgacct gatctatgta      2520
cacaaccccg tgttcaagcc cttcgagaag cccgtgatga tcagcatggg caacgagaac      2580
gtgctggaga tcaaggtgag gaacgccctg aacaccgtgc tgaatcacca gctgaagctg      2640
aaccccggga gccaccccca gttcgaaccc aagagctgtg acaagaccca cctgccccc      2700 ccttgccctg cccctgagct gctgggcgga cccagcgtgt tcctgttccc tcccaagcct      2760
aaggacaccc tgatgatcag cagaaccccc gaggtgacct gtgtggtggt ggatgtgagc      2820
cacgaggacc ctgaggtgaa gttcaactgg tacgtggacg gcgtggaggt gcacaatgcc      2880
aagaccaagc caggagga gcagtacaac agcacctacc gggtggtgtc cgtgctgacc      2940
gtgctgcacc aggattggct gaacggcaag gaatacaagt gtaaggtgtc caacaaggcc      3000
ctgcctgccc ctatcgagaa aaccatcagc aaggccaagg ccagcctag ggagccccag      3060 gtgtacaccc tgcccctag cagagatgag ctgaccaaga atcaggtgtc cctgacctgc      3120
ctggtgaagg gcttctaccc cagcgacatc gccgtggagt gggagagcaa cggccagccc      3180
gagaacaact acaagaccac cccccctgtg ctggacagcg atggcagctt cttcctgtac      3240
agcaagctga ccgtggataa gagcagatgg cagcagggca acgtgttcag ctgctccgtg      3300
atgcacgagg ccctgcacaa tcactacacc cagaagagcc tgagcctgtc ccctggcaag      3360
tgatgagcgg ccgc                                                       3374
```

<210> SEQ ID NO 79
<211> LENGTH: 1116
<212> TYPE: PRT
<213> ORGANISM: Homo sapiens

<400> SEQUENCE: 79

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140
```

-continued

```
Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
            165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
            195                 200                 205

His Pro Leu His Ser Ile Ser Val Arg Arg Leu Lys Glu Thr Lys Asp
            210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
            275                 280                 285

His Ser Tyr Met Glu Met Pro Leu Glu Cys Ile Leu Thr Glu Lys Arg
            290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
            355                 360                 365

Tyr Val Asn Asp Phe Phe Asn Lys Ile Val Asn Lys Asn Asn Val Arg
            370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
            435                 440                 445

Asp Leu Thr Ile Ala Asn Leu Gly Thr Ser Glu Gly Arg Phe Met Gln
            450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
            485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
            530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
```

-continued

```
                565                 570                 575
Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
            645                 650                 655

Pro Val Ile Thr Ser Ile Ser Pro Lys Tyr Gly Pro Met Ala Gly Gly
        660                 665                 670

Thr Leu Leu Thr Leu Thr Gly Asn Tyr Leu Asn Ser Gly Asn Ser Arg
    675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
            725                 730                 735

Ser Tyr Arg Glu Asp Pro Ile Val Tyr Glu Ile His Pro Thr Lys Ser
        740                 745                 750

Phe Ile Ser Gly Gly Ser Thr Ile Thr Gly Val Gly Lys Asn Leu Asn
    755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
            805                 810                 815

Thr Lys Ala Phe Phe Met Leu Asp Gly Ile Leu Ser Lys Tyr Phe Asp
        820                 825                 830

Leu Ile Tyr Val His Asn Pro Val Phe Lys Pro Phe Glu Lys Pro Val
    835                 840                 845

Met Ile Ser Met Gly Asn Glu Asn Val Leu Glu Ile Lys Val Arg Asn
850                 855                 860

Ala Leu Asn Thr Val Leu Asn His Gln Leu Lys Leu Asn Pro Trp Ser
865                 870                 875                 880

His Pro Gln Phe Glu Pro Lys Ser Cys Asp Lys Thr His Thr Cys Pro
            885                 890                 895

Pro Cys Pro Ala Pro Glu Leu Leu Gly Gly Pro Ser Val Phe Leu Phe
        900                 905                 910

Pro Pro Lys Pro Lys Asp Thr Leu Met Ile Ser Arg Thr Pro Glu Val
        915                 920                 925

Thr Cys Val Val Val Asp Val Ser His Glu Asp Pro Glu Val Lys Phe
    930                 935                 940

Asn Trp Tyr Val Asp Gly Val Glu Val His Asn Ala Lys Thr Lys Pro
945                 950                 955                 960

Arg Glu Glu Gln Tyr Asn Ser Thr Tyr Arg Val Val Ser Val Leu Thr
            965                 970                 975

Val Leu His Gln Asp Trp Leu Asn Gly Lys Glu Tyr Lys Cys Lys Val
        980                 985                 990
```

-continued

Ser Asn Lys Ala Leu Pro Ala Pro Ile Glu Lys Thr Ile Ser Lys Ala
        995                 1000                1005

Lys Gly Gln Pro Arg Glu Pro Gln Val Tyr Thr Leu Pro Pro Ser
    1010                1015                1020

Arg Asp Glu Leu Thr Lys Asn Gln Val Ser Leu Thr Cys Leu Val
    1025                1030                1035

Lys Gly Phe Tyr Pro Ser Asp Ile Ala Val Glu Trp Glu Ser Asn
    1040                1045                1050

Gly Gln Pro Glu Asn Asn Tyr Lys Thr Thr Pro Pro Val Leu Asp
    1055                1060                1065

Ser Asp Gly Ser Phe Phe Leu Tyr Ser Lys Leu Thr Val Asp Lys
    1070                1075                1080

Ser Arg Trp Gln Gln Gly Asn Val Phe Ser Cys Ser Val Met His
    1085                1090                1095

Glu Ala Leu His Asn His Tyr Thr Gln Lys Ser Leu Ser Leu Ser
    1100                1105                1110

Pro Gly Lys
    1115

<210> SEQ ID NO 80
<211> LENGTH: 72
<212> TYPE: DNA
<213> ORGANISM: Artificial Organism
<220> FEATURE:
<223> OTHER INFORMATION: Synthetic oligonucleotide

<400> SEQUENCE: 80
gtgggattcc tgcattcctc tcatgatgta aataaggaag ccagtgtaat tatgttattc      60
tcaggcttaa aa                                                         72

<210> SEQ ID NO 81
<211> LENGTH: 24
<212> TYPE: PRT
<213> ORGANISM: Homo sapiens

<400> SEQUENCE: 81

Val Gly Phe Leu His Ser Ser His Asp Val Asn Lys Glu Ala Ser Val
1               5                   10                  15

Ile Met Leu Phe Ser Gly Leu Lys
            20

<210> SEQ ID NO 82
<211> LENGTH: 47
<212> TYPE: DNA
<213> ORGANISM: Artificial Organism
<220> FEATURE:
<223> OTHER INFORMATION: Synthetic oligonucleotide

<400> SEQUENCE: 82
taagaaatgc tttaaacact gtcttaaatc atcagctcaa acttaat                   47

<210> SEQ ID NO 83
<211> LENGTH: 16
<212> TYPE: PRT
<213> ORGANISM: Homo sapiens

<400> SEQUENCE: 83

Val Arg Asn Ala Leu Asn Thr Val Leu Asn His Gln Leu Lys Leu Asn
1               5                   10                  15

The invention claimed is:

1. An isolated polypeptide having the amino acid sequence as set forth in SEQ ID NO:38.

2. A pharmaceutical composition comprising as an active ingredient the polypeptide sequence of claim 1, further comprising a pharmaceutically acceptable diluent or carrier.

3. A method for treating a Met related disease or disorder, comprising administering to a subject having the disease or disorder a therapeutically effective amount of the pharmaceutical composition of claim 2, thereby reducing the deleterious effects of the Met related disease or disorder, wherein the Met related disease or disorder is selected from the group consisting of malignant tumors and lymphoid malignancies.

4. The method according to claim 3, wherein the tumor is selected from the group consisting of carcinoma, lymphoma, leukemia, sarcoma and blastoma.

5. The method according to claim 3, wherein the tumor is selected from the group consisting of primary cancer, metastatic cancer, breast cancer, colon cancer, colorectal cancer, gastrointestinal tumors, esophageal cancer, cervical cancer, ovarian cancer, endometrial or uterine carcinoma, vulval cancer, liver cancer, hepatocellular cancer, bladder cancer, kidney cancer, hereditary and sporadic papillary renal cell carcinoma, pancreatic cancer, various types of head and neck cancer, lung cancer, prostate cancer, thyroid cancer, brain tumors, glioblastoma, glioma, malignant peripheral nerve sheath tumors, cancer of the peritoneum, cutaneous malignant melanoma, and salivary gland carcinoma.

6. The method according to claim 5 wherein the lung cancer is selected from the group consisting of non-small cell lung cancer, small cell lung cancer, squamous cell carcinoma and lung adenocarcinoma.

* * * * *